US010829452B2

(12) United States Patent
Yu et al.

(10) Patent No.: US 10,829,452 B2
(45) Date of Patent: Nov. 10, 2020

(54) HISTONE METHYLTRANSFERASE INHIBITORS

(71) Applicant: GLOBAL BLOOD THERAPEUTICS, INC., South San Francisco, CA (US)

(72) Inventors: Ming Yu, Foster City, CA (US); Zhe Li, San Diego, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/850,389

(22) Filed: Dec. 21, 2017

(65) Prior Publication Data
US 2018/0186745 A1    Jul. 5, 2018

Related U.S. Application Data

(60) Provisional application No. 62/438,121, filed on Dec. 22, 2016.

(51) Int. Cl.
| | |
|---|---|
| *C07D 215/38* | (2006.01) |
| *C07D 401/12* | (2006.01) |
| *C07D 471/04* | (2006.01) |
| *C07D 487/04* | (2006.01) |
| *C07D 491/048* | (2006.01) |
| *C07D 491/052* | (2006.01) |
| *C07D 401/14* | (2006.01) |
| *C07D 405/14* | (2006.01) |
| *C07D 413/12* | (2006.01) |
| *C07D 215/20* | (2006.01) |
| *C07D 215/227* | (2006.01) |
| *C07D 401/04* | (2006.01) |
| *C07D 405/04* | (2006.01) |
| *C07D 405/12* | (2006.01) |

(52) U.S. Cl.
CPC ......... *C07D 215/38* (2013.01); *C07D 215/20* (2013.01); *C07D 215/227* (2013.01); *C07D 401/04* (2013.01); *C07D 401/12* (2013.01); *C07D 401/14* (2013.01); *C07D 405/04* (2013.01); *C07D 405/12* (2013.01); *C07D 405/14* (2013.01); *C07D 413/12* (2013.01); *C07D 471/04* (2013.01); *C07D 487/04* (2013.01); *C07D 491/048* (2013.01); *C07D 491/052* (2013.01)

(58) Field of Classification Search
CPC ............................ C07D 401/14; C07D 401/12; C07D 215/227; C07D 215/18
See application file for complete search history.

(56) References Cited

U.S. PATENT DOCUMENTS

| | | |
|---|---|---|
| 4,107,288 A | 8/1978 | Oppenheim et al. |
| 5,145,684 A | 9/1992 | Liversidge et al. |
| 2002/0099068 A1 | 7/2002 | Ritzeler et al. |
| 2011/0142796 A1 | 6/2011 | Connors et al. |
| 2011/0275762 A1 | 11/2011 | Cmijanovic et al. |
| 2012/0208819 A1 | 8/2012 | Arndt et al. |
| 2012/0244110 A1 | 9/2012 | Chen et al. |
| 2013/0116273 A1 | 5/2013 | Frederick et al. |
| 2013/0231360 A1 | 9/2013 | Higgins et al. |
| 2015/0274660 A1 | 10/2015 | Pliushchev et al. |
| 2017/0002005 A1 | 1/2017 | Kroth et al. |

FOREIGN PATENT DOCUMENTS

| | | |
|---|---|---|
| EP | 2364983 | 9/2011 |
| WO | WO 2004/058759 A1 | 7/2004 |
| WO | WO 2005/020999 A1 | 3/2005 |
| WO | WO 2005/032484 A2 | 4/2005 |
| WO | WO 2005/032484 A3 | 4/2005 |
| WO | WO 2006/086449 A2 | 8/2006 |
| WO | WO 2008/101682 | 8/2008 |
| WO | WO 2015/192981 | 12/2015 |
| WO | WO 2017/085053 | 5/2017 |

OTHER PUBLICATIONS

Coulthard et al., "XCVI. The Chemotherapy of Derivatives of Harmine and Harmaline. I." Biochemical Journal (1933) 27:727-739.
Liu, F. et al., "Discovery of a 2,4-Diamino-7-aminoalkoxyquinazoline as a Potent and Selective Inhibitor of Histone Lysine Methyltransferase G9a", Journal of Medicinal Chemistry, (2009), pp. 7950-7953.
Liu, F. et al., "Optimization of Cellular Activity of G9a Inhibitors 7-Aminoalkoxy-quinazolines" Journal of Medicinal Chemistry, (2011), pp. 6139-6150.
Liu, F. et al., "Protein Lysine Methyltransferase G9a Inhibitors: Design Sybthesis and Structure Activity Relationships of 2,4-Diamino-7aminoalkoxy-quinazolines" Journal of Medicinal Chemistry, (2010), pp. 5844-5857.

(Continued)

*Primary Examiner* — Susanna Moore
(74) *Attorney, Agent, or Firm* — Alston & Bird LLP

(57) ABSTRACT

The present disclosure provides compounds of Formula (I) that are histone methyltransferases G9a and/or GLP inhibitors and are therefore useful for the treatment of diseases treatable by inhibition of G9a and/or GLP such as cancers and hemoglobinpathies (e.g., beta thalassemia and sickle cell disease). Also provided are pharmaceutical compositions containing such compounds and processes for preparing such compounds.

(I)

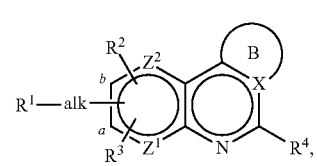

where $R^1$, alk, $R^2$, $Z^1$, $Z^2$, X, $R^3$, $R^4$, B, a, and b are as described herein.

16 Claims, No Drawings

(56) References Cited

OTHER PUBLICATIONS

Novak et al., "Characterization of the 2-(a-Carbolinyl)nitrenium Ion and Its Conjugate Base Produced during the Decomposition of the Model Carcinogen 2-N-(Pivaloyloxy)-2-amino-a-carboline in Aqueous Solution" J. Am. Chem. Soc. (2000) 122(15)3606-3616.
Reniers et al., "Synthesis and evaluation of b-carboline derivatives as potential monoamine oxidase inhibitors" Bioorganic & Medicinal Chemistry (2011) 19 134-144.
Song et al., "β-Carbolines as Specific Inhibitors of Cyclin-Dependent Kinases" Bioorganic & Medicinal Chemistry Letters (2002) 12:1229-1132.
Sweis et al. "Discovery and Development of Potent and Selective Inhibitors of Histone Methyltransferase G9a" ACS Med. Chem. Lett. (2014) 5(2):205-209.
Vedadi et al., "A chemical probe selectively inhibits G9a and GLP methyltransferase activity in cells" Nature Chemical Biology (2011) 7:566-574.
Antignano et al., "Methyltransferase G9A regulates T cell differentiation during murine intestinal in ammation," J. Clin. Invest. (2014) 124(5): 1945-55.
Agarwal et al., "G9a inhibition potentiates the anti-tumour activity of DNA double-strand break inducing agents by impairing DNA repair independent of p53 status" Cancer Letters (2016) 280:467-475.
Cascielle et al., "Functional role of G9a histone methyltransferase in cancer," Front Immunol. (2015) 6:Article 487:1-12.
Charache et al., "Hydroxyurea: Effects on Hemoglobin F Production in Patients With Sickle Cell Anemia" Blood (1992) 79(10):2555-2565.
Clark et al., "Synthetic Uses of the Sequential Ring Positional Reactivity in Pyridin-3-ol and Derivatives" Australian Journal of Chemistry (1981) 34(4):927-932.
Coburn et al., "Picrylamino-substituted Heterocycles V. Pyridines (1,2)," Journal of Heterocyclic Chemistry (1972) 9:1039-1044.
Gennaro, AR., Remington's Pharmaceutical Sciences, (1985) 17th Ed., Mack Publishing Co., Easton, PA, Cover and Table of Contents.
Gennaro, AR., Remington's Pharmaceutical Sciences (2000) 20th Ed., Lippincott Williams & Wilkins, Baltimore, MD, Cover and Table of Contents.
Greene, et al., Protective Groups in Organic Synthesis, (1999) 3rd. Ed., John Wiley & Sons, Cover and Table of Contents.
Imai et al., "Involvement of Histone H3 Lysine 9 (H3K9) Methyltransferase G9a in the Maintenance of HIV-1 Latency and Its Reactivation by BIX01294" J. Biol. Chem. (2010) 285(22):16538-16545.
Krivega et al., "Inhibition of G9a methyltransferase stimulates fetal hemoglobin production by facilitating LCR/γ-globin looping," Blood (2015) 126(5):665-672.
Lanman et al., "Phosphoinositide-3-kinase inhibitors: Evaluation of substituted alcohols as replacements for the piperazine sulfonamide portion of AMG 511" Bioorganic & Medicinal Chemistry Letters (2014) 24(24):5630-5634.
Ling et al., "Lysine methyltransferase G9a methylates the transcription factor MyoD and regulates skeletal muscle differentiation" PNAS (2012) 109(3):841-846.
Liu et al., "Discovery of an in Vivo Chemical Probe of the Lysine Methyltransferases G9a and GLP," J. Med Chem. (2013) 56(21):8931-8942.
Merkling et al., "The Epigenetic Regulator G9a Mediates Tolerance to RNA Virus Infection in *Drosophila*" PLoS Pathog. (2015) 11(4). e1004692.
Renneville et al., "EHMT1 and EHMT2 inhibition induces fetal hemoglobin expression," Blood (2015) 126(16):1930-1939.
Sankaran et al., "The Switch from Fetal to Adult Hemoglobin" Cold Spring Harb Perspect Med. (2013) 3(1): a011643.
Shankar et al., "G9a, a multipotent regulator of gene expression" Epigenetics (2013) 8(1):16-22.
Shinkai et al., "H3K9 methyltransferase G9a and the related molecule GLP" Genes & Dev. (2011) 25(8):781-788.
Wang et al., "Histone H3K9 methyltransferase G9a represses PPARγ expression and adipogenesis" EMBO J. (2013) 32(1):45-59.
Yang et al., "G9a coordinates with the RPA complex to promote DNA damage repair and cell survival" PNAS (2017):1700694114.
You et al., "Cancer Genetics and Epigenetics: Two Sides of the Same Coin'?," Cancer Cell (2012) 22(1):9-20.
Zhang et al., "Down-regulation of G9a triggers DNA damage response and inhibits colorectal cancer cells proliferation" Oncotarget (2015) 6(5): 2917-2927.
International Search Report and Written Opinion dated Apr. 5, 2018 for PCT Application No. PCT/US2017/067855, filed Dec. 21, 2017.
International Preliminary Report in Patentability dated Jul. 4, 2019 for PCT Application No. PCT/US2017/067855.
Chen et al., "Discovery, design and synthesis of 6H-anthra[1,9-cd]isoxazol-6-one scaffold as G9a inhibitor through a combination of shape-based virtual screening and structure-based molecular modification," Bioorganic & Medicinal Chemistry, 24(22):6102-6108, (2016).
EP Application No. 17829543.2, Article 94(3) Communication dated Jun. 2, 2020, 8 pages.

HISTONE METHYLTRANSFERASE INHIBITORS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

FIELD OF THE DISCLOSURE

The present disclosure provides certain angular tricyclic compounds that are histone methyltransferases G9a and/or GLP inhibitors, and are therefore useful for the treatment of diseases treatable by inhibition of G9a and/or GLP such as cancers and hemoglobinpathies (e.g., beta-thalassemia and sickle cell disease). Also provided are pharmaceutical compositions containing such compounds and processes for preparing such compounds.

BACKGROUND

Chromatin modification plays an essential role in transcriptional regulation. These modifications, including DNA methylation, histone acetylation and histone methylation, are important in a variety of biological processes including protein production and cellular differentiation, and are emerging as attractive drug targets in various human diseases. Two particular enzymes associated with histone methylation are G9a and GLP, also known as EHMT2 and EHMT1 (Euchromatic histone-lysine N-methyltransferase 2 and 1). G9a and GLP are the primary enzymes for mono- and dimethylation at Lys 9 of histone H3 (H3K9me1 and H3K9me2), and exist predominantly as a G9a-GLP heteromeric complex that appears to be a functional H3K9 methyltransferase in vivo. Structurally, either G9a or GLP is composed of a catalytic SET domain, a domain containing ankyrin repeats (involved in protein-protein interactions) and nuclear localization signals on the N-terminal region. The SET domain is responsible for the addition of methyl groups on H3, whereas the ankyrin repeats have been observed to represent mono- and dimethyl lysine binding regions. The G9a-GLP complex is thus not only able to both methylate histone tails but also able to recognize this modification, and can function as a scaffold for the recruitment of other target molecules on the chromatin [see Shinkai et al., Genes Dev. 2011 Apr. 15; 25(8):781-8. doi: 10.1101/gad.2027411. H3K9 methyltransferase G9a and the related molecule GLP; and Shankar et al., Epigenetics. 2013 January; 8(1):16-22. doi:10.4161/epi.23331. G9a, a multipotent regulator of gene expression].

Many studies have reported that G9a and GLP play critical roles in various biological processes. Several reports have highlighted its link to a variety of cancers [see Cascielle et al., Front Immunol. 2015 Sep. 25; 6:487. doi: 10.3389/fimmu.2015.00487. Functional Role of G9a Histone Methyltransferase in Cancer]. It is upregulated in hepatocellular carcinoma, B cell acute lymphoblastic leukemia, and lung cancers. In addition, elevated expression of G9a in aggressive lung cancer correlates with poor prognosis, while its knockdown in highly invasive lung cancer cells suppressed metastasis in an in vivo mouse model. In prostate cancer cells (PC3), G9a knockdown caused significant morphological changes and inhibition of cell growth. [see Liu et al., J. Med Chem. 2013 Nov. 14; 56(21):8931-42. doi: 10.1021/jm401480r. Epub 2013 Oct. 31. Discovery of an in vivo chemical probe of the lysine methyltransferases G9a and GLP; and Sweis et al., ACS Med Chem Lett. 2014 Jan. 2; 5(2):205-9. doi: 10.1021/ml400496h. eCollection 2014. Discovery and development of potent and selective inhibitors of histone methyltransferase g9a.] Loss of G9a has been demonstrated to impair DNA damage repair and enhance the sensitivity of cancer cells to radiation and chemotherapeutics. See Yang et al., Proc. Natl. Acad. Sci. USA, 2017, doi: 10.1073/pnas.1700694114.

Interestingly, recent studies have also shown that the inhibition of G9a and GLP by either genetic depletion or pharmacological intervention increased fetal hemoglobin (HbF) gene expression in erythroid cells [see Krivega et al., Blood. 2015 Jul. 30; 126(5):665-72. Inhibition of G9a methyltransferase stimulates fetal hemoglobin production by facilitating LCR/γ-globin looping; and Renneville et al., Blood. 2015 Oct. 15; 126(16):1930-9. EHMT1 and EHMT2 inhibition induces fetal hemoglobin expression]. Inducing fetal globin gene would be potentially therapeutically beneficial for the disease of hemoglobinpathies, including beta-thalassemia and sickle cell disease where the production of normal β-globin, a component of adult hemoglobin, is impaired. [see Sankaran et al., Cold Spring Harb Perspect Med. 2013 January; 3(1): a011643. doi:10.1101/cshperspect.a011643 The Switch from Fetal to Adult Hemoglobin]. Moreover, G9a or GLP inhibitions may potentiate other clinically used therapies, such as hydroxyurea or HDAC inhibitors. These agents may act, at least in part, by increasing γ-globin gene expression through different mechanisms [see Charache et al., Blood. 1992 May 15; 79(10):2555-65. Hydroxyurea: effects on hemoglobin F production in patients with sickle cell anemia]. Thus, there is a need for the development of small molecules that are capable of inhibiting the activity of G9a and/or GLP. The compounds of the present disclosure fulfill this and related needs.

SUMMARY

In one aspect provided is a compound of Formula (I):

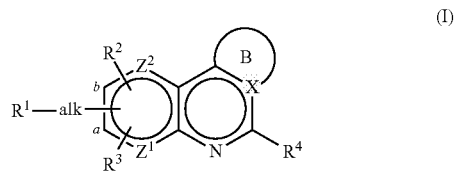

where:

$Z^1$ and $Z^2$ are independently C (when $R^2$ or $R^3$ is attached thereto), CH, or N;

alk is alkylene wherein one or two carbon atoms of the alkylene chain are optionally replaced by NR, O, S, or $SO_2$ (where R is hydrogen or alkyl), and the alkylene chain is optionally substituted with one or two substituents independently selected from halo, haloalkyl, haloalkoxy, hydroxy, and alkoxy, and wherein -alk-$R^1$ is attached to carbon (a) or (b);

$R^1$ is —$NR^6R^7$ (where $R^6$ and $R^7$ are independently hydrogen, alkyl, hydroxyalkyl, alkoxyalkyl, haloalkyl, or haloalkoxyalkyl), unsubstituted heterocyclyl, heterocyclyl substituted with 1, 2, or 3 of $R^a$, $R^b$, and $R^c$ wherein $R^a$, $R^b$, and $R^c$ are independently selected from alkyl, hydroxy, alkoxy, halo, haloalkyl, alkylcarbonyl, and haloalkylcarbonyl, or spiroheterocycloamino wherein a nitrogen atom of the spiroheterocycloamino is attached to alk;

$R^2$ is hydrogen, alkyl, cycloalkyl, halo, hydroxy, alkoxy, haloalkoxy, or cyano;

$R^3$ is hydrogen, alkyl, halo, alkoxy, alkylamino, dialkylamino, or cyano;

$R^4$ is hydrogen, deuterium, alkyl (optionally substituted with one to nine deuteriums), cycloalkyl (optionally substituted with one or two substituents independently selected from alkyl, hydroxy, halo, alkoxy, haloalkyl, and haloalkoxy), cycloalkenyl, phenyl (optionally substituted with one or two substituents independently selected from alkyl, halo, hydroxy, alkoxy, haloalkyl, and haloalkoxy), heteroaryl (optionally substituted with one or two substituents independently selected from alkyl, halo, hydroxy, and alkoxy), heterocyclyl (optionally substituted with one or two substituents independently selected from alkyl, halo, hydroxy, and alkoxy), —$OR^d$ (where $R^d$ is hydrogen, alkyl, haloalkyl, hydroxyalkyl, alkoxyalkyl, cycloalkyl, halocycloalkyl, cycloalkylalkyl, aryl, aralkyl, heteroaryl, heteroaralkyl, heterocyclyl, or heterocyclylalkyl), or $NR^eR^f$ (where $R^e$ is hydrogen or alkyl and $R^f$ is hydrogen, alkyl, deuterated alkyl, alkylthioalkyl, acyl, haloalkyl, hydroxyalkyl, alkoxyalkyl, aminoalkyl, cyanoalkyl, carboxyalkyl, alkoxycarbonylalkyl, cycloalkyl, cycloalkylalkyl, aryl, aralkyl, heteroaryl, heteroaralkyl, heterocyclyl, or heterocyclylalkyl), wherein the cycloalkyl, the aryl, the heteroaryl, and the heterocyclyl either alone or as part of the cycloalkylalkyl, the aralkyl, the heteroaralkyl and the heterocyclylalkyl in $R^d$ and $R^f$ are independently unsubstituted or substituted with 1, 2, or 3 of $R^g$, $R^h$, and $R^i$ wherein $R^g$, $R^h$, and $R^i$ are independently selected from alkyl, hydroxy, alkoxy, halo, haloalkyl, cyano, carboxy, alkoxycarbonyl, and haloalkoxy, and wherein the alkylene of the aralkyl, the heteroaralkyl, the heterocyclylalkyl, and the cycloalkylalkyl in $R^d$ and $R^f$ is optionally substituted with one to nine deuteriums;

X is carbon or nitrogen; and ring B is phenyl, 5- or 6-membered heteroaryl containing one, two, or three heteroatoms independently selected from nitrogen, oxygen, and sulfur, 5- or 6-membered cycloalkyl, spirocycloalkyl, spiroheterocycloamino, or 5-, 6-, or 7-membered saturated heterocyclyl, wherein each of the ring(s) of ring B is unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, cyano, alkoxy, halo, haloalkyl, and haloalkoxy; or a pharmaceutically acceptable salt thereof; provided the compound of Formula (I) is not:

5-aminobenzo[f][1,7]naphthyridine-8-methanamine or 10-ethoxy-8-(morpholinomethyl)-1,2,3,4-tetrahydrobenzo[h][1,6]naphthyridin-5-ol; or a salt thereof.

In a second aspect, this disclosure is directed to a pharmaceutical composition comprising a compound of Formula (I) (or any of the embodiments thereof described herein), or a pharmaceutically acceptable salt thereof; and a pharmaceutically acceptable excipient.

In a third aspect, this disclosure is directed to a method of treating a disease treatable by inhibition of G9a and/or GLP in a subject in need thereof, comprising administering a therapeutically effective amount of a compound of Formula (I) (or any of the embodiments thereof described herein), or a pharmaceutically acceptable salt thereof, or a pharmaceutical composition comprising a compound of Formula (I) (or any of the embodiments thereof described herein), or a pharmaceutically acceptable salt thereof, in a therapeutically effective amount, and a pharmaceutically acceptable excipient. In one embodiment, the disease can be a hemoglobinpathy, such as beta-thalassemia and sickle cell disease. See Krivega et al., Blood, 2015; 126(5):665-72 and Renneville et al., Blood. 2015 Oct. 15; 126(16):1930-9. In a second embodiment, the disease can be a cancer or tumor, for example, a cancer or tumor where G9a or GLP can be overexpressed. Examples of such cancers and tumors include, but are not limited to: Colorectal Cancer, Osteosarcoma Cancer, Acute Lymphoblastic Leukemia (ALL); Acute Myeloid Leukemia (AML); Adrenocortical Carcinoma, Kaposi Sarcoma (Soft Tissue Sarcoma); AIDS-Related Lymphoma (Lymphoma); Primary CNS Lymphoma; Anal Cancer; Gastrointestinal Carcinoid Tumors; Astrocytomas; Atypical Teratoid/Rhabdoid Tumor; Basal Cell Carcinoma of the Skin; Bile Duct Cancer; Bladder Cancer; Bone Cancer (includes Ewing Sarcoma and Osteosarcoma and Malignant Fibrous Histiocytoma); Brain Tumors; Breast Cancer; Bronchial Tumors—Burkitt Lymphoma; Cardiac Tumors; Embryonal Tumors (Brain Cancer); Germ Cell Tumor (Brain Cancer); Primary CNS Lymphoma; Cervical Cancer; Cholangiocarcinoma; Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell Lymphoma; Ductal Carcinoma In Situ (DCIS); Endometrial Cancer (Uterine Cancer); Ependymoma (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Retinoblastoma; Fallopian Tube Cancer; Fibrous Histiocytoma of Bone; Gallbladder Cancer; Gastric (Stomach) Gastrointestinal Stromal Tumors (GIST) (Soft Tissue Sarcoma); CNS Germ Cell Tumors (Brain Cancer); Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Hepatocellular (Liver) Cancer; Histiocytosis, Langerhans Cell; Hodgkin Lymphoma; Hypopharyngeal Cancer (Head and Neck Cancer); Intraocular Melanoma; Islet Cell Tumors, Pancreatic Neuroendocrine Tumors; Kidney (Renal Cell) Cancer; Langerhans Cell Histiocytosis; Laryngeal Cancer (Head and Neck Cancer); Leukemia; Lip and Oral Cavity Cancer (Head and Neck Cancer); Lung Cancer (Non-Small Cell and Small Cell); Lymphoma; Male Breast Cancer; Melanoma; Merkel Cell Carcinoma (Skin Cancer); Mesothelioma, Malignant Mesothelioma; Metastatic Squamous Neck Cancer with Occult Primary (Head and Neck Cancer); Midline Tract Carcinoma Involving NUT Gene; Mouth Cancer (Head and Neck Cancer); Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloproliferative Neoplasms, Chronic; Nasal Cavity and Paranasal Sinus Cancer (Head and Neck Cancer); Nasopharyngeal Cancer (Head and Neck Cancer); Nasopharyngeal Cancer—Neuroblastoma; Non-Hodgkin Lymphoma; Oral Cancer; Lip and Oral Cavity Cancer and Oropharyngeal Cancer (Head and Neck Cancer); Ovarian Cancer; Pancreatic Cancer; Papillomatosis; Paraganglioma; Paranasal Sinus and Nasal Cavity Cancer (Head and Neck Cancer); Parathyroid Cancer; Penile Cancer; Pharyngeal Cancer (Head and Neck Cancer); Pheochromocytoma; Pituitary Tumor; Plasma Cell Neoplasm/Multiple Myeloma; Pleuropulmonary Blastoma; Pregnancy and Breast Cancer; Primary CNS Lymphoma; Primary Peritoneal Cancer; Prostate Cancer; Rectal Cancer; Recurrent Cancer; Rhabdomyosarcoma (Soft Tissue Sarcoma); Salivary Gland Cancer (Head and Neck Cancer); Salivary Gland Tumors; Vascular Tumors (Soft Tissue Sarcoma); Uterine Sarcoma; Sézary Syndrome (Lymphoma); Small Intestine Cancer; Soft Tissue Sarcoma; Squamous Cell Carcinoma of the Skin; Skin Cancer; Squamous Neck Cancer with Occult Primary, Metastatic (Head and Neck Cancer); T-Cell Lymphoma, Cutaneous; Lymphoma (Mycosis Fungoides and Sézary Syndrome); Throat Cancer (Head and Neck Cancer); Nasopharyngeal Cancer; Oropharyngeal Cancer; Hypopharyngeal Cancer; Thymoma and Thymic Carcinoma; Thyroid Cancer; Urethral Cancer; Vaginal Cancer; Vascular Tumors (Soft Tissue Sarcoma); Vulvar Cancer; Myelodysplastic syndrome (MDS); and Wilms Tumor. Thus, the terms "cancerous cell," "cancer cell" or "tumor cell" as provided herein, includes a cell afflicted by any one of or related to the above identified conditions. See Cascielle et al., *Front. Immunol.* 2015; 6:487, Agarwal et al., *Cancer Letters* 2016: 467 and Zhang et al., *Oncotarget* 2015, 6(5): 2917. In a third embodiment, treating a cancer and/or tumor comprises increasing tumor free survival and/or reducing tumor mass and/or slowing tumor growth. In a fourth embodiment, the disease can be a cancer predisposition syndrome, such as Cowden syndrome. See You et al., *Cancer Cell,* 2012; 22(1):9-20. In a fifth embodiment, the disease can be an inflammatory and/or autoimmune disease, such as intestinal inflammation, arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis. See Antignano et al., *J. Clin. Invest.* 2014 4(5): 1945-55. In a sixth embodiment, the disease can be a metabolic disease, such as diabetes and/or obesity. See Wang et al., *EMBO J.* 2013; 32(1):45-59. In a seventh embodiment, the disease can be related to skeletal muscle development and regeneration. See Ling et al., *Proc. Natl. Acad. Sci. USA,* 2012; 109(3):841-6. In an eighth embodiment, the disease can be a viral disease, such as HIV-1 (human immunodeficiency virus 1) and HBV (Hepatitis B Virus). See Imai et al., *J. Biol. Chem.* 2010; 285(22):16538-45 and Merkling et al., *PLoS Pathog.* 2015; 11(4). The compounds and compositions described herein can be administered with one or more additional therapeutic agents including, but not limited to, anticancer agents and antiviral agents. See, e.g., Front Immunol. 2015; 6:487; Agarwal et al., Cancer Lett. 2016:467 and Zhang et al., Oncotarget 2015, 6(5):2917.

In a fourth aspect provided is the use of a compound of Formula (I) (or any of the embodiments thereof described herein), or a pharmaceutically acceptable salt thereof, in the treatment of the diseases provided in the third aspect herein.

In a fifth aspect, this disclosure is directed to a method of inhibiting G9a and/or GLP, comprising contacting a cell with a therapeutically effective amount of a compound of Formula (I) (or any of the embodiments thereof described herein), or a pharmaceutically acceptable salt thereof. In some embodiments, the cell suffers from one or more of the diseases provided in the third aspect herein.

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl (isopropyl), n-butyl, sec-butyl, iso-butyl, tert-butyl, pentyl (straight-chained or branched), hexyl (straight-chained or branched), and the like.

"Alkylene" means a linear saturated divalent hydrocarbon radical of one to six carbon atoms or a branched saturated divalent hydrocarbon radical of three to six carbon atoms unless otherwise stated, e.g., methylene, ethylene, propylene, 1-methylpropylene, 2-methylpropylene, butylene, pentylene, and the like.

"Alkylthioalkyl" means a —RSR' radical where R and R' are independently an alkyl as defined above.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means alkyl as defined above which is substituted with one or two alkoxy groups as defined above, e.g., methoxyethyl, ethoxyethyl, methoxypropyl, and the like.

"Alkylcarbonyl" or "Acyl" means a —COR radical where R is alkyl as defined above, e.g., methylcarbonyl, ethylcarbonyl, and the like.

"Alkoxycarbonyl" means a —C(=O)OR radical where —R is alkyl as defined above, e.g., methoxycarbonyl, ethoxycarbonyl, tert-butoxycarbonyl, and the like.

"Alkoxycarbonylalkyl" means alkyl as defined above which is substituted with one or two alkoxycarbonyl groups as defined above, e.g., methoxycarbonylethyl, ethoxycarbonylethyl, methoxycarbonylpropyl, and the like.

"Aryl" means a monovalent monocyclic or bicyclic aromatic hydrocarbon radical of 6 to 10 ring atoms, e.g., phenyl or naphthyl.

"Aralkyl" means a -(alkylene)-R radical where R is aryl as defined above, e.g., benzyl, phenethyl, and the like.

"Aminoalkyl" means a -(alkylene)-NR'R" radical where R' and R" are independently hydrogen or alkyl as defined above.

"Alkylamino" means a —NHR' radical where R' is alkyl as defined above.

"Cycloalkyl" means a cyclic saturated monovalent hydrocarbon radical of three to ten carbon atoms, unless stated otherwise, e.g., cyclopropyl, cyclobutyl, cyclopentyl, or cyclohexyl, and the like.

"Cycloalkylalkyl" means a -(alkylene)-R radical where R is cycloalkyl as defined above, e.g., cyclopropylmethyl, cyclohexylmethyl, and the like.

"Cycloalkenyl" means a cyclic hydrocarbon radical of three to ten carbon atoms containing a double bond, unless stated otherwise, e.g., cyclopropenyl, cyclobutenyl, cyclopentenyl, cyclohexenyl, and the like.

"Cyanoalkyl" means an alkyl radical as defined above that is substituted with a cyano group.

"Carboxy" means a —C(=O)OH group.

"Carboxyalkyl" means an alkyl radical as defined above that is substituted with a carboxy group.

"5- or 6-Membered cycloalkenyl" means a cyclic hydrocarbon radical of five or six carbon atoms containing a double bond.

"Deuterated alkyl" means an alkyl radical as defined above that is substituted with one, two or three deuterium atoms.

"Dialkylamino" means a —NRR' radical where R and R' are alkyl as defined above.

"Halo" or "halogen" means fluoro, chloro, bromo, or iodo, preferably fluoro or chloro.

"Haloalkyl" means an alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above, e.g., —OCF$_3$, —OCHF$_2$, —OCH$_2$F, and the like. When the haloalkyl of a haloalkoxy is an alkyl substituted with only fluoro, the haloalkoxy is referred to in this Application as fluoroalkoxy.

"Haloalkoxyalkyl" means alkyl as defined above which is substituted with one or two haloalkoxy groups as defined above, e.g., trifluormethoxyethyl, 2,2,2-trifluoroethoxyethyl, and the like.

"Haloalkylcarbonyl" means a —COR radical where R is haloalkyl as defined above, e.g., trifluoromethylcarbonyl, pentafluoroethylcarbonyl, and the like.

"Hydroxyalkyl" means alkyl as defined above which is substituted with one or two hydroxy groups as defined above, e.g., hydroxyethyl, hydroxyethyl, 1,3-dihydroxypropyl, and the like.

"Halocycloalkyl" means cycloalkyl group as defined above which is substituted with one, two or three halogen as defined above, e.g., 2,2-difluorocyclopropyl, and the like.

"Heterocyclyl" means a saturated or unsaturated monovalent monocyclic group of 4 to 8 ring atoms in which one or two ring atoms are heteroatom independently selected from N, O, and S(O)$_n$, where n is an integer from 0 to 2, and the remaining ring atoms are C, unless stated otherwise. Additionally, one or two ring carbon atoms in the heterocyclyl ring can optionally be replaced by a —C(=O)— group. More specifically the term heterocyclyl includes, but is not limited to, pyrrolidino, piperidino, homopiperidino, 2-oxpyrrolidinyl, 2-oxopiperidinyl, morpholino, piperazino, dihydropyranyl, thiomorpholino, and the like. When the heterocyclyl ring is unsaturated it can contain one or two ring double bonds provided that the ring is not aromatic. When the heterocyclyl group contains at least one nitrogen atom (e.g., pyrrolidine, piperidine, piperazine, and oxazolidine), the heterocyclyl ring can also be referred to herein as heterocycloamino and is a subset of the heterocyclyl group. When the heterocyclyl ring has no double bond, it is referred to herein as saturated heterocyclyl.

"Heterocyclylalkyl" or "heterocycloalkyl" means a -(alkylene)-R radical where R is heterocyclyl ring as defined above, e.g., tetrahydrofuranylmethyl, piperazinylmethyl, morpholinylethyl, and the like.

"5-, 6-, or 7-Membered heterocycloalkenyl or heterocyclylalkenyl" means a cyclic hydrocarbon radical of five, six, or seven carbon atoms containing a double bond and wherein one or two carbon atoms are independently replaced by N, O, or S(O). where n is an integer from 0 to 2.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. When the heteroaryl ring contains 5- or 6 ring atoms, it is also referred to herein as 5- or 6-membered heteroaryl.

"Heteroaralkyl" means a -(alkylene)-R radical where R is heteroaryl as defined above, e.g., pyridinylmethyl, and the like. When the heteroaryl ring in heteroaralkyl contains 5 or 6 ring atoms, the heteroaralkyl is also referred to herein as 5- or 6-membered heteroaralkyl.

"Oxo" means a =(O) radical. As would be readily apparent to one of skill in the art, "carbonyl" refers to an oxo radical attached to a carbon atom, i.e., —C(=O)—.

"Spiroheterocycloamino" means a saturated bicyclic ring having 7 to 10 ring atoms in which one, two, or three ring atoms are heteroatom selected from N, N-oxide, O, and S(O)$_n$, where n is an integer from 0 to 2, the remaining ring atoms being C, provided that at least one ring atom is N, and the rings are connected through only one atom. The connecting atom is also called the spiroatom, and is most often a quaternary carbon ("spiro carbon").

"Spirocycloalkyl" means a saturated bicyclic ring having 7 to 10 carbon ring atoms wherein the rings are connected through only one atom. The connecting atom is also called the spiroatom, and is most often a quaternary carbon ("spiro carbon").

It will be well recognized by a person skilled in the art that when ring B is cycloalkyl, heterocyclyl, or spirocycloalkyl, the carbon atoms in these rings that are shared with the adjacent ring (i.e., ring substituted with R$^4$ in Formula I) are sp$^2$ carbons.

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting group. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

The present disclosure also includes polymorphic forms and deuterated forms of the compound of the present disclosure, or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diastereomeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity, i.e., the (S) stereoisomer in less than about 5%, preferably 2% by wt. and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of the present disclosure are within the scope of this disclosure.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

It is to be understood that where compounds disclosed herein have unfilled valencies, then the valencies are to be filled with hydrogen.

Also provided herein are isotopologues (isotopically labeled analogues) of the compounds described herein. Substitution with isotopes such as deuterium may afford certain therapeutic advantages resulting from greater metabolic stability, such as, for example, increased in vivo half-life or reduced dosage requirements. In some embodiments, at any position of a compound described herein, or a pharmaceutically acceptable salt thereof, that has a hydrogen, the hydrogen atom can be replaced with hydrogen-2 (deuterium) or hydrogen-3 (tritium).

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

A "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees and apes, and, in particular, humans. In some embodiments, the subject can be human. In some embodiments, the subject can be a child and/or an infant, for example, a child or infant with a fever. In other embodiments, the subject can be an adult.

"Treating" or "treatment" of a disease includes:

(1) preventing the disease, i.e., causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure or a pharmaceutically acceptable salt thereof that, when administered to a subject for treating a disease, is sufficient to effect such treatment for the disease. The "therapeutically effective amount" will vary depending on the compound, the disease and its severity and the age, weight, etc., of the subject to be treated.

Embodiments

In further embodiments 1-54 below, the present disclosure includes:

1. In embodiment 1, the compounds of Formula (I), or a pharmaceutically acceptable salt thereof, are as defined in the Summary.

2. In embodiment 2, the compounds of embodiment 1, or a pharmaceutically acceptable salt thereof, are those wherein ring B is phenyl or phenyl substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 2, in one group of compounds, or a pharmaceutically acceptable salt thereof, ring B is phenyl substituted with 1, 2, 3, or 4 of $R^j$, $R^k$, $R^l$, and $R^m$ wherein $R^j$, $R^k$, $R^l$, and $R^m$ are independently selected from methyl, ethyl, fluoro, chloro, methoxy, trifluoromethyl, and trifluoromethoxy. Within embodiment 2, in another group of compounds, or a pharmaceutically acceptable salt thereof, ring B is phenyl.

3. In embodiment 3, the compounds of embodiment 1, or a pharmaceutically acceptable salt thereof, are those wherein ring B is an unsubstituted 5- or 6-membered cycloalkyl or a 5- or 6-membered cycloalkyl substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 3, ring B is cyclopentyl, cyclohexyl, cyclopentyl substituted with 1 or 2 of $R^j$ and $R^k$ wherein $R^j$ and $R^k$ are independently selected from fluoro, hydroxy, and methyl, or cyclohexyl substituted with 1 or 2 of $R^j$ and $R^k$ wherein $R^j$ and $R^k$ are independently selected from fluoro, hydroxy, and methyl. Within embodiment 3, in one group of compounds, or a pharmaceutically acceptable salt thereof, ring B is

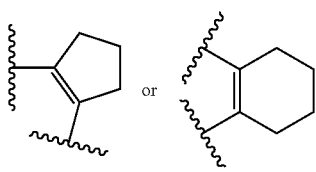 [SMILES: *C1=C(*)CCC1 ; *C1=C(*)CCCC1]

unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 3, in another group of compounds, or a pharmaceutically acceptable salt thereof, ring B is

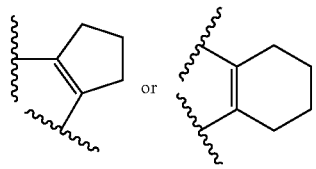 [SMILES: *C1=C(*)CCC1 ; *C1=C(*)CCCC1]

unsubstituted or substituted with 1 or 2 of $R^j$ and $R^k$ wherein $R^j$ and $R^k$ are independently selected from fluoro, hydroxy, and methyl. Within embodiment 3, in yet another group of compounds, or a pharmaceutically acceptable salt thereof, ring B is

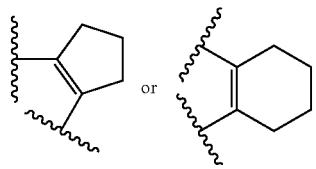 [SMILES: *C1=C(*)CCC1 ; *C1=C(*)CCCC1]

unsubstituted or substituted with one or two methyl groups. Within embodiment 3, in yet another group of compounds, or a pharmaceutically acceptable salt thereof, ring B is:

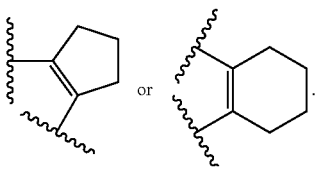 [SMILES: *C1=C(*)CCC1 ; *C1=C(*)CCCC1]

preferably

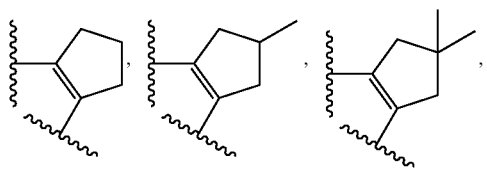

-continued

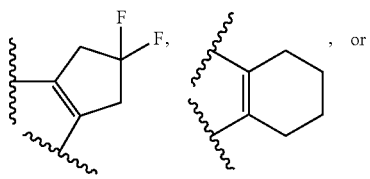

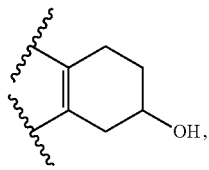

4. In embodiment 4, the compounds of embodiment 1, or a pharmaceutically acceptable salt thereof, are those wherein ring B is an unsubstituted 5-, 6- or 7-membered saturated heterocyclyl or a 5-, 6- or 7-membered saturated heterocyclyl substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 4 in yet another group of compounds, or a pharmaceutically acceptable salt thereof, ring B is:

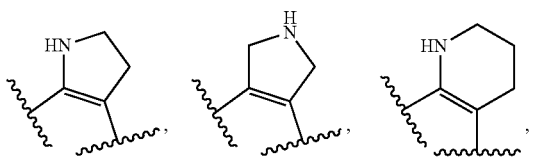

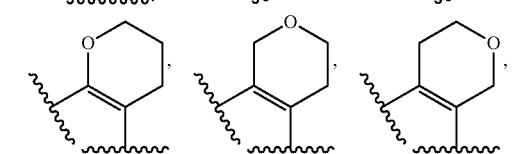

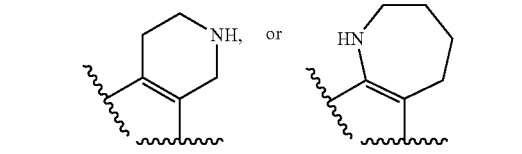

each ring is unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 4, in another one group of compounds, or a pharmaceutically acceptable salt thereof,

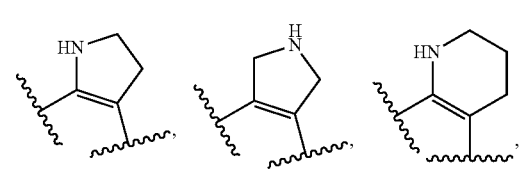

-continued

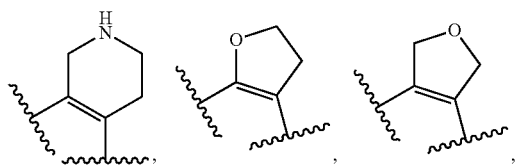

ring B is

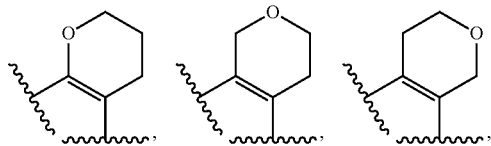

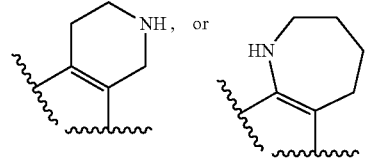

each ring is unsubstituted or substituted with 1 or 2 of $R^j$ and $R^k$ wherein $R^j$ and $R^k$ are independently selected from fluoro, chloro, hydroxy, and methyl. Within embodiment 4, in yet another group of compounds or a pharmaceutically acceptable salt thereof, ring B is:

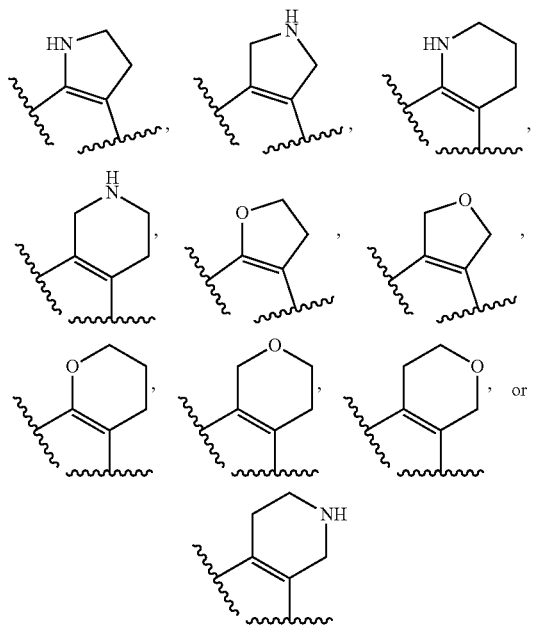

each ring is unsubstituted or substituted with one or two methyl groups. Within embodiment 4, in yet another group of compounds, or a pharmaceutically acceptable salt thereof, ring B is:

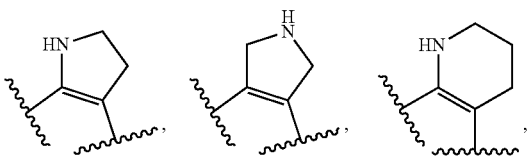

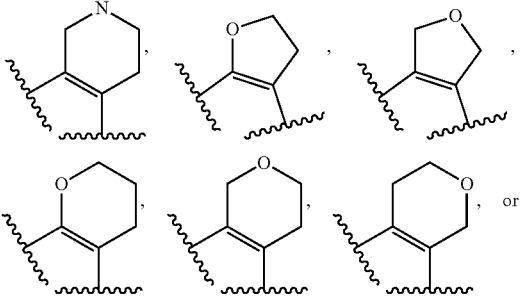

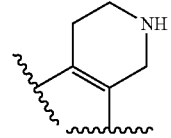

each ring is unsubstituted or substituted with one to four methyl groups. Within embodiment 4, in yet another group of compounds, or a pharmaceutically acceptable salt thereof, ring B is:

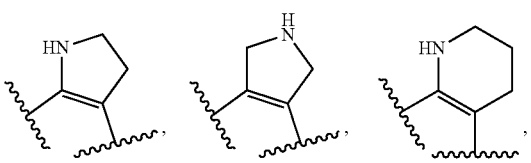

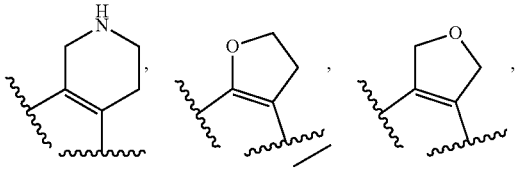

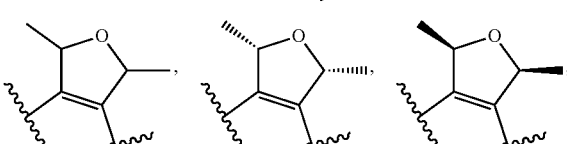

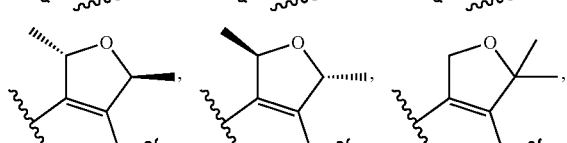

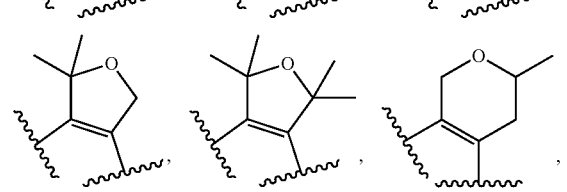

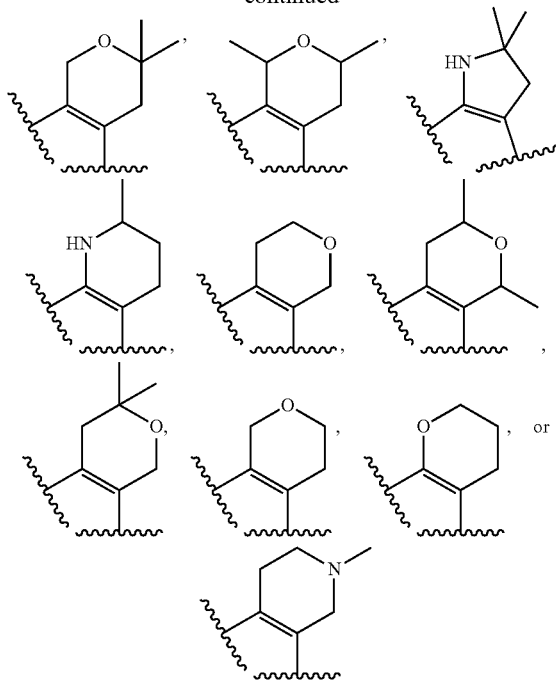

5. In embodiment 5, the compounds of embodiment 1, or a pharmaceutically acceptable salt thereof, are those wherein ring B is an unsubstituted 5- or 6-membered heteroaryl or a 5- or 6-membered heteroaryl substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 5, in one group of compounds, or a pharmaceutically acceptable salt thereof, ring B is pyridinyl, pyrazolyl, triazolyl, oxazolyl, or isoxazolyl either unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 5, in another one group of compounds, or a pharmaceutically acceptable salt thereof, ring B is pyridinyl, pyrazolyl, triazolyl, oxazolyl, or isoxazolyl either unsubstituted or substituted with 1 or 2 of $R^j$ and $R^k$ wherein $R^j$ and $R^k$ are independently selected from fluoro, chloro, hydroxy, and methyl. Within embodiment 5, in yet another group of compounds, or a pharmaceutically acceptable salt thereof, ring B is pyridinyl, pyrazolyl, triazolyl, oxazolyl, or isoxazolyl either unsubstituted or substituted with one or two methyl groups. Within embodiment 5, in yet another group of compounds, or a pharmaceutically acceptable salt thereof, ring B is pyridinyl, pyrazolyl, triazolyl, oxazolyl, or isoxazolyl, preferably

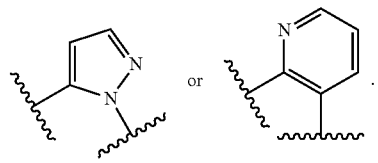 [SMILES: *c1ccnn1* ; *c1cccnc1*]

6. In embodiment 6, the compounds of embodiment 1, or a pharmaceutically acceptable salt thereof, are those wherein ring B is a spirocycloalkyl or a spiroheterocycloamino, wherein each of the rings is unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 6, in a group of compounds, or a pharmaceutically acceptable salt thereof, are those wherein ring B is a spirocycloalkyl wherein each of the rings is unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 6, in one group of compounds, or a pharmaceutically acceptable salt thereof, ring B is:

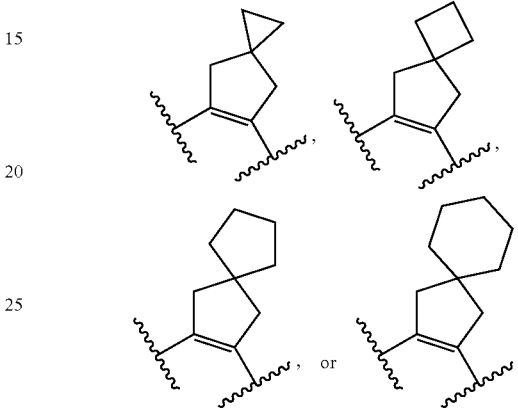

each ring is unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy. Within embodiment 6, in a group of compounds, or a pharmaceutically acceptable salt thereof, are those wherein ring B is a spiroheterocycloamino, wherein each of the rings is unsubstituted or substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy.

7. In embodiment 7, the compounds of any one of embodiments 1 to 6 and groups contained therein, or a pharmaceutically acceptable salt thereof, are those wherein $Z^1$ and $Z^2$ are independently C or CH. Within the groups of compounds in embodiment 7 in one group of compounds, or a pharmaceutically acceptable salt thereof, $Z^1$ and $Z^2$ are each CH. Within the groups of compounds in embodiment 7, or a pharmaceutically acceptable salt thereof, in one another group of compounds, $Z^1$ and $Z^2$ are each CH and -alk-$R^1$ is attached to carbon (a) in Formula (I). Within the groups of compounds in embodiment 7, or a pharmaceutically acceptable salt thereof, in yet another group of compounds $Z^1$ and $Z^2$ are each CH and -alk-$R^1$ is attached to carbon (a), and $R^2$ is attached to carbon (b) in Formula (I).

8. In embodiment 8, the compounds of any one of embodiments 1 to 6 and groups contained therein, or a pharmaceutically acceptable salt thereof, are those wherein one of $Z^1$ and $Z^2$ is N and the other is C or CH. In embodiment 8, in another group of compounds, the compounds of any one of embodiments 1 to 6 and groups contained therein, or a pharmaceutically acceptable salt thereof, are those wherein $Z^1$ and $Z^2$ are each N (nitrogen). Within the groups of compounds in embodiment 8, or a pharmaceutically acceptable salt thereof, in one another group of compounds, -alk-$R^1$ is attached to carbon (a) in Formula (I). Within the groups of compounds in embodiment 8, or a pharmaceutically acceptable salt thereof, in another group of compounds or a pharmaceutically acceptable salt thereof, -alk-$R^1$ is attached to carbon (a), and $R^2$ is attached to carbon (b) in Formula (I).

9. In embodiment 9, the compounds of any one of embodiments 1 to 8 and groups contained therein, or a pharmaceutically acceptable salt thereof, are those wherein alk in -(alk)-$R^1$ is —$(CH_2)_2$—*, —$(CH_2)_3$—*, —$(CH_2)_4$—*, —$CH_2CH(CH_3)CH_2$—*, *—$CH_2CH(CH_3)CH_2$—, —O—$(CH_2)$—*, —O—$(CH_2)_2$—*, —O—$(CH_2)_3$—*, —$OCH_2CH(CH_3)CH_2$—* —$OCH_2CH(F)CH_2$—*, —$OCH_2CH(OCH_3)CH_2$—* or —$OCH_2CH(OCF_3)CH_2$—*, preferably alk is —$(CH_2)_2$—*, —$(CH_2)_3$—*, —$(CH_2)_4$—*, —$CH_2CH(CH_3)CH_2$—*, —O—$(CH_2)_2$—*, or —O—$(CH_2)_3$—*, more preferably alk is —O—$(CH_2)_3$—*, wherein the * indicates the point of attachment to —$R^1$. Within embodiment 9, in one group of compounds, or a pharmaceutically acceptable salt thereof, $R^1$ is —$NR^6R^7$ where —$NR^6R^7$ is amino, methylamino, ethylamino, dimethylamino, or diethylamino. Within embodiment 9, or a pharmaceutically acceptably salt thereof, $R^1$ is an unsubstituted heterocyclyl. Within embodiment 9, or a pharmaceutically acceptable salt thereof, in another group of compounds, or a pharmaceutically acceptable salt thereof, $R^1$ is heterocyclyl substituted with 1, 2, or 3 of $R^a$, $R^b$, and $R^c$ wherein $R^a$, $R^b$, and $R^c$ are independently selected from alkyl, hydroxy, alkoxy, and halo. Preferably, $R^1$ is a saturated heterocyclyl such as azetidin-1-yl, pyrrolidin-1-yl, piperidin-1-yl, morpholin-4-yl, thiomorpholin-4-yl, or tetrahydrofuranyl, and each heterocyclyl is unsubstituted or substituted with 1 or 2 of $R^a$ and $R^b$ wherein $R^a$ and $R^b$ are independently selected from methyl, hydroxy, methoxy, and fluoro. Within embodiment 9, in another group of compounds, or a pharmaceutically acceptable salt thereof, -alk-$R^1$ is —O—$(CH_2)_3$-pyrrolidin-1-yl, —O—$(CH_2)_3$-piperidin-1-yl, or —O—$(CH_2)_3$-morpholin-4-yl wherein the pyrrolidin-1-yl, piperidin-1-yl and morpholin-4-yl of —O—$(CH_2)_3$-pyrrolidin-1-yl, —O—$(CH_2)_3$-piperidin-1-yl, and —O—$(CH_2)_3$-morpholin-4-yl are unsubstituted or substituted with 1 or 2 of $R^a$ and $R^b$ wherein $R^a$ and $R^b$ are independently selected from methyl, hydroxy, methoxy, and fluoro. Within embodiment 9, in yet another group of compounds, or a pharmaceutically acceptable salt thereof, -alk-$R^1$ is —O—$(CH_2)_3$—$R^1$ where $R^1$ is pyrrolidin-1-yl, 3-hydroxy-3-methylpyrrolidin-1-yl, 3-hydroxy-3-methylazetidin-1-yl, 3-fluoroazetidinyl, 3-fluoropyrrolidinyl, 3(R)-fluoropyrrolidinyl, 3(S)-fluoropyrrolidinyl, or 3,3-dimethylpyrrodin-1-yl, preferably pyrrolidin-1-yl. In embodiment 9, the compounds of any one of embodiments 1 to 8 and groups contained therein, or a pharmaceutically acceptable salt thereof, are those wherein -alk-$R^1$ is —O—$(CH_2)$—$R^1$ where $R^1$ is 1-methylpyrrolidin-3-yl or 1-methylpiperidin-3-yl.

10. In embodiment 10, the compounds of any one of embodiments 1 to 9 and groups contained therein, or a pharmaceutically acceptable salt thereof, are those wherein $R^2$ is alkyl, halo, hydroxy, or alkoxy. Within embodiment 10, in one group of compounds, or a pharmaceutically acceptable salt thereof, $R^2$ is alkyl, halo or alkoxy. Within embodiment 10, in another group of compounds, or a pharmaceutically acceptable salt thereof, $R^2$ is alkoxy, preferably methoxy or ethoxy. Within embodiment 10, in one group of compounds, or a pharmaceutically acceptable salt thereof, $R^2$ is halo, preferably chloro or fluoro. Within embodiment 10, in one group of compounds, or a pharmaceutically acceptable salt thereof, $R^2$ is alkyl, preferably methyl or ethyl.

11. In embodiment 11, the compounds of any one of embodiments 1 to 10 and groups contained therein, or a pharmaceutically acceptable salt thereof, are those wherein $R^4$ is hydrogen.

12. In embodiment 12, the compounds of any one of embodiments 1 to 10 and groups contained therein, or a pharmaceutically acceptable salt thereof, are those wherein $R^4$ is alkyl, preferably methyl or isopropyl.

13. In embodiment 13, the compounds of any one of embodiments 1 to 10 and groups contained therein, or a pharmaceutically acceptable salt thereof, are those wherein $R^4$ is —$OR^d$ (where $R^d$ is hydrogen, alkyl, cycloalkyl, cycloalkylalkyl, aryl, aralkyl, heteroaryl, heteroaralkyl, heterocyclyl, or heterocyclylalkyl), wherein the cycloalkyl, the aryl, the heteroaryl, and the heterocyclyl either alone or as part of the cycloalkylalkyl, the aralkyl, the heteroaralkyl and the heterocyclylalkyl in $R^d$ is unsubstituted or substituted with 1, 2, or 3 of $R^g$, $R^h$, and $R^i$ wherein $R^g$, $R^h$, and $R^i$ are independently selected from alkyl, hydroxy, alkoxy, halo, haloalkyl, cyano, and haloalkoxy. Within embodiment 13, in one group of compounds, or a pharmaceutically acceptable salt thereof, $R^4$ is —O-alkyl, preferably $R^4$ is methoxy, ethoxy, or n-propoxy, or isopropoxy. Within embodiment 13, in another group of compounds, or a pharmaceutically acceptable salt thereof, $R^4$ is —O-cycloalkyl, preferably $R^4$ is cyclopropoxy, cyclopentoxy, or cyclohexyloxy. Within embodiment 13, in yet another group of compounds, or a pharmaceutically acceptable salt thereof, $R^4$ is —O-heterocyclyl unsubstituted or substituted with 1, 2, or 3 of $R^g$, $R^h$, and $R^i$ wherein $R^g$, $R^h$, and $R^i$ are independently selected from alkyl, hydroxy, alkoxy, halo, haloalkyl, and haloalkoxy, preferably $R^4$ is piperidin-4-yloxy, tetrahydropyran-4-yloxy, tetrahydrofuran-3-yloxy, or 1-alkylpiperidin-4-yloxy. Within embodiment 13, in one group of compounds, or a pharmaceutically acceptable salt thereof, $R^4$ is hydroxy.

14. In embodiment 14, the compounds of any one of embodiments 1 to 10 and groups contained therein, or a pharmaceutically acceptable salt thereof, are those wherein $R^4$ is $NR^eR^f$ (where $R^e$ is hydrogen or alkyl, and $R^f$ is hydrogen, alkyl, cyanoalkyl, carboxyalkyl, alkoxycarbonlyalkyl, deuterated alkyl, alkylthioalkyl, acyl, haloalkyl, hydroxyalkyl, alkoxyalkyl, aminoalkyl, cycloalkyl, cycloalkylalkyl, aryl, aralkyl, heteroaryl, heteroaralkyl, heterocyclyl, or heterocyclylalkyl) wherein the cycloalkyl, the aryl, the heteroaryl, and the heterocyclyl either alone or as part of the cycloalkylalkyl, the aralkyl, the heteroaralkyl and the heterocyclylalkyl in $R^f$ is unsubstituted or substituted with 1, 2, or 3 of $R^g$, $R^h$, and $R^i$ wherein $R^g$, $R^h$, and $R^i$ are independently selected from alkyl, hydroxy, alkoxy, halo, haloalkyl, cyano, carboxy, alkoxycarbonyl, and haloalkoxy. Within embodiment 14, in one group of compounds, or a pharmaceutically acceptable salt thereof, $R^4$ is $NR^eR^f$ (where $R^e$ is hydrogen or alkyl, and $R^f$ is alkyl, cyanoalkyl, carboxyalkyl, alkoxycarbonylalkyl, deuterated alkyl, alkylthioalkyl, hydroxyalkyl, cycloalkyl, cycloalkylalkyl, aryl, aralkyl, heteroaryl, heteroaralkyl, heterocyclyl, or heterocyclylalkyl) wherein the cycloalkyl, the aryl, the heteroaryl, and the heterocyclyl either alone or as part of the cycloalkylalkyl, the aralkyl, the heteroaralkyl and the heterocyclylalkyl in $R^f$ is unsubstituted or substituted with 1, 2, or 3 of $R^g$, $R^h$, and $R^i$ wherein $R^g$, $R^h$, and $R^i$ are independently selected from alkyl, hydroxy, alkoxy, halo, haloalkyl, cyano, carboxy, alkoxycarbonyl, and haloalkoxy. Within embodiment 14, in another group of compounds, or a pharmaceutically acceptable salt thereof, $R^4$ is —$NR^e$-alkyl, preferably $R^4$ is —NH-alkyl or —N(alkyl)-alkyl, preferably $R^4$ is —NH-methyl, —NH-ethyl, —NH-n-propyl, —NH-isopropyl, —N(methyl)(isopropyl), —NH-n-butyl, —NH-isobutyl, —NH-tert-butyl, —NH—*CH(CH$_3$)CH$_2$CH$_3$ (where *C is (R) or (S)), or NH-pentyl (all isomers) more preferably —NH-methyl, —NH-ethyl, —NH-n-propyl, or —NH-isopropyl. Within embodiment 14, in another group of compounds, or a pharmaceutically acceptable salt thereof, R$^4$ is —NR$^e$-cyanoalkyl, preferably R$^4$ is —NH—(CH$_2$)$_2$—CN or —NH—(CH$_2$)$_3$—CN. Within embodiment 14, in another group of compounds, or a pharmaceutically acceptable salt thereof, R$^4$ is —NR$^e$-carboxyalkyl, preferably R$^4$ is —NH—(CH)—C(=O)OH. Within embodiment 14, in another group of compounds, or a pharmaceutically acceptable salt thereof, R$^4$ is —NR$^e$-alkoxycarbonylalkyl, preferably R$^4$ is —NH—(CH)—C(=O)—(CH$_2$)—CH$_3$. Within embodiment 14, in another group of compounds, or a pharmaceutically acceptable salt thereof, R$^4$ is —NR$^e$-(deterated alkyl), preferably R$^4$ is —NH—CD(CH$_3$)$_2$ (where D is deuterium). Within embodiment 14, in another group of compounds, or a pharmaceutically acceptable salt thereof, R$^4$ is —NR$^e$-alkylthioalkyl, preferably R$^4$ is —NH—(CH$_2$)$_2$—S—CH$_3$. Within embodiment 14, in another group of compounds, or a pharmaceutically acceptable salt thereof, R$^4$ is —NR$^e$-cycloalkyl, wherein the cycloalkyl is either unsubstituted or substituted with one or two of R$^g$ or R$^h$ wherein R$^g$ and R$^h$ are independently selected from alkyl, hydroxy, alkoxy, cyano, carboxy, carboxycarbonyl, halo, haloalkyl, and haloalkoxy, preferably R$^4$ is —NH-cyclopropyl, —NH(1-methylcyclopropyl), —NH(1-cyanocyclopropyl), —NH(2-cyanocyclopropyl), —NH(1-carboxycyclopropyl), —NH(1-[ethoxycarbonyl]cyclopropyl), —NH-cyclobutyl, —NH(3-hydroxycyclobutyl), —NH-cyclopentyl, —N(methyl)(cyclopentyl), —NH-cyclohexyl, —NH-(3-fluorocyclobutyl), —NH-(3,3-difluorocyclobutyl), or —NH-(3,3-dimethylcyclobutyl), more preferably —NH-cyclopropyl, NH-cyclopentyl, or NH-cyclohexyl. Within embodiment 14, in another group of compounds or a pharmaceutically acceptable salt thereof, R$^4$ is:

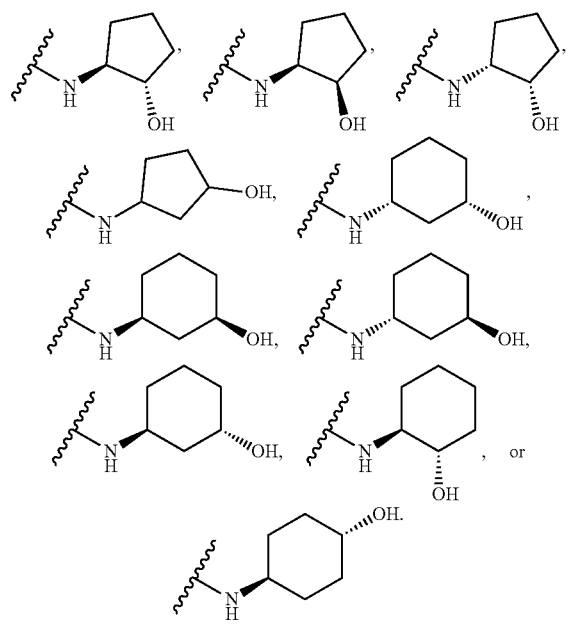

Within embodiment 14, in another group of compounds, or a pharmaceutically acceptable salt thereof, R$^4$ is —NH-heterocyclyl, wherein the heterocyclyl is unsubstituted or substituted with 1, 2, or 3 of R$^g$, R$^h$, and R$^i$ wherein R$^g$, R$^h$, and R$^i$ are independently selected from alkyl, hydroxy, alkoxy, halo, haloalkyl, and haloalkoxy, preferably R$^4$ is —NH-piperidin-4-yl, —NH-tetrahydropyran-4-yl, —NH-oxetan-3-yl, —NH-tetrahydrofuran-3-yl, —NH-(2,6-dimethyltetrahydropyran-4-yl), or —NH-(1-alkylpiperidin-4-yl). Within embodiment 14, in another group of compounds, or a pharmaceutically acceptable salt thereof, R$^4$ is —NH-cycloalkylalkyl, wherein the cycloalkyl of the cycloalkylalkyl is unsubstituted or substituted with 1 or 2 of R$^g$ and R$^h$ wherein R$^g$ and R$^h$ are independently selected from alkyl, hydroxy, alkoxy, halo, haloalkyl, and haloalkoxy, preferably R$^4$ is —NH—CH$_2$-cycloalkyl, wherein the cycloalkyl unsubstituted or substituted with 1 or 2 of R$^g$ and R$^h$ wherein R$^g$ and R$^h$ are independently selected from alkyl, hydroxy, alkoxy, halo, haloalkyl, and haloalkoxy, more preferably R$^4$ is —NH—CH$_2$-cyclopropyl, —NH—*CH(CH$_3$)cyclopropyl (where *C is (R) or (S)), —NH—CH$_2$-cyclobutyl, —NH—*CH(CH$_3$)cyclobutyl where *C is (R) or (S), —NH—CH$_2$-cyclopentyl, —NH—CH$_2$-cyclohexyl, —NH—CH$_2$-(3-fluorocyclobutyl), —NH—CH$_2$-(3,3-difluorocyclobutyl), —NH—CH$_2$-(3,3-dimethylcyclobutyl), —NH—CH$_2$-(1-methylcyclopropyl), —NH—CH$_2$-(1-methylcyclobutyl), —NH—(CH$_2$)$_2$-cyclopropyl, —NH—(CH$_2$)$_2$-cyclopentyl, or NH—(CH$_2$)$_2$-cyclohexyl, even more preferably —NH—CH$_2$-cyclopropyl or NH—CH$_2$-cyclobutyl. Within embodiment 14, in another group of compounds, or a pharmaceutically acceptable salt thereof, R$^4$ is —NH-(hydroxyalkyl) or —NH-(alkoxyalkyl), preferably R$^4$ is —NH-(2-hydroxyethyl), —NH-(2-hydroxybutyl), —NH-(2-hydroxy-2-methylbutyl), —NH-(2-hydroxy-2-methylpropyl), —NH-(2-methoxyethyl), —NH-(2-methoxypropyl), —NH-(2-methoxy-2-methylpropyl), or —NH-(2-methoxybutyl). Within embodiment 14, in another group of compounds, or a pharmaceutically acceptable salt thereof, R$^4$ is —NH-heterocyclylalkyl, wherein the heterocyclyl of the heterocyclylalkyl is unsubstituted or substituted with 1, 2, or 3 of R$^g$, R$^h$, and R$^i$ wherein R$^g$, R$^h$, and R$^i$ are independently selected from alkyl, hydroxy, alkoxy, halo, haloalkyl, and haloalkoxy, preferably R$^4$ is —NH—CH$_2$-oxetan-3-yl, —NH—CH$_2$-piperidin-4-yl, —NH—CH$_2$-tetrahydropyran-4-yl, —NH—CH$_2$-tetrahydrofuran-3-yl, —NH—CH$_2$-(1-alkylpiperidin-4-yl), —NH—(CH$_2$)$_2$-oxetan-3-yl, —NH—(CH$_2$)$_2$-piperidin-4-yl, —NH—(CH$_2$)$_2$-tetrahydropyran-4-yl, —NH—(CH$_2$)$_2$-tetrahydrofuran-3-yl, or —NH—(CH$_2$)$_2$-(1-alkylpiperidin-4-yl). Within embodiment 14, in another group of compounds, or a pharmaceutically acceptable salt thereof, R$^4$ is —NH-haloalkyl, preferably R$^4$ is —NH-2-fluoroethyl, —NH-2,2-difluoroethyl, —NH-(2,2,2-trifluoroethyl), —NH-(3-fluoropropyl), —NH-(3,3-difluoropropyl), or —NH-(3,3,3-trifluoropropyl). Within embodiment 14, in another group of compounds, or a pharmaceutically acceptable salt thereof, R$^4$ is —NH-heteroaralkyl unsubstituted or substituted with 1 or 2 of R$^g$ and R$^h$ wherein R$^g$ and R$^h$ are independently selected from alkyl, hydroxy, alkoxy, halo, haloalkyl, and haloalkoxy. Within embodiment 14, in another group of compounds, or a pharmaceutically acceptable salt thereof, R$^4$ is —NH-aralkyl unsubstituted or substituted with 1 or 2 of R$^g$ and R$^h$ wherein R$^g$ and R$^h$ are independently selected from alkyl, hydroxy, alkoxy, halo, haloalkyl, and haloalkoxy, preferably R$^4$ is —NH-(2-phenethyl), —NH-benzyl, or —NH-(2,4-dimethoxybenzyl). Within embodiment 14, in another group of compounds, or a pharmaceutically acceptable salt thereof, R$^4$ is —NH-methyl, —NH-ethyl, —NH-n-propyl, —NH-isopropyl, —N(methyl)(isopropyl), —NH-n-butyl, —NH-isobutyl, —NH-tert-butyl, NH-pentyl (all isomers), —NH-cyclopropyl, —NH-cyclobutyl, —NH(3-hydroxycyclobutyl), —NH-cyclopentyl, —N(methyl)(cyclopentyl), —NH-cyclohexyl, —NH-(3-fluorocyclobutyl), —NH-(3,3-difluorocyclobutyl), —NH-(3,3-dimethylcyclobutyl), —NH-piperidin-4-yl, —NH-tetrahydropyran-4-yl, —NH-oxetan-3-yl, —NH-tetrahydrofuran-3-yl, —NH-(2,6-dimethyltetrahydropyran-4-yl), —NH-(1-alkylpiperidin-4-yl), —NH—CH$_2$-cyclopropyl, —NH—CH$_2$-cyclobutyl, —NH—CH$_2$-cyclopentyl, —NH—CH$_2$-cyclohexyl, —NH—CH$_2$-(3-fluorocyclobutyl), —NH—CH$_2$-(3,3-difluorocyclobutyl), —NH—CH$_2$-(3,3-dimethylcyclobutyl), —NH—CH$_2$-(1-methylcyclopropyl), —NH—CH$_2$-(1-methylcyclobutyl), —NH—(CH$_2$)$_2$-cyclopropyl, —NH—(CH$_2$)$_2$-cyclopentyl, NH—(CH$_2$)$_2$-cyclohexyl, —NH-(2-hydroxyethyl), —NH-(2-hydroxybutyl), —NH-(2-hydroxy-2-methylbutyl), —NH-(2-methoxyethyl), —NH-(2-methoxy-2-methylbutyl), —NH-(2-methoxybutyl), —NH-2-fluoroethyl, —NH-2,2-difluoroethyl, —NH-(2,2,2-trifluoroethyl), —NH-(3-fluoropropyl), —NH-(3,3-difluoropropyl), —NH-(3,3,3-trifluoropropyl), —NH(2-phenethyl), —NH(2-phenethyl), pyrrolidin-1-yl, cyclopropyl, cyclobutyl, or cyclopentyl.

15. In embodiment 15, the compounds of any one of embodiments 1 to 10 and groups contained therein, or a pharmaceutically acceptable salt thereof, are those wherein R$^4$ is heteroaryl optionally substituted with one or two substituents independently selected from alkyl, halo, hydroxy, and alkoxy. Within embodiment 15, in one group of compounds, or a pharmaceutically acceptable salt thereof, R$^4$ is furanyl, pyridyl, pyrrolyl, or pyrimidinyl optionally substituted with one or two substituents independently selected from alkyl, halo, hydroxy, and alkoxy. Within embodiment 15, in another group of compounds, or a pharmaceutically acceptable salt thereof, R$^4$ is 3-pyridyl, 5-methylfuran-2-yl, or 5-methylfuran-3-yl.

16. In embodiment 16, the compounds of any one of embodiments 1 to 10 and groups contained therein, or a pharmaceutically acceptable salt thereof, are those wherein R$^4$ is phenyl optionally substituted with one or two substituents independently selected from alkyl, halo, hydroxy, and alkoxy.

17. In embodiment 17, the compounds of any one of embodiments 1 to 10 and groups contained therein, or a pharmaceutically acceptable salt thereof, are those wherein R$^4$ is heterocyclyl optionally substituted with 1 or 2 of R$^g$ or R$^h$ wherein R$^g$ and R$^h$ are independently selected from alkyl, hydroxy, alkoxy, halo, haloalkyl, and haloalkoxy, preferably R$^4$ is pyrrolidin-1-yl, tetrahydrofuranyl, or tetrahydropyranyl. Within embodiment 17, in another group of compounds, or a pharmaceutically acceptable salt thereof, R$^4$ is tetrahydrofuran-2-yl, tetrahydrofuran-3-yl, and tetrahydropyran-4-yl.

18. In embodiment 18, the compounds of any one of embodiments 1 to 10 and groups contained therein, or a pharmaceutically acceptable salt thereof, are those wherein R$^4$ is cycloalkyl optionally substituted with 1 or 2 of R$^g$ and R$^h$ wherein R$^g$ and R$^h$ are independently selected from alkyl, hydroxy, alkoxy, halo, haloalkyl, and haloalkoxy, preferably R$^4$ is cyclopropyl, cyclobutyl, cyclopentyl, 3-fluorocyclopentyl, 3,3-difluorocyclopentyl, cyclohexyl, or 4-fluorocyclohexyl.

19. In embodiment 19, the compounds of any one of embodiments 1 to 10 and groups contained therein, or a pharmaceutically acceptable salt thereof, are those wherein R$^4$ is cycloalkenyl, preferably R$^4$ is cyclopropenyl, cyclobutenyl, cyclopentenyl, 3-fluorocyclopentyl, 3,3-difluorocyclopentenyl, cyclohexenyl, or 4-fluorocyclohexenyl.

20. In embodiment 20, the compounds of any one of embodiments 1 to 19 and groups contained therein, or a pharmaceutically acceptable salt thereof, are those wherein R$^3$ is hydrogen, chloro, or —NH-isopropyl.

21. In embodiment 21, the compounds of any one of embodiments 1 to 20 and groups contained therein, or a pharmaceutically acceptable salt thereof, are those wherein X is carbon or nitrogen. Within embodiment 21, in a group of compounds, or a pharmaceutically acceptable salt thereof, wherein X is carbon. Within embodiment 21, in a group of compounds, or a pharmaceutically acceptable salt thereof, wherein X is nitrogen.

22. In some embodiments, the compounds of embodiment 1, or a pharmaceutically acceptable salt thereof, has the structure of Formula (Ia), or a pharmaceutically acceptable salt thereof:

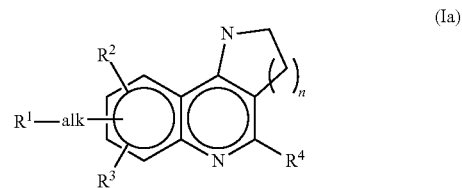

(Ia)

wherein: n is 1, 2, or 3; and R$^1$, R$^2$, R$^3$ and R$^4$ are as defined herein, for example, in embodiment 1. Within embodiment 22, alk is —O—(CH$_2$)$_{2-4}$, preferably —OCH$_2$CH$_2$CH$_2$—*, wherein * indicates the point of attachment to R$^1$. Within embodiment 22, R$^1$ is heterocyclyl, preferably a saturated, 5-membered nitrogen-containing heterocyclyl (for example, pyrrolidine). Within embodiment 22, R$^2$ is an unsubstituted C$_{1-4}$ alkoxy, preferably methoxy. Within embodiment 22, R$^3$ is H. Within embodiment 22, R$^4$ is alkyl, cycloalkyl, aryl, heteroaryl, OR$^d$, or NR$^e$R$^f$ as defined above. Within embodiment 22, Formula (Ia), or a pharmaceutically acceptable salt thereof, has the structure of Formula (Ic), or a pharmaceutically acceptable salt thereof:

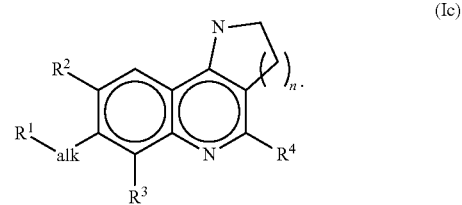

(Ic)

Within embodiment 22 and Formula (Ic), or a pharmaceutically acceptable salt thereof, alk is —O—(CH$_2$)$_{2-4}$, preferably —OCH$_2$CH$_2$CH$_2$—*, wherein * indicates the point of attachment to R$^1$; R$^1$ is heterocyclyl, preferably a saturated, 5-membered nitrogen-containing heterocyclyl (for example, pyrrolidine); R$^2$ is an unsubstituted C$_{1-4}$ alkoxy, preferably methoxy; R$^3$ is H; and R$^4$ is alkyl, cycloalkyl, aryl, heteroaryl, OR$^d$, or NR$^e$R$^f$ as defined above.

23. In some embodiments, the compounds of embodiment 1, or a pharmaceutically acceptable salt thereof, have the structure of Formula (Ib), or a pharmaceutically acceptable salt thereof:

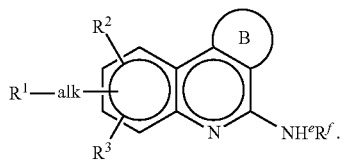

(Ib)

Where $R^1$, $R^2$, $R^3$, $R^e$, $R^f$ and ring B are as defined herein, for example, in embodiment 1. Within embodiment 23, alk is —O—$(CH_2)_{2-4}$, preferably —$OCH_2CH_2CH_2$—*, wherein * indicates the point of attachment to $R^1$. Within embodiment 23, $R^1$ is heterocyclyl, preferably a saturated, 5-membered nitrogen-containing heterocyclyl (for example, pyrrolidinyl). Within embodiment 23, $R^2$ is an unsubstituted $C_{1-4}$ alkoxy, preferably methoxy. Within embodiment 23, $R^3$ is H. Within embodiment 23, ring B is a 5-, 6-, or 7-membered nitrogen containing heterocyclyl that is optionally substituted. Within embodiment 23, ring B is a 5-, 6-, or 7-membered nitrogen containing heterocyclyl substituted with 1 to 4 substituents independently selected from $C_{1-4}$ alkyl, preferably methyl. Within embodiment 23, Formula (Ia), or a pharmaceutically acceptable salt thereof, has the structure of Formula (Id), or a pharmaceutically acceptable salt thereof:

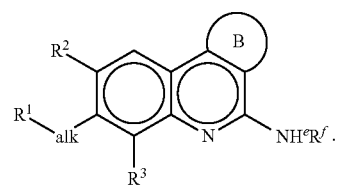

(Id)

Within embodiment 23 and Formula (Id), or a pharmaceutically acceptable salt thereof, alk is —O—$(CH_2)_{2-4}$, preferably —$OCH_2CH_2CH_2$—*, wherein * indicates the point of attachment to $R^1$; $R^1$ is heterocyclyl, preferably a saturated, 5-membered nitrogen-containing heterocyclyl (for example, pyrrolidine); $R^2$ is an unsubstituted $C_{1-4}$ alkoxy, preferably methoxy; $R^3$ is H; and ring B is a 5, 6 or 7 membered nitrogen containing heterocyclyl that is optionally substituted. Within embodiment 23 and Formula (Id), or a pharmaceutically acceptable salt thereof, $R^e$ is H or methyl, preferably H. Within embodiment 23 and Formula (Id), or a pharmaceutically acceptable salt thereof, $R^f$ is H, alkyl, haloalkyl, hydroxyalkyl, alkoxyalkyl, cycloalkyl, cycloalkylalkyl, aralkyl, or heterocyclyl, wherein the cycloalkyl, the cycloalkylalkyl, the arakyl, and the heterocyclyl are unsubstituted or substituted with one or two of methyl or hydroxy. Preferably, $R^f$ is methyl, ethyl, n-propyl, isopropyl, cyclopropyl, cyclopentyl, and cyclohexyl.

24. In embodiment 24, the compounds of Formula (I), or a pharmaceutically acceptable salt thereof, are those where: $Z^1$ and $Z^2$ are independently C (when $R^2$ or $R^3$ is attached thereto), CH, or N; alk is alkylene wherein one or two carbon atoms of the alkylene chain are optionally replaced by NR, O, S, or $SO_2$ (where R is hydrogen or alkyl), and the alkylene chain is optionally substituted with one or two substituents independently selected from halo, haloalkyl, haloalkoxy, hydroxyl, and alkoxy, and wherein -alk-$R^1$ is attached to carbon (a) or (b); $R^1$ is —$NR^6R^7$ (where $R^6$ and $R^7$ are independently hydrogen, alkyl, hydroxyalkyl, alkoxyalkyl, haloalkyl, or haloalkoxyalkyl), unsubstituted heterocyclyl, heterocyclyl substituted with 1, 2, or 3 of $R^a$, $R^b$, and $R^c$ wherein $R^a$, $R^b$, and $R^c$ are independently selected from alkyl, hydroxyl, alkoxy, halo, haloalkyl, alkylcarbonyl, and haloalkylcarbonyl), and spiroheterocycloamino wherein a nitrogen atom of the spiroheterocycloamino is attached to alk; $R^2$ is hydrogen, alkyl, cycloalkyl, halo, hydroxyl, alkoxy, haloalkoxy, or cyano; $R^3$ is hydrogen, alkyl, halo, alkoxy, alkylamino, dialkylamino, or cyano; $R^4$ is hydrogen, deuterium, alkyl (optionally substituted with one to nine deuteriums), cycloalkyl (optionally substituted with one or two substituents independently selected from alkyl, hydroxyl, halo, and alkoxy), cycloalkenyl, phenyl (optionally substituted with one or two substituents independently selected from alkyl, halo, hydroxyl, and alkoxy), heteroaryl (optionally substituted with one or two substituents independently selected from alkyl, halo, hydroxyl, and alkoxy), heterocyclyl (optionally substituted with one or two substituents independently selected from alkyl, halo, hydroxyl, and alkoxy), —$OR^d$ (where $R^d$ is hydrogen, alkyl, haloalkyl, hydroxyalkyl, alkoxyalkyl, cycloalkyl, halocycloalkyl, cycloalkylalkyl, aryl, aralkyl, heteroaryl, heteroaralkyl, heterocyclyl, or heterocyclylalkyl), or $NR^eR^f$ (where $R^e$ is hydrogen or alkyl and $R^f$ is hydrogen, alkyl, deuterated alkyl, acyl, haloalkyl, hydroxyalkyl, alkoxyalkyl, aminoalkyl, cyanoalkyl, carboxyalkyl, alkoxycarbonylalkyl, cycloalkyl, cycloalkylalkyl, aryl, aralkyl, heteroaryl, heteroaralkyl, heterocyclyl, or heterocyclylalkyl), wherein the cycloalkyl, the aryl, the heteroaryl, and the heterocyclyl either alone or as part of the cycloalkylalkyl, the aralkyl, the heteroaralkyl and the heterocyclylalkyl in $R^d$ and $R^f$ are independently unsubstituted or substituted with 1, 2, or 3 of $R^g$, $R^h$, and $R^i$ wherein $R^g$, $R^h$, and $R^i$ are independently selected from alkyl, hydroxyl, alkoxy, halo, haloalkyl, cyano, and haloalkoxy, and wherein the alkylene of the aralkyl, the heteroaralkyl, the heterocyclylalkyl, and the cycloalkylalkyl in $R^d$ and $R^f$ is optionally substituted with one to nine deuteriums; X is carbon or nitrogen; ring B is phenyl, 5- or 6-membered heteroaryl containing one two or three heteroatoms independently selected from nitrogen, oxygen, and sulfur, 5- or 6-membered cycloalkyl, spirocycloalkyl, or 5-, 6- or 7-membered saturated heterocyclyl, wherein each of the ring(s) of ring B are unsubstituted or substituted with 1, 2, or 3 of $R^j$, $R^k$, and $R^l$ wherein $R^j$, $R^k$, and $R^l$ independently selected from alkyl, hydroxyl cyano, alkoxy, halo, haloalkyl, and haloalkoxy; or a pharmaceutically acceptable salt thereof; provided the compound of Formula (I) is not: 5-aminobenzo[f][1,7]naphthyridine-8-methanamine or 10-ethoxy-8-(morpholinomethyl)-1,2,3,4-tetrahydrobenzo[h][1,6]naphthyridin-5-ol; or a salt thereof.

25. In embodiment 25, the compounds of embodiment 1, or a pharmaceutically acceptable salt thereof, are those wherein the compound, or a pharmaceutically acceptable salt thereof, is selected from compound numbers: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194 and 195 as shown in Table 1 or Table 2, or a parent compound of the salt as shown in Table 1 or Table 2, or a pharmaceutically acceptable salt of the parent compound.

26. In embodiment 26, the compounds of embodiment 1, or a pharmaceutically acceptable salt thereof, are those wherein the compound, or a pharmaceutically acceptable salt thereof, is selected from compound numbers: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125 and 126, as shown in Table 1, or a parent compound of the salt as shown in Table 1, or a pharmaceutically acceptable salt of the parent compound.

27. In embodiment 27, the compounds of embodiment 1, or a pharmaceutically acceptable salt thereof, are those wherein the compound, or a pharmaceutically acceptable salt thereof, is selected from compound numbers: 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194 and 195 as shown in Table 2, or a parent compound of the salt as shown in Table 2, or a pharmaceutically acceptable salt of the parent compound.

28. Embodiment 28 provides a pharmaceutical composition comprising a compound of any one of embodiments 1 to 27, or a pharmaceutically acceptable salt thereof, and a pharmaceutically acceptable excipient.

29. Embodiment 29 provides a method of inhibiting G9a, comprising contacting a cell with a therapeutically effective amount of a compound of any one embodiments 1 to 27, or a pharmaceutically acceptable salt thereof.

30. In embodiment 30, the cell of embodiment 29 can be a cancer cell.

31. Embodiment 31, provides a method of ameliorating and/or treating a hemoglobinpathy, comprising administering a therapeutically effective amount of a compound of any one of embodiments 1 to 27, or a pharmaceutically acceptable salt thereof, or the pharmaceutical composition of embodiment 28 to a subject in need thereof.

32. In embodiment 32, the hemoglobinpathy of embodiment 31 can be sickle cell disease or beta-thalassemia.

33. Embodiment 33, provides a method of ameliorating and/or treating a cancer, comprising administering a therapeutically effective amount of a compound of any one of embodiments 1 to 27, or a pharmaceutically acceptable salt thereof, or the pharmaceutical composition of embodiment 28 to a subject in need thereof.

34. In embodiment 34, the cancer of embodiment 33 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Fibrous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Fallopian Tube Cancer; a Fibrous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sézary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

35. In embodiment 35, the cancer of any one of embodiments 33 to 34 can be selected from: a Myelodysplastic Syndrome (MDS); an Acute Myeloid Leukemia (AML); an Ovarian Cancer; a Colon Cancer; and a Non-Small Cell Lung Cancer (NSCLC).

36. Embodiment 36, provides a method of ameliorating and/or treating an autoimmune or inflammatory disease in, comprising administering a therapeutically effective amount of a compound of any one of embodiments 1 to 27, or a pharmaceutically acceptable salt thereof, or the pharmaceutical composition of embodiment 28 to a subject in need thereof.

37. In embodiment 37, the autoimmune or inflammatory disease of embodiment 36 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

38. In embodiment 38, the autoimmune or inflammatory disease of any one of embodiments 36 to 37 can be Crohn's disease, rheumatoid arthritis, systemic lupus erythematosus, systemic sclerosis, primary biliary cirrhosis and graft-versus-host disease.

39. Embodiment 39, provides for the use of an effective amount of a compound of any one embodiments 1 to 27, or a pharmaceutically acceptable salt thereof, in the manufacture of a medicament for inhibiting the activity of G9a in a cell.

40. In embodiment 40, the cell of embodiment 39 can be a cancer cell.

41. Embodiment 41, provides an effective amount of a compound of any one embodiments 1 to 27, or a pharmaceutically acceptable salt thereof, for inhibiting the activity of G9a in a cell.

42. In embodiment 42, the cell of embodiment 41 can be a cancer cell.

43. Embodiment 43, provides for the use of an effective amount of a compound of any one embodiments 1 to 27, or a pharmaceutically acceptable salt thereof, or the pharmaceutical composition of embodiment 28, in the manufacture of a medicament for ameliorating and/or treating a hemoglobinpathy.

44. In embodiment 44, the hemoglobinpathy of embodiment 43 can be sickle cell disease or beta-thalassemia.

45. Embodiment 45, provides an effective amount of a compound of any one embodiments 1 to 27, or a pharmaceutically acceptable salt thereof, or the pharmaceutical composition of embodiment 28, for ameliorating and/or treating a hemoglobinpathy.

46. In embodiment 46, the hemoglobinpathy of embodiment 45 can be sickle cell disease or beta-thalassemia.

47. Embodiment 47, provides for the use of an effective amount of a compound of any one embodiments 1 to 27, or a pharmaceutically acceptable salt thereof, or the pharmaceutical composition of embodiment 28, in the manufacture of a medicament for ameliorating and/or treating a cancer.

48. In embodiment 48, the cancer of embodiment 47 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Fibrous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Fallopian Tube Cancer; a Fibrous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sézary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

49. In embodiment 49, the cancer of any one of embodiments 47 to 48 can be selected from: a Myelodysplastic Syndrome (MDS); an Acute Myeloid Leukemia (AML); an Ovarian Cancer; a Colon Cancer; and a Non-Small Cell Lung Cancer (NSCLC).

50. Embodiment 50, provides an effective amount of a compound of any one embodiments 1 to 27, or a pharmaceutically acceptable salt thereof, or the pharmaceutical composition of embodiment 28, for ameliorating and/or treating a cancer.

51. In embodiment 51, the cancer of embodiment 50 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Fibrous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Fallopian Tube Cancer; a Fibrous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sézary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

52. In embodiment 52, the cancer of any one of embodiments 50 to 51 can be selected from: a Myelodysplastic Syndrome (MDS); an Acute Myeloid Leukemia (AML); an Ovarian Cancer; a Colon Cancer; and a Non-Small Cell Lung Cancer (NSCLC).

53. Embodiment 53, provides for the use of an effective amount of a compound of any one embodiments 1 to 27, or a pharmaceutically acceptable salt thereof, or the pharmaceutical composition of embodiment 28, in the manufacture of a medicament for ameliorating and/or treating an autoimmune or inflammatory disease.

54. In embodiment 54, the autoimmune or inflammatory disease of embodiment 53 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

55. In embodiment 55, the autoimmune or inflammatory disease of any one of embodiments 53 to 54 can be selected from: Crohn's disease, rheumatoid arthritis, systemic lupus erythematosus, systemic sclerosis, primary biliary cirrhosis and graft-versus-host disease.

56. Embodiment 56, provides an effective amount of a compound of any one embodiments 1 to 27, or a pharmaceutically acceptable salt thereof, or the pharmaceutical composition of embodiment 28, for ameliorating and/or treating an autoimmune or inflammatory disease.

57. In embodiment 57, the autoimmune or inflammatory disease of embodiment 56 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

58. In embodiment 58, the autoimmune or inflammatory disease of any one of embodiments 56 to 57 can be selected from: Crohn's disease, rheumatoid arthritis, systemic lupus erythematosus, systemic sclerosis, primary biliary cirrhosis and graft-versus-host disease.

Representative compounds of Formula (I), or salts thereof, are disclosed in Tables 1 and 2 below. Although Tables 1 and 2 may show a specific salt of a compound of Formula (I), those skilled in the art will be able to recognize the parent compound (wherein the "parent compound" is a compound without a salt moiety present), and other salts, such as pharmaceutically acceptable salts, of those compounds in Tables 1 and 2.

TABLE 1

| Cmpd. # | Structure | Name | MS Found |
|---|---|---|---|
| 1 | formate | 8-methoxy-N-methyl-7-[3-(pyrrolidin-1-yl)propoxy]-1H,2H,3H-cyclopenta[c]quinolin-4-amine formate | 356.2 |
| 2 | formate | 2-methoxy-N-methyl-3-[3-(pyrrolidin-1-yl)propoxy]-7,8,9,10-tetrahydrophenanthridin-6-amine formate | 370.2 |
| 3 | trifluoroacetate | 8-methoxy-N-(propan-2-yl)-7-[3-(pyrrolidin-1-yl)propoxy]-1H,2H,3H-cyclopenta[c]quinolin-4-amine trifluoroacetate | 384.2 |
| 4 | trifluoroacetate | 2-({8-methoxy-7-[3-(pyrrolidin-1-yl)propoxy]-1H,2H,3H-cyclopenta[c]quinolin-4-yl}amino)ethan-1-ol trifluoroacetate | 386.3 |
| 5 | trifluoroacetate | 8-methoxy-N-(2-phenylethyl)-7-[3-(pyrrolidin-1-yl)propoxy]-1H,2H,3H-cyclopenta[c]quinolin-4-amine trifluoroacetate | 446.3 |
| 6 | formate | 8-methoxy-2-methyl-N-(propan-2-yl)-7-[3-(pyrrolidin-1-yl)propoxy]-1H,2H,3H-cyclopenta[c]quinolin-4-amine formate | 398.4 |

TABLE 1-continued

| Cmpd. # | Structure | Name | MS Found |
|---|---|---|---|
| 7 | (structure) formate | N-cyclobutyl-8-methoxy-7-[3-(pyrrolidin-1-yl)propoxy]-1H,2H,3H-cyclopenta[c]quinolin-4-amine formate | 396.4 |
| 8 | (structure) trifluoroacetate | N-cyclopentyl-8-methoxy-7-[3-(pyrrolidin-1-yl)propoxy]-1H,2H,3H-cyclopenta[c]quinolin-4-amine trifluoroacetate | 410.4 |
| 9 | (structure) trifluoroacetate | 8-methoxy-N-methyl-N-(propan-2-yl)-7-[3-(pyrrolidin-1-yl)propoxy]-1H,2H,3H-cyclopenta[c]quinolin-4-amine trifluoroacetate | 398.2 |
| 10 | (structure) formate | 1-{8-methoxy-7-[3-(pyrrolidin-1-yl)propoxy]-1H,2H,3H-cyclopenta[c]quinolin-4-yl}pyrrolidine formate | 396.2 |
| 11 | (structure) trifluoroacetate | 8-methoxy-7-[(1-methylpyrrolidin-3-yl)methoxy]-N-(propan-2-yl)-1H,2H,3H-cyclopenta[c]quinolin-4-amine trifluoroacetate | 370.4 |
| 12 | (structure) trifluoroacetate | 2-methoxy-N-(oxan-4-yl)-3-[3-(pyrrolidin-1-yl)propoxy]-7,8,9,10-tetrahydrophenanthridin-6-amine trifluoroacetate | 440.3 |

TABLE 1-continued

| Cmpd. # | Structure | Name | MS Found |
|---|---|---|---|
| 13 | formate | 2-methoxy-N-(propan-2-yl)-3-[3-(pyrrolidin-1-yl)propoxy]-7,8,9,10-tetrahydrophenanthridin-6-amine formate | 398.3 |
| 14 | trifluoroacetate | N-{8-methoxy-7-[3-(pyrrolidin-1-yl)propoxy]-1H,2H,3H-cyclopenta[c]quinolin-4-yl}acetamide trifluoroacetate | 384.2 |
| 15 | formate | 2-({2-methoxy-3-[3-(pyrrolidin-1-yl)propoxy]-7,8,9,10-tetrahydrophenanthridin-6-yl}amino)ethan-1-ol formate | 400.2 |
| 16 | trifluoroacetate | (1r,3r)-3-({8-methoxy-7-[3-(pyrrolidin-1-yl)propoxy]-1H,2H,3H-cyclopenta[c]quinolin-4-yl}amino)cyclobutan-1-ol trifluoroacetate | 412.3 |
| 17 | formate | 8-methoxy-N-[(3R)-oxolan-3-yl]-7-[3-(pyrrolidin-1-yl)propoxy]-1H,2H,3H-cyclopenta[c]quinolin-4-amine formate | 412.4 |
| 18 | formate | 8-methoxy-N-[(3S)-oxolan-3-yl]-7-[3-(pyrrolidin-1-yl)propoxy]-1H,2H,3H-cyclopenta[c]quinolin-4-amine formate | 412.4 |

TABLE 1-continued

| Cmpd. # | Structure | Name | MS Found |
|---|---|---|---|
| 19 | 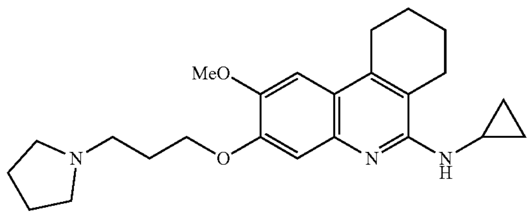 [SMILES: COc1cc2c3c(c(NC4CC4)nc2cc1OCCCN1CCCC1)CCCC3] | N-cyclopropyl-2-methoxy-3-[3-(pyrrolidin-1-yl)propoxy]-7,8,9,10-tetrahydrophenanthridin-6-amine formate | 396.2 |
| 20 | 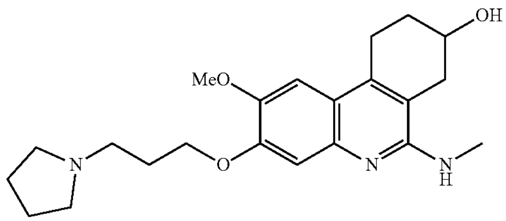 [SMILES: CNc1nc2cc(OCCCN3CCCC3)c(OC)cc2c2c1CC(O)CC2] | 2-methoxy-6-(methylamino)-3-[3-(pyrrolidin-1-yl)propoxy]-7,8,9,10-tetrahydrophenanthridin-8-ol formate | 386.2 |
| 21 | 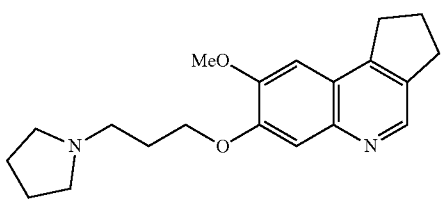 [SMILES: COc1cc2c3c(cnc2cc1OCCCN1CCCC1)CCC3] | 1-[3-({8-methoxy-1H,2H,3H-cyclopenta[c]quinolin-7-yl}oxy)propyl]pyrrolidine trifluoroacetate | 327.3 |
| 22 | 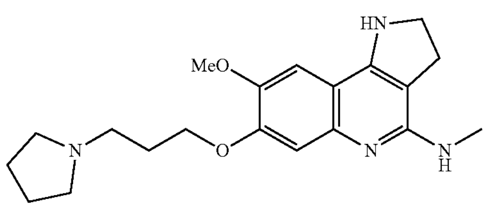 [SMILES: CNc1nc2cc(OCCCN3CCCC3)c(OC)cc2c2c1CCN2] | 8-methoxy-N-methyl-7-[3-(pyrrolidin-1-yl)propoxy]-1H,2H,3H-pyrrolo[3,2-c]quinolin-4-amine trifluoroacetate | 357.2 |
| 23 | 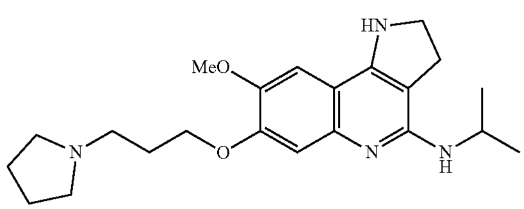 [SMILES: COc1cc2c3c(c(NC(C)C)nc2cc1OCCCN1CCCC1)CCN3] | 8-methoxy-N-(propan-2-yl)-7-[3-(pyrrolidin-1-yl)propoxy]-1H,2H,3H-pyrrolo[3,2-c]quinolin-4-amine trifluoroacetate | 385.2 |
| 24 | 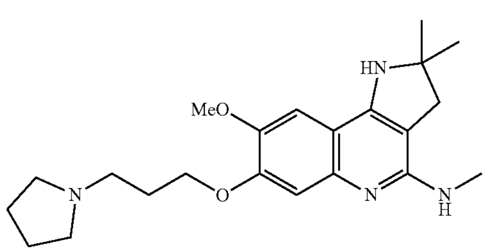 [SMILES: CNc1nc2cc(OCCCN3CCCC3)c(OC)cc2c2c1CC(C)(C)N2] | 8-methoxy-N,2,2-trimethyl-7-[3-(pyrrolidin-1-yl)propoxy]-1H,2H,3H-pyrrolo[3,2-c]quinolin-4-amine trifluoroacetate | 385.2 |

TABLE 1-continued

| Cmpd. # | Structure | Name | MS Found |
|---|---|---|---|
| 25 | 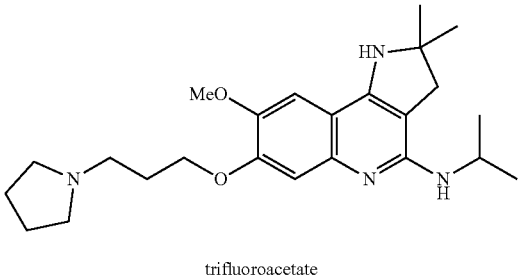 trifluoroacetate | 8-methoxy-2,2-dimethyl-N-(propan-2-yl)-7-[3-(pyrrolidin-1-yl)propoxy]-1H,2H,3H-pyrrolo[3,2-c]quinolin-4-amine trifluoroacetate | 413.2 |
| 26 | 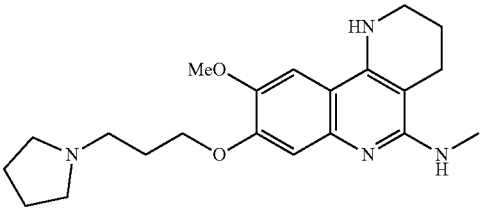 [SMILES: CNc1nc2cc(OCCCN3CCCC3)c(OC)cc2c2c1CCCN2] formate | 9-methoxy-N-methyl-8-[3-(pyrrolidin-1-yl)propoxy]-1H,2H,3H,4H-benzo[h]1,6-naphthyridin-5-amine formate | 371.1 |
| 27 | 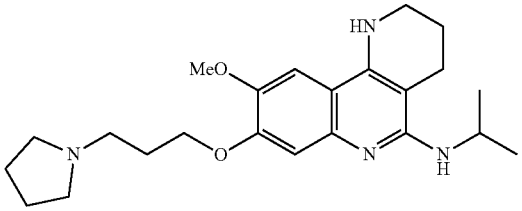 [SMILES: COc1cc2c3c(c(NC(C)C)nc2cc1OCCCN1CCCC1)CCCN3] trifluoroacetate | 9-methoxy-N-(propan-2-yl)-8-[3-(pyrrolidin-1-yl)propoxy]-1H,2H,3H,4H-benzo[h]1,6-naphthyridin-5-amine trifluoroacetate | 399.2 |
| 28 | 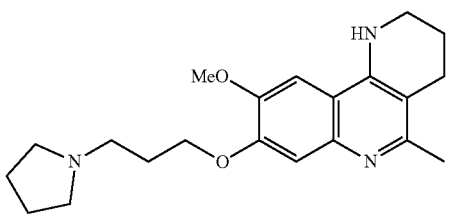 [SMILES: COc1cc2c3c(c(C)nc2cc1OCCCN1CCCC1)CCCN3] trifluoroacetate | 1-[3-({9-methoxy-5-methyl-1H,2H,3H,4H-benzo[h]1,6-naphthyridin-8-yl}oxy)propyl]pyrrolidine trifluoroacetate | 356.2 |
| 29 | 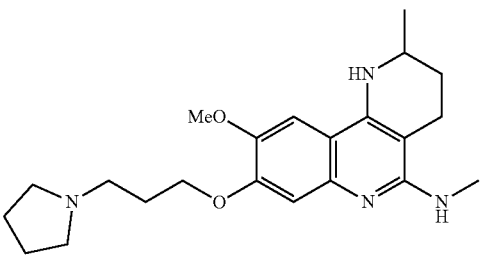 [SMILES: CNc1nc2cc(OCCCN3CCCC3)c(OC)cc2c2c1CCC(C)N2] formate | 9-methoxy-N,2-dimethyl-8-[3-(pyrrolidin-1-yl)propoxy]-1H,2H,3H,4H-benzo[h]1,6-naphthyridin-5-amine formate | 385.3 |

TABLE 1-continued

| Cmpd. # | Structure | Name | MS Found |
|---|---|---|---|
| 30 | formate | 9-methoxy-2-methyl-N-(propan-2-yl)-8-[3-(pyrrolidin-1-yl)propoxy]-1H,2H,3H,4H-benzo[h]1,6-naphthyridin-5-amine formate | 413.3 |
| 31 | trifluoroacetate | 1-[3-({9-methoxy-2,5-dimethyl-1H,2H,3H,4H-benzo[h]1,6-naphthyridin-8-yl}oxy)propyl]pyrrolidine trifluoroacetate | 370.2 |
| 32 | trifluoroacetate | 1-[3-({5-cyclopropyl-9-methoxy-2-methyl-1H,2H,3H,4H-benzo[h]1,6-naphthyridin-8-yl}oxy)propyl]pyrrolidine trifluoroacetate | 396.2 |
| 33 | formate | 10-methoxy-N-methyl-9-[3-(pyrrolidin-1-yl)propoxy]-1H,2H,3H,4H,5H-azepino[3,2-c]quinolin-6-amine formate | 385.2 |
| 34 | formate | 10-methoxy-N-(propan-2-yl)-9-[3-(pyrrolidin-1-yl)propoxy]-1H,2H,3H,4H,5H-azepino[3,2-c]quinolin-6-amine formate | 413.3 |

TABLE 1-continued

| Cmpd. # | Structure | Name | MS Found |
|---|---|---|---|
| 35 | formate | 1-[3-({8-methoxy-2,2-dimethyl-1H,2H,3H-pyrrolo[3,2-c]quinolin-7-yl}oxy)propyl]pyrrolidine formate | 356.2 |
| 36 | formate | 1-[3-({4-cyclopropyl-8-methoxy-2,2-dimethyl-1H,2H,3H-pyrrolo[3,2-c]quinolin-7-yl}oxy)propyl]pyrrolidine formate | 396.3 |
| 37 | trifluoroacetate | 8-methoxy-7-[3-(pyrrolidin-1-yl)propoxy]-1H,2H,3H-cyclopenta[c]quinolin-4-ol trifluoroacetate | 343.2 |
| 38 | trifluoroacetate | 2-methoxy-3-[3-(pyrrolidin-1-yl)propoxy]-7,8,9,10-tetrahydrophenanthridin-6-ol trifluoroacetate | 357.2 |
| 39 | trifluoroacetate | 2-methoxy-N-[1-(propan-2-yl)piperidin-4-yl]-3-[3-(pyrrolidin-1-yl)propoxy]-7,8,9,10-tetrahydrophenanthridin-6-amine trifluoroacetate | 481.4 |

TABLE 1-continued

| Cmpd. # | Structure | Name | MS Found |
|---|---|---|---|
| 40 | 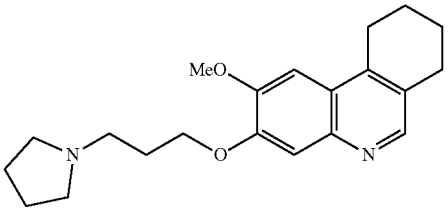 [SMILES: COc1cc2c3c(cnc2cc1OCCCN1CCCC1)CCCC3] trifluoroacetate | 2-methoxy-3-[3-(pyrrolidin-1-yl)propoxy]-7,8,9,10-tetrahydrophenanthridine trifluoroacetate | 341.3 |
| 41 | 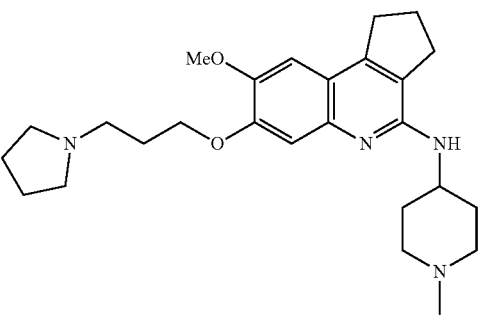 [SMILES: COc1cc2c3c(c(NC4CCN(C)CC4)nc2cc1OCCCN1CCCC1)CCC3] formate | 2-methoxy-N-(1-methylpiperidin-4-yl)-3-[3-(pyrrolidin-1-yl)propoxy]-7,8,9,10-tetrahydrophenanthridin-6-amine formate | 439.4 |
| 42 | 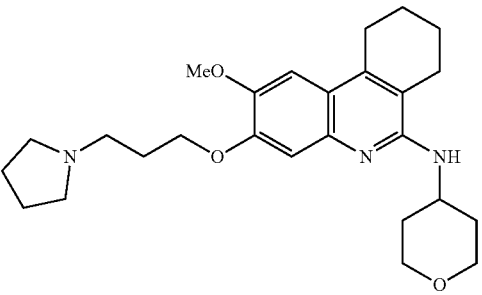 [SMILES: COc1cc2c3c(c(NC4CCOCC4)nc2cc1OCCCN1CCCC1)CCCC3] formate | 2-methoxy-N-(oxan-4-yl)-3-[3-(pyrrolidin-1-yl)propoxy]-7,8,9,10-tetrahydrophenanthridin-6-amine formate | 425.3 |
| 43 | 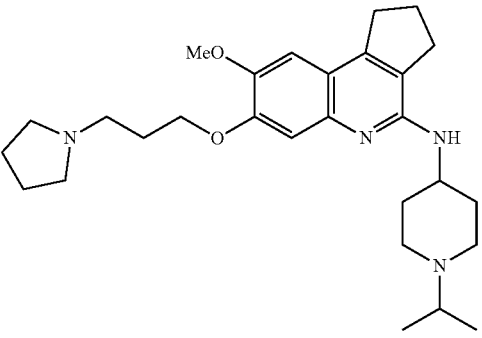 [SMILES: COc1cc2c3c(c(NC4CCN(C(C)C)CC4)nc2cc1OCCCN1CCCC1)CCC3] formate | N-{8-methoxy-7-[3-(pyrrolidin-1-yl)propoxy]-1H,2H,3H-cyclopenta[c]quinolin-4-yl}-1-(propan-2-yl)piperidin-4-amine formate | 467.4 |
| 44 | 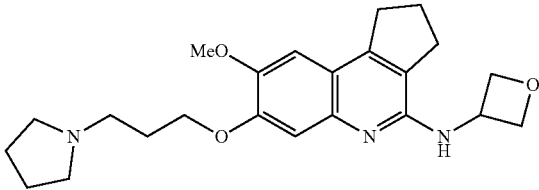 [SMILES: COc1cc2c3c(c(NC4COC4)nc2cc1OCCCN1CCCC1)CCC3] formate | 8-methoxy-N-(oxetan-3-yl)-7-[3-(pyrrolidin-1-yl)propoxy]-1H,2H,3H-cyclopenta[c]quinolin-4-amine formate | 398.3 |

TABLE 1-continued

| Cmpd. # | Structure | Name | MS Found |
|---|---|---|---|
| 45 | 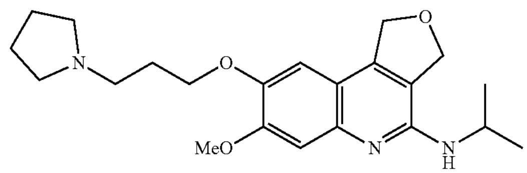 [SMILES: COc1cc2nc(NC(C)C)c3c(c2cc1OCCCN1CCCC1)COC3] | 7-methoxy-N-(propan-2-yl)-8-[3-(pyrrolidin-1-yl)propoxy]-1H,3H-furo[3,4-c]quinolin-4-amine | 386.3 |
| 46 | 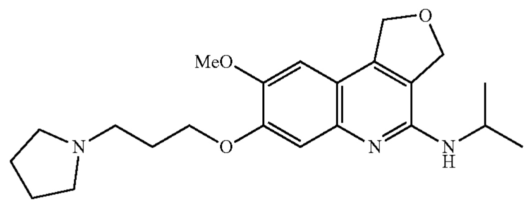 [SMILES: COc1cc2c3c(c(NC(C)C)nc2cc1OCCCN1CCCC1)COC3] | 8-methoxy-N-(propan-2-yl)-7-[3-(pyrrolidin-1-yl)propoxy]-1H,3H-furo[3,4-c]quinolin-4-amine | 386.4 |
| 47 | 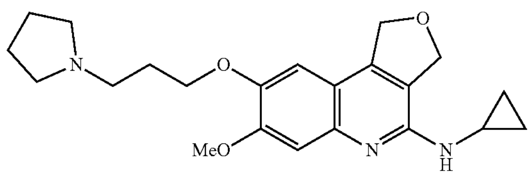 [SMILES: COc1cc2nc(NC3CC3)c3c(c2cc1OCCCN1CCCC1)COC3] | N-cyclopropyl-7-methoxy-8-[3-(pyrrolidin-1-yl)propoxy]-1H,3H-furo[3,4-c]quinolin-4-amine | 384.3 |
| 48 | 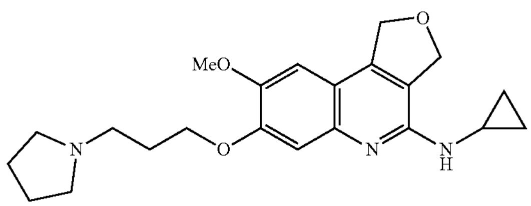 [SMILES: COc1cc2c3c(c(NC4CC4)nc2cc1OCCCN1CCCC1)COC3] | N-cyclopropyl-8-methoxy-7-[3-(pyrrolidin-1-yl)propoxy]-1H,3H-furo[3,4-c]quinolin-4-amine | 384.3 |
| 49 | formate | N-(cyclobutylmethyl)-8-methoxy-7-[3-(pyrrolidin-1-yl)propoxy]-1H,2H,3H-cyclopenta[c]quinolin-4-amine formate | 410.3 |
| 50 | formate | 9-methoxy-N-(propan-2-yl)-8-[3-(pyrrolidin-1-yl)propoxy]-1H,2H,4H-pyrano[3,4-c]quinolin-5-amine formate | 400.3 |
| 51 | formate | 2-methoxy-3-[(1-methylpyrrolidin-3-yl)methoxy]-N-(propan-2-yl)-7,8,9,10-tetrahydrophenanthridin-6-amine formate | 384.3 |

TABLE 1-continued

| Cmpd. # | Structure | Name | MS Found |
|---|---|---|---|
| 52 | formate | 9-methoxy-N-(propan-2-yl)-8-[3-(pyrrolidin-1-yl)propoxy]benzo[h]1,6-naphthyridin-5-amine formate | 395.4 |
| 53 | formate | 8-methoxy-N,2,2-trimethyl-7-[3-(pyrrolidin-1-yl)propoxy]-1H,2H,3H-cyclopenta[c]quinolin-4-amine formate | 384.3 |
| 54 | formate | 8-methoxy-2,2-dimethyl-N-(propan-2-yl)-7-[3-(pyrrolidin-1-yl)propoxy]-1H,2H,3H-cyclopenta[c]quinolin-4-amine formate | 412.3 |
| 55 | formate | N-cyclopropyl-9-methoxy-8-[3-(pyrrolidin-1-yl)propoxy]-1H,2H,4H-pyrano[3,4-c]quinolin-5-amine formate | 398.2 |
| 56 | formate | 9-methoxy-8-[3-(pyrrolidin-1-yl)propoxy]pyrazolo[1,5-c]quinazolin-5-ol formate | |
| 57 | formate | 9-methoxy-N-methyl-8-[3-(pyrrolidin-1-yl)propoxy]-1H,2H,4H-pyrano[3,4-c]quinolin-5-amine formate | 372.2 |

TABLE 1-continued

| Cmpd. # | Structure | Name | MS Found |
|---|---|---|---|
| 58 | 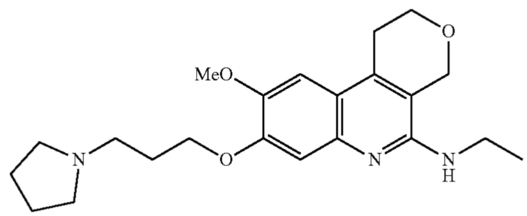 [SMILES: CCNc1nc2cc(OCCCN3CCCC3)c(OC)cc2c2c1COCC2] | N-ethyl-9-methoxy-8-[3-(pyrrolidin-1-yl)propoxy]-1H,2H,4H-pyrano[3,4-c]quinolin-5-amine formate | 386.2 |
| 59 | 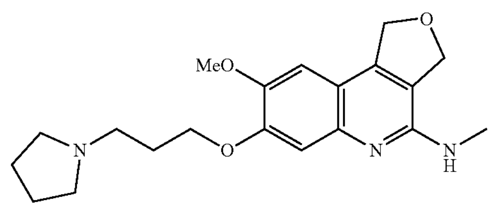 [SMILES: CNc1nc2cc(OCCCN3CCCC3)c(OC)cc2c2c1COC2] | 8-methoxy-N-methyl-7-[3-(pyrrolidin-1-yl)propoxy]-1H,3H-furo[3,4-c]quinolin-4-amine formate | 358.2 |
| 60 | 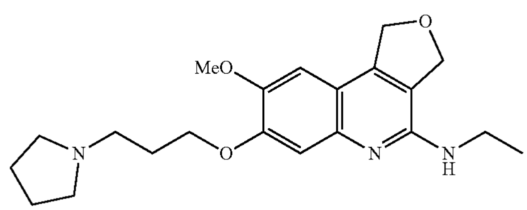 [SMILES: CCNc1nc2cc(OCCCN3CCCC3)c(OC)cc2c2c1COC2] | N-ethyl-8-methoxy-7-[3-(pyrrolidin-1-yl)propoxy]-1H,3H-furo[3,4-c]quinolin-4-amine formate | 372.2 |
| 61 | 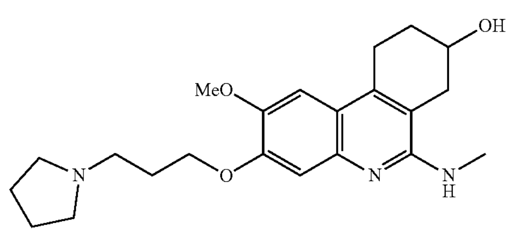 [SMILES: CNc1nc2cc(OCCCN3CCCC3)c(OC)cc2c2c1CC(O)CC2] | 2-methoxy-6-(methylamino)-3-[3-(pyrrolidin-1-yl)propoxy]-7,8,9,10-tetrahydrophenanthridin-8-ol formate | 386.2 |
| 62 | 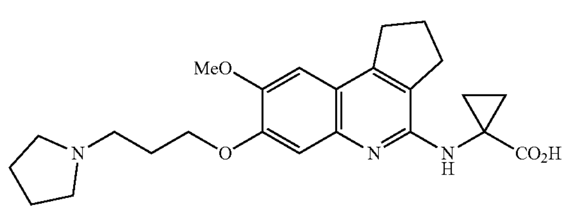 [SMILES: COc1cc2c3c(c(NC4(C(=O)O)CC4)nc2cc1OCCCN1CCCC1)CCC3] | 1-({8-methoxy-7-[3-(pyrrolidin-1-yl)propoxy]-1H,2H,3H-cyclopenta[c]quinolin-4-yl}amino)cyclopropane-1-carboxylic acid formate | 426.2 |
| 63 | 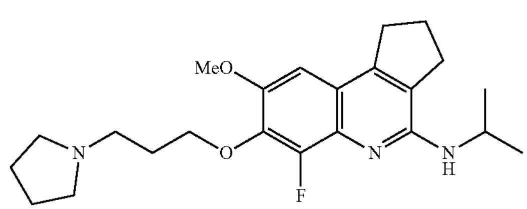 [SMILES: COc1cc2c3c(c(NC(C)C)nc2c(F)c1OCCCN1CCCC1)CCC3] | 6-fluoro-8-methoxy-N-(propan-2-yl)-7-[3-(pyrrolidin-1-yl)propoxy]-1H,2H,3H-cyclopenta[c]quinolin-4-amine formate | 402.2 |

TABLE 1-continued

| Cmpd. # | Structure | Name | MS Found |
|---|---|---|---|
| 64 | 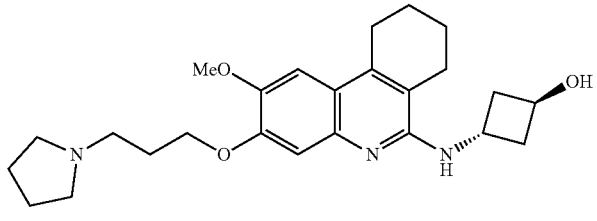 [SMILES: COc1cc2c3c(c(N[C@H]4C[C@H](O)C4)nc2cc1OCCCN1CCCC1)CCCC3]<br>formate | 3-({2-methoxy-3-[3-(pyrrolidin-1-yl)propoxy]-7,8,9,10-tetrahydrophenanthridin-6-yl}amino)cyclobutan-1-ol formate | 426.3 |
| 65 | 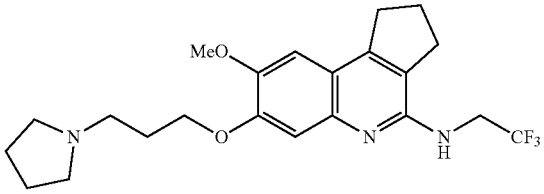 [SMILES: COc1cc2c3c(c(NCC(F)(F)F)nc2cc1OCCCN1CCCC1)CCC3]<br>formate | 8-methoxy-7-[3-(pyrrolidin-1-yl)propoxy]-N-(2,2,2-trifluoroethyl)-1H,2H,3H-cyclopenta[c]quinolin-4-amine formate | 424.3 |
| 66 | 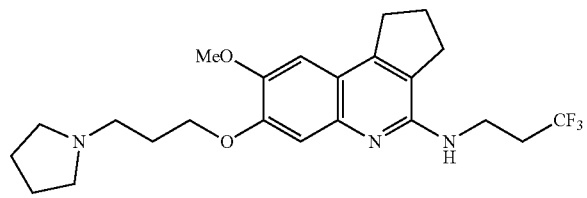 [SMILES: COc1cc2c3c(c(NCCC(F)(F)F)nc2cc1OCCCN1CCCC1)CCC3] | 8-methoxy-7-[3-(pyrrolidin-1-yl)propoxy]-N-(3,3,3-trifluoropropyl)-1H,2H,3H-cyclopenta[c]quinolin-4-amine | 438.4 |
| 67 | 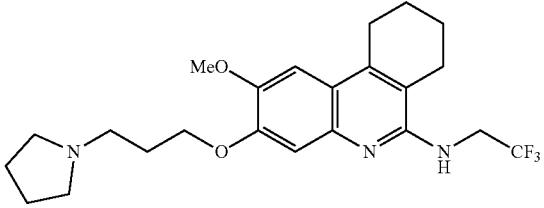 [SMILES: COc1cc2c3c(c(NCC(F)(F)F)nc2cc1OCCCN1CCCC1)CCCC3]<br>formate | 2-methoxy-3-[3-(pyrrolidin-1-yl)propoxy]-N-(2,2,2-trifluoroethyl)-7,8,9,10-tetrahydrophenanthridin-6-amine formate | 438.4 |
| 68 | 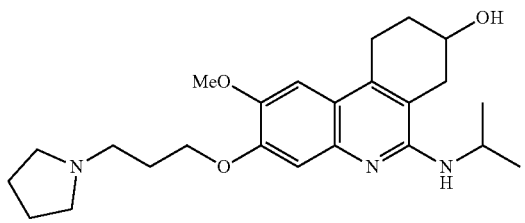 [SMILES: COc1cc2c3c(c(NC(C)C)nc2cc1OCCCN1CCCC1)CC(O)CC3]<br>trifluoroacetate | 2-methoxy-6-[(propan-2-yl)amino]-3-[3-(pyrrolidin-1-yl)propoxy]-7,8,9,10-tetrahydrophenanthridin-8-ol trifluoroacetate | 414.2 |
| 69 | 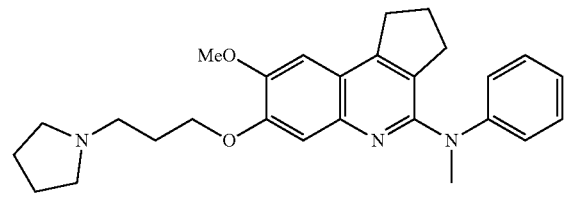 [SMILES: COc1cc2c3c(c(N(C)c4ccccc4)nc2cc1OCCCN1CCCC1)CCC3]<br>trifluoroacetate | 8-methoxy-N-methyl-N-phenyl-7-[3-(pyrrolidin-1-yl)propoxy]-1H,2H,3H-cyclopenta[c]quinolin-4-amine trifluoroacetate | 432.2 |

TABLE 1-continued

| Cmpd. # | Structure | Name | MS Found |
|---|---|---|---|
| 70 | 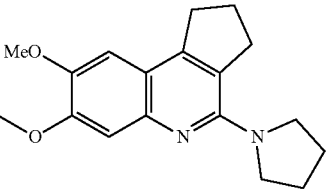 formate | 1-{8-methoxy-7-[3-(pyrrolidin-1-yl)propoxy]-1H,2H,3H-cyclopenta[c]quinolin-4-yl}pyrrolidine formate | 396.2 |
| 71 | 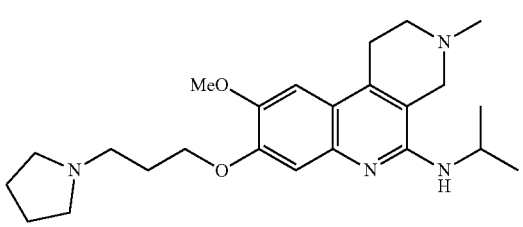 [SMILES: COc1cc2c3c(c(NC(C)C)nc2cc1OCCCN1CCCC1)CN(C)CC3] formate | 9-methoxy-3-methyl-N-(propan-2-yl)-8-[3-(pyrrolidin-1-yl)propoxy]-1H,2H,3H,4H-benzo[c]2,7-naphthyridin-5-amine formate | 413.3 |
| 72 | 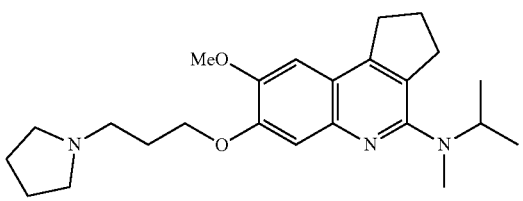 [SMILES: COc1cc2c3c(c(N(C)C(C)C)nc2cc1OCCCN1CCCC1)CCC3] trifluoroacetate | 8-methoxy-N-methyl-N-(propan-2-yl)-7-[3-(pyrrolidin-1-yl)propoxy]-1H,2H,3H-cyclopenta[c]quinolin-4-amine trifluoroacetate | 398.3 |
| 73 | 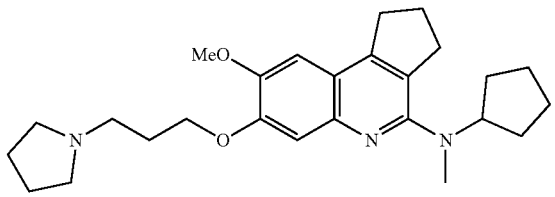 [SMILES: COc1cc2c3c(c(N(C)C4CCCC4)nc2cc1OCCCN1CCCC1)CCC3] trifluoroacetate | N-cyclopentyl-8-methoxy-N-methyl-7-[3-(pyrrolidin-1-yl)propoxy]-1H,2H,3H-cyclopenta[c]quinolin-4-amine trifluoroacetate | 424.3 |
| 74 | 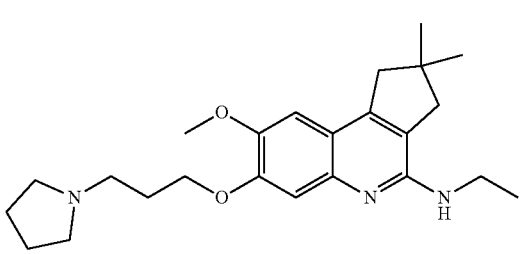 [SMILES: CCNc1nc2cc(OCCCN3CCCC3)c(OC)cc2c2c1CC(C)(C)C2] formate | N-ethyl-8-methoxy-2,2-dimethyl-7-[3-(pyrrolidin-1-yl)propoxy]-1H,2H,3H-cyclopenta[c]quinolin-4-amine formate | 398.3 |
| 75 | 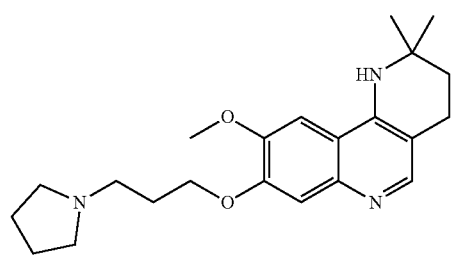 [SMILES: COc1cc2c3c(cnc2cc1OCCCN1CCCC1)CCC(C)(C)N3] Formate | 3-({9-methoxy-2,2-dimethyl-1H,2H,3H,4H-benzo[h]1,6-naphthyridin-8-yl}oxy)propyl]pyrrolidine formate | 370.2 |

TABLE 1-continued

| Cmpd. # | Structure | Name | MS Found |
|---|---|---|---|
| 76 | 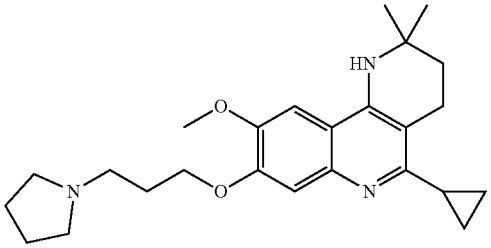 [SMILES: COc1cc2c3c(c(C4CC4)nc2cc1OCCCN1CCCC1)CCC(C)(C)N3] Formate | 1-[3-({5-cyclopropyl-9-methoxy-2,2-dimethyl-1H,2H,3H,4H-benzo[h]1,6-naphthyridin-8-yl)oxy)propyl]pyrrolidine formate | 410.5 |
| 77 | 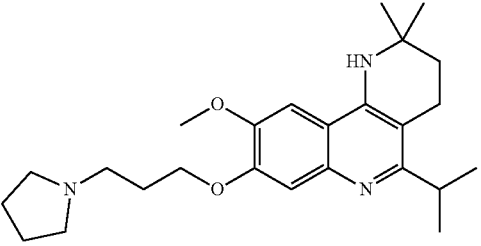 [SMILES: COc1cc2c3c(c(C(C)C)nc2cc1OCCCN1CCCC1)CCC(C)(C)N3] Formate | 1-(3-{[9-methoxy-2,2-dimethyl-5-(propan-2-yl)-1H,2H,3H,4H-benzo[h]1,6-naphthyridin-8-yl]oxy}propyl)pyrrolidine formate | 412.5 |
| 78 | 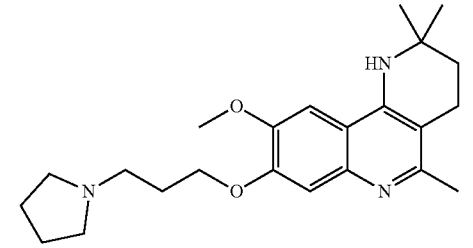 [SMILES: COc1cc2c3c(c(C)nc2cc1OCCCN1CCCC1)CCC(C)(C)N3] Formate | 1-[3-({9-methoxy-2,2,5-trimethyl-1H,2H,3H,4H-benzo[h]1,6-naphthyridin-8-yl}oxy)propyl]pyrrolidine formate | 384.4 |
| 79 | 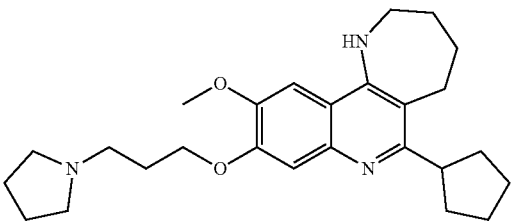 [SMILES: COc1cc2c3c(c(C4CCCC4)nc2cc1OCCCN1CCCC1)CCCCN3] Trifluroracetate | 1-[3-({6-cyclopentyl-10-methoxy-1H,2H,3H,4H,5H-azepino[3,2-c]quinolin-9-yl}oxy)propyl]pyrrolidine trifluoroacetate | 424.3 |
| 80 | 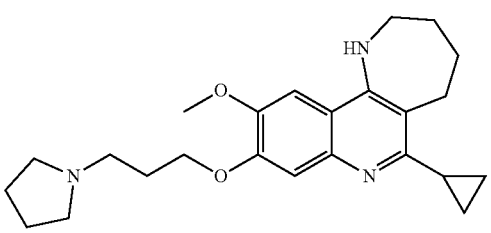 [SMILES: COc1cc2c3c(c(C4CC4)nc2cc1OCCCN1CCCC1)CCCCN3] trifluoroacetate | 1-[3-({6-cyclopropyl-10-methoxy-1H,2H,3H,4H,5H-azepino[3,2-c]quinolin-9-yl}oxy)propyl]pyrrolidine trifluoroacetate | 396.3 |

TABLE 1-continued

| Cmpd. # | Structure | Name | MS Found |
|---|---|---|---|
| 81 | trifluoroacetate | 1-(3-{[10-methoxy-6-(propan-2-yl)-1H,2H,3H,4H,5H-azepino[3,2-c]quinolin-9-yl]oxy}propyl)pyrrolidine trifluoroacetate | 398.2 |
| 82 | trifluoroacetate | 1-[3-({10-methoxy-6-methyl-1H,2H,3H,4H,5H-azepino[3,2-c]quinolin-9-yl}oxy)propyl]pyrrolidine trifluoroacetate | 370.2 |
| 83 | Formate | 1-(3-{[4-(cyclopent-1-en-1-yl)-8-methoxy-2,2-dimethyl-1H,2H,3H-pyrrolo[3,2-c]quinolin-7-yl]oxy}propyl)pyrrolidine formate | 422.1 |
| 84 | trifluoroacetate | 4-[(propan-2-yl)amino]-7-[3-(pyrrolidin-1-yl)propoxy]-1H,2H,3H-cyclopenta[c]quinolin-8-ol trifluoroacetate | 370.3 |
| 85 | Formate | 8-methoxy-7-[3-(piperidin-1-yl)propoxy]-N-(propan-2-yl)-1H,2H,3H-cyclopenta[c]quinolin-4-amine formate | 398.3 |
| 86 | Formate | 7-[3-(3,3-dimethylpyrrolidin-1-yl)propoxy]-8-methoxy-N-(propan-2-yl)-1H,2H,3H-cyclopenta[c]quinolin-4-amine formate | 412.3 |

TABLE 1-continued

| Cmpd. # | Structure | Name | MS Found |
|---|---|---|---|
| 87 | Formate | 8-methoxy-2,2-dimethyl-N-(3-methylbutyl)-7-[3-(pyrrolidin-1-yl)propoxy]-1H,2H,3H-cyclopenta[c]quinolin-4-amine formate | 440.1 |
| 88 | Formate | N-[(1S)-1-cyclopropylethyl]-8-methoxy-7-[3-(pyrrolidin-1-yl)propoxy]-1H,2H,3H-cyclopenta[c]quinolin-4-amine formate | 410.2 |
| 89 | Formate | N-[(1R)-1-cyclopropylethyl]-8-methoxy-7-[3-(pyrrolidin-1-yl)propoxy]-1H,2H,3H-cyclopenta[c]quinolin-4-amine formate | 410.2 |
| 90 | Formate | 1-(3-{[8-methoxy-4-(5-methylfuran-3-yl)-1H,2H,3H-cyclopenta[c]quinolin-7-yl]oxy}propyl)pyrrolidine formate | 407.2 |
| 91 | Formate | N-butyl-8-methoxy-2,2-dimethyl-7-[3-(pyrrolidin-1-yl)propoxy]-1H,2H,3H-cyclopenta[c]quinolin-4-amine formate | 426.1 |
| 92 | Formate | 7-[3-(dimethylamino)propoxy]-8-methoxy-N-(propan-2-yl)-1H,2H,3H-cyclopenta[c]quinolin-4-amine formate | 358.2 |

TABLE 1-continued

| Cmpd. # | Structure | Name | MS Found |
|---|---|---|---|
| 93 | Formate | 7-[3-(diethylamino)propoxy]-8-methoxy-N-(propan-2-yl)-1H,2H,3H-cyclopenta[c]quinolin-4-amine formate | 386.3 |
| 94 | Formate | N-tert-butyl-8-methoxy-7-[3-(pyrrolidin-1-yl)propoxy]-1H,2H,3H-cyclopenta[c]quinolin-4-amine formate | 398.2 |
| 95 | Formate | N-isobutyl-8-methoxy-2,2-dimethyl-7-(3-(pyrrolidin-1-yl)propoxy)-2,3-dihydro-1H-cyclopenta[c]quinolin-4-amine formate | 426.1 |
| 96 | Formate | N-(cyclobutylmethyl)-8-methoxy-2,2-dimethyl-7-(3-(pyrrolidin-1-yl)propoxy)-2,3-dihydro-1H-cyclopenta[c]quinolin-4-amine formate | 438.1 |
| 97 | Formate | N-(cyclopropylmethyl)-8-methoxy-2,2-dimethyl-7-[3-(pyrrolidin-1-yl)propoxy]-1H,2H,3H-cyclopenta[c]quinolin-4-amine formate | 424.1 |

TABLE 1-continued

| Cmpd. # | Structure | Name | MS Found |
|---|---|---|---|
| 98 | Formate | 1-(3-{[8-methoxy-4-(oxolan-3-yl)-1H,2H,3H-cyclopenta[c]quinolin-7-yl]oxy}propyl)pyrrolidine formate | 397.2 |
| 99 | Formate | N-[(2S)-butan-2-yl]-8-methoxy-7-[3-(pyrrolidin-1-yl)propoxy]-1H,2H,3H-cyclopenta[c]quinolin-4-amine formate | 398.4 |
| 100 | Formate | N-[(2R)-butan-2-yl]-8-methoxy-7-[3-(pyrrolidin-1-yl)propoxy]-1H,2H,3H-cyclopenta[c]quinolin-4-amine formate | 398.4 |
| 101 | Formate | N-(2,2-dimethylpropyl)-8-methoxy-7-[3-(pyrrolidin-1-yl)propoxy]-1H,2H,3H-cyclopenta[c]quinolin-4-amine formate | 412.3 |
| 102 | HCl | 8-methoxy-N-[(2-$^{2}$H)propan-2-yl]-7-[3-(pyrrolidin-1-yl)propoxy]-1H,2H,3H-cyclopenta[c]quinolin-4-amine hydrochloride | 385.2 |
| 103 | trifluoroacetate | 8-methoxy-N-(2-methylpropyl)-7-[3-(pyrrolidin-1-yl)propoxy]-1H,2H,3H-cyclopenta[c]quinolin-4-amine trifluoroacetate | 398.2 |

TABLE 1-continued

| Cmpd. # | Structure | Name | MS Found |
|---|---|---|---|
| 104 | Trifluoroacetic acid | 8-methoxy-N-propyl-7-[3-(pyrrolidin-1-yl)propoxy]-1H,2H,3H-cyclopenta[c]quinolin-4-amine trifluoroacetate | 384.2 |
| 105 | Trifluoroacetic acid | N-cyclopropyl-8-methoxy-7-[3-(pyrrolidin-1-yl)propoxy]-1H,2H,3H-cyclopenta[c]quinolin-4-amine trifluoroacetate | 382.2 |
| 106 | Trifluoroacetic acid | N-ethyl-8-methoxy-7-[3-(pyrrolidin-1-yl)propoxy]-1H,2H,3H-cyclopenta[c]quinolin-4-amine trifluoroacetate | 370.2 |
| 107 | Trifluoroacetic acid | N-cyclohexyl-8-methoxy-7-[3-(pyrrolidin-1-yl)propoxy]-1H,2H,3H-cyclopenta[c]quinolin-4-amine trifluoroacetate | 424.4 |
| 108 | Trifluoroacetic acid | N-(cyclopropylmethyl)-8-methoxy-7-[3-(pyrrolidin-1-yl)propoxy]-1H,2H,3H-cyclopenta[c]quinolin-4-amine trifluoroacetate | 396.4 |
| 109 | Formate | 1-[3-({4-cyclopentyl-8-methoxy-1H,2H,3H-cyclopenta[c]quinolin-7-yl}oxy)propyl]pyrrolidine formate | 395.2 |

TABLE 1-continued

| Cmpd. # | Structure | Name | MS Found |
|---|---|---|---|
| 110 | 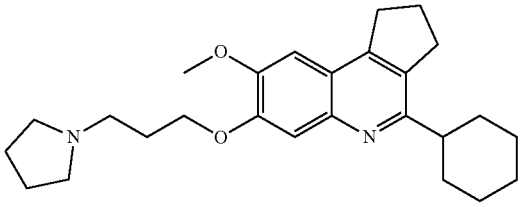 [SMILES: COc1cc2c3c(c(C4CCCCC4)nc2cc1OCCCN1CCCC1)CCC3]<br>trifluoroacetate | 1-[3-({4-cyclohexyl-8-methoxy-1H,2H,3H-cyclopenta[c]quinolin-7-yl}oxy)propyl]pyrrolidine trifluoroacetate | 409.3 |
| 111 | 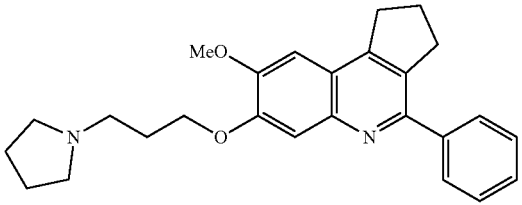 [SMILES: COc1cc2c3c(c(-c4ccccc4)nc2cc1OCCCN1CCCC1)CCC3]<br>Formate | 1-[3-({8-methoxy-4-phenyl-1H,2H,3H-cyclopenta[c]quinolin-7-yl}oxy)propyl]pyrrolidine formate | 403.1 |
| 112 | 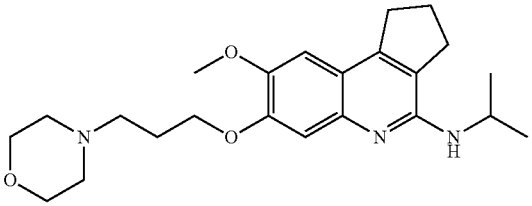 [SMILES: COc1cc2c3c(c(NC(C)C)nc2cc1OCCCN1CCOCC1)CCC3]<br>Trifluoroacetate | 8-methoxy-7-[3-(morpholin-4-yl)propoxy]-N-(propan-2-yl)-1H,2H,3H-cyclopenta[c]quinolin-4-amine trifluoroacetate | 400.2 |
| 113 | 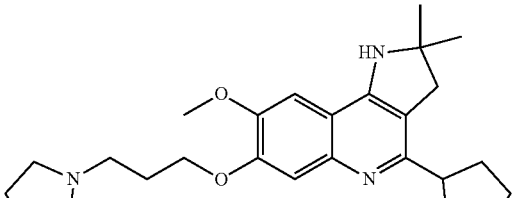<br>2 HCl | 1-[3-({4-cyclopentyl-8-methoxy-2,2-dimethyl-1H,2H,3H-pyrrolo[3,2-c]quinolin-7-yl}oxy)propyl]pyrrolidine hydrochloride | 424.1 |
| 114 | 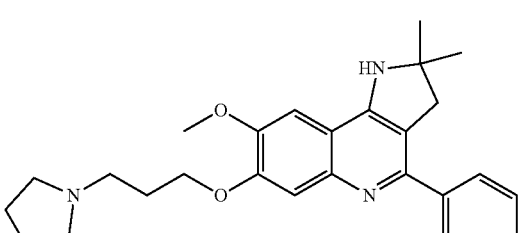<br>Formate | 1-[3-({8-methoxy-2,2-dimethyl-4-phenyl-1H,2H,3H-pyrrolo[3,2-c]quinolin-7-yl}oxy)propyl]pyrrolidine formate | 432.1 |

TABLE 1-continued

| Cmpd. # | Structure | Name | MS Found |
|---|---|---|---|
| 115 | Formate | N-[(2,4-dimethoxyphenyl)methyl]-8-methoxy-7-[3-(pyrrolidin-1-yl)propoxy]-1H,2H,3H-cyclopenta[c]quinolin-4-amine formate | 492.1 |
| 116 | Formate | 8-methoxy-7-[3-(pyrrolidin-1-yl)propoxy]-1H,2H,3H-cyclopenta[c]quinolin-4-amine formate | 342.1 |
| 117 | Formate | N-[(2,4-dimethoxyphenyl)methyl]-8-methoxy-2,2-dimethyl-7-[3-(pyrrolidin-1-yl)propoxy]-1H,2H,3H-cyclopenta[c]quinolin-4-amine formate | 520.1 |
| 118 | Formate | 8-methoxy-2,2-dimethyl-7-[3-(pyrrolidin-1-yl)propoxy]-1H,2H,3H-cyclopenta[c]quinolin-4-amine formate | 370.1 |
| 119 | Formate | 3-({8-methoxy-7-[3-(pyrrolidin-1-yl)propoxy]-1H,2H,3H-cyclopenta[c]quinolin-4-yl}amino)propanenitrile formate | 395.2 |
| 120 | Formate | 8-methoxy-N-[2-(methylsulfanyl)ethyl]-7-[3-(pyrrolidin-1-yl)propoxy]-1H,2H,3H-cyclopenta[c]quinolin-4-amine formate | 416.2 |

TABLE 1-continued

| Cmpd. # | Structure | Name | MS Found |
|---|---|---|---|
| 121 | | (1S,3R)-3-({8-methoxy-7-[3-(pyrrolidin-1-yl)propoxy]-1H,2H,3H-cyclopenta[c]quinolin-4-yl}amino)cyclohexan-1-ol formate and (1R,3S)-3-({8-methoxy-7-[3-(pyrrolidin-1-yl)propoxy]-1H,2H,3H-cyclopenta[c]quinolin-4-yl}amino)cyclohexan-1-ol (1:1 mixture) formate and | 440.2 |
| | (1:1 mixture as formate salt) and | | |
| | | (1S,3R)-3-({8-methoxy-7-[3-(pyrrolidin-1-yl)propoxy]-1H,2H,3H-cyclopenta[c]quinolin-4-yl}amino)cyclohexan-1-ol formate and (1R,3S)-3-({8-methoxy-7-[3-(pyrrolidin-1-yl)propoxy]-1H,2H,3H-cyclopenta[c]quinolin-4-yl}amino)cyclohexan-1-ol (1:1 mixture) formate | |
| | (1:1 mixture as formate salt) | | |
| 122 | Formate | (1S,2S)-2-({8-methoxy-7-[3-(pyrrolidin-1-yl)propoxy]-1H,2H,3H-cyclopenta[c]quinolin-4-yl}amino)cyclohexan-1-ol formate | 440.2 |
| 123 | Formate | (1R,4R)-4-({8-methoxy-7-[3-(pyrrolidin-1-yl)propoxy]-1H,2H,3H-cyclopenta[c]quinolin-4-yl}amino)cyclohexan-1-ol formate | 440.2 |

TABLE 1-continued

| Cmpd. # | Structure | Name | MS Found |
|---|---|---|---|
| 124 | Formate | (1S,2S)-2-({8-methoxy-7-[3-(pyrrolidin-1-yl)propoxy]-1H,2H,3H-cyclopenta[c]quinolin-4-yl}amino)cyclopentan-1-ol formate | 426.1 |
| 125 | 1:1 mixture in formate salt form | (1R,2S)-2-({8-methoxy-7-[3-(pyrrolidin-1-yl)propoxy]-1H,2H,3H-cyclopenta[c]quinolin-4-yl}amino)cyclopentan-1-ol formate | 426.1 |
| 126 | Formate | 3-({8-methoxy-7-[3-(pyrrolidin-1-yl)propoxy]-1H,2H,3H-cyclopenta[c]quinolin-4-yl}amino)cyclopentan-1-ol formate | 426.1 |

TABLE 2

| Cmpd # | Structure | Name |
|---|---|---|
| 127 | 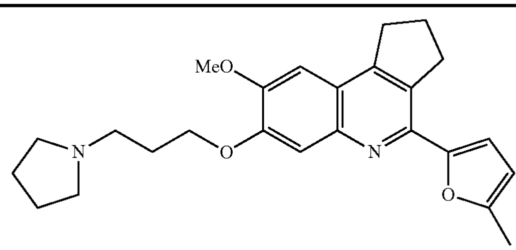 | 8-methoxy-4-(5-methylfuran-2-yl)-7-(3-(pyrrolidin-1-yl)propoxy)-2,3-dihydro-1H-cyclopenta[c]quinoline |
| 128 | 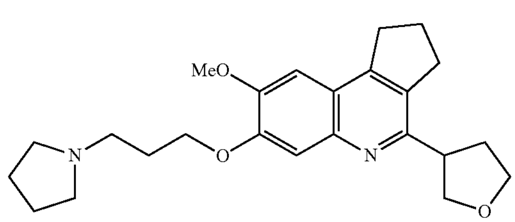 [SMILES: COc1cc2c3c(c(C4CCOC4)nc2cc1OCCCN1CCCC1)CCC3] | 8-methoxy-7-(3-(pyrrolidin-1-yl)propoxy)-4-(tetrahydrofuran-3-yl)-2,3-dihydro-1H-cyclopenta[c]quinoline |

TABLE 2-continued

| Cmpd # | Structure | Name |
|---|---|---|
| 129 | 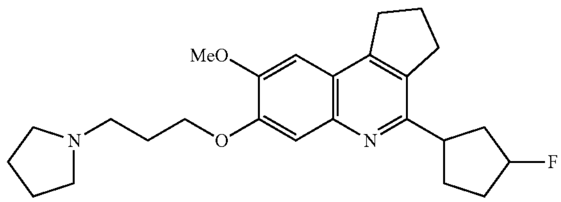 [SMILES: COc1cc2c3c(c(C4CCC(F)C4)nc2cc1OCCCN1CCCC1)CCC3] | 4-(3-fluorocyclopentyl)-8-methoxy-7-(3-(pyrrolidin-1-yl)propoxy)-2,3-dihydro-1H-cyclopenta[c]quinoline |
| 130 | 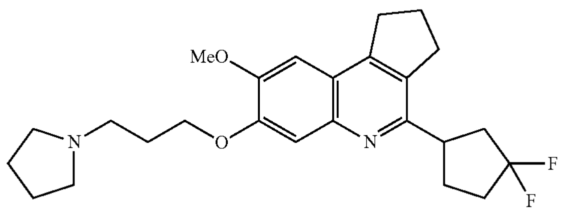 [SMILES: COc1cc2c3c(c(C4CCC(F)(F)C4)nc2cc1OCCCN1CCCC1)CCC3] | 4-(3,3-difluorocyclopentyl)-8-methoxy-7-(3-(pyrrolidin-1-yl)propoxy)-2,3-dihydro-1H-cyclopenta[c]quinoline |
| 131 | 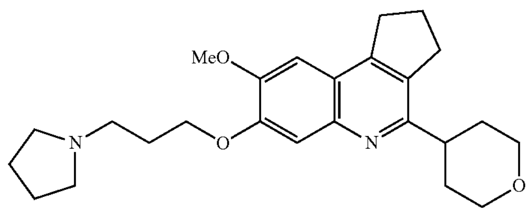 [SMILES: COc1cc2c3c(c(C4CCOCC4)nc2cc1OCCCN1CCCC1)CCC3] | 8-methoxy-7-(3-(pyrrolidin-1-yl)propoxy)-4-(tetrahydro-2H-pyran-4-yl)-2,3-dihydro-1H-cyclopenta[c]quinoline |
| 132 | 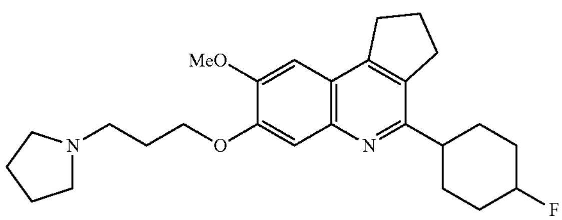 [SMILES: COc1cc2c3c(c(C4CCC(F)CC4)nc2cc1OCCCN1CCCC1)CCC3] | 4-(4-fluorocyclohexyl)-8-methoxy-7-(3-(pyrrolidin-1-yl)propoxy)-2,3-dihydro-1H-cyclopenta[c]quinoline |
| 133 | 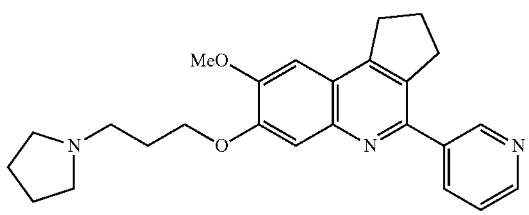 [SMILES: COc1cc2c3c(c(-c4cccnc4)nc2cc1OCCCN1CCCC1)CCC3] | 8-methoxy-4-(pyridin-3-yl)-7-(3-(pyrrolidin-1-yl)propoxy)-2,3-dihydro-1H-cyclopenta[c]quinoline |
| 134 | 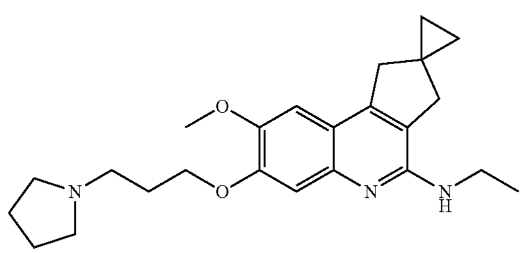 [SMILES: CCNc1nc2cc(OCCCN3CCCC3)c(OC)cc2c2c1CC1(CC1)C2] | N-ethyl-8-methoxy-7-(3-(pyrrolidin-1-yl)propoxy)-1,3-dihydrospiro[cyclopenta[c]quinoline-2,1'-cyclopropan]-4-amine |
| 135 | 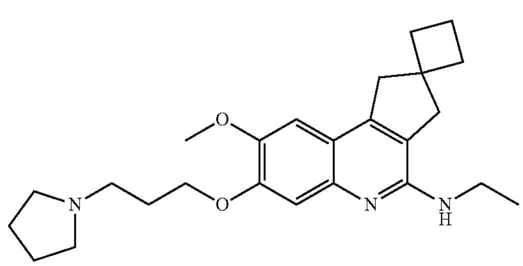 [SMILES: CCNc1nc2cc(OCCCN3CCCC3)c(OC)cc2c2c1CC1(CCC1)C2] | N-ethyl-8'-methoxy-7'-(3-(pyrrolidin-1-yl)propoxy)-1',3'-dihydrospiro[cyclobutane-1,2'-cyclopenta[c]quinolin]-4'-amine |

TABLE 2-continued

| Cmpd # | Structure | Name |
|---|---|---|
| 136 | 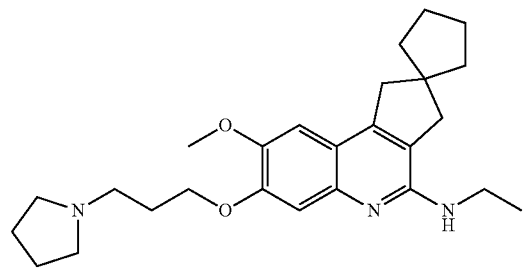 [SMILES: CCNc1nc2cc(OCCCN3CCCC3)c(OC)cc2c2c1CC1(CCCC1)C2] | N-ethyl-8'-methoxy-7'-(3-(pyrrolidin-1-yl)propoxy)-1',3'-dihydrospiro[cyclopentane-1,2'-cyclopenta[c]quinolin]-4'-amine |
| 137 | 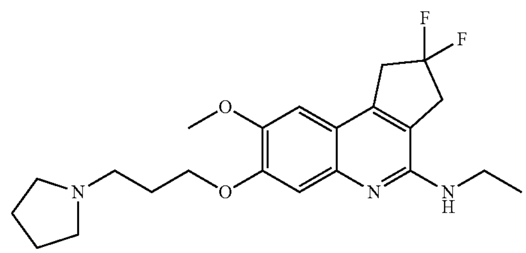 [SMILES: CCNc1nc2cc(OCCCN3CCCC3)c(OC)cc2c2c1CC(F)(F)C2] | N-ethyl-2,2-difluoro-8-methoxy-7-(3-(pyrrolidin-1-yl)propoxy)-2,3-dihydro-1H-cyclopenta[c]quinolin-4-amine |
| 138 | 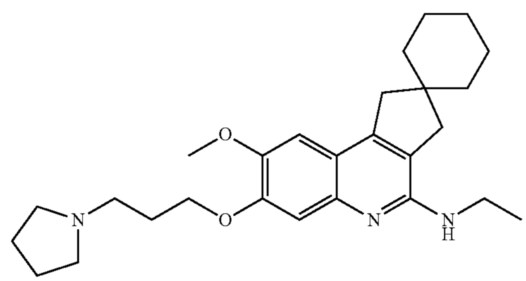 [SMILES: CCNc1nc2cc(OCCCN3CCCC3)c(OC)cc2c2c1CC1(CCCCC1)C2] | N-ethyl-8'-methoxy-7'-(3-(pyrrolidin-1-yl)propoxy)-1',3'-dihydrospiro[cyclohexane-1,2'-cyclopenta[c]quinolin]-4'-amine |
| 139 | 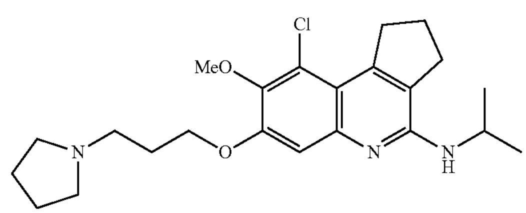 [SMILES: COc1c(OCCCN2CCCC2)cc2nc(NC(C)C)c3c(c2c1Cl)CCC3] | 9-chloro-8-methoxy-N-(propan-2-yl)-7-[3-(pyrrolidin-1-yl)propoxy]-1H,2H,3H-cyclopenta[c]quinolin-4-amine |
| 140 | 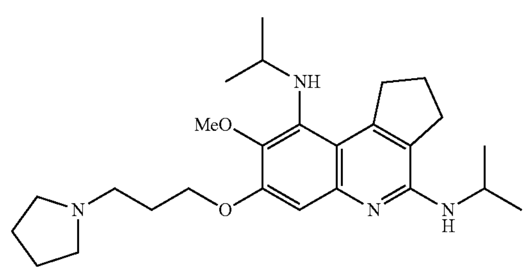 [SMILES: COc1c(OCCCN2CCCC2)cc2nc(NC(C)C)c3c(c2c1NC(C)C)CCC3] | 8-methoxy-N4,N9-bis(propan-2-yl)-7-[3-(pyrrolidin-1-yl)propoxy]-1H,2H,3H-cyclopenta[c]quinoline-4,9-diamine |
| 141 | 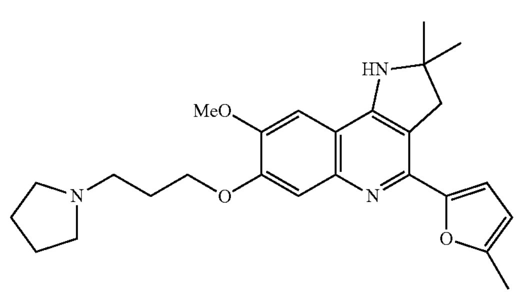 [SMILES: COc1cc2c3c(c(-c4ccc(C)o4)nc2cc1OCCCN1CCCC1)CC(C)(C)N3] | 8-methoxy-2,2-dimethyl-4-(5-methylfuran-2-yl)-7-(3-(pyrrolidin-1-yl)propoxy)-2,3-dihydro-1H-pyrrolo[3,2-c]quinoline |

TABLE 2-continued

| Cmpd # | Structure | Name |
|---|---|---|
| 142 | 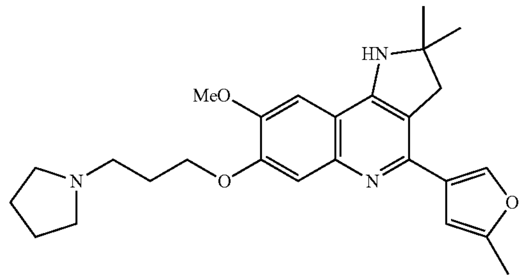 [SMILES: COc1cc2c3c(c(-c4coc(C)c4)nc2cc1OCCCN1CCCC1)CC(C)(C)N3] | 8-methoxy-2,2-dimethyl-4-(5-methylfuran-3-yl)-7-(3-(pyrrolidin-1-yl)propoxy)-2,3-dihydro-1H-pyrrolo[3,2-c]quinoline |
| 143 | 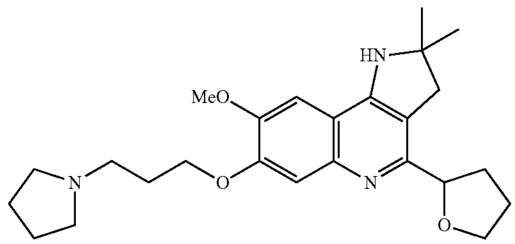 [SMILES: COc1cc2c3c(c(C4CCCO4)nc2cc1OCCCN1CCCC1)CC(C)(C)N3] | 8-methoxy-2,2-dimethyl-7-(3-(pyrrolidin-1-yl)propoxy)-4-(tetrahydrofuran-2-yl)-2,3-dihydro-1H-pyrrolo[3,2-c]quinoline |
| 144 | 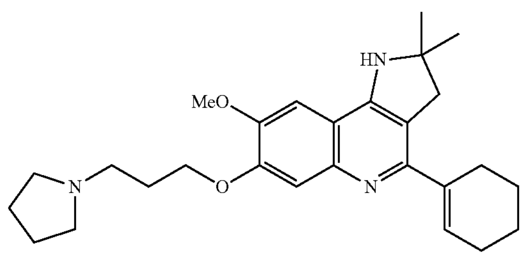 | 4-(cyclohex-1-en-1-yl)-8-methoxy-2,2-dimethyl-7-(3-(pyrrolidin-1-yl)propoxy)-2,3-dihydro-1H-pyrrolo[3,2-c]quinoline |
| 145 | 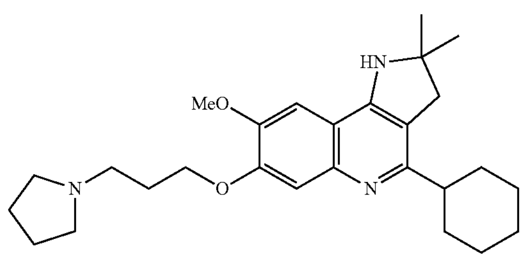 [SMILES: COc1cc2c3c(c(C4CCCCC4)nc2cc1OCCCN1CCCC1)CC(C)(C)N3] | 4-cyclohexyl-8-methoxy-2,2-dimethyl-7-(3-(pyrrolidin-1-yl)propoxy)-2,3-dihydro-1H-pyrrolo[3,2-c]quinoline |
| 146 | 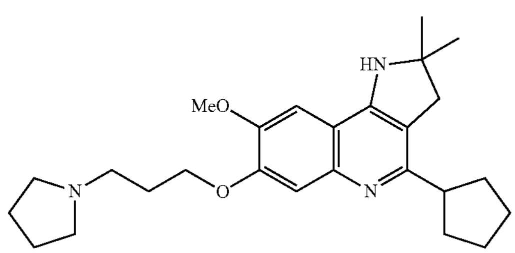 [SMILES: COc1cc2c3c(c(C4CCCC4)nc2cc1OCCCN1CCCC1)CC(C)(C)N3] | 4-cyclopentyl-8-methoxy-2,2-dimethyl-7-(3-(pyrrolidin-1-yl)propoxy)-2,3-dihydro-1H-pyrrolo[3,2-c]quinoline |
| 147 | 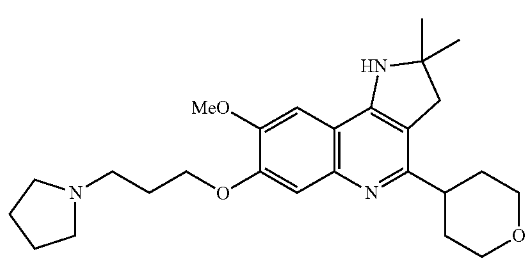 [SMILES: COc1cc2c3c(c(C4CCOCC4)nc2cc1OCCCN1CCCC1)CC(C)(C)N3] | 8-methoxy-2,2-dimethyl-7-(3-(pyrrolidin-1-yl)propoxy)-4-(tetrahydro-2H-pyran-4-yl)-2,3-dihydro-1H-pyrrolo[3,2-c]quinoline |

TABLE 2-continued

| Cmpd # | Structure | Name |
|---|---|---|
| 148 | 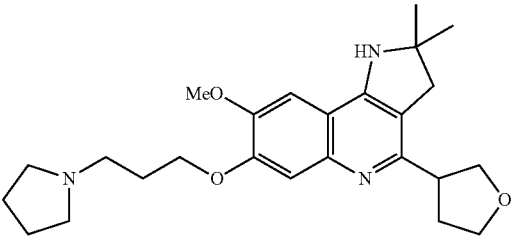 [SMILES: COc1cc2c3c(c(C4CCOC4)nc2cc1OCCCN1CCCC1)CC(C)(C)N3] | 8-methoxy-2,2-dimethyl-7-(3-(pyrrolidin-1-yl)propoxy)-4-(tetrahydrofuran-3-yl)-2,3-dihydro-1H-pyrrolo[3,2-c]quinoline |
| 149 | 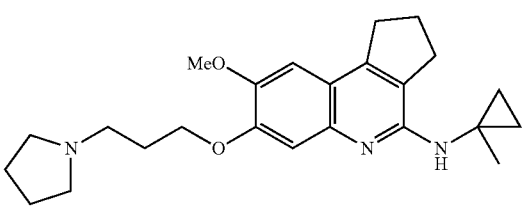 [SMILES: COc1cc2c3c(c(NC4(C)CC4)nc2cc1OCCCN1CCCC1)CCC3] | 8-methoxy-N-(1-methylcyclopropyl)-7-(3-(pyrrolidin-1-yl)propoxy)-2,3-dihydro-1H-cyclopenta[c]quinolin-4-amine |
| 150 | 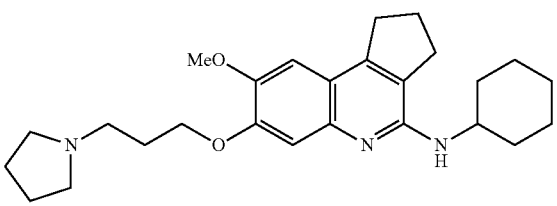 [SMILES: COc1cc2c3c(c(NC4CCCCC4)nc2cc1OCCCN1CCCC1)CCC3] | N-cyclohexyl-8-methoxy-7-(3-(pyrrolidin-1-yl)propoxy)-2,3-dihydro-1H-cyclopenta[c]quinolin-4-amine |
| 151 | 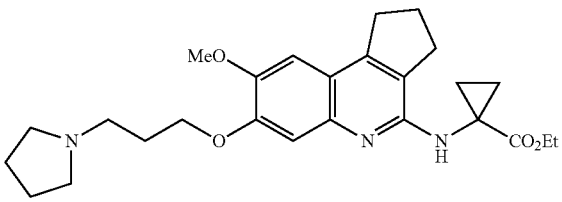 [SMILES: CCOC(=O)C1(Nc2nc3cc(OCCCN4CCCC4)c(OC)cc3c3c2CCC3)CC1] | ethyl 1-({8-methoxy-7-[3-(pyrrolidin-1-yl)propoxy]-1H,2H,3H-cyclopenta[c]quinolin-4-yl}amino)cyclopropane-1-carboxylate |
| 152 | 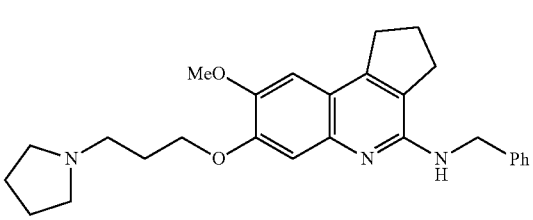 [SMILES: COc1cc2c3c(c(NCc4ccccc4)nc2cc1OCCCN1CCCC1)CCC3] | N-benzyl-8-methoxy-7-(3-(pyrrolidin-1-yl)propoxy)-2,3-dihydro-1H-cyclopenta[c]quinolin-4-amine |
| 153 | 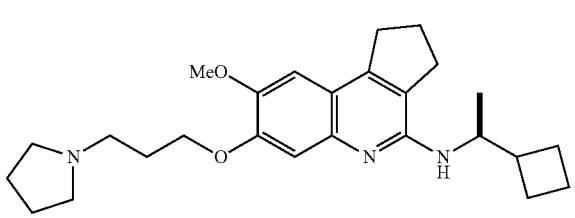 [SMILES: COc1cc2c3c(c(N[C@@H](C)C4CCC4)nc2cc1OCCCN1CCCC1)CCC3] | (S)-N-(1-cyclobutylethyl)-8-methoxy-7-(3-(pyrrolidin-1-yl)propoxy)-2,3-dihydro-1H-cyclopenta[c]quinolin-4-amine |
| 154 | 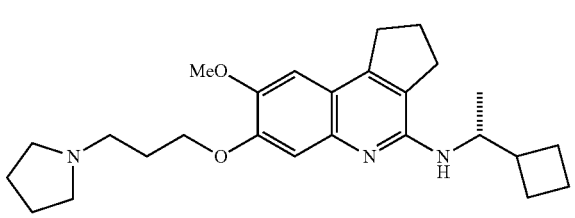 [SMILES: COc1cc2c3c(c(N[C@H](C)C4CCC4)nc2cc1OCCCN1CCCC1)CCC3] | (R)-N-(1-cyclobutylethyl)-8-methoxy-7-(3-(pyrrolidin-1-yl)propoxy)-2,3-dihydro-1H-cyclopenta[c]quinolin-4-amine |

TABLE 2-continued

| Cmpd # | Structure | Name |
|---|---|---|
| 155 | 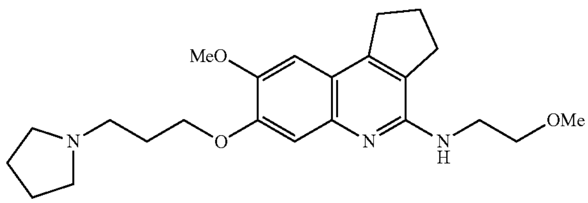 [SMILES: COCCNc1nc2cc(OCCCN3CCCC3)c(OC)cc2c2c1CCC2] | 8-methoxy-N-(2-methoxyethyl)-7-(3-(pyrrolidin-1-yl)propoxy)-2,3-dihydro-1H-cyclopenta[c]quinolin-4-amine |
| 156 | 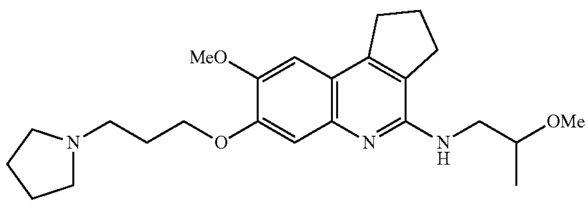 [SMILES: COc1cc2c3c(c(NCC(C)OC)nc2cc1OCCCN1CCCC1)CCC3] | 8-methoxy-N-(2-methoxypropyl)-7-(3-(pyrrolidin-1-yl)propoxy)-2,3-dihydro-1H-cyclopenta[c]quinolin-4-amine |
| 157 | 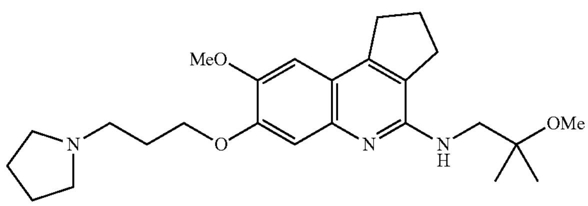 [SMILES: COc1cc2c3c(c(NCC(C)(C)OC)nc2cc1OCCCN1CCCC1)CCC3] | 8-methoxy-N-(2-methoxy-2-methylpropyl)-7-(3-(pyrrolidin-1-yl)propoxy)-2,3-dihydro-1H-cyclopenta[c]quinolin-4-amine |
| 158 | 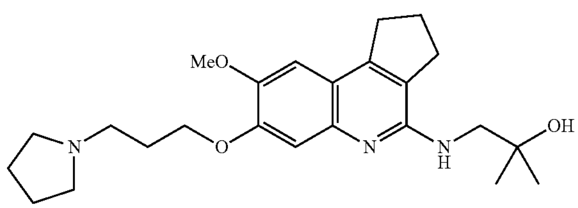 [SMILES: COc1cc2c3c(c(NCC(C)(C)O)nc2cc1OCCCN1CCCC1)CCC3] | 1-((8-methoxy-7-(3-(pyrrolidin-1-yl)propoxy)-2,3-dihydro-1H-cyclopenta[c]quinolin-4-yl)amino)-2-methylpropan-2-ol |
| 159 | 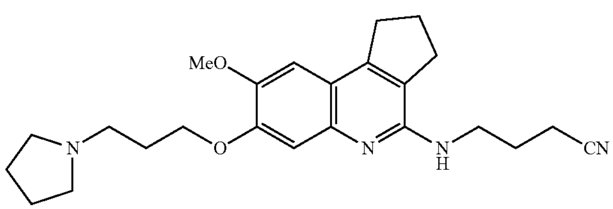 [SMILES: COc1cc2c3c(c(NCCCC#N)nc2cc1OCCCN1CCCC1)CCC3] | 4-((8-methoxy-7-(3-(pyrrolidin-1-yl)propoxy)-2,3-dihydro-1H-cyclopenta[c]quinolin-4-yl)amino)butanenitrile |
| 160 | 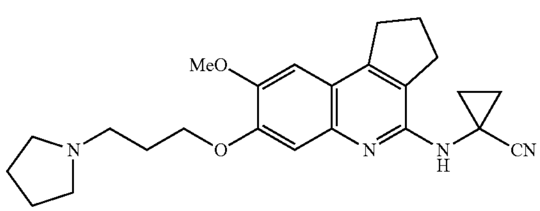 [SMILES: COc1cc2c3c(c(NC4(C#N)CC4)nc2cc1OCCCN1CCCC1)CCC3] | 1-((8-methoxy-7-(3-(pyrrolidin-1-yl)propoxy)-2,3-dihydro-1H-cyclopenta[c]quinolin-4-yl)amino)cyclopropane-1-carbonitrile |
| 161 | 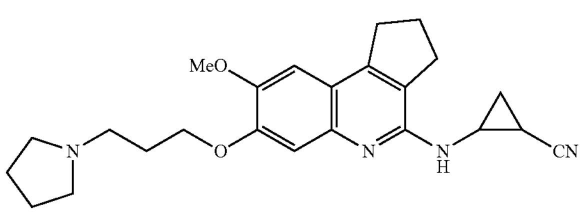 [SMILES: COc1cc2c3c(c(NC4CC4C#N)nc2cc1OCCCN1CCCC1)CCC3] | 2-((8-methoxy-7-(3-(pyrrolidin-1-yl)propoxy)-2,3-dihydro-1H-cyclopenta[c]quinolin-4-yl)amino)cyclopropane-1-carbonitrile |

TABLE 2-continued

| Cmpd # | Structure | Name |
| --- | --- | --- |
| 162 | 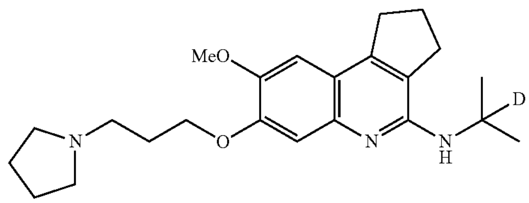 [SMILES: [2H]C(C)(C)Nc1nc2cc(OCCCN3CCCC3)c(OC)cc2c2c1CCC2] | 8-methoxy-N-(propan-2-yl-2-d)-7-(3-(pyrrolidin-1-yl)propoxy)-2,3-dihydto-1H-cyclopenta[c]quinolin-4-amilie |
| 163 | 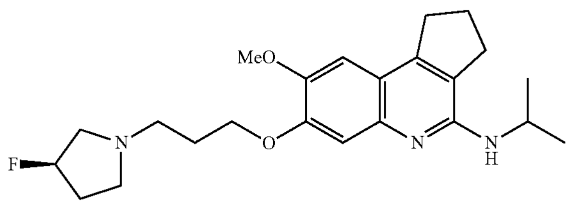 [SMILES: COc1cc2c3c(c(NC(C)C)nc2cc1OCCCN1CC[C@@H](F)C1)CCC3] | (R)-7-(3-(3-fluoropyrrolidin-1-yl)propoxy)-N-isopropyl-8-methoxy-2,3-dihydro-1H-cyclopenta[c]quinolin-4-amine |
| 164 | 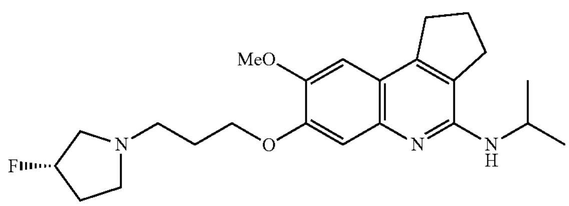 [SMILES: COc1cc2c3c(c(NC(C)C)nc2cc1OCCCN1CC[C@H](F)C1)CCC3] | (S)-7-(3-(3-fluoropyrrolidin-1-yl)propoxy)-N-isopropyl-8-methoxy-2,3-dihydro-1H-cyclopenta[c]quinolin-4-amine |
| 165 | 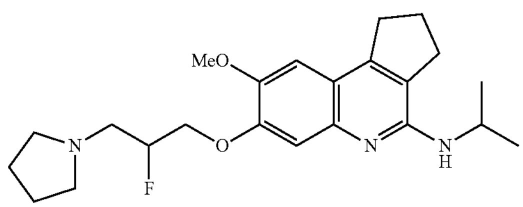 [SMILES: COc1cc2c3c(c(NC(C)C)nc2cc1OCC(F)CN1CCCC1)CCC3] | 7-(2-fluoro-3-(pyrrolidin-1-yl)propoxy)-N-isopropyl-8-methoxy-2,3-dihydro-1H-cyclopenta[c]quinolin-4-amine |
| 166 | 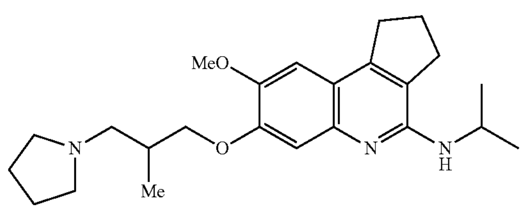 [SMILES: COc1cc2c3c(c(NC(C)C)nc2cc1OCC(C)CN1CCCC1)CCC3] | N-isopropyl-8-methoxy-7-(2-methyl-3-(pyrrolidin-1-yl)propoxy)-2,3-dihydro-1H-cyclopenta[c]quinolin-4-amine |
| 167 | 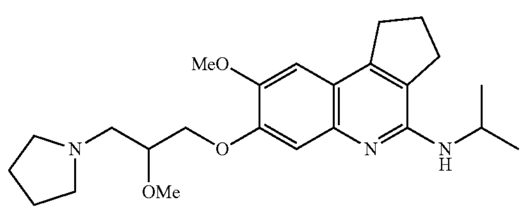 [SMILES: COc1cc2c3c(c(NC(C)C)nc2cc1OCC(CN1CCCC1)OC)CCC3] | N-isopropyl-8-methoxy-7-(2-methoxy-3-(pyrrolidin-1-yl)propoxy)-2,3-dihydro-1H-cyclopenta[c]quinolin-4-amine |
| 168 | 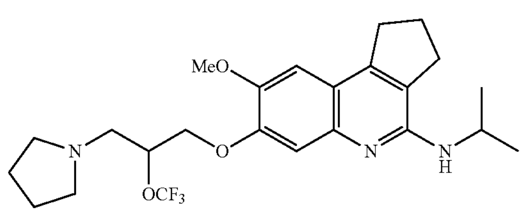 [SMILES: COc1cc2c3c(c(NC(C)C)nc2cc1OCC(CN1CCCC1)OC(F)(F)F)CCC3] | N-isopropyl-8-methoxy-7-(3-(pyrrolidin-1-yl)-2-(trifluoromethoxy)propoxy)-2,3-dihydro-1H-cyclopenta[c]quinolin-4-amine |

TABLE 2-continued

| Cmpd # | Structure | Name |
|---|---|---|
| 169 | 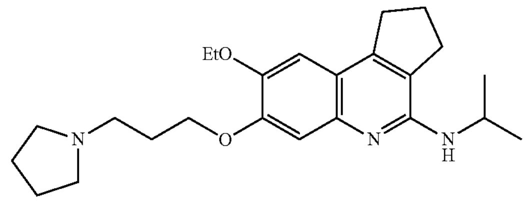 [SMILES: CCOc1cc2c3c(c(NC(C)C)nc2cc1OCCCN1CCCC1)CCC3] | 8-ethoxy-N-isopropyl-7-(3-(pyrrolidin-1-yl)propoxy)-2,3-dihydro-1H-cyclopenta[c]quinolin-4-amine |
| 170 | 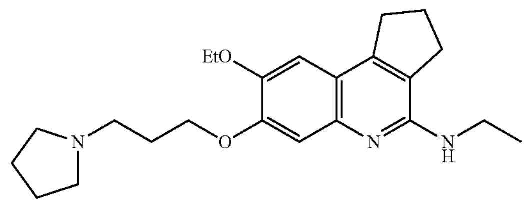 [SMILES: CCNc1nc2cc(OCCCN3CCCC3)c(OCC)cc2c2c1CCC2] | 8-ethoxy-N-ethyl-7-(3-(pyrrolidin-1-yl)propoxy)-2,3-dihydro-1H-cyclopenta[c]quinolin-4-amine |
| 171 | 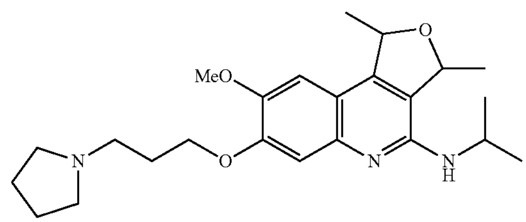 [SMILES: COc1cc2c3c(c(NC(C)C)nc2cc1OCCCN1CCCC1)C(C)OC3C] | N-isopropyl-8-methoxy-1,3-dimethyl-7-(3-(pyrrolidin-1-yl)propoxy)-1,3-dihydrofuro[3,4-c]quinolin-4-amine |
| 172 | 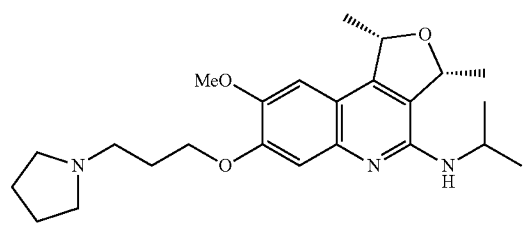 [SMILES: COc1cc2c3c(c(NC(C)C)nc2cc1OCCCN1CCCC1)[C@@H](C)O[C@H]3C] | (1S,3R)-N-isopropyl-8-methoxy-1,3-dimethyl-7-(3-(pyrrolidin-1-yl)propoxy)-1,3-dihydrofuro[3,4-c]quinolin-4-amine |
| 173 | 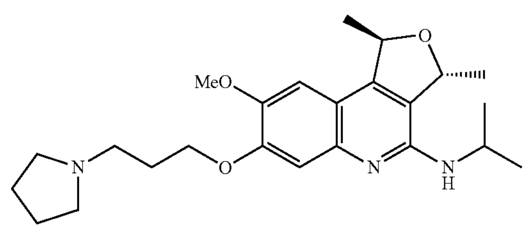 [SMILES: COc1cc2c3c(c(NC(C)C)nc2cc1OCCCN1CCCC1)[C@@H](C)O[C@@H]3C] | (1R,3R)-N-isopropyl-8-methoxy-1,3-dimethyl-7-(3-(pyrrolidin-1-yl)propoxy)-1,3-dihydrofuro[3,4-c]quinolin-4-amine |
| 174 | 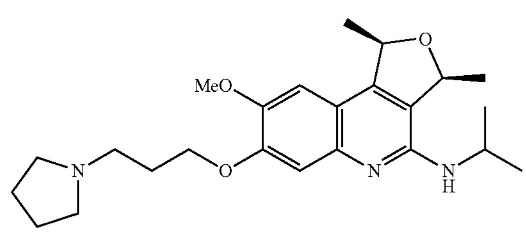 [SMILES: COc1cc2c3c(c(NC(C)C)nc2cc1OCCCN1CCCC1)[C@H](C)O[C@@H]3C] | (1R,3S)-N-isopropyl-8-methoxy-1,3-dimethyl-7-(3-(pyrrolidin-1-yl)propoxy)-1,3-dihydrofuro[3,4-c]quinolin-4-amine |
| 175 | 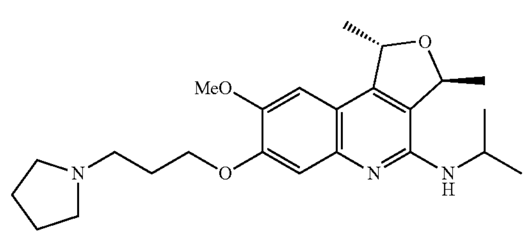 [SMILES: COc1cc2c3c(c(NC(C)C)nc2cc1OCCCN1CCCC1)[C@H](C)O[C@H]3C] | (1S,3S)-N-isopropyl-8-methoxy-1,3-dimethyl-7-(3-(pyrrolidin-1-yl)propoxy)-1,3-dihydrofuro[3,4-c]quinolin-4-amine |

TABLE 2-continued

| Cmpd # | Structure | Name |
|---|---|---|
| 176 | 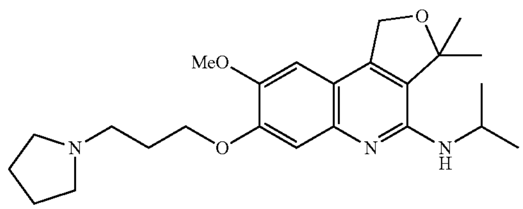 [SMILES: COc1cc2c3c(c(NC(C)C)nc2cc1OCCCN1CCCC1)C(C)(C)OC3] | N-isopropyl-8-methoxy-3,3-dimethyl-7-(3-(pyrrolidin-1-yl)propoxy)-1,3-dihydrofuro[3,4-c]quinolin-4-amine |
| 177 | 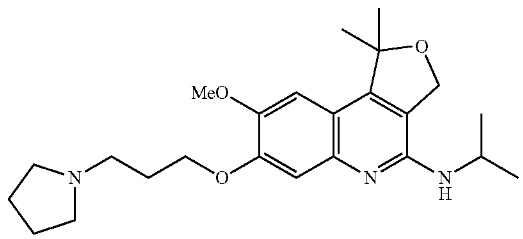 [SMILES: COc1cc2c3c(c(NC(C)C)nc2cc1OCCCN1CCCC1)COC3(C)C] | N-isopropyl-8-methoxy-1,1-dimethyl-7-(3-(pyrrolidin-1-yl)propoxy)-1,3-dihydrofuro[3,4-c]quinolin-4-amine |
| 178 | 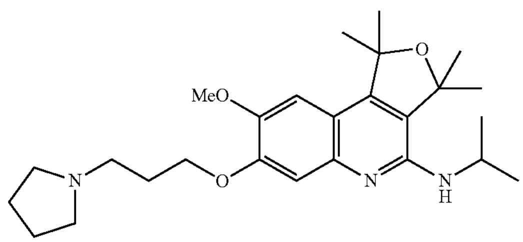 [SMILES: COc1cc2c3c(c(NC(C)C)nc2cc1OCCCN1CCCC1)C(C)(C)OC3(C)C] | N-isopropyl-8-methoxy-1,1,3,3-tetramethyl-7-(3-(pyrrolidin-1-yl)propoxy)-1,3-dihydrofuro[3,4-c]quinolin-4-amine |
| 179 | 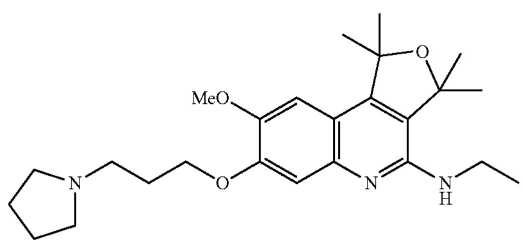 [SMILES: CCNc1nc2cc(OCCCN3CCCC3)c(OC)cc2c2c1C(C)(C)OC2(C)C] | N-ethyl-8-methoxy-1,1,3,3-tetramethyl-7-(3-(pyrrolidin-1-yl)propoxy)-1,3-dihydrofuro[3,4-c]quinolin-4-amine |
| 180 | 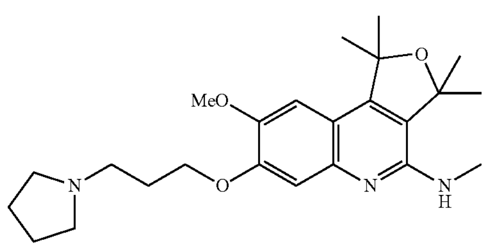 [SMILES: CNc1nc2cc(OCCCN3CCCC3)c(OC)cc2c2c1C(C)(C)OC2(C)C] | 8-methoxy-N,1,1,3,3-pentamethyl-7-(3-(pyrrolidin-1-yl)propoxy)-1,3-dihydrofuro[3,4-c]quinolin-4-amine |
| 181 | 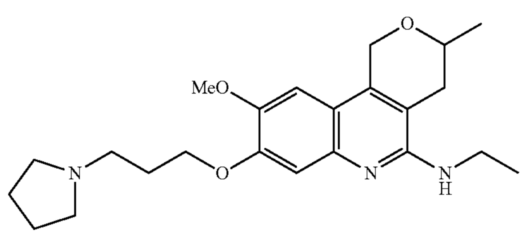 [SMILES: CCNc1nc2cc(OCCCN3CCCC3)c(OC)cc2c2c1CC(C)OC2] | N-ethyl-9-methoxy-3-methyl-8-(3-(pyrrolidin-1-yl)propoxy)-3,4-dihydro-1H-pyrano[4,3-c]quinolin-5-amine |

TABLE 2-continued

| Cmpd # | Structure | Name |
| --- | --- | --- |
| 182 | 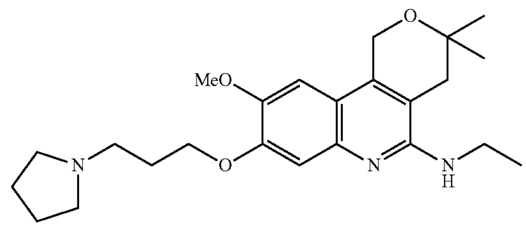 [SMILES: CCNc1nc2cc(OCCCN3CCCC3)c(OC)cc2c2c1CC(C)(C)OC2] | N-ethyl-9-methoxy-3,3-dimethyl-8-(3-(pyrrolidin-1-yl)propoxy)-3,4-dihydro-1H-pyrano[4,3-c]quinolin-5-amine |
| 183 | 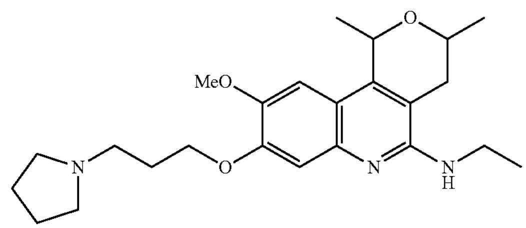 [SMILES: CCNc1nc2cc(OCCCN3CCCC3)c(OC)cc2c2c1CC(C)OC2C] | N-ethyl-9-methoxy-1,3-dimethyl-8-(3-(pyrrolidin-1-yl)propoxy)-3,4-dihydro-1H-pyrano[4,3-c]quinolin-5-amine |
| 184 | 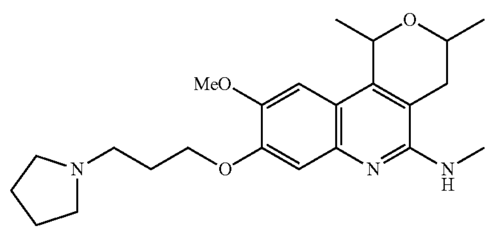 [SMILES: CNc1nc2cc(OCCCN3CCCC3)c(OC)cc2c2c1CC(C)OC2C] | 9-methoxy-N,1,3-trimethyl-8-(3-(pyrrolidin-1-yl)propoxy)-3,4-dihydro-1H-pyrano[4,3-c]quinolin-5-amine |
| 185 | 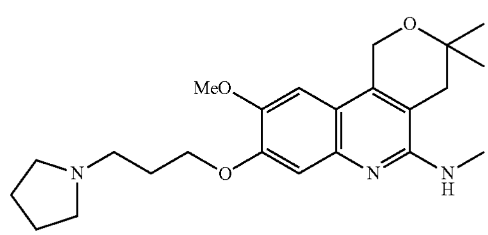 [SMILES: CNc1nc2cc(OCCCN3CCCC3)c(OC)cc2c2c1CC(C)(C)OC2] | 9-methoxy-N,3,3-trimethyl-8-(3-(pyrrolidin-1-yl)propoxy)-3,4-dihydro-1H-pyrano[4,3-c]quinolin-5-amine |
| 186 | 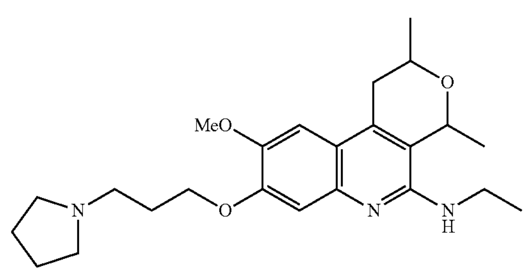 [SMILES: CCNc1nc2cc(OCCCN3CCCC3)c(OC)cc2c2c1C(C)OC(C)C2] | N-ethyl-9-methoxy-2,4-dimethyl-8-(3-(pyrrolidin-1-yl)propoxy)-1,4-dihydro-2H-pyrano[3,4-c]quinolin-5-amine |
| 187 | 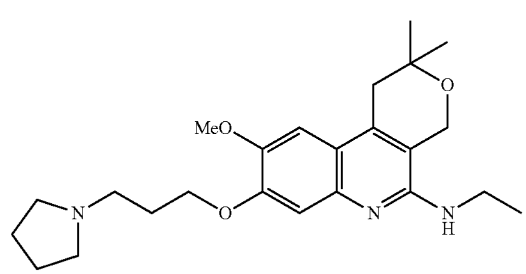 [SMILES: CCNc1nc2cc(OCCCN3CCCC3)c(OC)cc2c2c1COC(C)(C)C2] | N-ethyl-9-methoxy-2,2-dimethyl-8-(3-(pyrrolidin-1-yl)propoxy)-1,4-dihydro-2H-pyrano[3,4-c]quinolin-5-amine |

TABLE 2-continued

| Cmpd # | Structure | Name |
| --- | --- | --- |
| 188 | 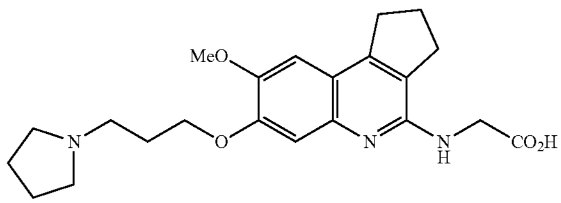 [SMILES: COc1cc2c3c(c(NCC(=O)O)nc2cc1OCCCN1CCCC1)CCC3] | 2-({8-methoxy-7-[3-(pyrrolidin-1-yl)propoxy]-1H,2H,3H-cyclopenta[c]quinolin-4-yl}amino)acetic acid |
| 189 | 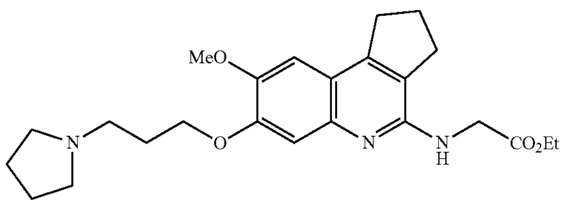 [SMILES: CCOC(=O)CNc1nc2cc(OCCCN3CCCC3)c(OC)cc2c2c1CCC2] | ethyl 2-({8-methoxy-7-[3-(pyrrolidin-1-yl)propoxy]-1H,2H,3H-cyclopenta[c]quinolin-4-yl}amino)acetate |
| 190 | 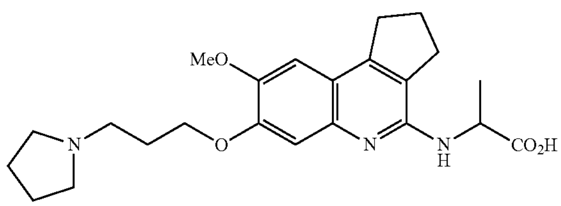 [SMILES: COc1cc2c3c(c(NC(C)C(=O)O)nc2cc1OCCCN1CCCC1)CCC3] | 2-({8-methoxy-7-[3-(pyrrolidin-1-yl)propoxy]-1H,2H,3H-cyclopenta[c]quinolin-4-yl}amino)propanoic acid |
| 191 | 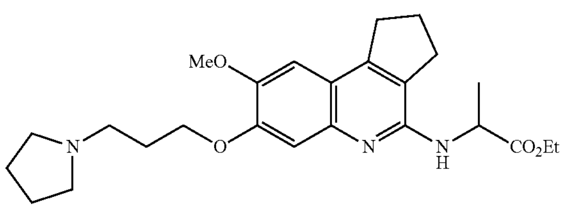 [SMILES: CCOC(=O)C(C)Nc1nc2cc(OCCCN3CCCC3)c(OC)cc2c2c1CCC2] | ethyl 2-({8-methoxy-7-[3-(pyrrolidin-1-yl)propoxy]-1H,2H,3H-cyclopenta[c]quinolin-4-yl}amino)propanoate |
| 192 | 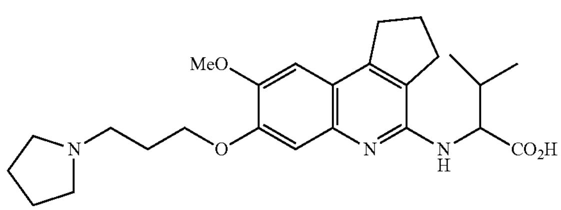 [SMILES: COc1cc2c3c(c(NC(C(=O)O)C(C)C)nc2cc1OCCCN1CCCC1)CCC3] | 2-({8-methoxy-7-[3-(pyrrolidin-1-yl)propoxy]-1H,2H,3H-cyclopenta[c]quinolin-4-yl}amino)-3-methylbutanoic acid |
| 193 | 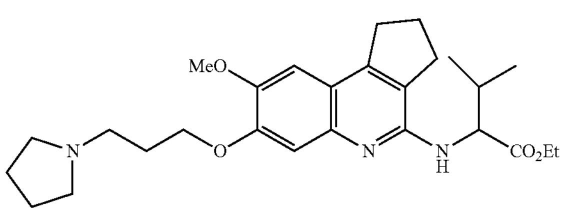 [SMILES: CCOC(=O)C(Nc1nc2cc(OCCCN3CCCC3)c(OC)cc2c2c1CCC2)C(C)C] | ethyl 2-({8-methoxy-7-[3-(pyrrolidin-1-yl)propoxy]-1H,2H,3H-cyclopenta[c]quinolin-4-yl}amino)-3-methylbutanoate |
| 194 | 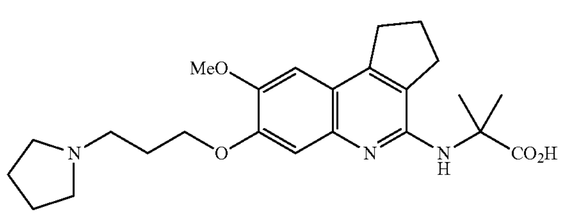 [SMILES: COc1cc2c3c(c(NC(C)(C)C(=O)O)nc2cc1OCCCN1CCCC1)CCC3] | 2-({8-methoxy-7-[3-(pyrrolidin-1-yl)propoxy]-1H,2H,3H-cyclopenta[c]quinolin-4-yl}amino)-2-methylpropanoic acid |

TABLE 2-continued

| Cmpd # | Structure | Name |
|---|---|---|
| 195 | 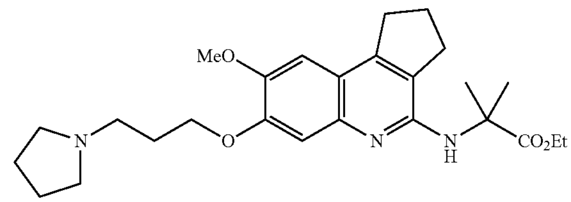 [SMILES: CCOC(=O)C(C)(C)Nc1nc2cc(OCCCN3CCCC3)c(OC)cc2c2c1CCC2] | ethyl 2-({8-methoxy-7-[3-(pyrrolidin-1-yl)propoxy]-1H,2H,3H-cyclopenta[c]quinolin-4-yl}amino)-2-methylpropanoate |

General Synthetic Scheme

Compounds of this disclosure can be made by the methods depicted in the reaction schemes shown below.

The starting materials and reagents used in preparing these compounds are either available from commercial suppliers such as Sigma-Aldrich Chemical Co., (Milwaukee, Wis.), Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials, the intermediates, and the final products of the reaction(s) may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) where ring B is cycloalkyl or 5-, 6-, or 7-membered saturated heterocyclyl, $Z^1$ and $Z^2$ are independently selected from CH or C (wherein a substituent is attached), X is C, and $R^1$, $R^2$, $R^3$, and $R^4$ are as defined in the Summary, can be prepared by the following procedure described in Scheme 1 below.

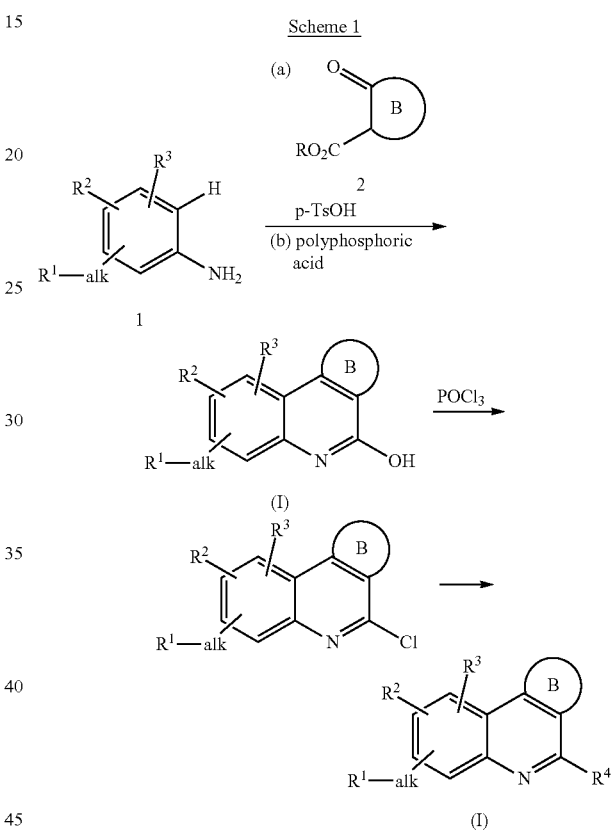

Scheme 1

Reaction of a compound of formula 1 where -alk-$R^1$, $R^2$ and $R^3$ are as defined in the Summary, or a precursor group thereof with 2-oxocycloalkylcarboxylate or 2-oxo heterocyclylcarboxylate of formula 2 wherein R is alkyl and ring B is unsubstituted or substituted with $R^j$, $R^k$, $R^l$, and/or $R^m$ as defined in the Summary, in the presence of catalytic amount of an acid, such as p-toluenesulfonic acid, followed by treating the resulting intermediate with poly phosphoric acid at 90° C. to refluxing temperature provides an annular tricyclic compound of Formula (I) where $R^4$ is hydroxy. Compounds of formula 1 can be prepared from commercially available materials such as 2-methoxy-5-nitrophenol by methods well known in the art (see references in the synthetic examples below). Compounds of formula 2 such as methyl 2-oxocyclopentane-1-carboxylate, methyl 2-oxocyclohexane-1-carboxylate, methyl 4-oxotetrahydrofuran-3-carboxylate, and methyl 1-methyl-4-oxopiperidine-3-carboxylate are commercially available. Other compounds of formula 2 are readily available through synthetic procedures well known to those in the art (e.g., methyl 4,4-dimethyl-2-oxocyclopentane-1-carboxylate and the close analogs, see Gellman et al, Organic Letters, 2004, Vol 6, No. 24, page 4411-4414). Compound of Formula (I) where $R^4$ is hydroxy can be converted to other compounds of Formula (I) by first converting it into a corresponding compound where $R^4$ is halo, e.g., chloro, followed by other transformations. The reaction conditions used for these transformations depend on the nature of the $R^4$ groups. For example, compounds of Formula (I) where $R^4$ is $NR^eR^f$ (where $R^e$ and $R^f$ are as defined in the Summary) can be prepared by reacting the corresponding compound where $R^4$ is halo, such as chloro, with an amine of formula $NHR^eR^f$ under Buchwald coupling reaction condition. Compounds of Formula (I) where $R^4$ is alkyl, cycloalkyl, -cycloalkenyl, heterocyclyl, phenyl, or heteroaryl, can be prepared by reacting corresponding compound where $R^4$ is chloro with either a boronic reagents under Suzuki coupling reaction conditions, Zn reagent under Negishi coupling, or tin derivatives under Stille coupling reaction conditions. It will be recognized by a person skilled in the art that, $R^1$, $R^2$, and $R^3$ groups can be modified, as necessary, during the above synthetic route.

Alternatively, compounds of Formula (I) where $Z^1$ and $Z^2$ are independently selected from CH or C (wherein a substituent is attached), X is C, and ring B, $R^1$, $R^2$, $R^3$, and $R^4$ are as defined in the Summary, can be prepared by the following procedure described in Scheme 2 below.

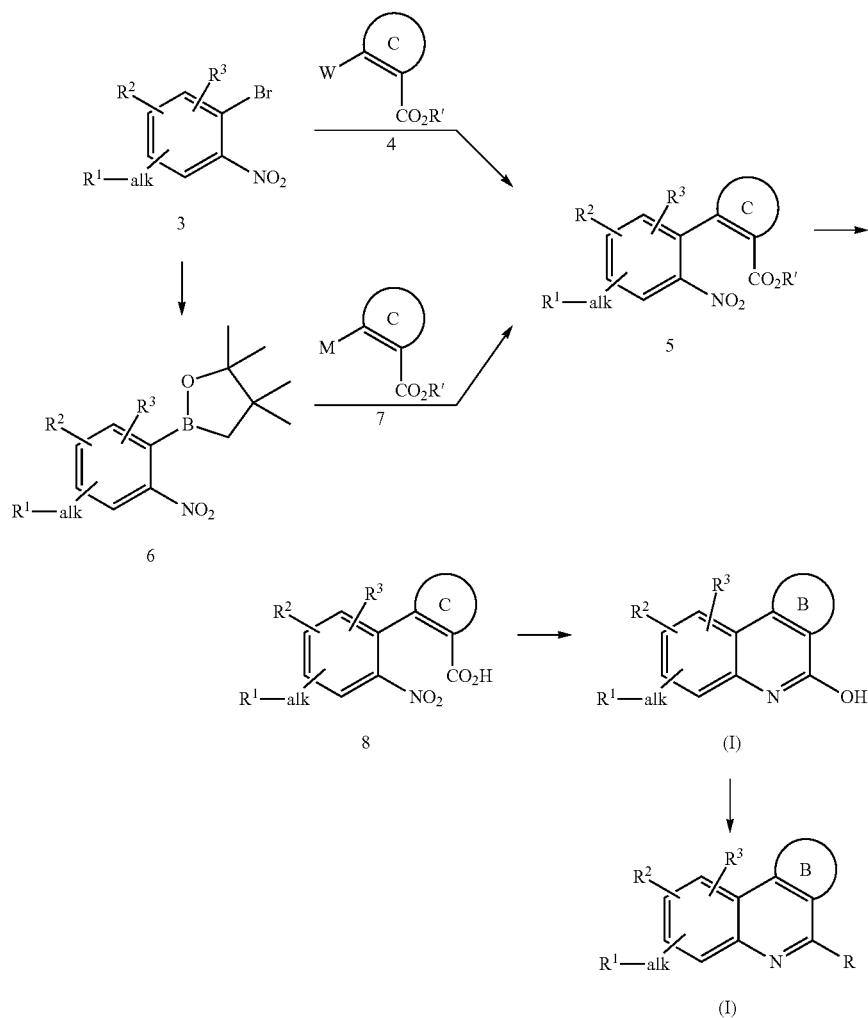

Compounds of Formula (I) can also be prepared following the synthetic routes depicted in Scheme 2. Coupling reaction of compound of formula 3 where -alk-$R^1$, $R^2$ and $R^3$ are as defined in the Summary or a precursor group thereof, with a compound of formula 4 (wherein ring C is phenyl, 5- or 6-membered heteroaryl, 5- or 6-membered cycloalkenyl, or 5-, 6-, or 7-membered heterocycloalkenyl each aforementioned ring substituted with $R^j$, $R^k$, $R^l$, and/or $R^m$ as defined in the Summary, W is —$B(OH)_2$, 4,4,5,5-tetramethyl-1,3,2-dioxaborolanyl-, tributylstannyl or other appropriate functional groups and R' is H or alkyl) in the presence of appropriate catalysts such as tetrakis(triphenylphosphine)palladium(0) or [1,1'-bis(diphenylphosphino)ferrocene]-dichloropalladium(II) gives an intermediate compound of formula 5. Compound of formula 3 such as 1-[3-(4-bromo-2-methoxy-5-nitrophenoxy)propyl]pyrrolidine can be made from commercially available material, such as 4-bromo-2-methoxyphenol, through methods well known to those skilled in the art (see synthetic examples below for reference). Compounds of formula 4 can be purchased from commercial resources. Alternatively, compound 4 where W is 4,4,5,5-tetramethyl-1,3,2-dioxaborolanyl or 1,1,1-tributylstannane can be made from compound of formula 7 (where M is halo and R' is as defined above) by reacting compound 7 with appropriate reagents such as 4,4,4',4',5,5,5',5'-octamethyl-2,2'-bi(1,3,2-dioxaborolane) or 1,1,1,2,2,2-hexabutyldistannane in the presence of a suitable catalyst such as tetrakis(triphenylphosphine) palladium (0) or [1,1'-bis(diphenylphosphino)ferrocene]-dichloropalladium(II), respectively. Compound 4 where W is 4,4,5,5-tetramethyl-1,3,2-dioxaborolanyl can be subjected to hydrolysis to give corresponding compound of formula 4 where W is —B(OH)$_2$. Compounds of formula 7 where M is Br or Cl, such as ethyl 4-chlorothiazole-5-carboxylate, methyl 2-bromobenzoate, methyl 4-chloro-1H-imidazole-5-carboxylate, methyl 2-chloronicotinate, methyl 3-chloropyrazine-2-carboxylate, methyl 4-chloropyrimidine-5-carboxylate, ethyl 5-chloro-1H-pyrazole-4-carboxylate, 3-bromothiophene-2-carboxylic acid, or 2-bromo-3-thiophenecarboxylic acid are commercially available. Compound 7 where M is —OTf can be made from the corresponding commercially available starting material of 2-oxocycloalkylcarboxylate or 2-oxo heterocyclocarboxylate, such as 1-tert-butyl 3-methyl 4-oxopiperidine-1,3-dicarboxylate, by methods well known to those skilled in the art (see Organic Letters, 2012, 14(12): 2940-2943; and Organic letters, 2003, 5(1):59-61).

Alternatively, compound of formula 5 can be prepared by reacting an organoborane compound of formula 6 with a compound of formula 7 under coupling conditions described above. Compound of Formula (I) is made from compound 5 by reduction of the nitro group under suitable reduction conditions such as treatment with Zn, Fe, tin(II) chloride, or under hydrogenation conditions, such as Pd/C under hydrogen atmosphere, followed by hydrolysis of the ester group (where R'=alkyl) under basic reaction conditions (for example, sodium hydroxide (NaOH) or lithium hydroxide (LiOH)) to give an amino compound of formula 8. Intramolecular amide coupling reaction of compound 8 facilitated by amide coupling reagents well known to those skilled in the art, such as 1-[bis(dimethylamino)-methylene]-1H-1,2,3-triazolo[4,5-b]pyridinium 3-oxide hexafluorophosphate (HATU) and hydroxybenzotriazole (HOBt), 1-ethyl-3-(3-dimethyl-aminopropyl)carbodiimide (EDCI) and HOBt, or benzotriazol-1-yl-oxytripyrrolidino-phosphonium hexafluorophosphate (PyBOP) in an appropriate solvent, such as dimethylformamide (DMF) or 1,4-dioxane, at ambient temperature provides a compound of Formula (I) where R$^4$ is hydroxy which can be converted to other compound of Formula (I) as described above in Scheme 1.

Alternatively, compounds of Formula (I) where Z$^1$ and Z$^2$ are independently selected from CH and C (wherein a substituent is attached), X is C, ring B is saturated heterocyclyl shown in the structure below and R$^1$, R$^2$, R$^3$, and R$^4$ are as defined in the Summary, can be prepared by the following procedure described in Scheme 3.

Scheme 3

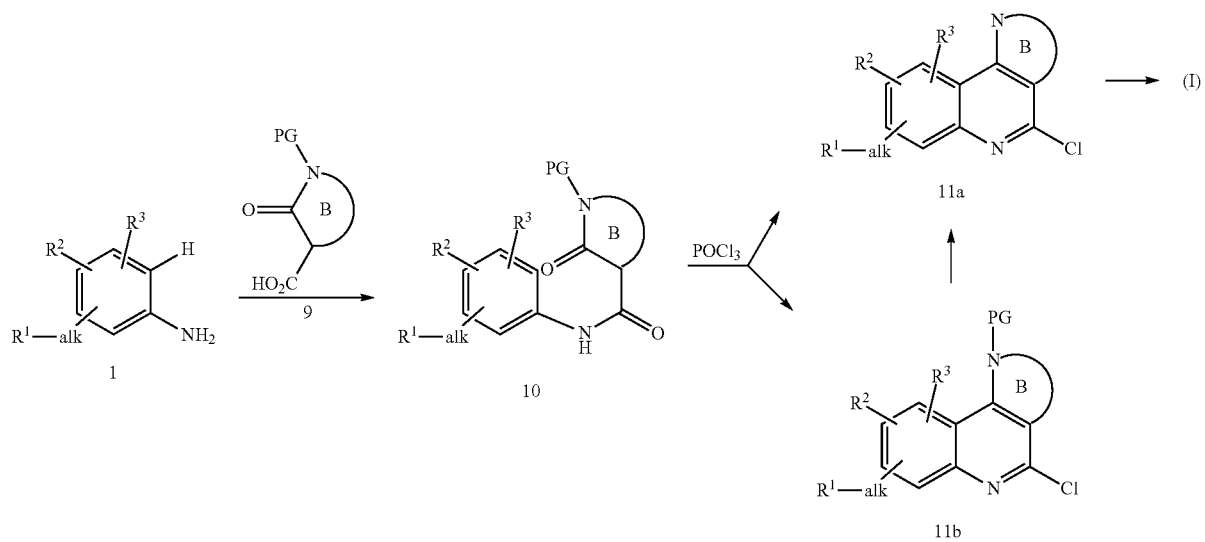

Reaction of a compound of formula 1 where -alk-R$^1$, R$^2$ and R$^3$ are as defined in the Summary or a precursor group thereof, with a 5-, 6-, or 7-membered heterocycloalkyl compound of formula 9 unsubstituted or substituted with R$^j$, R$^k$, R$^l$, and/or R$^m$ as defined in the Summary, e.g., pyrrolidine-3-carboxylic acid, 2-oxopiperidine-3-carboxylic acid or 2-oxoazepane-3-carboxylic acid where PG is a suitable nitrogen protecting group (such as benzyl, p-methoxybenzyl or Boc) in the presence of an amide coupling agent (such as 1-[bis(dimethylamino)-methylene]-1H-1,2,3-triazolo[4,5-b]pyridinium 3-oxide hexafluorophosphate (HATU) and hydroxybenzotriazole (HOBt), 1-ethyl-3-(3-dimethyl-aminopropyl)carbodiimide (EDCI) and HOBt, or benzotriazol-1-yl-oxytripyrrolidino-phosphonium hexafluorophosphate (PyBOP)) in an appropriate solvent (such as dimethylformamide (DMF) or 1,4-dioxane) at ambient temperature gives compound 10.

Compounds of formula 9 can be prepared as shown below:

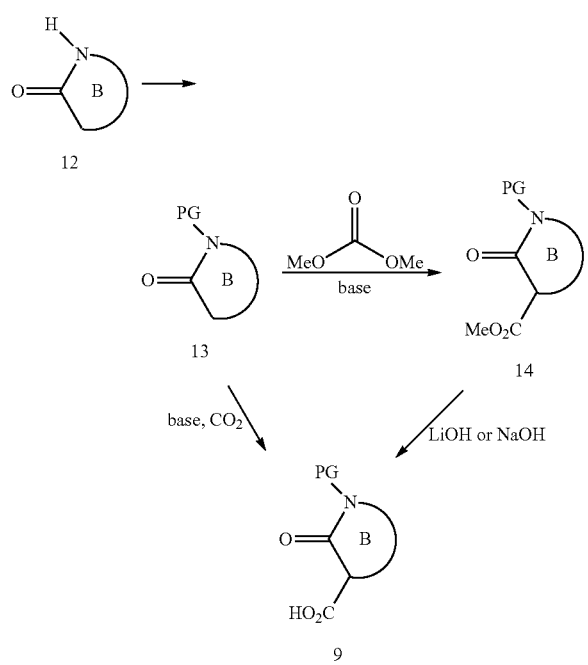

Compounds of formula 9 can be prepared from a 5-, 6-, or 7-membered heterocyclyl compound of formula 13 by deprotonation of compound 13 with a suitable base such as $^t$BuLi or lithium diisopropylamide (LDA) followed by treatment with dry $CO_2$ gas (see Zhang et. al., Organic Letters, 2016, 18(3):348-351 for a representative method.). Compounds of formula 13 such as 1-benzyl-2-pyrrolidinone and 1-benzylpiperidin-2-one are commercially available. Compounds of formula 13 can also be made by protecting the nitrogen atom of a commercially available lactam of formula 12 (such as azepan-2-one, 2-piperidinone, 6-methyl-2-piperidinone, 6,6-dimethylpiperidin-2-one, and 5,5-dimethylpyrrolidin-2-one), e.g., by reacting 12 under alkylating reaction conditions (such as with either benzyl chloride (BnCl) or p-methoxy benzyl chloride (PMBCl) under sodium hydride (NaH) or potassium carbonate ($K_2CO_3$) mediated condition) in appropriate solvents, such as tetrahydrofuran (THF) or dimethylformamide (DMF). Compounds of formula 13 where PG is Boc can be made by treating a lactam of formula 12 (such as azepan-2-one, 2-pyrrolidinone, 2-piperidinone, 6-methyl-2-piperidinone, 6,6-dimethylpiperidin-2-one, 5,5-dimethylpyrrolidin-2-one, etc.) with di-tert-butyl dicarbonate in the presence of 4-dimethylaminopyridine in appropriate solvent(s), such as acetonitrile or dimethylformamide (DMF).

Alternatively, compounds of formula 9 can be made by hydrolysis of the ester group in compounds of formula 14 with a base, such as sodium hydroxide (NaOH) or lithium hydroxide (LiOH). Compounds of formula 14 can be made by deprotonation of compound 12 with bases, such as $^t$BuLi or lithium diisopropylamide (LDA), followed by treatment with dimethyl carbonate.

Treatment of compound 10 with $POCl_3$ at 90° C. to refluxing temperature for up to 16 h provides a compound of Formula 11a where $R^4$ is chloro (when PG is Boc or methoxybenzyl) or formula 11b (when PG is benzyl). Removal of the amino protecting group in 11b provides a compound of formula 11a. Compounds of formula 11a can be converted to compounds of Formula (I) as described herein.

Compounds of Formula (I) where $Z^1$ is N, $Z^2$ is CH or C (wherein a substituent is attached), X is C, and ring B, $R^1$, $R^2$, $R^3$, and $R^4$ are as defined in the Summary, can be prepared by the following procedure described in Scheme 4 below.

Scheme 4

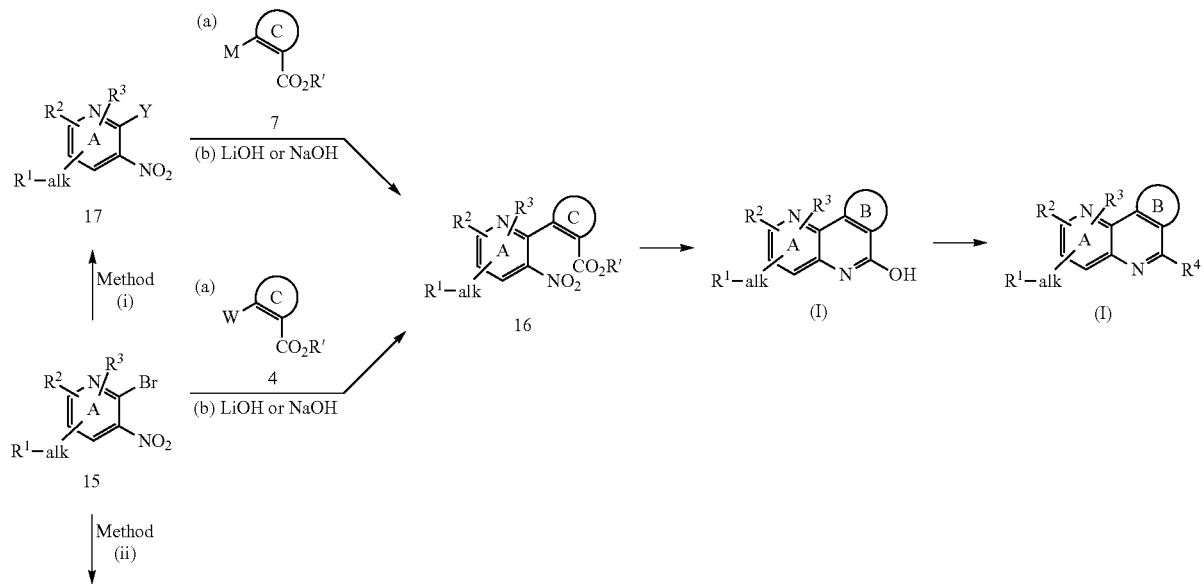

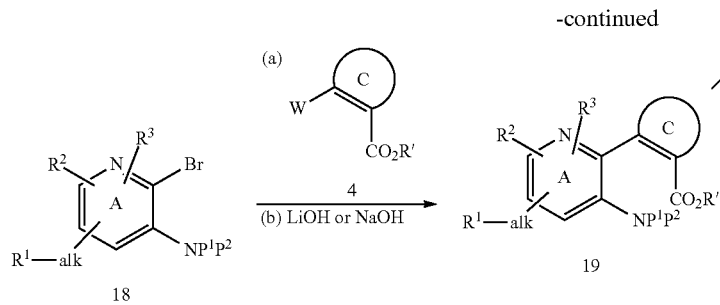

Reaction of a compound of formula 15 where -alk-R$^1$, R$^2$ and R$^3$ are as defined in the Summary or a precursor group thereof, with a compound of formula 4 under reaction conditions described in Scheme 2 provides a compound of formula 16. Compounds of formula 15 can be made by methods well known in the art. For example, 2-bromo-6-methoxy-3-nitro-5-[3-(pyrrolidin-1-yl)propoxy]pyridine and 6-bromo-2-methoxy-5-nitro-N-[3-(pyrrolidin-1-yl)propyl]pyridin-3-amine can be made from the commercially available 3-hydroxy-pyridine and 3-aminopyridine by methods known to those skilled in the art (see literature procedures such as Australian Journal of Chemistry, 1981, 34(4): 927-932; Bioorganic and Medicinal Chemistry Letters, 2014, 24(24):5630-5634; WO 2008/101682 A2, and Journal of Heterocyclic Chemistry, 1972, 9:1039-1043). Compound 16 can be converted to compound of Formula (I) where R$^4$ is hydroxy as described in Scheme 2 herein and other compound of Formula (I) as described in Scheme 1 herein.

Alternatively, compound 15 can be converted to a compound of Formula (I) following the method illustrated in Methods (i) and (ii) herein.

In Method (i), Compound 15 is first converted to a compound of formula 17 where Y is 4,4,5,5-tetramethyl-1,3,2-dioxaborolanyl-, —B(OH)$_2$, -tributylstannyl, or other appropriate functional groups. Compound 17 is then reacted with a compound of formula 7 as described in Scheme 2 herein to give a compound of formula 16, which after nitro group reduction, ester hydrolysis, and intramolecular amide coupling reaction provides compound of Formula (I) (where R$^4$ is hydroxy) which can be converted to other compound of Formula (I) as described above in Scheme 1.

In Method (ii), compound 15 is converted to a compound of formula 18 (where P$^1$ and P$^2$ are independently selected from H and Boc) by reduction of the nitro group with a suitable reducing agent, such as tin(II) chloride, followed by reaction of the resulting amino compound 18 (where P$^1$ and P$^2$ are each hydrogen) with di-tert-butyl dicarbonate in the presence of 4-dimethylaminopyridine to give the corresponding compound 18 (where P$^1$ and/or P$^2$ is Boc). Compound 18 is reacted with compound 4 under conditions similar as described above in Scheme 2 to provide a compound of formula 19 which is then converted to a compound of Formula (I) wherein R$^4$ is hydroxy after removal of the amino protecting group(s) and/or intramolecular amide coupling, if needed, as described above. Compound of Formula (I) wherein R$^4$ is hydroxy is further transformed into compound of Formula (I) wherein R$^4$ is other appropriate groups following the procedure similar to those described above.

Compounds of Formula (I) where Z$^1$ is N, CH or C, Z$^2$ is N, X is C, and ring B, R$^1$, R$^2$, R$^3$, and R$^4$ are as defined in the Summary, can be prepared by the following procedure described in Scheme 5.

Scheme 5

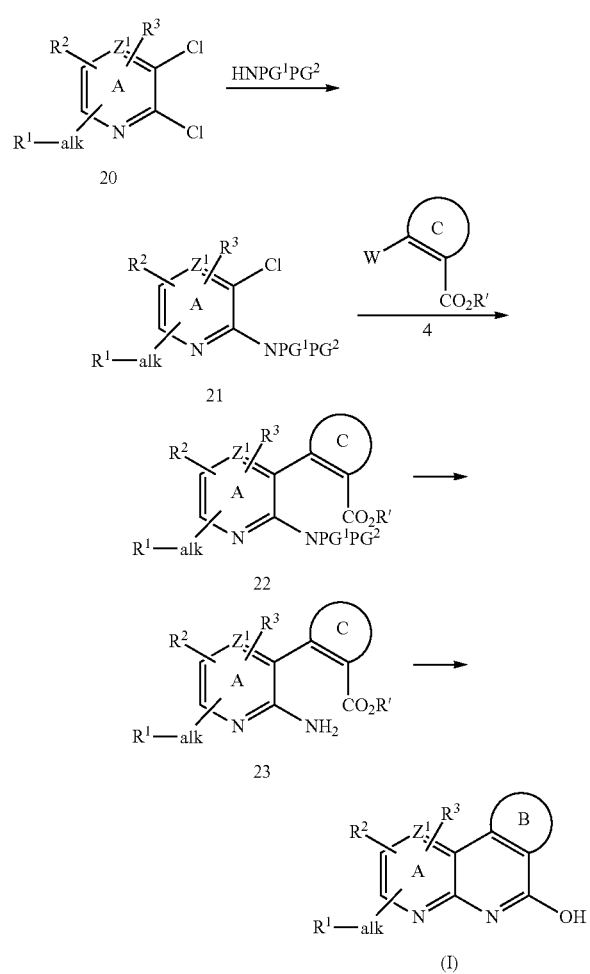

Reaction of a compound of formula 20 (wherein -alk-R$^1$, R$^2$ and R$^3$ are as defined in the Summary or a precursor group thereof, and Z$^1$ is either N, C or CH), with a compound of formula NHPG$^1$PG$^2$ (where PG$^1$ and PG$^2$ are either H or a suitable nitrogen protecting group such as benzyl, p-methoxybenzyl or Boc), followed by coupling reaction of the resulting amino compound 21 with compound 4 under reaction conditions described herein provides a compound of formula 22. Removal of the amino protecting groups (for example, with acid such as TFA or HCl when PG$^1$ and/or PG$^2$ is -p-methoxybenzyl) provides a compound of formula 23, which can be converted to a compound of Formula (I)

subsequently by ester hydrolysis (for example, with a base such as NaOH or LiOH, when R' is alkyl) and intramolecular amide coupling reaction under conditions described herein if needed. In some cases, the intermediate compound 23 (wherein R' is not H) can cyclize directly into compound of Formula (I). Compounds of formula 20 (such as 2,3-dichloro-5-methoxy-6-[3-(pyrrolidin-1-yl)propoxy]pyridine and 2,3-dichloro-5-methoxy-6-[3-(pyrrolidin-1-yl)propoxy] pyrazine) can be made from commercially available material, such as perchloropyrazine and 2,3,5,6-tetrachloropyridine, through procedures known to those skilled in the art. Other compounds of formula 20 can also be made from starting material, such as 5,6-dimethoxypyridin-2-amine, 6-amino-5-chloro-3-(trifluoromethoxy)pyridin-2-ol, 6-amino-5-chloro-2-(trifluoromethoxy)pyridin-3-ol, 2,5-dichloro-6-methyl-nicotinonitrile, and 5,6-dichloronicotinonitrile. through procedures known to those skilled in the art.

Testing

The G9a inhibitory activity of the compounds of the present disclosure can be tested using the in vitro assay described in Biological Examples 1 below. The ability of the compounds of the disclosure to stimulated fetal hemoglobin can be tested using the in vitro assay described in Biological Example 2 below.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg subject body weight per day, which can be administered in single or multiple doses. A suitable dosage level may be from about 0.1 to about 250 mg/kg per day or about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, or 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents and/or anti-cancer therapies. In some embodiments, the anti-cancer therapies can be surgery and/or radiation therapy. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as docetaxel (Taxotere™). Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, or axitinib; EGFR inhibitor such as afatinib, brivanib, carbozatinib, erlotinib, gefitinib, neratinib, or lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, or TG100-115; MTOR inhibitor such as rapamycin (sirolimus), temsirolimus, everolimus, XL388, XL765, AZD2013, PF04691502, PKI-587, BEZ235, or GDC0349; MEK inhibitor such as AZD6244, trametinib, PD184352, pimasertinib, GDC-0973, or AZD8330; and proteasome inhibitor such as carfilzomib, MLN9708, delanzomib, or bortezomib.

Other anti-cancer agents that can be employed in combination with a compound of this disclosure include Adriamycin; Dactinomycin; Bleomycin; Vinblastine; Cisplatin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or RiI2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer agents that can be employed in combination with a compound of the disclosure such as 20-epianalogues of 1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+diethylstilbe cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; $R_{11}$ retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan, etc.), nitrosoureas (e.g., carmustine, lomusitne, etc.), or triazenes (decarbazine, etc.). Examples of antimetabolites include but are not limited to folic acid analog (e.g., methotrexate), pyrimidine analogs (e.g., cytarabine, etc.), or purine analogs (e.g., mercaptopurine, thioguanine, pentostatin, etc.).

Examples of natural products useful in combination with a compound of this disclosure include but are not limited to vinca alkaloids (e.g., vincristine, etc.), epipodophyllotoxins (e.g., etoposide, etc.), antibiotics (e.g., daunorubicin, doxorubicin, bleomycin, etc.), enzymes (e.g., L-asparaginase, etc.), or biological response modifiers (e.g., interferon alpha, etc.).

Examples of alkylating agents that can be employed in combination a compound of this disclosure include, but are not limited to, nitrogen mustards (e.g., mechloroethamine, cyclophosphamide, chlorambucil, melphalan, etc.), ethylenimine and methylmelamines (e.g., hexamethylmelamine, thiotepa, etc.), alkyl sulfonates (e.g., busulfan, etc.), nitrosoureas (e.g., carmustine, lomusitne, semustine, streptozocin, etc.), or triazenes (decarbazine, etc.). Examples of antimetabolites include, but are not limited to folic acid analog (e.g., methotrexate, etc.), pyrimidine analogs (e.g., fluorouracil, floxuridine, cytarabine, etc.), or purine analogs (e.g., mercaptopurine, thioguanine, pentostatin, etc.).

Examples of hormones and antagonists useful in combination a compound of this disclosure include, but are not limited to, adrenocorticosteroids (e.g., prednisone, etc.), progestins (e.g., hydroxyprogesterone caproate, megestrol acetate and medroxyprogesterone acetate, etc.), estrogens (e.g., diethylstilbestrol and ethinyl estradiol, etc.), antiestrogen (e.g., tamoxifen, etc.), androgens (e.g., testosterone propionate, fluoxymesterone, etc.), antiandrogen (e.g., flutamide, etc.) and gonadotropin releasing hormone analog (e.g., leuprolide, etc.). Other agents that can be used in the methods and compositions described herein for the treatment or prevention of cancer include platinum coordination complexes (e.g., cisplatin, carboblatin, etc.), anthracenedione (e.g., mitoxantrone, etc.), substituted urea (e.g., hydroxyurea, etc.), methyl hydrazine derivative (e.g., procarbazine, etc.) and adrenocortical suppressant (e.g., mitotane, aminoglutethimide, etc.).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8 and Spongistatin 9), Cemadotin hydrochloride (also known as LU-103793 and NSC-D-669356), Epothilones (such as Epothilone A, Epothilone B, Epothilone C (also known as desoxyepothilone A or dEpoA)), Epothilone D (also referred to as KOS-862, dEpoB and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone, Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes) and SSR-250411 (Sanofi).

EXAMPLES

The following preparations of compounds of Formula (I) (Examples) and intermediates (References) are given to enable those skilled in the art to more clearly understand and to practice the present disclosure. They should not be considered as limiting the scope of the disclosure, but merely as being illustrative and representative thereof.

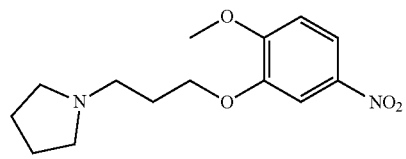

Intermediate I-1

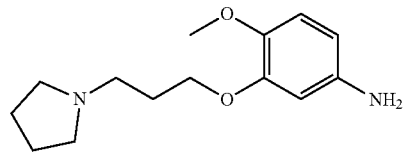

Intermediate I-2

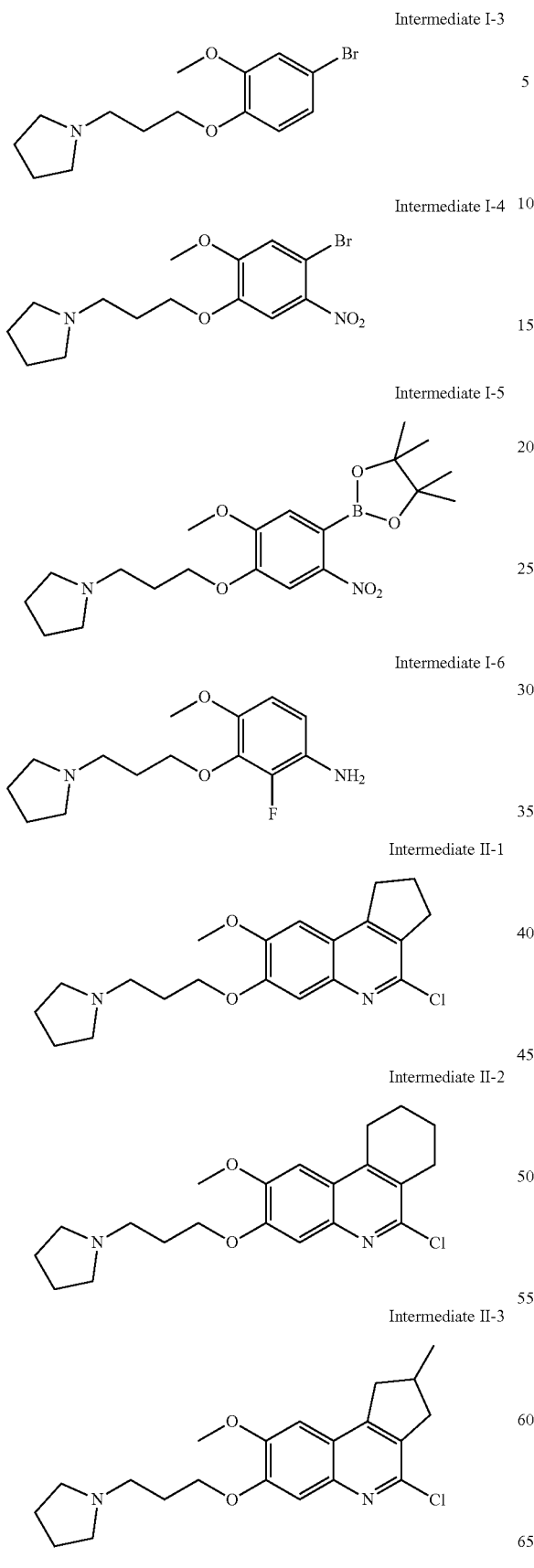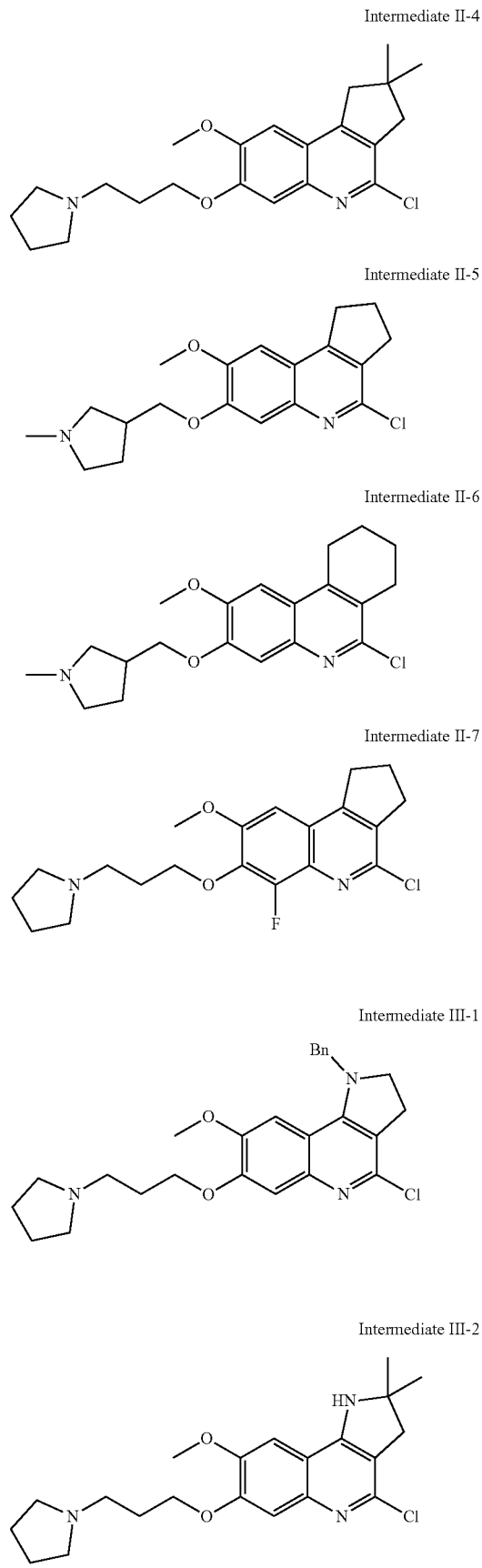

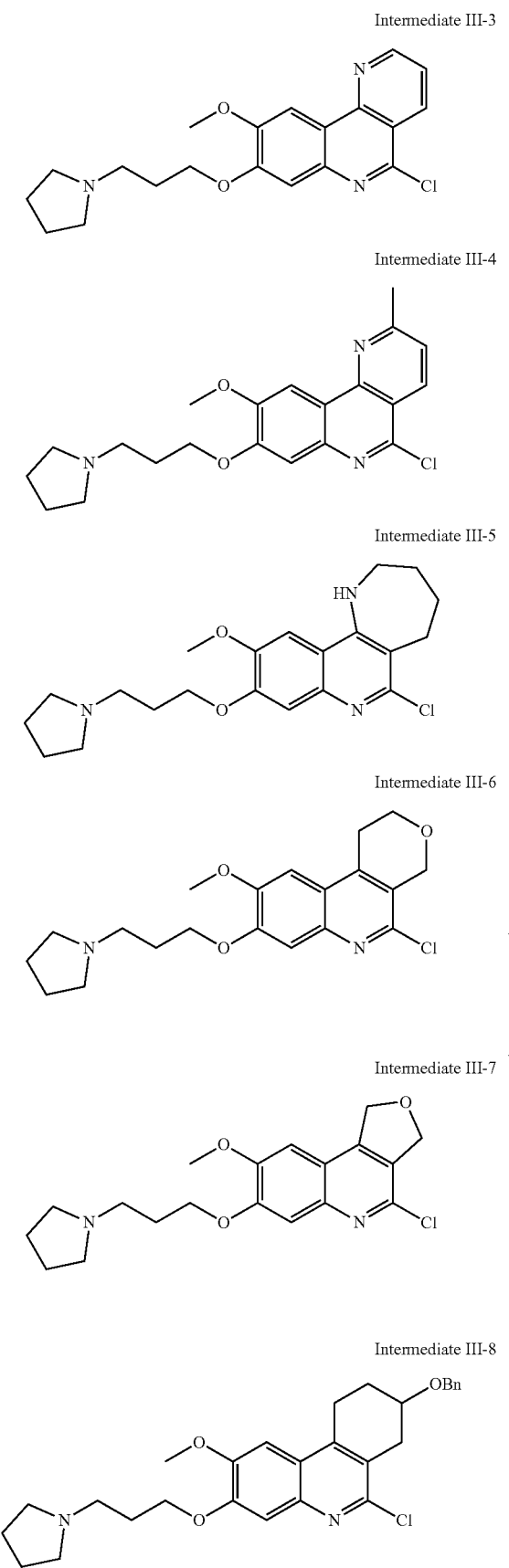
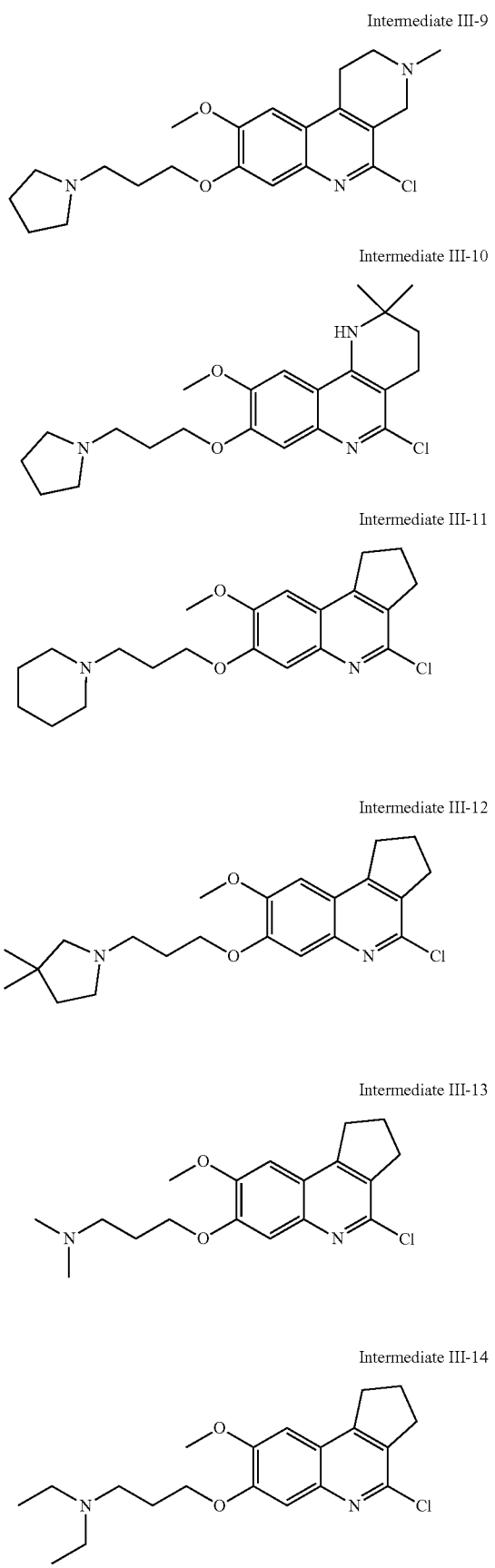

Intermediate III-15

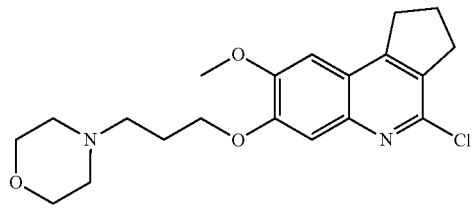

Reference 1

Synthesis of 1-[3-(2-methoxy-5-nitrophenoxy)propyl]pyrrolidine (Intermediate I-1)

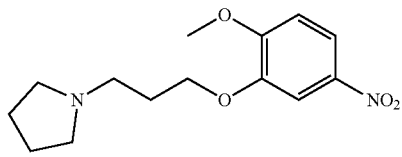 [SMILES: COc1ccc([N+](=O)[O-])cc1OCCCN1CCCC1]

Into a 250-mL round-bottom flask was placed a mixture of 2-methoxy-5-nitrophenol (5.00 g, 29.56 mmol, 1.00 eq.), N,N-dimethylformamide (60 mL), potassium carbonate (8.10 g, 58.61 mmol, 2.00 eq.) and 1-(3-chloropropyl)pyrrolidine (5.99 g, 40.57 mmol, 1.10 eq.). The resulted mixture was allowed to stir at 80° C. for 12 h. The reaction mixture was cooled to rt, diluted with $H_2O$ and extracted with ethyl acetate thrice. The combined organic layers were dried over anhydrous sodium sulfate and concentrated under reduced pressure. The residue was purified by flash chromatography on silica gel column with 10% $MeOH/CH_2Cl_2$ as the eluent to provide 1-[3-(2-methoxy-5-nitrophenoxy)propyl]pyrrolidine as yellow oil (4.80 g, 58%). LCMS (ES) [M+1]+ m/z 281.

Reference 2

Synthesis of 4-methoxy-3-[3-(pyrrolidin-1-yl)propoxy]aniline (Intermediate I-2)

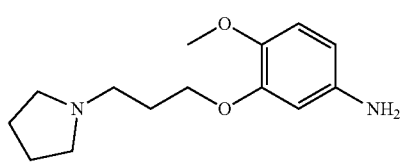

Into a 250-mL round-bottom flask, was placed a mixture of 1-[3-(2-methoxy-5-nitrophenoxy)-propyl]pyrrolidine (Intermediate I-1) (4.80 g, 17.12 mmol, 1.00 eq.), methanol (100 mL) and 10% Pd/C (500 mg). The flask was degassed and purged with $H_2$ for 5 times. The mixture was allowed to stir under $H_2$ atmosphere at rt for 4 h, and the solid was filtered off. Removal of organic solvents under reduced pressure provided 4-methoxy-3-[3-(pyrrolidin-1-yl)propoxy]aniline as tan oil (4.10 g, 96%). LCMS (ES) [M+1]+ m/z 251.2.

Reference 3

Synthesis of 1-[3-(4-bromo-2-methoxyphenoxy)propyl]pyrrolidine (Intermediate I-3)

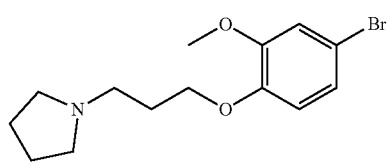 [SMILES: COc1cc(Br)ccc1OCCCN1CCCC1]

Into a 1-L round-bottom flask, was placed a mixture of 4-bromo-2-methoxyphenol (15.0 g, 73.88 mmol, 1.00 eq.), N,N-dimethylformamide (300 mL), 1-(3-chloropropyl)pyrrolidine hydrochloride (13.60 g, 73.88 mmol, 1.00 eq.), potassium iodide (12.26 g, 73.88 mmol, 1.00 eq.) and potassium carbonate (20.4 g, 147.76 mmol, 2.00 eq.). The resulting mixture was allowed to stir for 5 h at 70° C. The mixture was filtered and the filtrate was concentrated under reduced pressure. The residue was diluted with water and extracted with ethyl acetate. The combined organic layer was washed with brine, dried over anhydrous sodium sulfate and concentrated under reduced pressure. The residue was purified by flash chromatography on silica gel column eluted with dichloromethane/methanol (6/1) to provide 1-[3-(4-bromo-2-methoxyphenoxy)propyl]pyrrolidine (Intermediate I-3) as a brown oil (18.5 g, 80%). LCMS (ES) [M+1]+ m/z 314.0.

Reference 4

Synthesis of 1-[3-(4-bromo-2-methoxy-5-nitrophenoxy)propyl]pyrrolidine (Intermediate I-4)

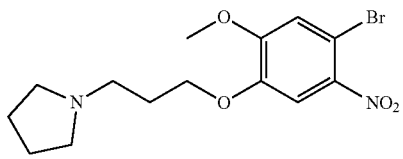 [SMILES: COc1cc(Br)c([N+](=O)[O-])cc1OCCCN1CCCC1]

Into a 500-mL 3-necked round-bottom flask, was placed a solution of 1-[3-(4-bromo-2-methoxyphenoxy)propyl]pyrrolidine (Intermediate I-3) (18.0 g, 57.29 mmol, 1.00 eq.) in acetic acid (100 mL). To the stirring solution was added $HNO_3$ (50 mL) dropwise at 15° C. The resulting solution was allowed to stir for 3 h at 25° C. The reaction was then quenched by the addition of ice water. The precipitate was collected by filtration to provide 1-[3-(4-bromo-2-methoxy-5-nitrophenoxy)propyl]pyrrolidine as a yellow solid (18.1 g, 88%). LCMS (ES) [M+1]+ m/z 359.0.

Reference 5

Synthesis of 1-{3-[4-(4,4-dimethyl-1,3,2-dioxaborolan-2-yl)-2-methoxy-5-nitrophenoxy]-propyl}pyrrolidine (Intermediate I-5)

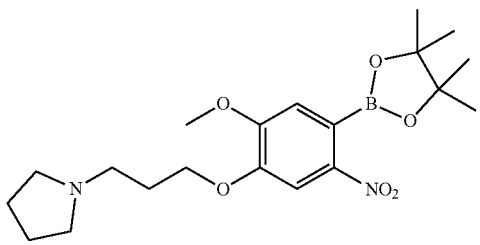 [SMILES: COc1cc(B2OC(C)(C)C(C)(C)O2)c([N+](=O)[O-])cc1OCCCN1CCCC1]

Into a 500-mL 3-necked round-bottom flask purged and maintained with an inert atmosphere of nitrogen, was placed a mixture of 1-[3-(4-bromo-2-methoxy-5-nitrophenoxy)propyl]pyrrolidine (Intermediate I-4) (8.0 g, 22.27 mmol, 1.00 eq.), 1.4-dioxane (200 mL), BPD (8.51 g, 33.51 mmol, 1.50 eq.), KOAc (4.38 g, 44.63 mmol, 2.00 eq.) and Pd(dppf)Cl$_2$ (1.63 g, 2.23 mmol, 0.10 eq.). The resulting mixture was allowed to stir under N$_2$ at 110° C. for 3 h. The mixture was concentrated under reduced pressure. The residue was purified by flash chromatography on silica gel column eluted with dichloromethane/methanol (10/1) to provide 1-{3-[4-(4,4-dimethyl-1,3,2-dioxaborolan-2-yl)-2-methoxy-5-nitrophenoxy]propyl}pyrrolidine (Intermediate I-5) as a gray solid (6.1 g, 67%). LCMS (ES) [M+1]$^+$ m/z 407.2.

Reference 6

Synthesis of 2-fluoro-4-methoxy-3-[3-(pyrrolidin-1-yl)propoxy]aniline (Intermediate I-6)

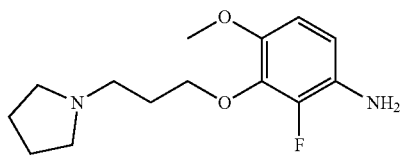 [SMILES: COc1ccc(N)c(F)c1OCCCN1CCCC1]

Step 1

Into a 250-mL round-bottom flask, was placed a mixture of 2-fluoro-6-methoxyphenol (4.6 g, 32.36 mmol, 1.00 eq.), acetonitrile (150 mL), 3-(pyrrolidin-1-yl)propan-1-ol hydrochloride (10.73 g, 58.26 mmol, 1.80 eq.), potassium carbonate (12.3 g, 89.00 mmol, 2.75 eq.) and potassium iodide (9.67 g, 58.26 mmol, 1.80 eq.). The resulting mixture was allowed to stir at 80° C. for 3 h. The solids were filtered off. The filtrate was concentrated under reduced pressure. The residue was purified by flash chromatography on silica gel column eluted with ethyl acetate/petroleum ether (1/3) to provide 1-[3-(2-fluoro-6-methoxyphenoxy)propyl]pyrrolidine as a yellow solid (4.35 g, 53%). LCMS (ES) [M+1]$^+$ m/z 254.1.

Step 2

Into a 50-mL round-bottom flask placed in 0° C. ice bath was added 1-[3-(2-fluoro-6-methoxy-phenoxy)propyl]pyrrolidine (4.35 g, 17.17 mmol, 1.00 eq.). To the resulting mixture was added nitric acid (10 mL) slowly. The resulting solution was allowed to stir at room temperature for 1 h. The reaction mixture was poured into ice water (50 mL). The pH value of the solution was adjusted to 8 with sodium bicarbonate aqueous solution (1.0 M). The resulting mixture was extracted with ethyl acetate (3×100 mL). The combined organic layers was washed with brine, dried over anhydrous sodium sulfate and concentrated under reduced pressure. The residue was purified by flash chromatography on silica gel column eluted with ethyl acetate/petroleum ether (1/5) to afford 1-[3-(2-fluoro-6-methoxy-3-nitrophenoxy)propyl]pyrrolidine as a yellow oil (1.52 g, 30%). LCMS (ES) [M+1]$^+$ m/z 299.2.

Step 3

Into a 100-mL round-bottom flask, was placed a mixture of 1-[3-(2-fluoro-6-methoxy-3-nitrophenoxy)propyl]pyrrolidine (1.52 g, 5.10 mmol, 1.00 eq.), methanol (30 mL) and 10% Pd/C (500 mg). The mixture was degassed and purged with hydrogen thrice. The resulting mixture was allowed to stir under H$_2$ atmosphere at room temperature for 2 h. The reaction mixture was diluted with MeOH (50 mL) and filtered through a pad of celite. The filtrate was concentrated under reduced pressure to provide 2-fluoro-4-methoxy-3-[3-(pyrrolidin-1-yl)propoxy]aniline (Intermediate I-6) as a yellow oil (1.27 g, 93%). LCMS (ES) [M+1]$^+$ m/z 269.2.

Reference 7

Synthesis of 1-[3-({4-chloro-8-methoxy-1H,2H,3H-cyclopenta[c]quinolin-7-yl}oxy)-propyl]pyrrolidine (Intermediate II-1)

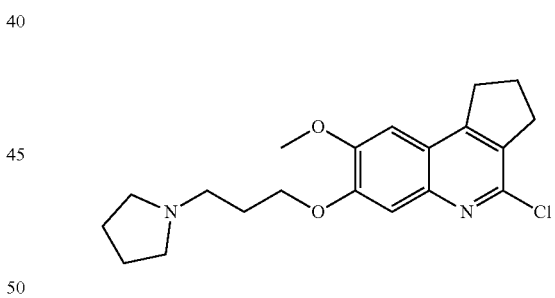

Into a 50-mL round-bottom flask was placed a mixture of 8-methoxy-7-[3-(pyrrolidin-1-yl)propoxy]-1H,2H,3H-cyclopenta[c]quinolin-4-ol (Example 37 below) (346 mg, 1.01 mmol, 1.00 eq.) and POCl$_3$ (4.5 mL). The resulted solution was allowed to stir at 100° C. for 2 h. After removal of volatiles under reduced pressure, the residue was poured into water. The mixture was adjusted with aqueous sodium bicarbonate solution (2 N) to pH=8, and extracted with CH$_2$Cl$_2$ thrice. The combined organic layers were dried over anhydrous sodium sulfate. The solid was filtered off, and the solution was concentrated under reduced pressure. The residue was purified by flash chromatography on silica gel column with 25% MeOH/CH$_2$Cl$_2$ (0.1% NH$_4$OH) as the eluent to provide the desired product (Intermediate II-1) as a yellow solid (214 mg, 59%). LCMS (ES) [M+1]$^+$ m/z 361.2.

Reference 8

Synthesis of 6-chloro-2-methoxy-3-[3-(pyrrolidin-1-yl)propoxy]-7,8,9,10-tetrahydrophenanthridine (Intermediate II-2)

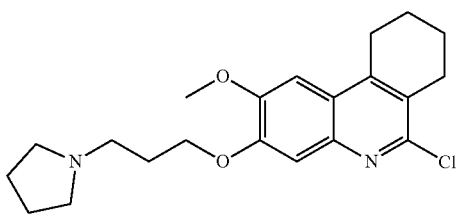 [SMILES: COc1cc2c3c(c(Cl)nc2cc1OCCCN1CCCC1)CCCC3]

The title compound was made from 2-methoxy-3-[3-(pyrrolidin-1-yl)propoxy]-7,8,9,10-tetrahydrophenanthridin-6-ol (Example 38 below) following a procedure similar as described for the synthesis of Intermediate II-1 above. The crude product was purified by flash chromatography on silica gel column with 25% MeOH/CH$_2$Cl$_2$ (0.1% NH$_4$OH) as the eluent to provide the desired product as a brown solid. LCMS (ES) [M+1]$^+$ m/z 375.2.

Reference 9

Synthesis of 1-[3-({4-chloro-8-methoxy-2-methyl-1H,2H,3H-cyclopenta[c]quinolin-7-yl}oxy)propyl]pyrrolidine (Intermediate II-3)

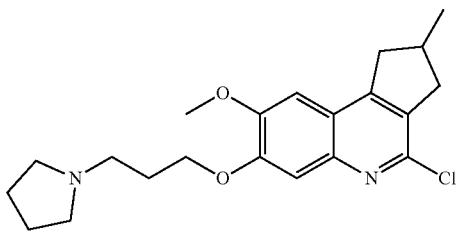 [SMILES: COc1cc2c3c(c(Cl)nc2cc1OCCCN1CCCC1)CC(C)C3]

Step 1

Into a −78° C. solution of 3-methylcyclopent-2-en-1-one (14.40 g, 150.0 mmol, 1.0 eq.) in tetrahydrofuran (200 mL) under N$_2$ atmosphere was added lithium diisopropylamide (LDA) (150 mL, 2.0 M in THF, 300.0 mmol, 2.00 eq.) over 20 min. The resulting solution was allowed to stir at −78° C. for 1 h. A solution of dimethyl carbonate (14.85 g, 165.0 mmol, 1.10 eq.) in THF (150 mL) was added dropwise over 20 min. The resulting solution was allowed to warm from −78° C. to rt and allowed to stir for additional 3 h. The reaction mixture was poured into HCl aqueous solution (1.0 N) at 0° C. The organic layer was separated. The water layer was back extracted with ethyl acetate. The combined organic layers were washed with brine, dried over anhydrous sodium sulfate and concentrated under reduced pressure. The residue was purified by flash chromatography on silica gel column eluted with ethyl acetate/petroleum ether (1/1) to provide methyl 4-methyl-2-oxocyclopent-3-ene-1-carboxylate as a light brown oil (6.13 g, 27%). LCMS (ES) [M+1]$^+$ m/z 155.1.

Step 2

Into a 250-mL round-bottom flask, was placed a mixture of methyl 4-methyl-2-oxocyclopent-3-ene-1-carboxylate (6.13 g, 39.81 mmol, 1.00 eq.), methanol (100 mL) and 10% Pd/C (400 mg). The flask was flushed with nitrogen thrice, followed by hydrogen twice. The mixture was allowed to stir under hydrogen atmosphere at room temperature for 1 h. The solids were filtered off. The filtrate was concentrated under reduced pressure. The residue was purified by flash chromatography on silica gel column eluted with ethyl acetate/petroleum ether (1/2) to afford methyl 4-methyl-2-oxocyclopentane-1-carboxylate as a colorless oil (3.87 g, 62%). LCMS (ES) [M+1]$^+$ m/z 157.2.

Step 3

The title compound was made from methyl 4-methyl-2-oxocyclopentane-1-carboxylate and 4-methoxy-3-[3-(pyrrolidin-1-yl)propoxy]aniline (Intermediate I-2) following conditions similar as described in Example 37 below and Reference 7 above, except that the final crude product was purified by flash chromatography on silica gel column eluted with dichloromethane/methanol (8/1) to provide the desired product as a light brown solid. LCMS (ES) [M+1]$^+$ m/z 375.2.

Reference 10

Synthesis of 1-[3-({4-chloro-8-methoxy-2,2-dimethyl-1H,2H,3H-cyclopenta[c]quinolin-7-yl}oxy)propyl]pyrrolidine (Intermediate II-4)

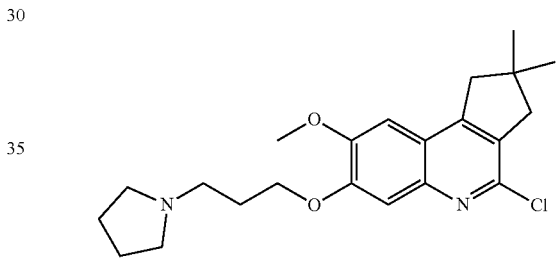

The title compound was made from methyl 4,4-dimethyl-2-oxocyclopentane-1-carboxylate (prepared according to literature procedure reported in Organic Letters, 2004, Vol 6, No. 24, page 44411-4414) and 4-methoxy-3-[3-(pyrrolidin-1-yl)propoxy]aniline (Intermediate I-2) following a procedure similar as described in Reference 9 above, except that final crude product was purified by flash chromatography on silica gel column eluted with 10-20% MeOH/dichloromethane (0.1% NH$_4$OH) to provide the title product as a light brown solid. LCMS (ES) [M+1]$^+$ m/z 389.2.

Reference 11

Synthesis of 3-[({4-chloro-8-methoxy-1H,2H,3H-cyclopenta[c]quinolin-7-yl}oxy)methyl]-1-methylpyrrolidine (Intermediate II-5)

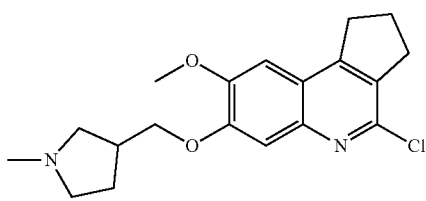 [SMILES: COc1cc2c3c(c(Cl)nc2cc1OCC1CCN(C)C1)CCC3]

Step 1

Into a 500-mL round-bottom flask, was placed a solution of methyl 2-oxocyclopentanel-carboxylate (14.2 g, 99.89 mmol, 1.00 eq.), toluene (150 mL), ethane-1,2-diol (12.4 g, 199.78 mmol, 2.00 eq.) and TsOH (860 mg, 4.99 mmol, 0.05 eq.). The solution was allowed to reflux overnight. The reaction mixture was cooled to room temperature, diluted with water (100 mL), and extracted with ethyl acetate thrice. The combined organic layers were dried over anhydrous sodium sulfate and concentrated under reduced pressure. The residue was purified by flash chromatography on silica gel column eluted with 25% ethyl acetate/petroleum ether (1/3) to provide methyl 1,4-dioxaspiro[4.4]nonane-6-carboxylate as a colorless oil (6.5 g. 35%).

Step 2

Into a 100-mL round-bottom flask, was placed a solution of methyl 1,4-dioxaspiro[4.4]-nonane-6-carboxylate (6.5 g, 34.9 mmol, 1.00 eq.), methanol (60 mL), water (30 mL) and sodium hydroxide (2.78 g, 69.7.00 mmol, 2.00 eq.). The resulting solution was allowed to stir at 80° C. for 2 h. The mixture was concentrated under reduced pressure. The residue was diluted with water and treated with saturated aqueous NaH$_2$PO$_4$ solution to pH=5~6). The mixture was extracted with ethyl acetate thrice. The combined organic layers were dried over anhydrous sodium sulfate and concentrated under reduced pressure to provide 1,4-dioxaspiro[4.4]nonane-6-carboxylic acid as a white solid (3.94 g, 66%).

Step 3

Into a 250-mL round-bottom flask purged and maintained under atmosphere of nitrogen, was placed a solution of 2-methoxy-5-nitrophenol (5.0 g, 29.56 mmol, 1.00 eq.), dichloromethane (70 mL), (1-methylpyrrolidin-3-yl)methanol (6.8 g, 59.09 mmol, 2.00 eq.) and PPh3 (15.5 g, 59.09 mmol, 2.00 eq.). To this stirring solution was added a solution of di-t-butyl azodicarboxylate (13.6 g, 59.09 mmol, 2.00 eq.) in dichloromethane (30 mL) dropwise at 0° C. under N$_2$. The resulting solution was allowed to stir for 4 h at room temperature and concentrated under reduced pressure. The residue was purified by flash chromatography on silica gel column eluted with MeOH/CH$_2$Cl$_2$ (1/8) to provide 3-(2-methoxy-5-nitrophenoxymethyl)-1-methylpyrrolidine as a light yellow solid (5.5 g, 70%). LCMS (ES) [M+1]$^+$ m/z 267.1.

Step 4

Into a 250-mL round-bottom flask, was placed a mixture of 3-(2-methoxy-5-nitrophenoxy-methyl)-1-methylpyrrolidine (5.5 g, 20.65 mmol, 1.00 eq.), methanol (100 mL) and 10% Pd/C (500 mg). The flask was flushed with nitrogen thrice followed by with hydrogen twice. The mixture was allowed to stir under H$_2$ atmosphere at rt overnight. The solids were filtered off. The filtrate was concentrated under reduced pressure to provide 4-methoxy-3-[(1-methylpyrrolidin-3-yl)methoxy]aniline as a light brown oil (4.8 g, 98%). LCMS (ES) [M+1]$^+$ m/z 237.2.

Step 5

Into a 250-mL round-bottom flask, was placed a solution of 1,4-dioxaspiro[4.4]nonane-6-carboxylic acid (made in Step 2) (3.5 g, 20.31 mmol, 1.00 eq.), N,N-dimethylformamide (50 mL), 4-methoxy-3-[(1-methylpyrrolidin-3-yl)methoxy]aniline (4.8 g, 20.31 mmol, 1.00 eq.), DIEA (5.24 g, 40.62 mmol, 2.00 eq.) and HATU (9.3 g, 24.46 mmol, 1.20 eq.). The resulting solution was allowed to stir at room temperature for 2 h. The crude reaction mixture was filtered and subjected to purification on reverse phase preparative MPLC (Prep-C18, 20-45 µM, 120 g, Tianjin Bonna-Agela Technologies; gradient elution of 15-25% MeCN in water over a 10 min period, where both solvents contain 0.05% TFA) to provide N-[4-methoxy-3-[(1-methylpyrrolidin-3-yl)methoxy]phenyl]-1,4-dioxaspiro[4.4]nonane-6-carboxamide in form of TFA salt as a yellow oil (3.4 g, 43%). LCMS (ES) [M-TFA+1]$^+$ m/z 390.2.

Step 6

Into a 250-mL round-bottom flask, was placed a solution of N-[4-methoxy-3-[(1-methylpyrrolidin-3-yl)methoxy]phenyl]-1,4-dioxaspiro[4.4]nonane-6-carboxamide (3.4 g, 8.71 mmol, 1.00 eq.), MeCN (50 mL), aqueous HCl solution (17.5 mL, 2.0 N, 34.9 mmol, 4.00 eq.). The resulting solution was allowed to stir at 50° C. for 5 h. The mixture was concentrated under reduced pressure to provide crude N-[4-methoxy-3-[(1-methylpyrrolidin-3-yl)methoxy]phenyl]-2-oxocyclopentane-1-carboxamide hydrochloride salt as a yellow oil (3.05 g, 91%). LCMS (ES) [M+1]$^+$ m/z 347.2.

Step 7

Into a 100-mL round-bottom flask, was placed a solution of N-[4-methoxy-3-[(1-ethylpyrrolidin-3-yl)methoxy]phenyl]-2-oxocyclopentane-1-carboxamide hydrochloride salt (3.05 g, 8.80 mmol, 1.00 eq.), toluene (30 mL), and polyphosphoric acid (3 mL). The resulting mixture was allowed to stir at 100° C. for 2 h. The mixture was concentrated under reduced pressure. The residue was diluted with water (100 mL) and basified with aqueous NaOH solution (2.0 N) to pH ~8. The mixture was extracted with dichloromethane/methanol (10/1) thrice. The combined organic layers were dried over anhydrous sodium sulfate and concentrated under reduced pressure. The residue was purified by flash chromatography on silica gel column eluted with ethyl dichloromethane/methanol (8/1) to provide 8-methoxy-7-[(1-methylpyrrolidin-3-yl)methoxy]-1H,2H,3H-cyclopenta[c]quinolin-4-ol as yellow oil (2.6 g, 90%). LCMS (ES) [M+1]$^+$ m/z 328.2.

Step 8

Into a 100-mL round-bottom flask, was placed a solution of 8-methoxy-7-[(1-methylpyrrolidin-3-yl)methoxy]-1H,2H,3H-cyclopenta[c]quinolin-4-ol (2.6 g, 7.92 mmol, 1.00 eq.) and POCl$_3$ (30 mL). The resulting solution was allowed to stir at 100° C. for 2 h. The resulting mixture was concentrated under reduced pressure. The residue was diluted with 100 mL of dichloromethane, added into ice water (100 mL) dropwise and basified with aqueous NaOH solution (2.0 N) to pH=~9. The resulting mixture was extracted with dichloromethane thrice. The combined organic layers were dried over anhydrous sodium sulfate and concentrated under reduced pressure. The residue was purified by flash chromatography on silica gel column eluted with ethyl dichloromethane/methanol (8/1) to provide the title product as a light yellow solid (1.35 g, 49%). LCMS (ES) [M+1]$^+$ m/z 347.1.

Reference 12

Synthesis of 6-chloro-2-methoxy-3-[(1-methylpyrrolidin-3-yl)methoxy]-7,8,9,10-tetrahydrophenanthridine (Intermediate II-6)

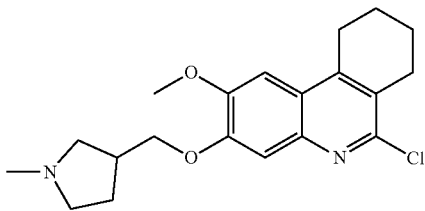 [SMILES: COc1cc2c3c(c(Cl)nc2cc1OCC1CCN(C)C1)CCCC3]

The title compound was made from 4-methoxy-3-[(1-methylpyrrolidin-3-yl)methoxy]aniline (prepared in the synthesis of Intermediate II-5, step 4) following synthetic procedure described for the synthesis of 1-[3-({4-chloro-8-methoxy-1H,2H,3H-cyclopenta[c]quinolin-7-yl}oxy)propyl]pyrrolidine (Intermediate II-1), except that methyl 2-oxocyclohexane-1-carboxylate was used in the place of methyl 2-oxocyclopentanel-carboxylate. LCMS (ES) [M+1]+ m/z 361.2.

Reference 13

Synthesis of 1-[3-({4-chloro-6-fluoro-8-methoxy-1H,2H,3H-cyclopenta[c]quinolin-7-yl}oxy)propyl]pyrrolidine (Intermediate II-7)

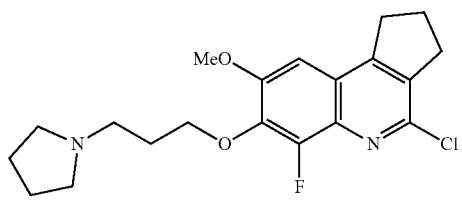 [SMILES: COc1cc2c3c(c(Cl)nc2c(F)c1OCCCN1CCCC1)CCC3]

The title compound was made as described in Reference 11, Steps 5-8, except that 2-fluoro-4-methoxy-3-[3-(pyrrolidin-1-yl)propoxy]aniline (Intermediate I-6) was used in the place of 4-methoxy-3-[(1-methylpyrrolidin-3-yl)methoxy]aniline. LCMS (ES) [M+1]+ m/z 379.2.

Reference 14

Synthesis of 1-[3-({1-benzyl-4-chloro-8-methoxy-1H,2H,3H-pyrrolo[3,2-c]quinolin-7-yl}oxy)propyl]pyrrolidine (Intermediate III-1)

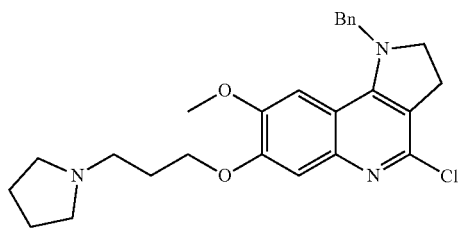 [SMILES: COc1cc2c3c(c(Cl)nc2cc1OCCCN1CCCC1)CCN3Cc1ccccc1]

Step 1

Into a −20° C. solution of 1-benzylpyrrolidin-2-one (1.00 g, 5.71 mmol, 1.00 eq.) in THF (20 mL) under $N_2$ was added lithium diisopropylamide (LDA) (6.3 mL, 2.0 M in THF, 12.6 mmol, 2.20 eq.) dropwise over 5 min. The resulting mixture was allowed to stir at −20° C. under $N_2$ for 1.5 h. Dry carbon dioxide gas was run through this solution at −20° C. for 0.5 h. The reaction was then quenched by saturated aqueous $NH_4Cl$ solution (6.3 mL) and then diluted with water. The pH was adjusted to 2-3 with concentrated HCl. The resulting solution was extracted with EtOAc thrice. The combined organic layers were dried over anhydrous sodium sulfate. The solids were filtered off. The filtrate was concentrated under reduced pressure to provide 1-benzyl-2-oxopyrrolidine-3-carboxylic acid as a colorless oil (700 mg, 56%). LCMS (ES) [M+1]+ m/z 220.2.

Step 2

Into a 40-mL vial charged with solution of 1-benzyl-2-oxopyrrolidine-3-carboxylic acid (700 mg, 3.19 mmol, 1.00 eq.) in dichloromethane (15 mL) was added 4-methoxy-3-[3-(pyrrolidin-1-yl)propoxy]aniline (Intermediate I-2) (839 mg, 3.35 mmol, 1.05 eq.), diisopropylethylamine (825 mg, 6.38 mmol, 2.00 eq.) and HATU (1.46 g, 3.84 mmol, 1.20 eq.). The resulting mixture was allowed to stir at rt for 0.5 h. The solution was diluted with dichloromethane, washed with saturated aqueous $NaHCO_3$. The organic layer was separated, dried over anhydrous sodium sulfate and concentrated under reduced pressure to provide 1-benzyl-N-[4-methoxy-3-[3-(pyrrolidin-1-yl)propoxy]phenyl]-2-oxopyrrolidine-3-carboxamide as a brown oil (1.15 g, 80%). LCMS (ES) [M+1]+ m/z 452.4.

Step 3

Into a 50-mL round-bottom flask, was placed a mixture of 1-benzyl-N-[4-methoxy-3-[3-(pyrrolidin-1-yl)propoxy]phenyl]-2-oxopyrrolidine-3-carboxamide (1.15 g, 2.55 mmol, 1.00 eq.) and $POCl_3$ (23 mL). The resulting mixture was allowed to stir at 110° C. under condenser for 3 h. The reaction was concentrated under reduced pressure and quenched with ice water (20 mL). The pH value of the solution was adjusted to 8 with saturated aqueous $NaHCO_3$. The resulting solution was extracted with a mixed solution of dichloromethane/MeOH (V/V=10/1) thrice. The organic layers were combined, dried over anhydrous sodium sulfate and concentrated under reduced pressure. The residue was purified by flash chromatography on silica gel column eluted with petroleum ether/THF (5% TEA) (1/4) to provide 1-[3-({1-benzyl-4-chloro-8-methoxy-1H,2H,3H-pyrrolo[3,2-c]quinolin-7-yl}oxy)propyl]pyrrolidine (Intermediate III-1) as a brown solid (600 mg, 52%). LCMS (ES) [M+1]+ m/z 452.2.

Reference 15

Synthesis of 1-[3-({4-chloro-8-methoxy-2,2-dimethyl-1H,2H,3H-pyrrolo[3,2-c]quinolin-7-yl}oxy)propyl]pyrrolidine (Intermediate III-2)

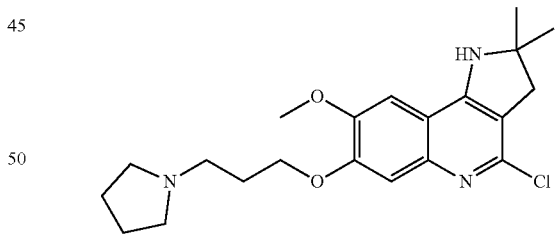

Step 1

To a solution of 5,5-dimethylpyrrolidin-2-one (2.0 g, 17.67 mmol, 1.00 eq.) in N,N-dimethylformamide (50 mL) was added sodium hydride (848 mg, 21.20 mmol, 1.20 eq.) in portions at 0° C. The resulting solution was allowed to stir under $N_2$ at 0° C. for 0.5 h. To the above solution was added a solution of p-methoxybenzyl chloride (3.32 g, 21.20 mmol, 1.20 eq.) in N,N-dimethylformamide (10 mL) dropwise over 5 min. The solution was allowed to stir at room temperature for 16 h before being quenched by water. The mixture was extracted with EtOAc thrice. The combined organic layer was washed with brine, dried over anhydrous sodium sulfate and concentrated under reduced pressure.

The residue was purified by reverse phase preparative MPLC (Prep-C18, 20-45 µM, 120 g, Tianjin Bonna-Agela Technologies; gradient elution of 40-60% MeCN in water over a 8 min period, where both solvents contain 0.1% formic acid (FA)) to provide 1-[(4-methoxyphenyl)methyl]-5,5-dimethylpyrrolidin-2-one as a yellow oil (2.87 g, 70%). LCMS (ES) [M+1]⁺ m/z 234.1.

Step 2

Into a 100-mL 3-necked round-bottom flask, was placed a solution of 1-[(4-methoxyphenyl)-methyl]-5,5-dimethyl-pyrrolidin-2-one (2.00 g, 8.57 mmol, 1.00 eq.) in dry THF (40 mL). To the above solution was added a solution of t-BuLi (12.3 mL, 1.6 M in pentane, 19.7 mmol, 2.3 eq.) dropwise with stirring at −78° C. The resulting solution was allowed to stir for 1.5 h at −78° C. under N₂. Dry CO₂ gas was allowed to run through the above solution at −78° C. for 0.5 h. After warming to 0° C., the reaction mixture was quenched by saturated aqueous NH₄Cl solution and diluted with water. The pH was adjusted to 2-3 with concentrated HCl and then extracted with EtOAc thrice. The combined organic layers were dried over anhydrous sodium sulfate and concentrated under reduced pressure to provide 1-[(4-methoxyphenyl)methyl]-5,5-dimethyl-2-oxopyrrolidine-3-carboxylic acid as a colorless oil (2.10 g, 87%). LCMS (ES) [M+1]⁺ m/z 278.2.

Step 3

Into a 50-mL round-bottom flask, was placed a mixture of 1-[(4-methoxyphenyl)methyl]-5,5-dimethyl-2-oxopyrrolidine-3-carboxylic acid (2.10 g, 7.57 mmol, 1.00 eq.), 4-methoxy-3-[3-(pyrrolidin-1-yl)propoxy]aniline (Intermediate I-2) (1.90 g, 7.59 mmol, 1.00 eq.), dichloromethane (30 mL), DIEA (1.96 g, 15.17 mmol, 2.00 eq.) and HATU (3.46 g, 9.10 mmol, 1.20 eq.). The resulting solution was allowed to stir at rt for 0.5 h. The solution was diluted with dichloromethane and washed with saturated aqueous NaHCO₃ solution. The organic layer was separated, dried over anhydrous sodium sulfate, concentrated under reduced pressure and purified by silica gel column chromatography with petroleum ether/THF (5% TEA) (1/2) as the eluents to provide N-[4-methoxy-3-[3-(pyrrolidin-1-yl)propoxy]phenyl]-1-[(4-methoxyphenyl)methyl]-5,5-dimethyl-2-oxopyrrolidine-3-carboxamide as a brown oil (2.10 g, 54%). LCMS (ES) [M+1]⁺ m/z 510.2.

Step 4

Into a 100-mL round-bottom flask, was placed a mixture of N-[4-methoxy-3-[3-(pyrrolidin-1-yl)propoxy]phenyl]-1-[(4-methoxyphenyl)methyl]-5,5-dimethyl-2-oxopyrrolidine-3-carboxamide (1.50 g, 2.94 mmol, 1.00 eq.) and POCl₃ (30 mL). The resulting solution was allowed to stir under reflux for overnight. The solution was concentrated under reduced pressure. To the residue was added ice water and the pH value was adjusted to 8 with NaHCO₃ (solid). The mixture was extracted with a mixed solution of 10% MeOH/dichloromethane (3×30 mL). The combined organic layers were dried over anhydrous sodium sulfate and concentrated under reduced pressure. The residue was purified by flash chromatography on silica gel column with petroleum ether/THF (1/2) (mixed with 5% TEA) to provide 1-[3-(([4-chloro-8-methoxy-2,2-dimethyl-1H,2H,3H-pyrrolo[3,2-c]quinolin-7-yl]oxy)propyl]pyrrolidine (Intermediate III-2) as a brown oil (700 mg, 61%). LCMS (ES) [M+1]⁺ m/z 390.2.

Reference 16

Synthesis of 1-[3-({5-chloro-9-methoxybenzo[h]1,6-naphthyridin-8-yl}oxy)propyl]pyrrolidine (Intermediate III-3)

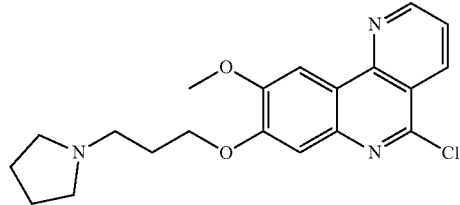 [SMILES: COc1cc2c(cc1OCCCN1CCCC1)nc(Cl)c1cccnc12]

Step 1

Into a 250-mL 3-necked round-bottom flask purged and maintained with an inert atmosphere of nitrogen was placed a mixture of 1-{3-[4-(4,4-dimethyl-1,3,2-dioxaborolan-2-yl)-2-methoxy-5-nitrophenoxy]propyl}pyrrolidine (Intermediate I-5) (2.8 g, 6.89 mmol, 1.00 eq.), 1,4-dioxane (100 mL), methyl 2-chloropyridine-3-carboxylate (1.77 g, 10.32 mmol, 1.50 eq.), potassium carbonate (1.9 g, 13.75 mmol, 2.00 eq.), and Pd(PPh₃)₄ (797 mg, 0.69 mmol, 0.10 eq.). The resulting mixture was allowed to stir at 100° C. under N₂ for 4 h. The mixture was concentrated under reduced pressure. The residue was purified by flash chromatography on silica gel column eluted with 10% MeOH/CH₂Cl₂ to provide methyl 2-[5-methoxy-2-nitro-4-[3-(pyrrolidin-1-yl)propoxy]phenyl]pyridine-3-carboxylate (1.6 g, 56%) as a gray solid. LCMS (ES) [M+1]⁺ m/z 416.1.

Step 2

Into a 100-mL round-bottom flask, was placed a mixture of methyl 2-[5-methoxy-2-nitro-4-[3-(pyrrolidin-1-yl)propoxy]phenyl]pyridine-3-carboxylate (1.3 g, 3.13 mmol, 1.00 eq.), ethanol (50 mL), water (5 mL), Iron powder (1.75 g, 31.30 mmol, 10.00 eq.) and NH₄Cl (830 mg, 15.52 mmol, 5.00 eq.). The resulting mixture was allowed to stir at 90° C. for 6 h. The solids were filtered off. The filtrate was concentrated under reduced pressure. The residue was purified by flash chromatography on silica gel column eluted with 10-15% MeOH/CH₂Cl₂ to provide 9-methoxy-8-[3-(pyrrolidin-1-yl)propoxy]-5H,6H-benzo[h]1,6-naphthyridin-5-one as a red solid (780 mg, 71%). LCMS (ES) [M+1]⁺ m/z 354.1.

Step 3

Into a 50-mL round-bottom flask, was placed 9-methoxy-8-[3-(pyrrolidin-1-yl)propoxy]-5H,6H-benzo[h]1,6-naphthyridin-5-one (740 mg, 2.09 mmol, 1.00 eq.) and POCl₃ (10 mL). The resulting solution was allowed to stir at 100° C. for 6 h. The resulting mixture was concentrated under reduced pressure. To the residue was added ice water. The pH value of the mixture was adjusted to 7 with Na₂CO₃ (solid). The resulting mixture was concentrated under reduced pressure. The residue was purified by flash chromatography on silica gel column eluted with 10-15% MeOH/dichloromethane to provide 1-[3-({5-chloro-9-methoxybenzo[h]1,6-naphthyridin-8-yl}oxy)propyl]pyrrolidine (Intermediate III-3) as a light yellow solid (430 mg, 55%). LCMS (ES) [M+1]⁺ m/z 372.1.

Reference 17

Synthesis of 1-[3-({5-chloro-9-methoxy-2-methyl-benzo[h]1,6-naphthyridin-8-yl}oxy)-propyl]pyrrolidine (Intermediate III-4)

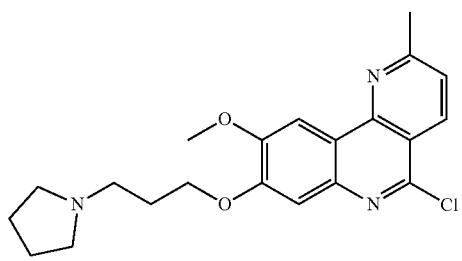 [SMILES: COc1cc2c(cc1OCCCN1CCCC1)nc(Cl)c1ccc(C)nc12]

The title compound was made following a synthetic procedure similar as described in Reference 16 above except that methyl 2-chloro-6-methylpyridine-3-carboxylate was used in the place of methyl 2-chloropyridine-3-carboxylate. LCMS (ES) [M+1]+ m/z 386.2.

Reference 18

Synthesis of 1-[3-({6-chloro-10-methoxy-1H,2H,3H,4H,5H-azepino[3,2-c]quinolin-9-yl}oxy)propyl]pyrrolidine (Intermediate III-5)

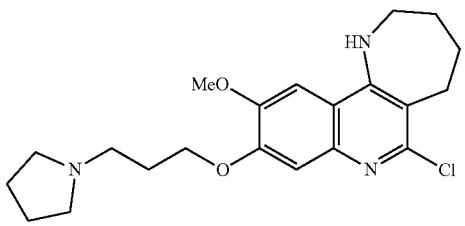 [SMILES: COc1cc2c3c(c(Cl)nc2cc1OCCCN1CCCC1)CCCCN3]

Step 1

Into a 0° C. mixture of sodium hydride (7.78 g, 60% in mineral oil, 194.58 mmol, 1.10 eq.) in THF (200 mL) under $N_2$ was added a solution of azepan-2-one (12.0 g, 106.1 mmol, 1.00 eq.) in THF (100 mL) dropwise over 30 min. The resulting mixture was allowed to stir for 30 min at 0° C. To this resulting mixture was added a solution of p-methoxybenzyl chloride (18.2 g, 116.21 mmol, 1.10 eq.) in THF (100 mL) dropwise over 20 min. The resulting solution was allowed to stir at room temperature for 3 h, and was quenched with water under $N_2$ atmosphere. The resulting mixture was concentrated under reduced pressure. The residue was purified by flash chromatography on silica gel column eluted with ethyl acetate/petroleum ether (1/1) to provide 1-[(4-methoxyphenyl)methyl]azepan-2-one as a light yellow oil (7.2 g, 29%). LCMS (ES) [M+1]+ m/z 234.1.

Step 2

Into a 500-mL 3-necked round-bottom flask, was placed a solution of 1-[(4-methoxyphenyl)-methyl]azepan-2-one (7.3 g, 31.29 mmol, 1.00 eq.) in THF (150 mL). To the resulting solution at −78° C. under $N_2$ was added lithium diisopropylamide (LDA) (39.2 mL, 2 M, 78.3 mmol, 2.5 eq.) dropwise. The resulting solution was allowed to stir at −78° C. for 30 min. To the above solution was added a solution of dimethyl carbonate (5.6 g, 62.6 mmol, 2.0 eq.) in THF (50 mL) at −78° C. The resulting mixture was allowed to warm to room temperature and stirred for 2 h. The reaction was then quenched by saturated aqueous $NH_4Cl$, extracted with 105 $MeOH/CH_2Cl_2$ twice. The combined organic layers were concentrated under reduced pressure. The residue was purified by flash chromatography on silica gel column eluted with ethyl acetate/petroleum ether (1/1) to provide methyl 1-[(4-methoxyphenyl)methyl]-2-oxoazepane-3-carboxylate as yellow oil (6.8 g, 75%). LCMS (ES) [M+1]+ m/z 292.1.

Step 3

Into a 250-mL round-bottom flask, was placed a mixture of methyl 1-[(4-methoxyphenyl)-methyl]-2-oxoazepane-3-carboxylate (6.7 g, 23.00 mmol, 1.00 eq.), methanol (100 mL) and sodium hydroxide (2.76 g, 69.00 mmol, 3.00 eq.). The resulting solution was allowed to stir for 3 h at room temperature. The pH of the reaction mixture was adjusted to ~6 with aqueous HCl (1.0 M) and then concentrated under reduced pressure. The residue was purified by flash chromatography on silica gel column eluted with 10% MeOH/dichloromethane to provide 1-[(4-methoxyphenyl)methyl]-2-oxoazepane-3-carboxylic acid a yellow solid (6.1 g, 96%). LCMS (ES) [M+1]+ m/z 278.1.

Step 4

Into a 1-L round-bottom flask, was placed a mixture of 1-[(4-methoxyphenyl)methyl]-2-oxoazepane-3-carboxylic acid (6.1 g, 22.00 mmol, 1.00 eq.), $CH_2Cl_2$ (300 mL), 4-methoxy-3-[3-(pyrrolidin-1-yl)propoxy]aniline (Intermediate I-2) (6.1 g, 24.13 mmol, 1.10 eq.), N,N-diisopropylethylamine (DIEA) (14.2 g, 109.87 mmol, 5.00 eq.) and HATU (9.2 g, 24.20 mmol, 1.10 eq.). The resulting solution was allowed to stir at rt for 4 h. The solution was washed with $H_2O$ (2×50 mL) and concentrated under reduced pressure. The residue was purified by flash chromatography on silica gel column using 10% MeOH/dichloromethane as the eluents to provide N-[4-methoxy-3-[3-(pyrrolidin-1-yl)propoxy]phenyl]-1-[(4-methoxyphenyl)-methyl]-2-oxoazepane-3-carboxamide as yellow oil (8.1 g, 72%). LCMS (ES) [M+1]+ m/z 510.3.

Step 5

Into a 100-mL round-bottom flask, was placed a solution of N-[4-methoxy-3-[3-(pyrrolidin-1-yl)propoxy]phenyl]-1-[(4-methoxyphenyl)methyl]-2-oxoazepane-3-carboxamide (2.5 g, 4.91 mmol, 1.00 eq.) and $POCl_3$ (30 mL). The resulting solution was allowed to stir at 100° C. for 10 h. The mixture was concentrated under reduced pressure. The residue was diluted with ice water (30 mL). The reaction mixture was treated with potassium carbonate (solid) till pH-99 and extracted with a mixed solution of 20% dichloromethane/80% MeOH thrice. The combined organic layers were dried over anhydrous sodium sulfate and concentrated under reduced pressure. The residue was purified by flash chromatography on silica gel column eluted with 10-20% MeOH/dichloromethane/methanol (0.1% $NH_4OH$) to provide the title compound (Intermediate III-5) as a yellow solid (0.9 g, 47%). LCMS (ES) [M+1]+ m/z 390.2.

Reference 19

Synthesis of 1-[3-({5-chloro-9-methoxy-1H,2H,4H-pyrano[3,4-c]quinolin-8-yl}oxy)-propyl]pyrrolidine (Intermediate III-6)

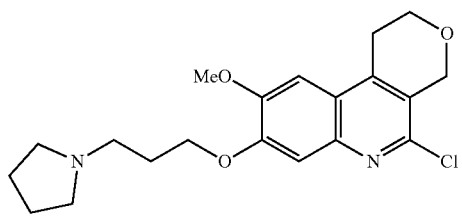 [SMILES: COc1cc2c3c(c(Cl)nc2cc1OCCCN1CCCC1)COCC3]

Step 1

Into a 250-mL round-bottom flask, was placed a mixture of methyl 4-oxo-tetrahydro-2H-pyran-3-carboxylate (5.64 g, 35.69 mmol, 1.00 eq.), toluene (100 mL), ethane-1,2-diol (4.43 g, 71.39 mmol, 2.0 eq.), p-TsOH (615 mg, 3.57 mmol, 0.10 eq.). The resulting mixture was allowed to stir for 24 h with reflux under a dean stark trap. The mixture was concentrated and the residue was purified by a silica gel column eluted with 20% ethyl acetate/petroleum ether to afford methyl 1,4,8-trioxaspiro[4.5]decane-6-carboxylate as a colorless oil (6.7 g, 93%). LCMS (ES) [M+1]+ m/z 203.1.

Step 2

Into a mixture of methyl 1,4,8-trioxaspiro[4.5]decane-6-carboxylate (6.70 g, 33.16 mmol, 1.00 eq.) in MeOH/THF/H$_2$O (50 mL/50 mL/50 mL) was added NaOH (2.65 g, 66.32 mmol, 2.0 eq.). The resulting solution was allowed to stir at room temperature for 4 h. The organic solvents were removed under reduced pressure. The resulting mixture was acidified to pH 5~6 with aqueous HCl (1.0 N), extracted with ethyl acetate thrice The combined organic layer was washed with brine, dried over anhydrous sodium sulfate and concentrated under reduced pressure to provide 1,4,8-trioxaspiro[4.5]decane-6-carboxylic acid as white solid (3.97 g, 64%). LCMS (ES) [M−1]− m/z 187.1.

Step 3

The title compound was made following a procedure similar as described above in Reference 11, Steps 5-8 but using 1,4,8-trioxaspiro[4.5]decane-6-carboxylic acid and 4-methoxy-3-[3-(pyrrolidin-1-yl)propoxy]aniline (Intermediate I-2).The final crude product was purified by flash chromatography on silica gel column eluted with 10% MeOH/CH$_2$Cl$_2$ (0.1% NH$_4$OH) to afford the title compound as a white solid. LCMS (ES) [M+1]+ m/z 377.2.

Reference 20

Synthesis of 1-[3-({4-chloro-8-methoxy-1H,3H-furo[3,4-c]quinolin-7-yl}oxy)propyl]pyrrolidine (Intermediate III-7)

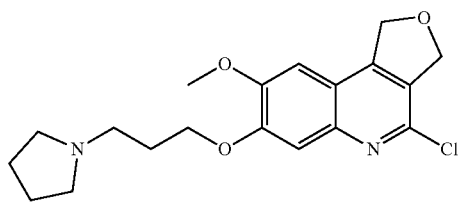 [SMILES: COc1cc2c3c(c(Cl)nc2cc1OCCCN1CCCC1)COC3]

The title compound was prepared from 4-methoxy-3-[3-(pyrrolidin-1-yl)propoxy]aniline (Intermediate I-2) and ethyl 4-oxotetrahydrofuran-3-carboxylate following a synthetic sequences similar as described for the synthesis of 8-methoxy-7-[3-(pyrrolidin-1-yl)propoxy]-1H,2H,3H-cyclopenta[c]quinolin-4-ol in Example 37 below and (Intermediate II-1 above, except that final crude product was purified by reverse phase preparative MPLC (Prep-C18, 20-45 μM, 120 g, Tianjin Bonna-Agela Technologies; gradient elution of 25-45% MeCN in water over a 12 min period, where both solvents contain 0.1% formic acid (FA)) to provide the desired compound of 1-[3-({4-chloro-8-methoxy-1H,3H-furo[3,4-c]quinolin-7-yl}oxy)propyl]pyrrolidine (Intermediate III-7) as formate salt. LCMS (ES) [M-FA+1]+ m/z 363.2.

Reference 21

Synthesis of 8-(benzyloxy)-6-chloro-2-methoxy-3-[3-(pyrrolidin-1-yl)propoxy]-7,8,9,10-tetrahydrophenanthridine (Intermediate III-8)

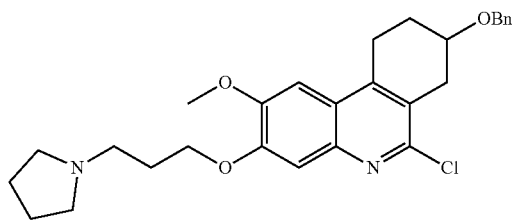 [SMILES: COc1cc2c3c(c(Cl)nc2cc1OCCCN1CCCC1)CC(OCc1ccccc1)CC3]

Step 1

Into a 250-mL round-bottom flask was placed a solution of 4-(benzyloxy)cyclohexan-1-one (10.0 g, 48.96 mmol, 1.00 eq.) in THF (100 mL). The flask was placed into ice bath, to the solution was added sodium hydride (2.35 g, 60% dispersion in mineral oil, 58.75 mmol, 1.20 eq.) and dimethyl carbonate (6.62 g, 73.49 mmol, 1.50 eq.) under N2 atmosphere. The resulting mixture was allowed to stir in an oil bath at 80° C. for 2 h. After cooling the reaction to room temperature, the reaction mixture was quenched with water and extracted with ethyl acetate thrice. The combined organic layers were washed with brine, dried over anhydrous sodium sulfate and concentrated under reduced pressure to provide methyl 5-(benzyloxy)-2-oxocyclohexane-1-carboxylate as a colorless oil (12.5 g, 97%). LCMS (ES) [M+1]+ m/z 263.1.

Step 2

Into a 250-mL round-bottom flask, was placed a mixture of methyl 5-(benzyloxy)-2-oxo-cyclohexane-1-carboxylate (9.18 g, 35.00 mmol, 1.00 eq.), ethane-1,2-diol (21.7 g, 349.62 mmol, 10.00 eq.), p-TsOH (1.81 g, 10.50 mmol, 0.30 eq.) and toluene (100 mL). The resulting solution was allowed to stir at 125° C. for 16 h with Dean-Stark trap to remove water. The reaction mixture was allowed to cool for rt and concentrated under reduced pressure. The remaining residue was diluted with 200 mL of H$_2$O, and the mixture was extracted with of ethyl acetate thrice. The combined organic layers were washed with brine, dried over anhydrous sodium sulfate and concentrated under reduced pressure to provide the desired crude product of methyl 8-(benzyloxy)-1,4-dioxaspiro[4.5]decane-6-carboxylate as a yellow oil (10.8 g).

Step 3

Into a 250-mL round-bottom flask, was placed a solution of methyl 8-(benzyloxy)-1,4-dioxaspiro[4.5]decane-6-carboxylate (5.50 g, 17.95 mmol, 1.00 eq.), methanol (100 mL), water (10 mL) and sodium hydroxide (3.59 g, 89.75 mmol, 5.00 eq.) in portions. The resulting solution was allowed to stir at 60° C. for 2 h and then concentrated under reduced pressure. The residue was diluted with 100 mL of H$_2$O. The pH value of the solution was adjusted to 5 with aqueous HCl (2.0 N). The mixture was extracted with 10% MeOH/CH$_2$Cl$_2$ five times. The combined organic layers were dried over anhydrous sodium sulfate and concentrated under reduced pressure to provide the desired crude product of 8-(benzyloxy)-1,4-dioxaspiro[4.5]decane-6-carboxylic acid as yellow oil (4.75 g, 91%). LCMS (ES) [M+1]$^+$ m/z 293.1.

Step 4

Into a 250-mL round-bottom flask, was placed a mixture of 8-(benzyloxy)-1,4-dioxaspiro-[4.5]decane-6-carboxylic acid (4.50 g, 15.39 mmol, 1.00 eq.), N,N-dimethylformamide (60 mL), 4-methoxy-3-[3-(pyrrolidin-1-yl)propoxy]aniline (3.85 g, 15.34 mmol, 1.00 eq.), N,N-diisopropylethylamine (DIEA) (5.96 g, 46.12 mmol, 3.00 eq.) and HATU (8.78 g, 23.09 mmol, 1.50 eq.). The mixture was allowed to stir at rt for 1.0 h. The resulting mixture was diluted with H$_2$O and extracted with ethyl acetate thrice. The combined organic layers were washed with water and brine, dried over anhydrous sodium sulfate and concentrated under reduced pressure to provide 8-(benzyloxy)-N-[4-methoxy-3-[3-(pyrrolidin-1-yl)propoxy]phenyl]-1,4-dioxaspiro[4.5]decane-6-carboxamide as yellow oil (5.13 g, 64%) of. LCMS (ES) [M+1]$^+$ m/z 525.3.

Step 5

Into a 0° C. mixture of 8-(benzyloxy)-N-[4-methoxy-3-[3-(pyrrolidin-1-yl)propoxy]phenyl]-1,4-dioxaspiro[4.5]decane-6-carboxamide (5.13 g, 9.78 mmol, 1.00 eq.) in THF (50 mL) was added aq. HCl (37% 15 mL) dropwise over 5 min. The solution was allowed to stir at rt for 0.5 h. The resulting mixture was then concentrated under reduced pressure. The residue was diluted with 100 mL of H$_2$O. The pH value of the solution was adjusted to 8 with aq. NaOH (2.0 N). The resulting mixture was extracted with 10% MeOH/CH$_2$Cl$_2$ four times. The combined organic layers were dried over anhydrous sodium sulfate and concentrated under reduced pressure to provide 5-(benzyloxy)-N-[4-methoxy-3-[3-(pyrrolidin-1-yl)propoxy]phenyl]-2-oxocyclohexane-1-carboxamide as brown crude oil (4.56 g, 97%). LCMS (ES) [M+1]$^+$ m/z 481.3.

Step 6

Into a 50-mL round-bottom flask, was placed a mixture of 5-(benzyloxy)-N-[4-methoxy-3-[3-(pyrrolidin-1-yl)propoxy]phenyl]-2-oxocyclohexane-1-carboxamide (4.56 g, 9.49 mmol, 1.00 eq.) and POCl$_3$ (15 mL). The resulting solution was allowed to stir for at 100° C. for 2 hand then concentrated under reduced pressure. To the residue was added 100 mL of ice water. The pH value of the solution was adjusted to 8 with aq. NaOH (2.0 N), and the mixture was extracted with 10% MeOH/CH$_2$Cl$_2$ four times. The combined organic layers were dried over anhydrous sodium sulfate and concentrated under reduced pressure to provide crude -(benzyloxy)-6-chloro-2-methoxy-3-[3-(pyrrolidin-1-yl)propoxy]-7,8,9,10-tetrahydrophenanthridine (Intermediate III-8) as brown crude oil (4.12 g, 90%). LCMS (ES) [M+1]$^+$ m/z 481.2.

Reference 22

Synthesis of 1-[3-({5-chloro-9-methoxy-3-methyl-1H,2H,3H,4H-benzo[c]2,7-naphthyridin-8-yl}oxy)propyl]pyrrolidine (Intermediate III-9)

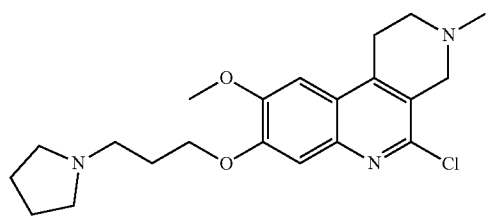 [SMILES: COc1cc2c3c(c(Cl)nc2cc1OCCCN1CCCC1)CN(C)CC3]

Step 1

Into a −78° C. solution of 1-tert-butyl 3-methyl 4-oxopiperidine-1,3-dicarboxylate (2.0 g, 7.78 mmol, 1.00 eq.),in CH$_2$Cl$_2$ (50 mL) was added N,N-diisopropylethylamine (DIEA) (2.0 g, 15.56 mmol, 2.0 eq.) followed by Tf$_2$O (3.28 g, 11.67 mmol, 1.50 eq.) dropwise. The resulting mixture was allowed to warm to rt and to stir for 3 h. The reaction mixture was quenched by H$_2$O and extracted with CH$_2$Cl$_2$. The combined organic layers were dried over the anhydrous Na$_2$SO$_4$, filtered and concentrated under reduced pressure. The residue was purified by flash chromatography on silica gel column eluted with 25% ethyl acetate/petroleum ether to provide 1-(tert-butyl)-3-methyl-4-(((trifluoromethyl)-sulfonyl)oxy)-5,6-dihydropyridine-1,3(2H)-dicarboxylate as yellow oil (2.4 g, 80%). LCMS (ES) [M+1]$^+$ m/z 390.1.

Step 2

Into a 50-mL round-bottom flask was placed a mixture of 1-(tert-butyl)-3-methyl-4-(((trifluoromethyl)sulfonyl)oxy)-5,6-dihydropyridine-1,3(2H)-dicarboxylate (479 mg, 1.23 mmol, 1.00 eq.), dioxane (8 mL), water (2 mL), 1-{3-[4-(4,4-dimethyl-1,3,2-dioxaborolan-2-yl)-2-methoxy-5-nitrophenoxy]propyl}pyrrolidine (Intermediate I-5) (500 mg, 1.23 mmol, 1.0 eq.), Pd(PPh$_3$)$_4$ (141 mg, 0.123 mmol, 0.1 eq.) and Na$_2$CO$_3$ (326 mg, 3.07 mmol, 2.5 eq.). The mixture was allowed to stir at reflux under N$_2$ for overnight. The resulting mixture was concentrated under reduced pressure. The residue was purified by flash chromatography on silica gel column eluted with 50% ethyl acetate/petroleum ether to provide 1-(tert-butyl) 3-methyl-4-(5-methoxy-2-nitro-4-(3-(pyrrolidin-1-yl)propoxy)phenyl)-5,6-dihydropyridine-1,3(2H)-dicarboxylate as brown solid (216 mg, 34%). LCMS (ES) [M+1]$^+$ m/z 520.3.

Step 3

Into a 50-mL round-bottom flask, was placed a mixture of 1-(tert-butyl) 3-methyl-4-(5-methoxy-2-nitro-4-(3-(pyrrolidin-1-yl)propoxy)phenyl)-5,6-dihydropyridine-1,3(2H)-dicarboxylate (216 mg, 0.415 mmol, 1.00 eq.), MeOH (10 mL) and 10% Pd/C (50 mg). The mixture was degassed and purged with hydrogen. The resulting mixture was allowed to stir under H$_2$ atmosphere at rt for overnight. The reaction mixture was diluted with MeOH (10 mL) and filtered through a small pad of celite. The filtrate was concentrated under reduced pressure to provide tert-butyl 5-hydroxy-9-methoxy-8-(3-(pyrrolidin-1-yl)propoxy)-1,2-dihydrobenzo[c][2,7]naphthyridine-3(4H)-carboxylate as brown oil (200 mg, 95%). LCMS (ES) [M+1]$^+$ m/z 458.3.

Step 4

Into a 25-mL round-bottom flask was placed tert-butyl 5-hydroxy-9-methoxy-8-(3-(pyrrolidin-1-yl)propoxy)-1,2- dihydrobenzo[c][2,7]naphthyridine-3(4H)-carboxylate (200 mg, 0.436 mmol, 1.00 eq.) followed by POCl$_3$ (10 mL). The resulting solution was allowed to stir at 110° C. for 2 h. The organic volatiles were reduced under reduced pressure. To the residue was added 5 mL of ice/water and the pH value was adjusted to 8 with Na$_2$CO$_3$ (solid). The precipitate was collected through filtration to afford 5-chloro-9-methoxy-8-(3-(pyrrolidin-1-yl)propoxy)-1,2,3,4-tetrahydrobenzo[c][2,7]naphthyridine (180 mg, 91%). LCMS (ES) [M+1]$^+$ m/z 376.1.

Step 5

Into a 25-mL round-bottom flask, were placed a mixture of 5-chloro-9-methoxy-8-(3-(pyrrolidin-1-yl)propoxy)-1,2,3,4-tetrahydrobenzo[c][2,7]naphthyridine (180 mg, 0.478 mmol, 1.00 eq.), acetonitrile (5 mL), water (2 mL), CH$_2$O (37% (aq.), 0.2 mL) and NaBH$_3$CN (74.6 mg, 1.18 mmol, 2.5 eq.). The resulting mixture was allowed to stir at rt for 4 h. The mixture was filtered and subjected to reverse phase preparative MPLC (Prep-C18, 20-45 µM, 120 g, Tianjin Bonna-Agela Technologies; gradient elution of 20-40% MeCN in water over a 7 min period, where both solvents contain 0.1% formic acid (FA)) to provide the title compound (Intermediate III-9) in form of formate salt as a brown solid (110 mg, 59%). LCMS (ES) [M+1]$^+$ m/z 390.3.

Reference 23

Synthesis of 1-[3-({5-chloro-9-methoxy-2,2-dimethyl-1H,2H,3H,4H-benzo[h]1,6-naphthyridin-8-yl}oxy)propyl]pyrrolidine (Intermediate III-10)

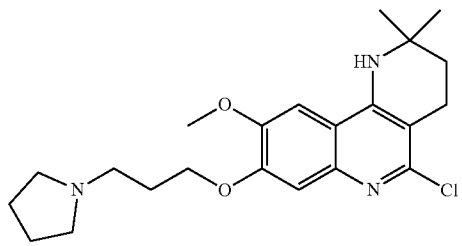 [SMILES: COc1cc2c3c(c(Cl)nc2cc1OCCCN1CCCC1)CCC(C)(C)N3]

Step 1

To a solution of 3-[[(tert-butoxy)carbonyl]amino]-3-methylbutanoic acid (50.0 g, 230.4 mmol, 1.00 eq.) in dichloromethane (1200 mL) was added 2,2-dimethyl-1,3-dioxane-4,6-dione (33.1 g, 230.4 mmol, 1.00 eq.), EDCI (48.7 g, 253.4 mmol, 1.10 eq.) and 4-dimethylaminopyridine (30.9 g, 253.4 mmol, 1.10 eq.). The resulting solution was allowed to stir for at room temperature for 16 h. The solution was washed with H$_2$O (3×200 mL), dried over anhydrous sodium sulfate and concentrated under vacuum to provide tert-butyl 4-(2,2-dimethyl-4,6-dioxo-1,3-dioxan-5-yl)-2-methyl-4-oxobutan-2-ylcarbamate as an off-white solid (60.5 g, 77%). LCMS (ES) [M−1]$^−$ m/z 342.1.

Step 2

To a 0° C. solution of tert-butyl N-[4-(2,2-dimethyl-4,6-dioxo-1,3-dioxan-5-yl)-2-methyl-4-oxobutan-2-yl]carbamate (60.5 g, 176.2 mmol, 1.00 eq.) in AcCN/AcOH (600 mL, V/V=3:1) was added NaBH$_4$ (20.1 g, 528.6 mmol, 3.00 eq.) in portions over 15 min. The resulting solution was stirred at rt for 16 h. The mixture was concentrated under vacuum. The residue was subjected to reverse preparative HPLC (Prep-C18, 20-45 µM, 120 g, Tianjin Bonna-Agela Technologies; gradient elution of 40% MeCN in water to 71% MeCN in water over a 9 min period, where both solvents contain 0.1% TFA) to provide tert-butyl 4-(2,2-dimethyl-4,6-dioxo-1,3-dioxan-5-yl)-2-methylbutan-2-ylcarbamate as a white solid (35.5 g, 61%). LCMS (ES) [M−1]$^−$ m/z 328.1.

Step 3

To a solution of tert-butyl N-[4-(2,2-dimethyl-4,6-dioxo-1,3-dioxan-5-yl)-2-methylbutan-2-yl]carbamate (35.5 g, 107.9 mmol, 1.00 eq.) in methanol (150 mL) was added dioxane (150 mL) which was freshly saturated with hydrochloride (gas). The resulting solution was allowed to stir rt for 16 h. The solution was concentrated under vacuum to provide dimethyl 2-(3-amino-3-methylbutyl)malonate hydrochloride as a white solid (23.5 g, 86%). LCMS (ES) [M+1]$^+$ m/z 218.1.

Step 4

Into a 250-mL round-bottom flask, was placed a solution of methanol (150 mL), 1,3-dimethyl 2-(3-amino-3-methylbutyl)propanedioate hydrochloride (23.5 g, 92.9 mmol, 1.00 eq.) and TEA (28.1 g, 278.7 mmol, 3.00 eq.). The resulting solution was allowed to stir at 65° C. for 24 h. The volatiles were removed under vacuum. The residue was re-dissolved in with EtOAc (200 mL), washed with brine (2×50 mL), and dried over anhydrous sodium sulfate. Revoal of the organic solvents under reduced pressure provided methyl 6,6-dimethyl-2-oxopiperidine-3-carboxylate as a white solid (20.3 g, crude). LCMS (ES) [M+1]$^+$ m/z 186.2.

Step 5

To a solution of methyl 6,6-dimethyl-2-oxopiperidine-3-carboxylate (10.0 g, 54.0 mmol 1.00 eq.) in a mixed solution of THF/MeOH/H$_2$O (100 mL, V/V/V=5:5:1) was added lithium hydroxide monohydrate (4.54 g, 108.0 mmol, 2.00 eq.). The resulting mixture was allowed to stir at rt for 16 h. The mixture was concentrated under vacuum. The residue was diluted with H$_2$O (20 mL), acidified carefully with aqueous HCl (1.0 N) to pH ~4, and the resulting mixture was extracted with CH$_2$Cl$_2$/MeOH (V/V=5:1, 3×50 mL). The combined organic layers were dried over anhydrous sodium sulfate and concentrated under vacuum to provide 6,6-dimethyl-2-oxopiperidine-3-carboxylic acid as a white solid (7.8 g, 84%). LCMS (ES) [M+1]$^+$ m/z 172.2.

Step 6

To a solution of 6,6-dimethyl-2-oxopiperidine-3-carboxylic acid (8.0 g, 46.7 mmol, 1.00 eq.) in N,N-dimethylformamide (150 mL) was added TEA (12.0 g, 116.8 mmol, 2.50 eq.), 4-methoxy-3-[3-(pyrrolidin-1-yl)propoxy]aniline (14.0 g, 56.0 mmol, 1.20 eq.), HOBt (9.5 g, 70.0 mmol, 1.50 eq.) and EDCI (13.4 g, 70.0 mmol, 1.50 eq.). The resulting solution was stirring for 16 h at room temperature. The crude reaction mixture was filtered and subjected to reverse preparative HPLC (Prep-C18, 20-45 µM, 120 g, Tianjin Bonna-Agela Technologies; gradient elution of 5% MeCN in water to 30% MeCN in water over a 7 min period, where both solvents contain 0.1% TFA) over multiple runs to provide N-(4-methoxy-3-(3-(pyrrolidin-1-yl)propoxy)phenyl)-6,6-dimethyl-2-oxopiperidine-3-carboxamide as a white solid (16.8 g, 89%). LCMS (ES) [M+1]$^+$ m/z 404.2.

Step 7

Into a 250-mL sealed tube, was placed a solution of POCl$_3$ (100 mL) and N-[4-methoxy-3-[3-(pyrrolidin-1-yl)propoxy]phenyl]-6,6-dimethyl-2-oxopiperidine-3-carboxamide (10.0 g, 24.8 mmol, 1.00 eq.). The resulting solution was stirred at 170° C. for 7 h and then concentrated under reduced pressure. The residue was pured into ice water (50 mL) and carefully basified with aqueous solution NaOH (2.0 N) (pH ~8) and extracted with CH$_2$Cl$_2$/MeOH (V/V=5:1, 3×200 mL). The combined organic layers were dried over anhydrous sodium sulfate and concentrated under vacuum. The crude was diluted with DMF (50 mL), filtered and subjected to reverse preparative HPLC (Prep-C18, 20-45 μM, 120 g, Tianjin Bonna-Agela Technologies; gradient elution of 40% MeCN in water to 71% MeCN in water over a 7 min period, where both solvents contain 0.1% TFA) over multiple runs to provide the title compound as an off-white solid. The compound was further purified by a silica gel column eluted with DCM/MeOH (4/1) to provide the title compound as a brown solid (0.5447 g, 5%). $^1$H NMR (300 MHz, CD$_3$OD-d$_4$) δ 7.20 (s, 1H), 6.80 (s, 1H), 4.75 (s, 1H), 4.17 (t, J=5.9 Hz, 2H), 4.00 (s, 3H), 3.25-3.10 (m, 6H), 2.92 (t, J=6.6 Hz, 2H), 2.39-2.33 (m, 2H), 2.07-2.02 (m, 5H), 1.83 (t, J=6.6 Hz, 2H), 1.37 (s, 6H). LCMS (ES) [M+1]$^+$ m/z 404.2.

Reference 24

Synthesis of 1-[3-({4-chloro-8-methoxy-1H,2H,3H-cyclopenta[c]quinolin-7-yl}oxy)propyl]piperidine (Intermediate III-11)

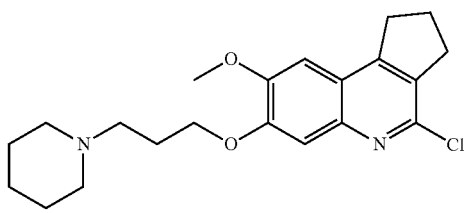 [SMILES: COc1cc2c3c(c(Cl)nc2cc1OCCCN1CCCCC1)CCC3]

The title compound was made from 2-methoxy-5-nitrophenol and 1-(3-chloropropyl)piperidine hydrogen chloride following a procedure similar as described above for Intermediate II-1. The crude product was purified by a silica gel column eluted with dichloromethane/methanol (10/1) to provide the title compound as light brown solid. LCMS (ES) [M+1]$^+$ m/z 375.1.

Reference 25

Synthesis of 1-[3-({4-chloro-8-methoxy-1H,2H,3H-cyclopenta[c]quinolin-7-yl}oxy)propyl]-3,3-dimethylpyrrolidine (Intermediate III-12)

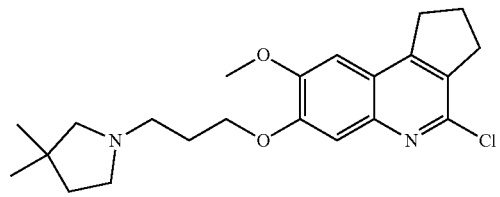 [SMILES: COc1cc2c3c(c(Cl)nc2cc1OCCCN1CCC(C)(C)C1)CCC3]

Step 1

Into a 500-mL round-bottom flask, was placed a mixture of 2-methoxy-5-nitrophenol (10.0 g, 59.17 mmol, 1.00 eq.), CH$_3$CN (200 mL), 1-chloro-3-iodopropane (18.11 g, 88.76 mmol, 1.50 eq.) and potassium carbonate (16.33 g, 118.34 mmol, 2.00 eq.). The resulting mixture was allowed to stir at 85° C. for 3 h and cooled to room temperature. The solids were filtered off and the filtrate was concentrated under vacuum. The residue was purified by a silica gel column eluted with ethyl acetate/petroleum ether (1/2) to provide 2-(3-chloropropoxy)-1-methoxy-4-nitrobenzene as an off-white solid (7.86 g, 54%).

Step 2

Into a 250-mL round-bottom flask, was placed a mixture of 2-(3-chloropropoxy)-1-methoxy-4-nitrobenzene (5.0 g, 20.41 mmol, 1.00 eq.), CH$_3$CN (100 mL), 3,3-dimethylpyrrolidine hydrochloride (2.76 g, 20.41 mmol, 1.00 eq.), Cs$_2$CO$_3$ (13.31 g, 40.82 mmol, 2.00 eq.) and KI (6.78 g, 40.82 mmol, 2.00 eq.). The resulting mixture was allowed to stir for 16 h at 80° C. and cooled to room temperature. The solids were filtered off, and the filtrate was concentrated under vacuum. The residue was purified by a silica gel column eluted with dichloromethane/methanol (10/1) to provide 1-[3-(2-methoxy-5-nitrophenoxy)propyl]-3,3-dimethylpyrrolidine as a yellow solid (5.21 g, 83%). LCMS (ES) m/z 309.1 [M+1]$^+$.

Step 3~Step 6

The title compound was made from 1-[3-(2-methoxy-5-nitrophenoxy)propyl]-3,3-dimethylpyrrolidine following a procedure similar as described for the synthesis of Intermediate II-1 above. The crude product was purified by a silica gel column eluted with dichloromethane/methanol (10/1) to provide the title compound as a yellow solid. LCMS (ES) m/z 389.2 [M+1]$^+$.

Reference 26

Synthesis of [3-({4-chloro-8-methoxy-1H,2H,3H-cyclopenta[c]quinolin-7-yl}oxy)propyl]dimethylamine (Intermediate III-13)

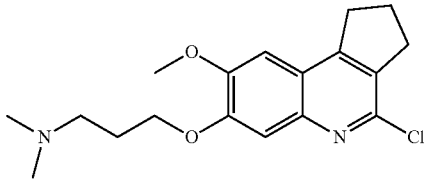 [SMILES: COc1cc2c3c(c(Cl)nc2cc1OCCCN(C)C)CCC3]

The title compound was made from 2-methoxy-5-nitrophenol and 3-chloro-N,N-dimethylpropan-1-amine hydrogen chloride following a procedure similar as described above for the synthesis of Intermediate II-1. The crude product was purified by column chromatography on silica gel eluted with dichloromethane/methanol (10/1) to provide the title compound as an off-white solid. $^1$H NMR (300 MHz, DMSO-d$_6$): 7.33 (s, 1H), 7.14 (s, 1H), 4.15 (t, J=6.0 Hz, 2H), 3.93 (s, 3H), 3.32-3.27 (m, 4H), 3.05 (t, J=6.9 Hz, 2H), 2.44-2.39 (m, 2H), 2.18 (s, 6H), 1.96-1.91 (m, 2H). LCMS (ES) [M+1]$^+$ m/z 335.1.

Reference 27

Synthesis of [3-([4-chloro-8-methoxy-1H,2H,3H-cyclopenta[c]quinolin-7-yl]oxy)propyl]diethylamine (Intermediate III-14)

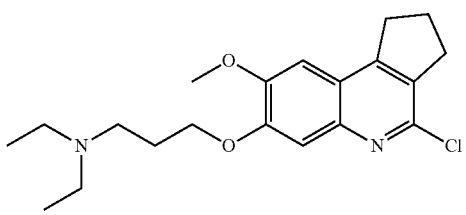 [SMILES: CCN(CC)CCCOc1cc2nc(Cl)c3c(c2cc1OC)CCC3]

The title compound was made from 2-methoxy-5-nitrophenol and 3-chloro-N,N-diethylpropan-1-amine following a procedure similar as described above for the synthesis of Intermediate II-1. The crude product was purified by column chromatography on silica gel eluted with dichloromethane/methanol (10/1) to provide the title compound as an off-white solid. $^1$H NMR (300 MHz, DMSO-d$_6$): 7.32 (s, 1H), 7.09 (s, 1H), 4.17 (t, J=6.0 Hz, 2H), 3.92 (s, 3H), 3.25 (t, J=7.2 Hz, 2H), 3.02 (t, J=7.5 Hz, 2H), 2.80-2.55 (m, 6H), 2.25-2.15 (m, 2H), 2.02-1.91 (m, 2H), 1.10-0.98 (m, 6H). LCMS (ES) [M+1]$^+$ m/z 363.2.

Reference 28

Synthesis of 4-[3-([4-chloro-8-methoxy-1H,2H,3H-cyclopenta[c]quinolin-7-yl]oxy)propyl]morpholine (Intermediate III-15)

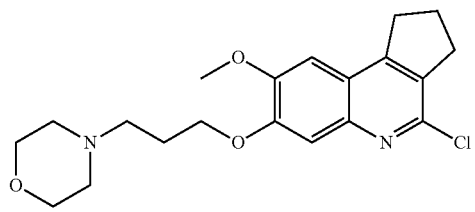 [SMILES: COc1cc2c3c(c(Cl)nc2cc1OCCCN1CCOCC1)CCC3]

The title compound was made from 2-methoxy-5-nitrophenol and 4-(3-chloropropyl)morpholine following a procedure similar as described for the synthesis of Intermediate II-1 above. The crude product was purified by column chromatography on silica gel eluted with dichloromethane/methanol (10/1) to provide the title compound as an off-white solid. The crude product was purified by column chromatography on silica gel eluted with dichloromethane/methanol (10/1) to provide the title compound as a light yellow solid. LCMS (ES) [M+1]$^+$ m/z 377.2.

Example 1

Synthesis of 8-methoxy-N-methyl-7-[3-(pyrrolidin-1-yl)propoxy]-1H,2H,3H-cyclopenta[c]quinolin-4-amine formate

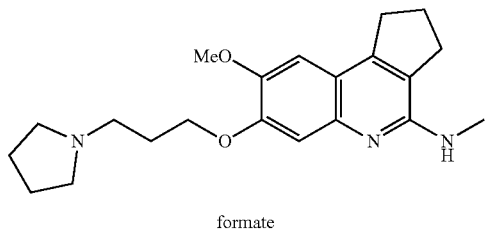 [SMILES: CNc1nc2cc(OCCCN3CCCC3)c(OC)cc2c2c1CCC2]

formate

The title compound was made from 1-[3-({4-chloro-8-methoxy-1H,2H,3H-cyclopenta[c]-quinolin-7-yl}oxy)propyl]pyrrolidine (Intermediate II-1) and methyl amine (2.0 N in THF), following a procedure similar as described in n Example 3 below, except that the crude product was purified by reverse preparative HPLC (Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as brown syrup. LCMS (ES) [M+1]$^+$ m/z 356.2.

Example 2

Synthesis of 2-methoxy-N-methyl-3-[3-(pyrrolidin-1-yl)propoxy]-7,8,9,10-tetrahydrophenanthridin-6-amine formate

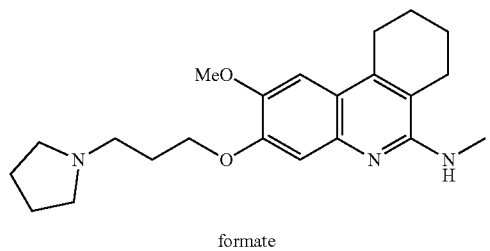 [SMILES: CNc1nc2cc(OCCCN3CCCC3)c(OC)cc2c2c1CCCC2]

formate

The title compound was made from 6-chloro-2-methoxy-3-[3-(pyrrolidin-1-yl)propoxy]-7,8,9,10-tetrahydrophenanthridine (Intermediate II-2) and methyl amine (2.0 N in THF), following a procedure similar as described in Example 3 below, except the reaction was conducted in microwave reactor at 80° C. for 2 h. The crude product was purified by reverse preparative HPLC (Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as brown syrup. LCMS (ES) [M+1]$^+$ m/z 370.2.

Example 3

Synthesis of 8-methoxy-N-(propan-2-yl)-7-[3-(pyrrolidin-1-yl)propoxy]-1H,2H,3H-cyclopenta-[c]quinolin-4-amine trifluoroacetate

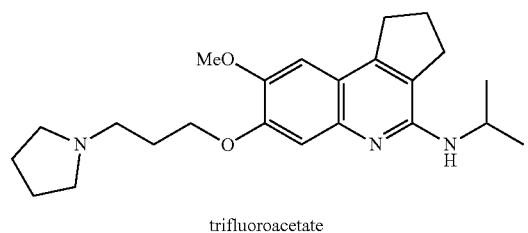 [SMILES: COc1cc2c3c(c(NC(C)C)nc2cc1OCCCN1CCCC1)CCC3]

trifluoroacetate

A mixture of 1-[3-({4-chloro-8-methoxy-1H,2H,3H-cyclopenta[c]quinolin-7-yl}oxy)propyl]-pyrrolidine (Intermediate II-1) (250 mg, 0.69 mmol, 1.00 eq.), 1,4-dioxane (5 mL), and t-BuONa (331 mg, 3.45 mmol, 5.00 eq.) in a microwave reaction vial was purged with N$_2$ for 5 min. To the solution was added propan-2-amine (285 mg, 4.83 mol, 7.00 eq.), and 3rd Generation BrettPhos pre-catalyst (64 mg, 0.07 mmol, 0.10 eq.). After being purged with N$_2$ for additional 2 min, the resulting solution was sealed and subjected to microwave reactor (120° C., 1.5 h). The reaction mixture was allowed to cool to rt and quenched with H$_2$O. After removal of the volatiles under reduced pressure, the residue was re-dissolved in DMSO, filtered and subjected to reverse preparative HPLC (Prep-C18, 5 mM XBridge column, 19×150 mm, waters; gradient elution of 10-25% MeCN in water over a 10 min period, where both solvents contain 0.1% trifluoroacetic acid (TFA)) to provide the title compound as brown oil (70 mg, 15%). LCMS (ES) [M+1]+ m/z 384.

Example 4

Synthesis of 2-({8-methoxy-7-[3-(pyrrolidin-1-yl)propoxy]-1H,2H,3H-cyclopenta[c]quinolin-4-yl}amino)ethan-1-oltrifluoroacetate trifluoroacetate

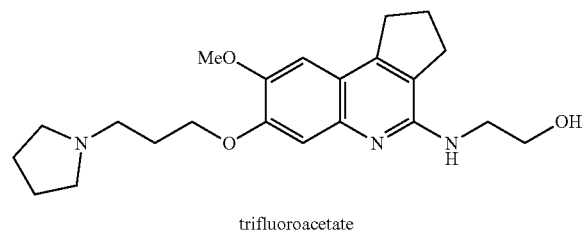 [SMILES: COc1cc2c3c(c(NCCO)nc2cc1OCCCN1CCCC1)CCC3]

trifluoroacetate

The title compound was made from 1-[3-({4-chloro-8-methoxy-1H,2H,3H-cyclopenta[c]-quinolin-7-yl}oxy)propyl]pyrrolidine (Intermediate II-1) and 2-aminoethane-1-ol, following a procedure similar as described in Example 3 above. The crude product was purified by reverse preparative HPLC (Prep-C18, 5 mM XBridge column, 19×150 mm, waters; gradient elution of 10-25% MeCN in water over a 10 min period, where both solvents contain 0.1% trifluoroacetic acid (TFA)) to provide the title compound as brown oil. LCMS (ES) [M+1]+ m/z 386.3.

Example 5

Synthesis of 8-methoxy-N-(2-phenylethyl)-7-[3-(pyrrolidin-1-yl)propoxy]-1H,2H,3H-cyclopenta[c]quinolin-4-amine trifluoroacetate

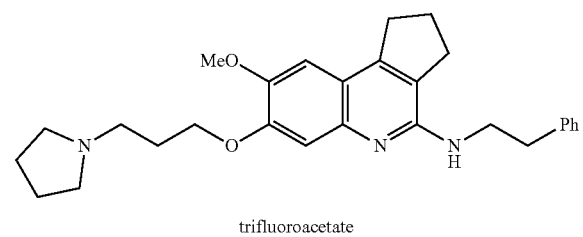 [SMILES: COc1cc2c3c(c(NCCc4ccccc4)nc2cc1OCCCN1CCCC1)CCC3]

trifluoroacetate

Into a 50-mL round-bottom flask maintained under atmosphere of dry nitrogen was placed 1-[3-({4-chloro-8-methoxy-1H,2H,3H-cyclopenta[c]quinolin-7-yl}oxy)propyl]pyrrolidine (Intermediate II-1) (150 mg, 0.42 mmol, 1.00 eq.), 1,4-dioxane (10 mL), 2-phenylethan-1-amine (103 mg, 0.85 mmol, 2.00 eq.), $Cs_2CO_3$ (277 mg, 0.85 mmol, 2.00 eq.), $Pd_2(dba)_3CHCl_3$ (43 mg, 0.05 mmol, 0.10 eq.) and 2,2'-Bis(diphenylphosphino)-1,1'-binaphthyl (26 mg, 0.04 mmol, 0.10 eq.) subsequently. The resulting mixture was allowed to stir at 100° C. under $N_2$ for overnight. The crude reaction mixture was cooled to rt, and treated with water (5 mL). After removal of volatiles, the residue was re-dissolved in DMSO, filtered and subjected to purification on reverse phase preparative HPLC (Prep-C18, 5 μM SunFire column, 19×150 mm, Waters; gradient elution of 5-20% MeCN in water over a 1 min period and 20%-43% MeCN in water over a 6.5 min period, where both solvents contain 0.1% trifluoroacetic acid (TFA)) to provide the title compound as a yellow semi-solid (102.0 mg, 36%). LCMS (ES) [M+1]+ m/z 446.3.

Example 6

Synthesis of 8-methoxy-2-methyl-N-(propan-2-yl)-7-[3-(pyrrolidin-1-yl)propoxy]-1H,2H,3H-cyclopenta[c]quinolin-4-amine formate

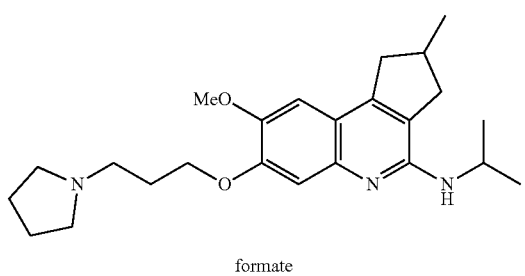 [SMILES: COc1cc2c3c(c(NC(C)C)nc2cc1OCCCN1CCCC1)CC(C)C3]

formate

Into a 50-mL round-bottom flask, was placed a mixture of propan-2-amine (248 mg, 4.20 mmol, 2.00 eq.), 1,4-dioxane (20 mL), sodium sulfate (895 mg, 6.30 mmol, 3.00 eq.), tBuONa (604 mg, 6.30 mol, 3.00 eq.), 3rd Generation BrettPhos precatalyst (381 mg, 0.42 mmol, 0.20 eq.) and 1-[3-({4-chloro-8-methoxy-2-methyl-1H,2H,3H-cyclopenta[c]quinolin-7-yl}oxy)propyl]pyrrolidine (Intermediate II-3) (787 mg, 2.10 mmol, 1.00 eq.). The resulting mixture was allowed to stir at 90° C. under $N_2$ for 2 h. The mixture was cooled to rt, filtered and subjected to purification on reverse phase preparative HPLC (Prep-C18, 5 μM SunFire column, 19×150 mm, Waters; gradient elution of 17-34% MeCN in water over a 7 min period, where both solvents contain 0.1% FA) to provide the title compound as a yellow solid (102.8 mg, 12.3%). LCMS (ES) [M+1]+ m/z 398.4.

Example 7

Synthesis of N-cyclobutyl-8-methoxy-7-[3-(pyrrolidin-1-yl)propoxy]-1H,2H,3H-cyclopenta[c]quinolin-4-amine formate

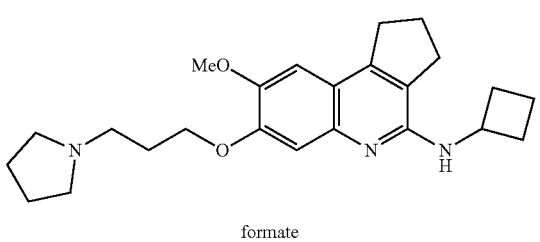 [SMILES: COc1cc2c3c(c(NC4CCC4)nc2cc1OCCCN1CCCC1)CCC3]

formate

The title compound was made from 1-[3-({4-chloro-8-methoxy-1H,2H,3H-cyclopenta-[c]quinolin-7-yl}oxy)propyl]pyrrolidine (Intermediate II-1) and cyclobutylamine, following a procedure similar as described in Example 5 above, except that reaction solution was allowed to stir at 100° C. under $N_2$ atmosphere for 16 h. The crude product was purified by reverse preparative HPLC (Prep-C18, 5 µM XBridge column, 19×150 mm, Waters; gradient elution of 8-24% MeCN in water over a 7 min period, where both solvents contain 0.1% FA) to provide the title compound as an off-white solid (153.8 mg, 19%). LCMS (ES) [M+1]$^+$ m/z 396.4.

Example 8

Synthesis of N-cyclopentyl-8-methoxy-7-[3-(pyrrolidin-1-yl)propoxy]-1H,2H,3H-cyclopenta[c]quinolin-4-amine trifluoroacetate

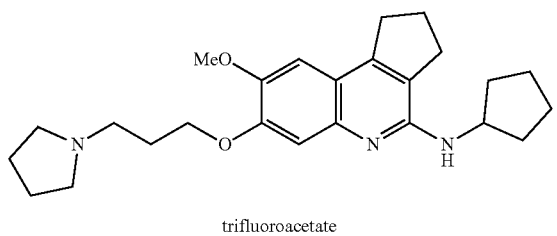 [SMILES: COc1cc2c3c(c(NC4CCCC4)nc2cc1OCCCN1CCCC1)CCC3]

trifluoroacetate

The title compound was made from 1-[3-({4-chloro-8-methoxy-1H,2H,3H-cyclopenta[c]-quinolin-7-yl}oxy)propyl]pyrrolidine (Intermediate II-1) and cyclopentylamine, following the procedure described above in Example 3, except that the reaction was conducted in microwave reactor at 130° C. for 2.5 h. The crude reaction solution was concentrated under reduced pressure. The residue was purified by flash chromatography on silica gel column eluted with 10% MeOH/CH$_2$Cl$_2$. The desired fractions were combined and concentrated under reduced pressure. The resulting crude product was further purified by prep-HPLC (SunFire Prep-C18, 5 µM XBridge column, 19×150 mm, Waters; gradient elution of 36-49% MeCN in water over a 8 min period, where both solvents contain 0.05% TFA) to provide the title compound as an off-white solid (522.9 mg, 49%). LCMS (ES) [M+1]$^+$ m/z 410.4.

Example 9

Synthesis of 8-methoxy-N-methyl-N-(propan-2-yl)-7-[3-(pyrrolidin-1-yl)propoxy]-1H,2H,3H-cyclopenta[c]quinolin-4-amine trifluoroacetate

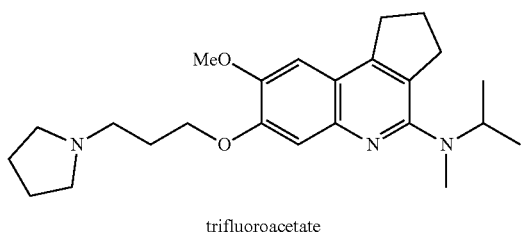 [SMILES: COc1cc2c3c(c(N(C)C(C)C)nc2cc1OCCCN1CCCC1)CCC3]

trifluoroacetate

Into a 50-mL seal tube was placed a mixture of 8-methoxy-N-(propan-2-yl)-7-[3-(pyrrolidin-1-yl)propoxy]-1H,2H,3H-cyclopenta[c]quinolin-4-amine (Example 3) (110 mg, 0.29 mmol, 1.00 eq.), ethanol (10 mL), CH$_2$O (aq. 37%) (0.23 mL, 2.90 mmol, 10.00 eq.) and NaBH$_3$CN (54 mg, 0.86 mmol, 3.00 eq.). The resulting solution was allowed to stir at 120° C. for 16 h. The crude reaction mixture was filtered and subjected to purification on reverse phase preparative HPLC (Prep-C18, 5 µM SunFire column, 19×150 mm, Waters; gradient elution of 20-32% MeCN in water over a 9.5 min period, where both solvents contain 0.1% trifluoroacetic acid (TFA)) to provide the title compound as a yellow solid (18.5 mg, 10%). LCMS (ES) [M+1]$^+$ m/z 398.2.

Example 10

Synthesis of 1-{8-methoxy-7-[3-(pyrrolidin-1-yl)propoxy]-1H,2H,3H-cyclopenta[c]quinolin-4-yl}pyrrolidine formate

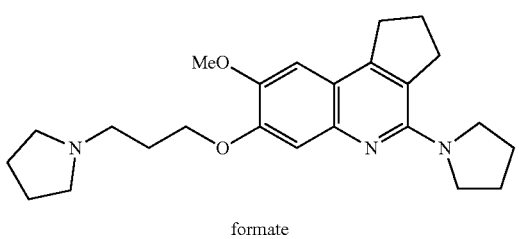 [SMILES: COc1cc2c3c(c(N4CCCC4)nc2cc1OCCCN1CCCC1)CCC3]

formate

The title compound was made from 1-[3-({4-chloro-8-methoxy-1H,2H,3H-cyclopenta[c]-quinolin-7-yl}oxy)propyl]pyrrolidine (Intermediate II-1) and pyrrolidine, following the procedure described above in Example 3, except that reaction solution was left stirring at 100° C. under N$_2$ atmosphere for 14 h. The crude reaction mixture was filtered and subjected to purification on reverse phase preparative HPLC (Prep-C18, 5 µM XBridge column, 19×150 mm, Waters; gradient elution of 5-22% MeCN in water over a 7 min period, where both solvents contain 0.1% formic acid (FA)) to provide the title compound as a dark green solid (119.3 mg, 65%). LCMS (ES) [M+1]$^+$ m/z 396.2.

Example 11

Synthesis of 8-methoxy-7-[(1-methylpyrrolidin-3-yl)methoxy]-N-(propan-2-yl)-1H,2H,3H-cyclopenta[c]quinolin-4-amine trifluoroacetate

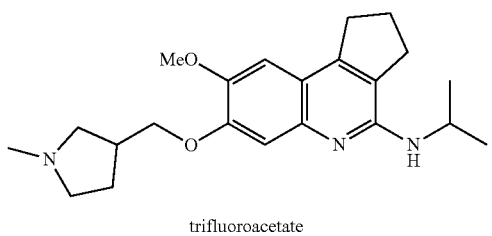 [SMILES: COc1cc2c3c(c(NC(C)C)nc2cc1OCC1CCN(C)C1)CCC3]

trifluoroacetate

Into a 40-mL vial was placed 3-[({4-chloro-8-methoxy-1H,2H,3H-cyclopenta[c]quinolin-7-yl}oxy)methyl]-1-methylpyrrolidine (Intermediate II-5) (300 mg, 0.86 mmol, 1.00 eq.), 1,4-dioxane (6 mL), propan-2-amine (255 mg, 4.31 mmol, 5.00 eq.), t-BuONa (165 mg, 1.72 mmol, 2.00 eq.) and 3$^{rd}$ Brettphos precatalyst (78.4 mg, 0.086 mmol, 0.10 eq.) subsequently. The resulting mixture was purged with N$_2$ for 5 min, sealed and allowed to stir at 90° C. for 2 h. The crude reaction mixture was concentrated under reduced pressure. The remaining residue was re-dissolved in DMSO, filtered and subjected to purification on reverse phase preparative HPLC (Prep-C18, 5 µM XBridge column, 19×150 mm, Waters; gradient elution of 19-24% MeCN in water over a 7 min period, where both solvents contain 0.1% trifluoroacetic acid (TFA)) to provide the title compound as brown oil (203.1 mg, 39%). LCMS (ES) [M+1]+ m/z 370.4.

Example 12

Synthesis of 2-methoxy-N-(oxan-4-yl)-3-[3-(pyrrolidin-1-yl)propoxy]-7,8,9,10-tetrahydrophenanthridin-6-amine trifluoroacetate

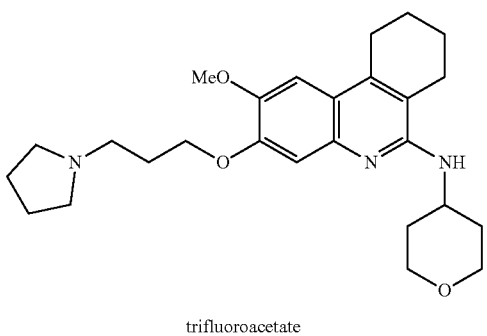 [SMILES: COc1cc2c3c(c(NC4CCOCC4)nc2cc1OCCCN1CCCC1)CCCC3]

trifluoroacetate

The title compound was made from 6-chloro-2-methoxy-3-[3-(pyrrolidin-1-yl)propoxy]-7,8,9,10-tetrahydrophenanthridine (Intermediate II-2) and tetrahydro-2H-pyran-4-amine as described above in Example 3. The crude product was purified by reverse preparative HPLC (Prep-C18, 5 mM XBridge column, 19×150 mm, waters; gradient elution of 10-33% MeCN in water over a 10 min period, where both solvents contain 0.1% trifluoroacetic acid (TFA)) to provide the title compound as brown syrup. LCMS (ES) [M+1]+ m/z 440.3.

Example 13

Synthesis of 2-methoxy-N-(propan-2-yl)-3-[3-(pyrrolidin-1-yl)propoxy]-7,8,9,10-tetrahydrophenanthridin-6-amine formate

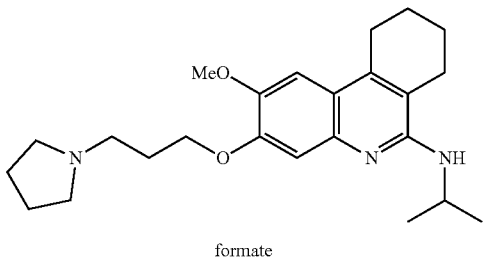 [SMILES: COc1cc2c3c(c(NC(C)C)nc2cc1OCCCN1CCCC1)CCCC3]

formate

The title compound was made from 6-chloro-2-methoxy-3-[3-(pyrrolidin-1-yl)propoxy]-7,8,9,10-tetrahydrophenanthridine (Intermediate II-2) and propan-2-amine following a procedure as described above in Example 3. The crude product was purified by reverse preparative HPLC (Prep-C18, 5 µM XBridge column, 19×150 mm, Waters; gradient elution of 5-30% MeCN in water over a 7 min period, where both solvents contain 0.1% formic acid (FA)) to provide the title compound as brown syrup. LCMS (ES) [M+1]+ m/z 398.3.

Example 14

Synthesis of N-{8-methoxy-7-[3-(pyrrolidin-1-yl)propoxy]-1H,2H,3H-cyclopenta[c]quinolin-4-yl}acetamide trifluoroacetate

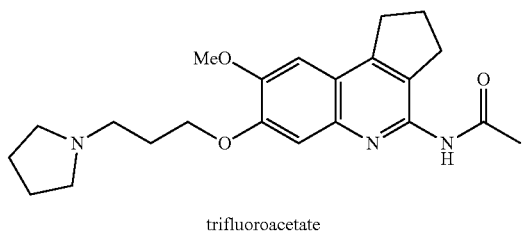 [SMILES: COc1cc2c3c(c(NC(C)=O)nc2cc1OCCCN1CCCC1)CCC3]

trifluoroacetate

The title compound was made from 1-[3-({4-chloro-8-methoxy-1H,2H,3H-cyclopenta-[c]quinolin-7-yl}oxy)propyl]pyrrolidine (Intermediate II-1) and acetamide, following a procedure similar as described in Example 5 above except that crude product was purified by reverse preparative HPLC (Prep-C18, 20-45 µM, 120 g, Tianjin Bonna-Agela Technologies; gradient elution of 15-45% MeCN in water over a 9 min period, where both solvents contain 0.1% trifluoroacetic acid (TFA)) to provide the title compound as brown syrup. LCMS (ES) [M+1]+ m/z 384.2.

Example 15

Synthesis of 2-({2-methoxy-3-[3-(pyrrolidin-1-yl)propoxy]-7,8,9,10-tetrahydrophenanthridin-6-yl}amino)ethan-1-ol formate

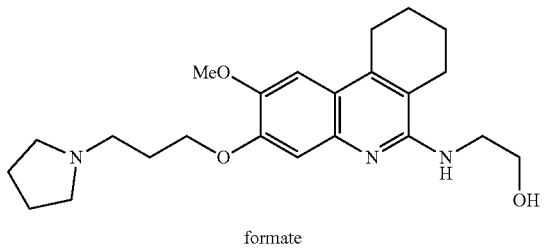 [SMILES: COc1cc2c3c(c(NCCO)nc2cc1OCCCN1CCCC1)CCCC3]

formate

The title compound was made from 6-chloro-2-methoxy-3-[3-(pyrrolidin-1-yl)propoxy]-7,8,9,10-tetrahydrophenanthridine (Intermediate II-2) and 2-aminoethane-1-ol, following a procedure similar as described in Example 3 above, except that the crude product was purified by reverse preparative HPLC (Prep-C18, 5 µM OBD column, 19×250 mm, waters; gradient elution of 0-25% MeCN in water over a 20 min period, where both solvents contain 0.1% formic acid (FA), flow rate: 20 mL/min) to provide the title compound as brown syrup. LCMS (ES) [M+1]+ m/z 400.2.

Example 16

Synthesis of (1r,3r-3-({8-methoxy-7-[3-(pyrrolidin-1-yl)propoxy]-1H,2H,3H-cyclopenta[c]quinolin-4-yl}amino)cyclobutan-1-ol trifluoroacetate

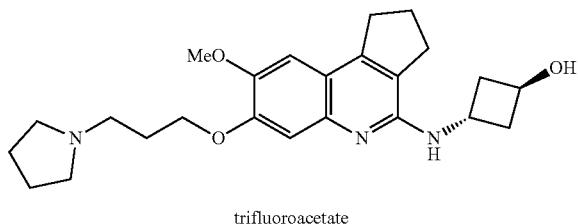 [SMILES: COc1cc2c3c(c(N[C@H]4C[C@H](O)C4)nc2cc1OCCCN1CCCC1)CCC3]

trifluoroacetate

The title compound was made from 1-[3-({4-chloro-8-methoxy-1H,2H,3H-cyclopenta[c]quinolin-7-yl}oxy)propyl]pyrrolidine (Intermediate II-1) and trans-3-aminocyclobutane-1-ol, following a procedure similar as described in Example 3 above, except that the crude product was purified by reverse preparative HPLC (Prep-C18, 20-45 µM, 120 g, Tianjin Bonna-Agela Technologies; gradient elution of 6-31% MeCN in water over a 9 min period, where both solvents contain 0.1% trifluoroacetic acid (TFA)) to provide the title compound as a brown syrup. LCMS (ES) [M+1]$^+$ m/z 412.3.

Example 17

Synthesis of 8-methoxy-N-[(3R)-oxolan-3-yl]-7-[3-(pyrrolidin-1-yl)propoxy]-1H,2H,3H-cyclopenta[c]quinolin-4-amine formate

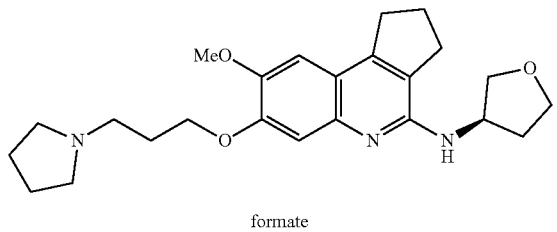 [SMILES: COc1cc2c3c(c(N[C@@H]4CCOC4)nc2cc1OCCCN1CCCC1)CCC3]

formate

The title compound was made from 1-[3-({4-chloro-8-methoxy-1H,2H,3H-cyclopenta[c]-quinolin-7-yl}oxy)propyl]pyrrolidine (Intermediate II-1) and (R)-tetrahydrofuran-3-amine, following a procedure similar as described in Example 3, except that reaction mixture was allowed to stir at 100° C. under N$_2$ for 16 h. The crude product was subjected to reverse phase preparative HPLC (Prep-C18, 5 µM XBridge column, 19×150 mm, Waters; gradient elution of 11-28% MeCN in water over a 7 min period, where both solvents contain 0.1% formic acid (FA)) to provide the title compound as a light yellow solid (138.4 mg, 33%). LCMS (ES) [M+1]$^+$ m/z: 412.4.

Example 18

Synthesis of 8-methoxy-N-[(3S)-oxolan-3-yl]-7-[3-(pyrrolidin-1-yl)propoxy]-1H,2H,3H-cyclopenta[c]quinolin-4-amine formate

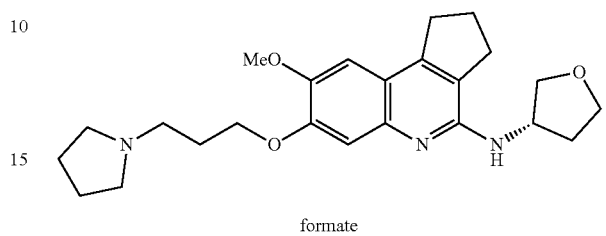

formate

The title compound was made from 1-[3-({4-chloro-8-methoxy-1H,2H,3H-cyclopenta-[c]quinolin-7-yl}oxy)propyl]pyrrolidine (Intermediate II-1) and (S)-tetrahydrofuran-3-amine, following a procedure similar as described in Example 3 above, except that reaction mixture was allowed to stir at 100° C. under N$_2$ for 16 h. The crude product was subjected to reverse phase preparative HPLC (Prep-C18, 5 µM XBridge column, 19×150 mm, Waters; gradient elution of 11-28% MeCN in water over a 7 min period, where both solvents contain 0.1% formic acid (FA)) to provide the title compound as a brown syrup. LCMS (ES) [M+1]$^+$ m/z 412.4.

Example 19

Synthesis of N-cyclopropyl-2-methoxy-3-[3-(pyrrolidin-1-yl)propoxy]-7,8,9,10-tetrahydrophenanthridin-6-amine formate

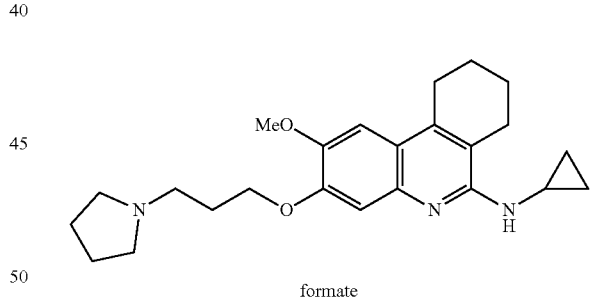

formate

The title compound was made from 6-chloro-2-methoxy-3-[3-(pyrrolidin-1-yl)propoxy]-7,8,9,10-tetrahydrophenanthridine (Intermediate II-2) and cyclopropanamine following a procedure similar as described in Example 3 above, except that the crude product was purified by reverse preparative HPLC (Prep-C18, 5 µM XBridge column, 19×150 mm, Waters; gradient elution of 10-35% MeCN in water over a 7 min period, where both solvents contain 0.1% formic acid (FA)) to provide the title compound as a brown syrup. LCMS (ES) [M+1]$^+$ m/z 396.2.

Example 20

Synthesis of 2-methoxy-6-(methylamino)-3-[3-(pyrrolidin-1-yl)propoxy]-7,8,9,10-tetrahydrophenanthridin-8-ol formate

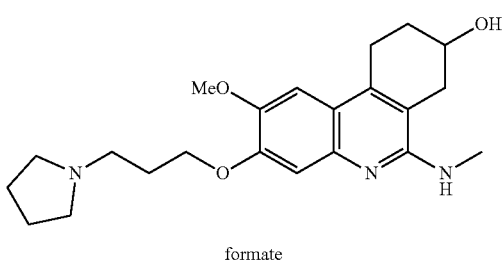 [SMILES: CNc1nc2cc(OCCCN3CCCC3)c(OC)cc2c2c1CC(O)CC2]

formate

The title compound was made from 8-(benzyloxy)-6-chloro-2-methoxy-3-[3-(pyrrolidin-1-yl)propoxy]-7,8,9,10-tetrahydrophenanthridine (Intermediate III-8) and methylamine (2.0 M in THF), following a procedure similar as described in Example 61, except that the crude product was purified by reverse preparative HPLC (Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as a brown syrup. LCMS (ES) [M+1]$^+$ m/z 386.2.

Example 21

Synthesis of 1-[3-({8-methoxy-1H,2H,3H-cyclopenta[c]quinolin-7-yl}oxy)propyl]pyrrolidine trifluoroacetate

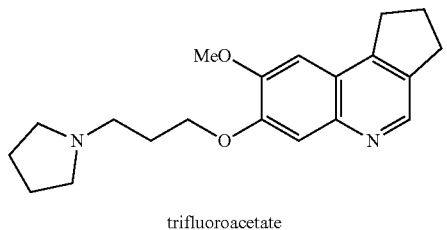 [SMILES: COc1cc2c3c(cnc2cc1OCCCN1CCCC1)CCC3]

trifluoroacetate

Into a 25-mL round-bottom flask, was placed a mixture of 1-[3-({4-chloro-8-methoxy-1H,2H,3H-cyclopenta[c]quinolin-7-yl}oxy)propyl]pyrrolidine (Intermediate II-1) (250 mg, 0.69 mmol, 1.00 eq.), N,N-dimethylformamide (10 mL), t-BuONa (331 mg, 3.45 mmol, 5.00 eq.), propan-2-amine (285 g, 4.83 mol, 7.00 eq.), Pd$_2$(dba)$_3$ (321 mg, 0.35 mmol, 0.50 eq.) and PCy$_3$ (26 mg, 0.069 mmol, 0.10 eq.). The resulting solution was allowed to stir for 5 h at 90° C. under N$_2$. The mixture was filtered and subjected to reverse preparative HPLC (Prep-C18, 5 μM XBridge column, 19×150 mm, Waters; gradient elution of 8-32% MeCN in water over a 7 min period, where both solvents contain 0.1% trifluoroacetic acid (TFA)) to provide the title compound as a brown oil (66.4 mg, 22%). LCMS (ES) [M+1]$^+$ m/z 327.3.

Example 22

Synthesis of 8-methoxy-N-methyl-7-[3-(pyrrolidin-1-yl)propoxy]-1H,2H,3H-pyrrolo[3,2-c]quinolin-4-amine trifluoroacetate

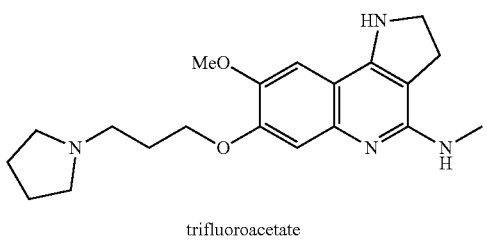 [SMILES: CNc1nc2cc(OCCCN3CCCC3)c(OC)cc2c2c1CCN2]

trifluoroacetate

Step 1

Into a 8 mL seal tube under N$_2$ was added a mixture of 1-[3-({1-benzyl-4-chloro-8-methoxy-1H,2H,3H-pyrrolo[3,2-c]quinolin-7-yl}oxy)propyl]pyrrolidine (Intermediate III-1) (300 mg, 0.66 mmol, 1.00 eq.), 1.4-dioxane (4 mL), MeNH$_2$ (1.6 mL, 2.0 M in THF, 3.32 mmol, 5.00 eq.), t-BuONa (127 mg, 1.32 mmol, 2.00 eq.) and 3rd Brettphos precatalyst (30 mg, 0.0332 mmol, 0.05 eq.) subsequently. The vial was sealed and the solution was allowed to stir at 90° C. for 1 h. The resulting mixture was concentrated and the residue was purified by flash chromatography on silica gel column with 33% petroleum ether in THF (both containing 5% trimethylamine) to provide the desired product of 1-benzyl-8-methoxy-N-methyl-7-[3-(pyrrolidin-1-yl)propoxy]-1H,2H,3H-pyrrolo[3,2-c]quinolin-4-amine as a light brown solid. LCMS (ES) [M+1]$^+$ m/z 447.2.

Step 2

To a solution of 1-benzyl-8-methoxy-N-methyl-7-[3-(pyrrolidin-1-yl)propoxy]-1H,2H,3H-pyrrolo[3,2-c]quinolin-4-amine (115 mg, 0.26 mmol, 1.00 eq.) in MeOH (3 mL) and CH$_3$CO$_2$H (0.1 mL) was added 10% Pd/C (10 mg). The mixture was degassed and purged with H$_2$ for several times. The resulting mixture was allowed to stir at room temperature under hydrogen atmosphere for 3 h. The reaction mixture was diluted with MeOH (5 mL), filtered and subjected to purification on reverse phase preparative HPLC (Prep-C18, 5 μM SunFire column, 19×150 mm, Waters; gradient elution of 13-35% MeCN in water over a 7 min period, where both solvents contain 0.1% trifluoroacetic acid (TFA)) to provide the title compound as a light brown oil (32.7 mg, 22%). LCMS (ES) [M+1]$^+$ m/z 357.2.

Example 23

Synthesis of 8-methoxy-N-(propan-2-yl)-7-[3-(pyrrolidin-1-yl)propoxy]-1H,2H,3H-pyrrolo[3,2c]-quinolin-4-amine trifluoroacetate

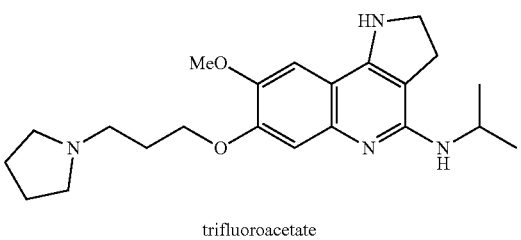 [SMILES: COc1cc2c3c(c(NC(C)C)nc2cc1OCCCN1CCCC1)CCN3]

trifluoroacetate

The title compound was made from 1-[3-({1-benzyl-4-chloro-8-methoxy-1H,2H,3H-pyrrolo[3,2-c]quinolin-7-yl}oxy)propyl]pyrrolidine (Intermediate III-1), as described in Example 22, Step 1 above, except that propan-2-amine was used in place of methylamine. The crude product was purified by reverse preparative HPLC (Prep-C18, 5 μM SunFire column, 19×150 mm, Waters; gradient elution of 5-40% MeCN in water over a 7 min period, where both solvents contain 0.1% trifluoroacetic acid (TFA)) to provide the title compound as a light brown oil (22.5 mg, 13%). LCMS (ES) [M+1]$^+$ m/z 385.2.

Example 24

Synthesis of 8-methoxy-N,2,2-trimethyl-7-[3-(pyrrolidin-1-yl)propoxy]-1H,2H,3H-pyrrolo[3,2-c]quinolin-4-amine trifluoroacetate

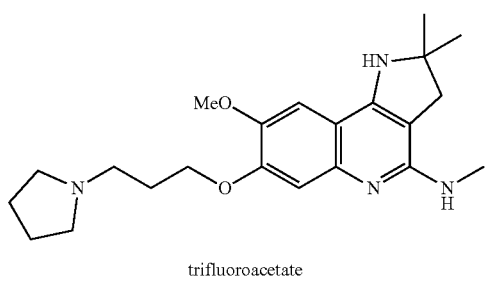 [SMILES: CNc1nc2cc(OCCCN3CCCC3)c(OC)cc2c2c1CC(C)(C)N2]

trifluoroacetate

The title compound was made from 1-[3-([4-chloro-8-methoxy-2,2-dimethyl-1H,2H,3H-pyrrolo[3,2-c]quinolin-7-yl]oxy)propyl]pyrrolidine (Intermediate III-2) and methylamine (1.0 N in THF), following a procedure similar as described in Example 22 Step 1 above, except that the crude reaction mixture was filtered and subjected to purification on reverse phase preparative HPLC (Prep-C18, 5 μM SunFire column, 19×150 mm, Waters; gradient elution of 15-32% MeCN in water over a 7 min period, where both solvents contain 0.1% trifluoroacetic acid (TFA)) to provide the title compound as a brown oil (85.5 mg, 18%). LCMS (ES) [M+1]$^+$ m/z 385.2.

Example 25

Synthesis of 8-methoxy-2,2-dimethyl-N-(propan-2-yl)-7-[3-(pyrrolidin-1-yl)propoxy]-1H,2H,3H-pyrrolo[3,2-c]quinolin-4-amine trifluoroacetate

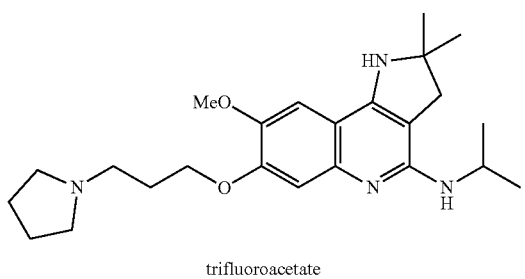 [SMILES: COc1cc2c3c(c(NC(C)C)nc2cc1OCCCN1CCCC1)CC(C)(C)N3]

trifluoroacetate

The title compound was made from 1-[3-([4-chloro-8-methoxy-2,2-dimethyl-1H,2H,3H-pyrrolo[3,2-c]quinolin-7-yl]oxy)propyl]pyrrolidine (Intermediate III-2) and propan-2-amine, following a procedure similar as described in Example 22, Step 1 above. The crude reaction mixture was diluted with N,N-dimethylformamide, filtered and subjected to purification on reverse phase preparative HPLC (Prep-C18, 5 μM SunFire column, 19×150 mm, Waters; gradient elution of 19-35% MeCN in water over a 7 min period, where both solvents contain 0.1% trifluoroacetic acid (TFA)) to provide the title compound as a brown oil (118.1 mg, 24%). LCMS (ES) [M+1]$^+$ m/z 413.2.

Example 26

Synthesis of 9-methoxy-N-methyl-8-[3-(pyrrolidin-1-yl)propoxy]-1H,2H,3H,4H-benzo[h]1,6-naphthyridin-5-amine formate

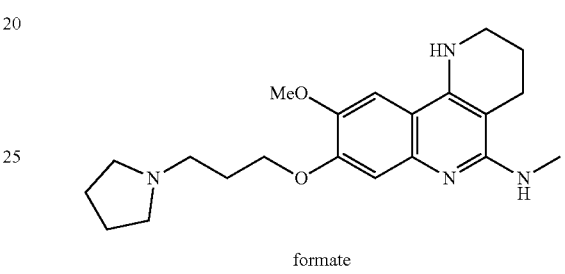

formate

Step 1

Into a 40-mL sealed tube maintained with an inert atmosphere of nitrogen was added mixture of 1-[3-({5-chloro-9-methoxybenzo[h]1,6-naphthyridin-8-yl}oxy)propyl]pyrrolidine (Intermediate III-3) (210 mg, 0.56 mmol, 1.00 eq.), Cs$_2$CO$_3$ (368 mg, 1.13 mmol, 2.00 eq.), 1,4-dioxane (10 mL), MeNH$_2$/THF (1M in THF, 1.7 mL, 1.68 mmol, 3.00 eq.), 2,2'-bis(diphenylphosphino)-1,1'-binaphthyl (35 mg, 0.06 mmol, 0.10 eq.), Pd$_2$(dba)$_3$CHCl$_3$ (59 mg, 0.06 mmol, 0.10 eq.). The resulting mixture was allowed to stir at 100° C. under N$_2$ for 16 h. The mixture was concentrated under reduced pressure and the residue was purified by flash chromatography on silica gel column eluted with 10-20% MeOH/CH$_2$Cl$_2$ to provide the desired product of 9-methoxy-N-methyl-8-[3-(pyrrolidin-1-yl)propoxy]benzo[h]1,6-naphthyridin-5-amine as a yellow oil (116 mg, 56%). LCMS (ES) [M+1]$^+$ m/z 367.2.

Step 2

Into a 50-mL round-bottom flask, was placed a mixture of 9-methoxy-N-methyl-8-[3-(pyrrolidin-1-yl)propoxy]benzo[h]1,6-naphthyridin-5-amine (111 mg, 0.30 mmol, 1.00 eq.), methanol (10 mL) and 10% Pd/C (50 mg). The mixture was degassed and purged with hydrogen for three times. The resulting mixture was allowed to stir at rt for 6 h. The mixture was diluted with MeOH (50 mL) and the solids were filtered off through a pad of celite. The filtrate was concentrated under reduced pressure. The residue was dissolved in N,N-dimethylformamide (5 mL), filtered and subjected to purification on reverse phase preparative HPLC (Prep-C18, 5 μM XBridge column, 19×150 mm, Waters; a gradient elution of 5% MeCN in water over a 1.5 min period and 5-20% MeCN in water over a 7 min period, where both solvents contain 0.1% formic acid (FA)) to provide the title compound as a light yellow solid (57.1 mg, 41%). LCMS (ES) [M+1]$^+$ m/z 371.1.

Example 27

Synthesis of 9-methoxy-N-(propan-2-yl)-8-[3-(pyrrolidin-1-yl)propoxy]-1H,2H,3H,4H-benzo[h]1,6-naphthyridin-5-amine trifluoroacetate

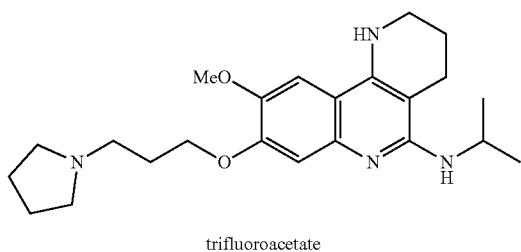 [SMILES: COc1cc2c3c(c(NC(C)C)nc2cc1OCCCN1CCCC1)CCCN3]

trifluoroacetate

The title compound was made from 1-[3-({5-chloro-9-methoxybenzo[h]1,6-naphthyridin-8-yl}oxy)propyl]pyrrolidine (Intermediate III-3) following a procedure similar as described above in Example 26, except that propan-2-amine was used in place of methylamine in Step 1. The final crude product was purified by reverse preparative HPLC (Prep-C18, 5 µM SunFire column, 19×150 mm, Waters; gradient elution of 5% MeCN in water over a 1 min period and 5-25% MeCN in water over a 7 min period where both solvents contain 0.1% trifluoroacetic acid (TFA)) to provide the title compound as a yellow oil. LCMS (ES) [M+1]$^+$ m/z 399.2.

Example 28

Synthesis of 1-[3-({9-methoxy-5-methyl-1H,2H,3H,4H-benzo[h]1,6-naphthyridin-8-yl}oxy)propyl]pyrrolidine trifluoroacetate

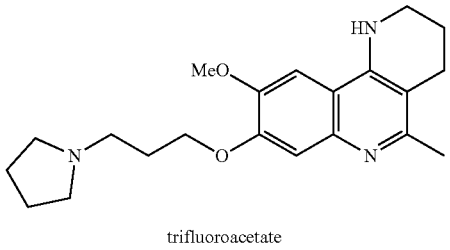 [SMILES: COc1cc2c3c(c(C)nc2cc1OCCCN1CCCC1)CCCN3]

trifluoroacetate

Step 1

Into a 50-mL 3-necked round-bottom flask purged and maintained with an inert atmosphere of nitrogen, was placed a mixture of 1-[3-({5-chloro-9-methoxybenzo[h]1,6-naphthyridin-8-yl}oxy)-propyl]pyrrolidine (Intermediate III-3) (220 mg, 0.59 mmol, 1.00 eq.), 1,4-dioxane (20 mL), trimethyl-1,3,5,2,4,6-trioxatriborinane (598 mg, 50%/W in THF, 2.37 mmol, 4.00 eq.), Cs$_2$CO$_3$ (580 mg, 1.78 mmol, 3.00 eq.) and Pd(PPh$_3$)$_4$ (69 mg, 0.06 mmol, 0.10 eq.) subsequently. The resulting mixture was allowed at 110° C. under N$_2$ for 3 h, and then concentrated under reduced pressure. The residue was dissolved in DMSO, filtered and subjected to purification by flash chromatography on silica gel column eluted with 10-15% MeOH/CH$_2$Cl$_2$ to provide the desired product of 1-[3-([9-methoxy-5-methylbenzo[h] 1,6-naphthyridin-8-yl]oxy)propyl]pyrrolidine as a yellow solid (155 mg, 75%). LCMS (ES) [M+1]$^+$ m/z 352.2.

Step 2

Into a 50-mL round-bottom flask, was placed a solution of 1-[3-([9-methoxy-5-methylbenzo[h]1,6-naphthyridin-8-yl]oxy)propyl]pyrrolidine (150 mg, 0.43 mmol, 1.00 eq.), methanol (10 mL), 10% Pd/C (15 mg). The mixture was degassed and purged with H$_2$ for several times and then stirred at rt under H$_2$ atmosphere (balloon) for 4 h. The crude reaction mixture was filtered and subjected to purification on reverse phase preparative HPLC (Prep-C18, 5 µM SunFire column, 19×150 mm, Waters; gradient elution of 12-25% MeCN in water over a 8 min period, where both solvents contain 0.1% trifluoroacetic acid (TFA)) to provide the title compound as a yellow oil (20.4 mg, 8%). LCMS (ES) [M+1]$^+$ m/z 356.2.

Example 29

Synthesis of 9-methoxy-N,2-dimethyl-8-[3-(pyrrolidin-1-yl)propoxy]-1H,2H,3H,4H-benzo[h]1,6-naphthyridin-5-amine formate

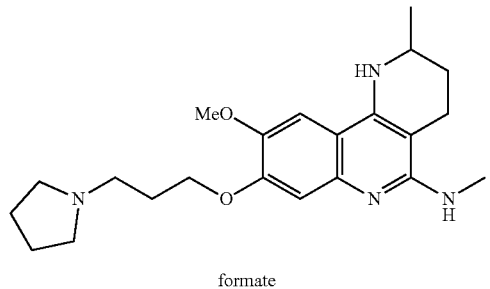 [SMILES: CNc1nc2cc(OCCCN3CCCC3)c(OC)cc2c2c1CCC(C)N2]

formate

Step 1

Into a seal tube was placed a solution of 1-[3-({5-chloro-9-methoxy-2-methylbenzo[h]1,6-naphthyridin-8-yl}oxy) propyl]pyrrolidine (Intermediate III-4) (200 mg, 0.52 mmol, 1.00 eq.), DMSO (10 mL) and CH$_3$NH$_2$ (5.2 mL, 1M in THF, 5.2 mmol, 10.00 eq.). The resulting solution was sealed and allowed to stir at 120° C. overnight. The reaction solution was diluted with water and extracted with a mixed solution of 20% MeOH/CH$_2$Cl$_2$. The organic layers were combined, dried over anhydrous sodium sulfate and concentrated under reduced pressure. The residue was purified by flash chromatography on silica gel column eluted with 5-20% MeOH/CH$_2$Cl$_2$ to provide the desired product of 9-methoxy-N,2-dimethyl-8-[3-(pyrrolidin-1-yl)propoxy] benzo[h]1,6-naphthyridin-5-amine as a yellow solid (125 mg, 63%). LCMS (ES) [M+1]$^+$ m/z 381.3.

Step 2

Into a 50-mL round-bottom flask, was placed a solution of 9-methoxy-N,2-dimethyl-8-[3-(pyrrolidin-1-yl)propoxy] benzo[h]1,6-naphthyridin-5-amine (125 mg, 0.33 mmol, 1.00 eq.), methanol (10 mL) and 10% Pd/C (15 mg). The resulting mixture was degassed and purged with H$_2$ for several time, and allowed to stir at rt under H$_2$ atmosphere for 6 h. The crude reaction mixture was filtered and subjected to purification on reverse phase preparative HPLC (Prep-C18, 5 µM XBridge column, 19×150 mm, Waters; gradient elution of 5-17% MeCN in water over a 7 min period, where both solvents contain 0.1% formic acid (FA)) to provide the title compound as a white solid (23.3 mg, 16%). LCMS (ES) [M+1]$^+$ m/z 385.3.

Example 30

Synthesis of 9-methoxy-2-methyl-N-(propan-2-yl)-8-[3-(pyrrolidin-1-yl)propoxy]-1H,2H,3H,4H-benzo[h]1,6-naphthyridin-5-amine formate

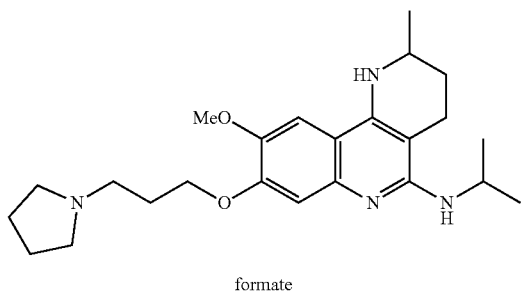 [SMILES: COc1cc2c3c(c(NC(C)C)nc2cc1OCCCN1CCCC1)CCC(C)N3]

formate

The title compound was made from 1-[3-({5-chloro-9-methoxy-2-methylbenzo[h]1,6-naphthyridin-8-yl}oxy)propyl]pyrrolidine (Intermediate III-4), following the procedure described in Example 29 above, except that propan-2-amine was used in place of methyl amine. The final crude product was purified by reverse preparative HPLC (Prep-C18, 5 μM XBridge column, 19×150 mm, Waters; gradient elution of 5-25% MeCN in water over a 7.5 min period, where both solvents contain 0.1% formic acid (FA)) to provide the title compound as a white solid (33.1 mg, 24%). LCMS (ES) $[M+1]^+$ m/z 413.3.

Example 31

Synthesis of 1-[3-({9-methoxy-2,5-dimethyl-1H,2H,3H,4H-benzo[h]1,6-naphthyridin-8-yl}oxy)propyl]pyrrolidine trifluoroacetate

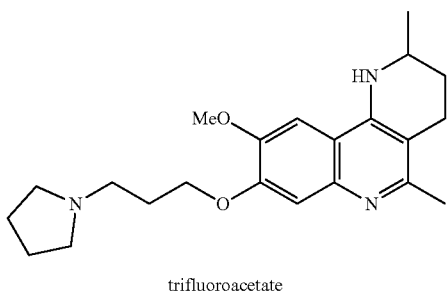 [SMILES: COc1cc2c3c(c(C)nc2cc1OCCCN1CCCC1)CCC(C)N3]

trifluoroacetate

The title compound was made from 1-[3-({5-chloro-9-methoxy-2-methylbenzo[h]1,6-naphthyridin-8-yl}oxy)propyl]pyrrolidine (Intermediate III-4), following a procedure similar as described in Example 28 above. The final crude product was purified by reverse preparative HPLC (Prep-C18, 5 μM SunFire column, 19×150 mm, Waters; gradient elution of 5-35% MeCN in water over a 7 min period, where both solvents contain 0.1% trifluoroacetic acid (TFA)) to provide the title compound as a yellow semi-solid (31.4 mg, 17%). LCMS (ES) $[M+1]^+$ m/z 370.2.

Example 32

Synthesis of 1-[3-({5-cyclopropyl-9-methoxy-2-methyl-1H,2H,3H,4H-benzo[h]1,6-naphthyridin-8-yl}oxy)propyl]pyrrolidine trifluoroacetate

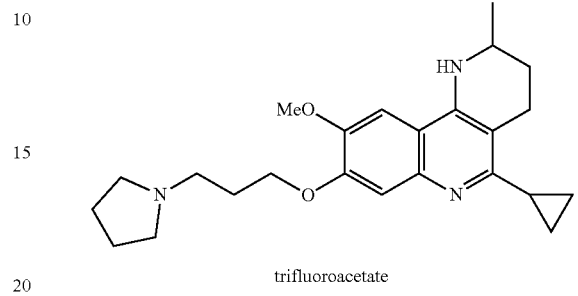

trifluoroacetate

Step 1

Into a 50-mL round-bottom flask purged and maintained with an inert atmosphere of nitrogen, was added 1-[3-({5-chloro-9-methoxy-2-methylbenzo[h]1,6-naphthyridin-8-yl}oxy)propyl]-pyrrolidine (Intermediate III-4) (210 mg, 0.54 mmol, 1.00 eq.), 1,4-dioxane (20 mL), cyclopropylboronic acid (94 mg, 1.09 mmol, 2.00 eq.), $Cs_2CO_3$ (356 mg, 1.09 mmol, 2.00 eq.) and $Pd(PPh_3)_4$ (63 mg, 0.05 mmol, 0.10 eq.) subsequently. The resulting mixture was allowed to stir at 110° C. under $N_2$ for 4 h. The resulting mixture was concentrated under reduced pressure. The residue was purified by flash chromatography on silica gel column eluted with 5-20% MeOH/$CH_2Cl_2$ to provide the desired product of 1-[3-([5-cyclopropyl-9-methoxy-2-methylbenzo[h]1,6-naphthyridin-8-yl]oxy)propyl]pyrrolidine as a yellow solid (135 mg, 63%). LCMS (ES) $[M+1]^+$ m/z 392.2.

Step 2

Into a rt solution of 1-[3-([5-cyclopropyl-9-methoxy-2-methylbenzo[h]1,6-naphthyridin-8-yl]oxy)propyl]pyrrolidine (95 mg, 0.24 mmol, 1.00 eq.) in 1,4-dioxane (5 mL) was added a solution of 1,4-dioxane (1 mL) saturated with HCl (gas). The resulting solution was allowed to stir at rt for 1 h and then concentrated under reduced pressure to provide the corresponding HCl salt of 1-[3-([5-cyclopropyl-9-methoxy-2-methylbenzo[h]1,6-naphthyridin-8-yl]oxy)propyl]pyrrolidine. To a 50-mL round-bottom flask was placed a solution of the above HCl salt in methanol (10 mL) and 10% Pd/C (10 mg). The resulting mixture was degassed and purged with $H_2$ for several times and was then allowed to stir at rt under $H_2$ atmosphere for 6 h. The crude reaction mixture was filtered and subjected to purification on reverse phase preparative HPLC (Prep-C18, 5 μM SunFire column, 19×150 mm, Waters; gradient elution of 20-33% MeCN in water over a 7.5 min period, where both solvents contain 0.1% trifluoroacetic acid (TFA)) to provide the title compound as a dark yellow solid. LCMS (ES) $[M+1]^+$ m/z 396.2.

Example 33

Synthesis of 10-methoxy-N-methyl-9-[3-(pyrrolidin-1-yl)propoxy]-1H,2H,3H,4H,5H-azepino[3,2-c]quinolin-6-amine formate

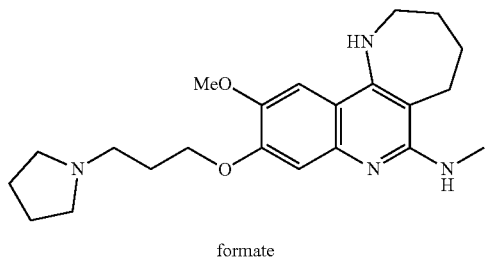 [SMILES: CNc1nc2cc(OCCCN3CCCC3)c(OC)cc2c2c1CCCCN2]

formate

The title compound was made from 1-[3-({6-chloro-10-methoxy-1H,2H,3H,4H,5H-azepino[3,2-c]quinolin-9-yl}oxy)propyl]pyrrolidine (Intermediate III-5) and methylamine (1.0 N in THF), following a procedure similar as described in Example 22, Step 1. The crude mixture was filtered and subjected to purification on reverse phase preparative HPLC (Prep-C18, 5 μM XBridge column, 19×150 mm, Waters; gradient elution of 5-17% MeCN in water over a 7 min period, where both solvents contain 0.1% formic acid (FA)) to provide the title compound as a gray solid LCMS (ES) [M+1]$^+$ m/z 385.2.

Example 34

Synthesis of 10-methoxy-N-(propan-2-yl)-9-[3-(pyrrolidin-1-yl)propoxy]-1H,2H,3H,4H,5H-azepino[3,2-c]quinolin-6-amine formate

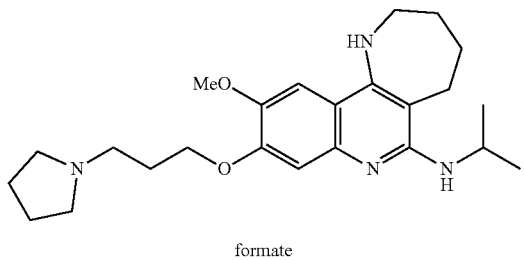 [SMILES: COc1cc2c3c(c(NC(C)C)nc2cc1OCCCN1CCCC1)CCCCN3]

formate

The title compound was made from 1-[3-({6-chloro-10-methoxy-1H,2H,3H,4H,5H-azepino[3,2-c]quinolin-9-yl}oxy)propyl]pyrrolidine (Intermediate III-5) following a procedure similar as described in Example 22, Step 1, except that propan-2-amine was used in the place of methyl amine. The crude mixture was filtered and subjected to purification on reverse phase preparative HPLC (Prep-C18, 5 μM XBridge column, 19×150 mm, Waters; gradient elution of 5-21% MeCN in water over a 7 min period, where both solvents contain 0.1% formic acid (FA)) to provide the title compound as a gray solid. LCMS (ES) [M+1]$^+$ m/z 413.3.

Example 35

Synthesis of 1-[3-({8-methoxy-2,2-dimethyl-1H,2H,3H-pyrrolo[3,2-c]quinolin-7-yl}oxy)propyl]pyrrolidine formate

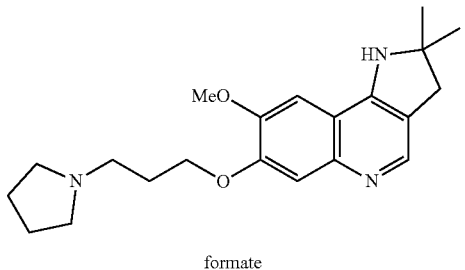 [SMILES: COc1cc2c3c(cnc2cc1OCCCN1CCCC1)CC(C)(C)N3]

formate

To a mixture of 1-[3-([4-chloro-8-methoxy-2,2-dimethyl-1H,2H,3H-pyrrolo[3,2-c]quinolin-7-yl]oxy)propyl]pyrrolidine (Intermediate III-2) (80.00 mg; 0.21 mmol) and zinc (300 mg, 4.6 mmol, 22 eq.) in MeOH was added aqueous HCl (37%, 0.5 mL). The mixture was left stirring at rt for 72 h and filtered through a small pad of celite. After removal of the solvents under reduced pressure, the residue was filtered and purified by reverse preparative HPLC (Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as a brown solid. LCMS (ES) [M+1]$^+$ m/z 356.2.

Example 36

Synthesis of 1-[3-({4-cyclopropyl-8-methoxy-2,2-dimethyl-1H,2H,3H-pyrrolo[3,2-c]quinolin-7-yl}oxy)propyl]pyrrolidine formate

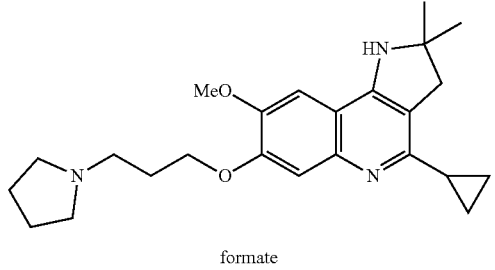 [SMILES: COc1cc2c3c(c(C4CC4)nc2cc1OCCCN1CCCC1)CC(C)(C)N3]

formate

A mixture of 1-[3-({4-chloro-8-methoxy-2,2-dimethyl-1H,2H,3H-pyrrolo[3,2-c]quinolin-7-yl}oxy)propyl]pyrrolidine (Intermediate III-2) (80.00 mg; 0.21 mmol; 1.00 eq.), cyclopropylboronic acid (44.06 mg; 0.51 mmol; 2.50 eq.) and K$_2$CO$_3$ (87 mg, 0.63 mmol, 3.0 eq.) in a mixed solvent of N,N-dimethylformamide (2.5 mL) and water (1.0 mL) in a seal vial was purged with N$_2$ for 10 min. To the resulting mixture was added Pd$_2$(dba)$_3$ (62 mg, 0.067 mmol, 0.32 eq.). The vial was sealed and the mixture was allowed to stir at 100° C. for 3 h. The crude reaction mixture was cooled to rt, quenched with water, and extracted with 30% PrOH/chloroform. The organic layers were combined and concentrated under reduced pressure. The residue was dissolved in DMSO and subjected to purification by reverse preparative HPLC (Prep-C18, 5 µM OBD column, 19×250 mm, waters; gradient elution of 0-40% MeCN in water over a 20 min period, where both solvents contain 0.1% formic acid, flow rate: 20 mL/min) to provide the title compound as a brown solid. LCMS (ES) [M+1]+ m/z 396.4.

Example 37

Synthesis of 8-methoxy-7-[3-(pyrrolidin-1-yl) propoxy]-1H,2H,3H-cyclopenta[c]quinolin-4-ol trifluoroacetate

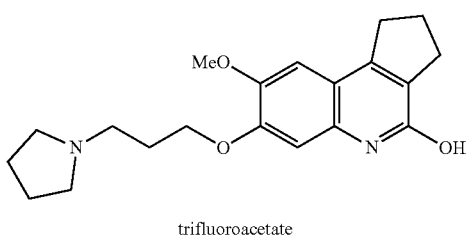 [SMILES: COc1cc2c3c(c(O)nc2cc1OCCCN1CCCC1)CCC3]

trifluoroacetate

Into a 50-mL round-bottom flask, was placed a mixture of 4-methoxy-3-[3-(pyrrolidin-1-yl)propoxy]aniline (Intermediate I-2) (1.00 g, 3.99 mmol, 1.00 eq.), ethyl 2-oxocyclopentane-1-carboxylate (655 mg, 4.19 mmol, 1.05 eq.), p-TsOH (69 mg, 0.20 mmol, 0.05 eq.) and toluene (15 mL). The resulting mixture was allowed to stir at 110° C. for 1 h. After the starting material was consumed completely, the mixture was cooled to rt. To the mixture was added polyphosphoric acid (1 mL). The mixture was allowed to stir at 100° C. for 1.0 h. After removal of volatiles under reduced pressure, the residue was diluted with 100 mL of H2O and the pH value of the solution was adjusted to 9 with aqueous NaOH solution (2 N). The mixture was extracted with a mixed solvent of 20% iPrOH/80% CHCl3. The combined organic layers were dried over anhydrous sodium sulfate and concentrated under reduced pressure. The residue was subjected for purification on reverse preparative HPLC (Prep-C18, 5 µM XBridge column, 19×150 mm, Waters; gradient elution of 17-32% MeCN in water over 7 min, where both solvents contain 0.1% trifluoroacetic acid (TFA), flow rate: 20 mL/min, detector UV wavelength: 254 nm) to afford the title compound as a gray solid. LCMS (ES) [M+1]+ m/z 343.2.

Example 38

Synthesis of 2-methoxy-3-[3-(pyrrolidin-1-yl) propoxy]-7,8,9,10-tetrahydrophenanthridin-6-ol trifluoroacetate

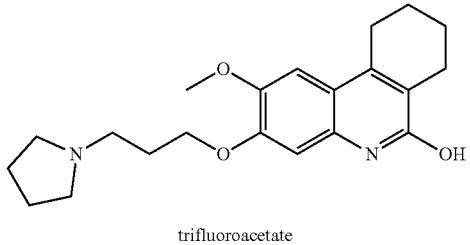 [SMILES: COc1cc2c3c(c(O)nc2cc1OCCCN1CCCC1)CCCC3]

trifluoroacetate

The title compound was made from 4-methoxy-3-[3-(pyrrolidin-1-yl)propoxy]aniline (Intermediate I-2) following a procedure similar as described in Example 37, except that ethyl 2-oxocyclohexane-1-carboxylate was used in place of ethyl 2-oxocyclopentane-1-carboxylate. LCMS (ES) [M+1]+ m/z 375.2.

Example 39

Synthesis of 2-methoxy-N-[1-(propan-2-yl)piperidin-4-yl]-3-[3-(pyrrolidin-1-yl)propoxy]-7,8,9,10-tetrahydrophenanthridin-6-amine trifluoroacetate

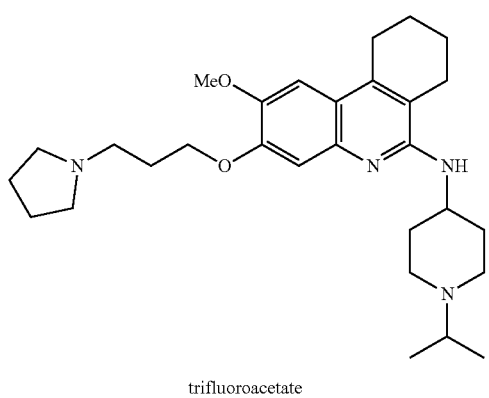 [SMILES: COc1cc2c3c(c(NC4CCN(C(C)C)CC4)nc2cc1OCCCN1CCCC1)CCCC3]

trifluoroacetate

The title compound was made from 6-chloro-2-methoxy-3-[3-(pyrrolidin-1-yl)propoxy]-7,8,9,10-tetrahydrophenanthridine (Intermediate II-2) and 1-isopropylpiperidin-4-amine, following a procedure described in Example 3, except that the crude product was purified by reverse preparative HPLC (Prep-C18, 5 µM SunFire column, 19×150 mm, Waters; gradient elution of 10-30% MeCN in water over a 7.5 min period, where both solvents contain 0.1% trifluoroacetic acid (TFA)) to provide the title compound as a brown solid. LCMS (ES) [M+1]+ m/z 481.4.

Example 40

Synthesis of 2-methoxy-3-[3-(pyrrolidin-1-yl) propoxy]-7,8,9,10-tetrahydrophenanthridine trifluoroacetate

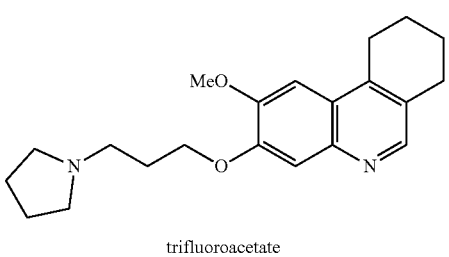 [SMILES: COc1cc2c3c(cnc2cc1OCCCN1CCCC1)CCCC3]

trifluoroacetate

The title compound was made from 6-chloro-2-methoxy-3-[3-(pyrrolidin-1-yl)propoxy]-7,8,9,10-tetrahydrophenanthridine (Intermediate II-2) following a procedure similar as described in Example 21. The crude product was purified by reverse HPLC (Prep-C18, 5 µM XBridge column, 19×150 mm, Waters; gradient elution of 8-32% MeCN in water over a 7 min period, where both solvents contain 0.1% trifluoroacetic acid (TFA)) to provide the title compounds as a light brown oil. LCMS (ES) [M+1]+ m/z 341.3.

Example 41

Synthesis of N-{8-methoxy-7-[3-(pyrrolidin-1-yl)propoxy]-1H,2H,3H-cyclopenta[c]quinolin-4-yl}-1-methylpiperidin-4-amine formate

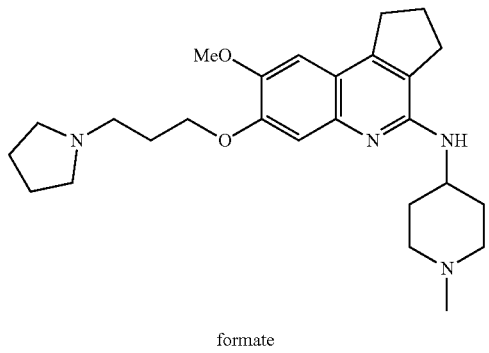 [SMILES: COc1cc2c3c(c(NC4CCN(C)CC4)nc2cc1OCCCN1CCCC1)CCC3]

formate

The title compound was made from 1-[3-({4-chloro-8-methoxy-1H,2H,3H-cyclopenta[c]-quinolin-7-yl}oxy)propyl]pyrrolidine (Intermediate II-1) and 1-methylpiperidin-4-amine, following a procedure similar as described Example 3, except that the crude product was purified by reverse preparative (Prep-C18, 5 µM OBD column, 19×250 mm, waters; gradient elution of 0-40% MeCN in water over a 20 min period, where both solvents contain 0.1% formic acid, flow rate: 20 mL/min) to provide the title compound as a white solid. LCMS (ES) [M+1]+ m/z 439.4.

Example 42

Synthesis of 2-methoxy-N-(oxan-4-yl)-3-[3-(pyrrolidin-1-yl)propoxy]-7,8,9,10-tetrahydrophenanthridin-6-amine formate

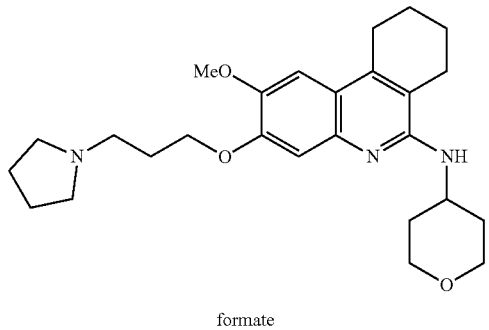 [SMILES: COc1cc2c3c(c(NC4CCOCC4)nc2cc1OCCCN1CCCC1)CCCC3]

formate

The title compound was made from 6-chloro-2-methoxy-3-[3-(pyrrolidin-1-yl)propoxy]-7,8,9,10-tetrahydrophenanthridine (Intermediate II-2) and tetrahydro-2H-pyran-4-amine, following a procedure similar as described in Example 3. The crude product was purified by reverse preparative (Prep-C18, 5 µM OBD column, 19×250 mm, waters; gradient elution of 0-40% MeCN in water over a 20 min period, where both solvents contain 0.1% formic acid, flow rate: 20 mL/min) to provide the title compound as a white solid. LCMS (ES) [M+1]+ m/z 440.3.

Example 43

Synthesis of N-{8-methoxy-7-[3-(pyrrolidin-1-yl)propoxy]-1H,2H,3H-cyclopenta[c]quinolin-4-yl}-1-(propan-2-yl)piperidin-4-amine formate

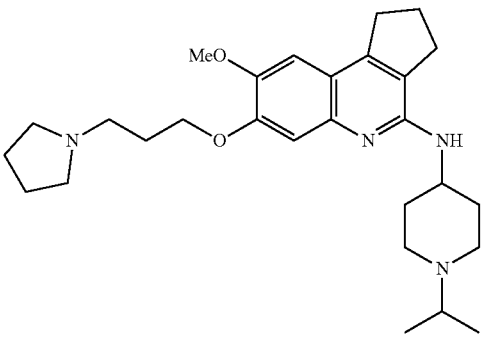

formate

The title compound was made from 1-[3-({4-chloro-8-methoxy-1H,2H,3H-cyclopenta[c]-quinolin-7-yl}oxy)propyl]pyrrolidine (Intermediate II-1) and 1-isopropylpiperidin-4-amine following a procedure similar as described in Example 3. The crude product was purified by reverse preparative (Prep-C18, 5 µM OBD column, 19×250 mm, waters; gradient elution of 0-40% MeCN in water over a 20 min period, where both solvents contain 0.1% formic acid, flow rate: 20 mL/min) to provide the title compound as a white solid. LCMS (ES) [M+1]+ m/z 467.4.

Example 44

Synthesis of 8-methoxy-N-(oxetan-3-yl)-'7-[3-(pyrrolidin-1-yl)propoxy]-1H,2H,3H-cyclopenta[c]quinolin-4-amine formate

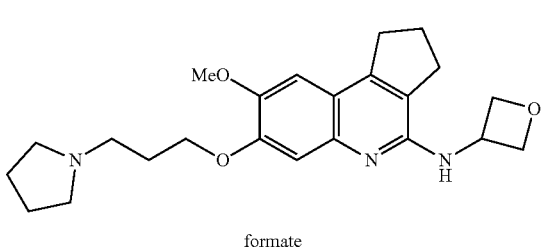 [SMILES: COc1cc2c3c(c(NC4COC4)nc2cc1OCCCN1CCCC1)CCC3]

formate

The title compound was made from 1-[3-({4-chloro-8-methoxy-1H,2H,3H-cyclopenta-[c]quinolin-7-yl}oxy)propyl]pyrrolidine (Intermediate II-1) and oxetan-3-amine, following a procedure similar as described above in Example 3. The crude product was purified by reverse preparative (Prep-C18, 5 µM OBD column, 19×250 mm, waters; gradient elution of 5-38% MeCN in water over a 20 min period, where both solvents contain 0.1% formic acid, flow rate: 20 mL/min) to provide the title compound as a brown solid. LCMS (ES) [M+1]+ m/z 398.3.

Examples 45 and 46

Synthesis of 7-methoxy-N-(propan-2-yl)-8-[3-(pyrrolidin-1-yl)propoxy]-1H,3H-furo[3,4-c]quinolin-4-amine (45) and 8-methoxy-N-(propan-2-yl)-7-[3-(pyrrolidin-1-yl)propoxy]-1H,3H-furo[3,4-c]quinolin-4-amine (46)

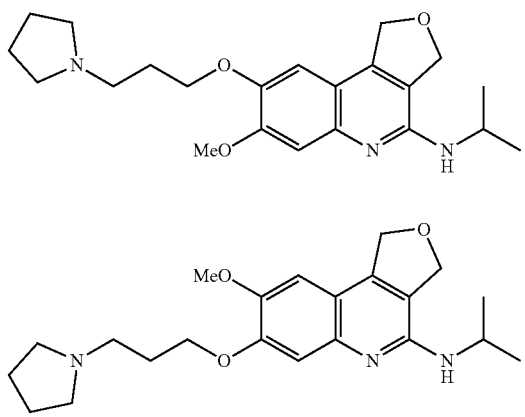

Step 1

Into a 250-mL round-bottom flask, was placed a solution of 3,4-dimethoxybenzenamine (7.5 g, 48.96 mmol, 1.00 eq.), toluene (100 mL), ethyl 4-oxo-tetrahydrofuran-3-carboxylate (9.3 g, 58.75 mmol, 1.20 eq.) and p-TsOH.H$_2$O (932 mg, 4.90 mmol, 0.1 eq.) subsequently. The resulting mixture was allowed to stir under reflux with Dean-Stark for 4 h. The resulting mixture was concentrated under reduced pressure. The residue was dissolved in ethyl acetate, washed with saturated aqueous sodium carbonate, brine and dried over anhydrous sodium sulfate. After removal of the organic solvents under reduced pressure, the resulting brown solid was dissolved in toluene. To the solution was added poly phosphoric acid (PPA) (20 mL). The resulting mixture was stirred at 100° C. for 4 h and then concentrated under reduced pressure. The residue was diluted with water and the pH value of the solution was adjusted to 7 with saturated aqueous sodium bicarbonate solution. The mixture was extracted with ethyl acetate. The combined organic layers were washed with brine, dried over anhydrous sodium sulfate and concentrated under reduced pressure to provide crude 7,8-dimethoxy-1,3-dihydrofuro[3,4-c]quinolin-4-ol as a brown thick oil (7.1 g). LCMS (ES) [M+1]+ m/z 248.1.

Step 2

Into a 250-mL round-bottom flask charge with crude 7,8-dimethoxy-1,3-dihydrofuro[3,4-c]quinolin-4-ol (7.1 g, crude, 28.72 mmol, 1.00 eq.) was added POCl$_3$ (100 mL). The resulting solution was allowed to stir at 100° C. for 4 h. After removal of volatiles under reduced pressure, the residue was treated with ice/water and the pH value of the solution was adjusted to 7 with aqueous NaHCO$_3$ (1.0 M) solution. The resulting mixture was extracted with ethyl acetate thrice. The combined organic layers were washed with brine, dried over anhydrous sodium sulfate and concentrated under reduced pressure. The residue was purified by column chromatography on silica gel eluted with ethyl acetate/petroleum ether (1/2) to provide 4-chloro-7,8-dimethoxy-1,3-dihydrofuro[3,4-c]quinoline as a yellow solid (3.5 g, 27%, 2 steps). LCMS (ES) [M+1]$^+$ m/z 266.1.

Step 3

Into a 100-mL round-bottom flask, was placed a mixture of 4-chloro-7,8-dimethoxy-1,3-dihydrofuro[3,4-c]quinoline (3.5 g, 13.17 mmol, 1.00 eq.), dichloroethane (50 mL) and AlCl$_3$ (1.75 g, 13.17 mmol, 1.0 eq.). The resulting mixture was allowed to stir at 40° C. for 6 h, cooled to rt, diluted with CH$_2$Cl$_2$ and then treated with ice water. The mixture was filtered through a pad of celite and the filter cake was washed with CH$_2$Cl$_2$. The filtrated was concentrated under reduced pressure and the residue was purified by flash chromatography on silica gel column eluted with 5% MeOH/CH$_2$Cl$_2$ to afford a mixture of 4-chloro-8-methoxy-7-(3-(pyrrolidin-1-yl)propoxy)-1,3-dihydrofuro[3,4-c]quinolone and 4-chloro-7-methoxy-8-(3-(pyrrolidin-1-yl)propoxy)-1,3-dihydrofuro[3,4-c]quinolone (1:1) as a yellow oil (1.40 g). LCMS (ES) [M+1]$^+$ m/z 252.1.

Step 4

Into a 50-mL round-bottom flask, was placed a mixture of 4-chloro-8-methoxy-7-(3-(pyrrolidin-1-yl)propoxy)-1,3-dihydrofuro[3,4-c]quinolone and 4-chloro-7-methoxy-8-(3-(pyrrolidin-1-yl)propoxy)-1,3-dihydrofuro[3,4-c]quinolone (1:1, 1.40 g, 5.56 mmol, 1.00 eq.), potassium carbonate (2.30 g, 16.69 mmol, 3.0 eq.), acetonitrile (30 mL), 3-(pyrrolidin-1-yl)propan-1-ol hydrochloride (1.84 g, 10.01 mmol, 1.80 eq.) and potassium iodide (1.66 g, 10.01 mmol, 1.80 eq.). The resulting mixture was allowed to stir at 80° C. for 3 h. The solids were filtered off, and the filter cake was washed with acetonitrile (2×30 mL). The filtrate was concentrated under reduced pressure and the resulting residue was purified by flash chromatography on silica gel column eluted with 10% MeOH/CH$_2$Cl$_2$ to provide a mixture of 1-[3-({4-chloro-8-methoxy-1H,3H-furo[3,4-c]quinolin-7-yl}oxy)propyl]pyrrolidine and 1-[3-({4-chloro-7-methoxy-1H,3H-furo[3,4-c]quinolin-8-yl}oxy)propyl]pyrrolidine (1:1, 0.99 g) as a brown solid. LCMS (ES) [M+1]$^+$ m/z 363.2.

Step 5

Into a 8-mL seal tube was added 1-[3-({4-chloro-8-methoxy-1H,3H-furo[3,4-c]quinolin-7-yl}oxy)propyl]pyrrolidine and 1-[3-({4-chloro-7-methoxy-1H,3H-furo[3,4-c]quinolin-8-yl}oxy)propyl]pyrrolidine (1:1, 330 mg, 0.91 mmol, 1.0 eq.), dry 1,4-dioxane (4 mL), propan-2-amine (269 mg, 4.56 mmol, 5.00 eq.), t-BuONa (175 mg, 1.82 mmol, 2.00 eq.), 4 Å MS (50 mg) and 3rd-BrettPhos precatalyst (56 mg, 0.063 mmol, 0.05 eq.) subsequently. The resulting mixture was allowed to stir at 90° C. under N$_2$ for 2 h. The mixture was concentrated under reduced pressure. The residue was purified by a silica gel column eluted with 10% MeOH/CH$_2$Cl$_2$ to provide a mixture of the two crude desired products (326 mg). Purification of this crude mixture by chiral-Prep-HPLC with the conditions (Phenomenex Lux Cellulose-4 column, 21.2×250 mm; Mobile phase: 70% n-Hexane (0.1% diethylamine)/30% Ethanol; Flow rate: 20 mL/min; Detector 254 nm) to provide two fractions as below:

The first fraction was collected (Rt=6.5 min) to provide 7-methoxy-N-(propan-2-yl)-8-[3-(pyrrolidin-1-yl)propoxy]-1H,3H-furo[3,4-c]quinolin-4-amine (45) as a light yellow solid (82.5 mg). LCMS (ES) [M+1]$^+$ m/z 386.3.

The second fraction was collected (Rt=7.2 min) to provide 8-methoxy-N-(propan-2-yl)-7-[3-(pyrrolidin-1-yl)propoxy]-1H,3H-furo[3,4-c]quinolin-4-amine (46) as a light yellow solid. LCMS (ES) [M−1]$^+$ m/z 386.4.

Examples 47 and 48

Synthesis of N-cyclopropyl-7-methoxy-8-[3-(pyrrolidin-1-yl)propoxy]-1H,3H-furo[3,4-c]quinolin-4-amine (47) and N-cyclopropyl-8-methoxy-7-[3-(pyrrolidin-1-yl)propoxy]-1H,3H-furo[3,4-c]quinolin-4-amine (48)

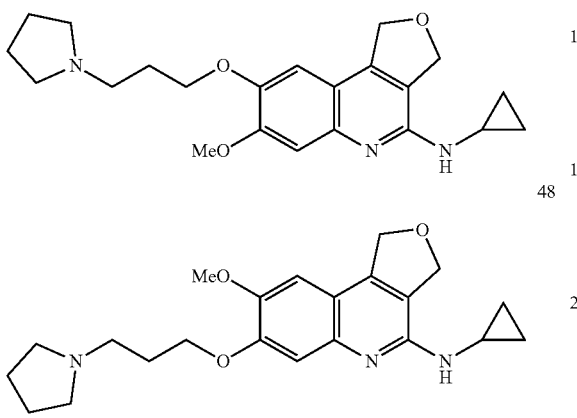

The title compounds were made from a mixture of 1-[3-({4-chloro-8-methoxy-1H,3H-furo[3,4-c]quinolin-7-yl}oxy)propyl]pyrrolidine and 1-[3-({4-chloro-7-methoxy-1H,3H-furo[3,4-c]quinolin-8-yl}oxy)propyl]pyrrolidine (1:1.) (prepared in Example 45 and 46, Step 4), following a procedure similar as described above in Example 45 and 46, Step 5, except that cyclopropanamine was used in the place of propan-2-amine.

The crude mixture was purified by a silica gel column eluted with 10% MeOH/CH$_2$Cl$_2$ to provide a mixture containing both the desired products. Purification of this crude mixture by chiral-Prep-HPLC with the conditions (Phenomenex Lux Cellulose-4 column, 21.2×250 mm; Mobile phase: 70% n-Hexane (0.1% diethylamine)/30% Ethanol; Flow rate: 20 mL/min; Detector 254 nm) to provide two fractions as below:

The first fraction was collected (Rt=15.0 min) to provide N-cyclopropyl-7-methoxy-8-[3-(pyrrolidin-1-yl)propoxy]-1H,3H-furo[3,4-c]quinolin-4-amine (47) as a light yellow solid (82.5 mg). LCMS (ES) [M+1]$^+$ m/z 384.3.

The second fraction was collected (Rt=17.8 min) to provide N-cyclopropyl-8-methoxy-7-[3-(pyrrolidin-1-yl)propoxy]-1H,3H-furo[3,4-c]quinolin-4-amine (48) as a light yellow solid. LCMS (ES) [M−1]$^+$ m/z 384.3.

Example 49

Synthesis of N-(cyclobutylmethyl)-8-methoxy-7-[3-(pyrrolidin-1-yl)propoxy]-1H,2H,3H-cyclopenta[c]quinolin-4-amine formate

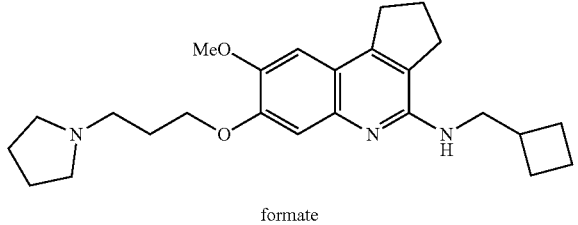 [SMILES: COc1cc2c3c(c(NCC4CCC4)nc2cc1OCCCN1CCCC1)CCC3]

formate

The title compound was made from 1-[3-({4-chloro-8-methoxy-1H,2H,3H-cyclopenta[c]quinolin-7-yl}oxy)propyl]pyrrolidine (Intermediate II-1) and cyclobutylmethanamine, following a procedure similar as described above in Example 3. The crude product was purified by reverse preparative (Prep-C18, 5 μM OBD column, 19×250 mm, waters; gradient elution of 0-35% MeCN in water over a 20 min period, where both solvents contain 0.1% formic acid, flow rate: 20 mL/min) to provide the title compound as a brown solid. LCMS (ES) [M+1]$^+$ m/z 410.3.

Example 50

Synthesis of 9-methoxy-N-(propan-2-yl)-8-[3-(pyrrolidin-1-yl)propoxy]-1H,2H,4H-pyrano[3,4-c]quinolin-5-amine formate

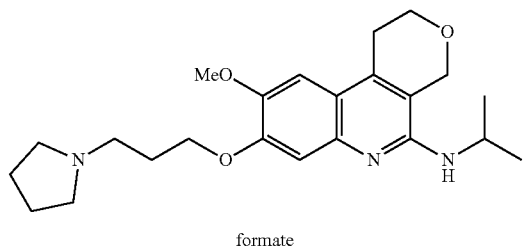 [SMILES: COc1cc2c3c(c(NC(C)C)nc2cc1OCCCN1CCCC1)COCC3]

formate

The title compound was made from 1-[3-({5-chloro-9-methoxy-1H,2H,4H-pyrano[3,4-c]quinolin-8-yl}oxy)propyl]pyrrolidine (Intermediate III-6) and propan-2-amine, following a procedure similar as described above in Example 3 except that reaction was conducted in microwave reactor at 80° C. for 3 h. The crude product was purified by reverse preparative HPLC (Prep-C18, 5 μM XBridge column, 19×150 mm, Waters; gradient elution of 13-35% MeCN in water over a 7 min period, where both solvents contain 0.1% formic acid) to provide the title compound as a yellow solid. LCMS (ES) [M+1]$^+$ m/z 400.3.

Example 51

Synthesis of 2-methoxy-3-[(1-methylpyrrolidin-3-yl)methoxy]-N-(propan-2-yl)-7,8,9,10-tetrahydrophenanthridin-6-amine formate

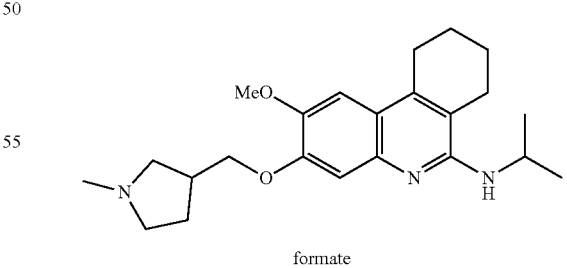

formate

The title compound was made from 6-chloro-2-methoxy-3-[(1-methylpyrrolidin-3-yl)methoxy]-7,8,9,10-tetrahydrophenanthridine (Intermediate II-6) and propan-2-amine, following a procedure similar as described above in Example 3. The crude product was purified by reverse preparative HPLC (Prep-C18, 5 μM SunFire column, 19×150 mm, Waters; gradient elution of 17-34% MeCN in water over a 7 min period, where both solvents contain 0.1% FA) to provide the title compound as a dark green solid. LCMS (ES) [M+1]$^+$ m/z 384.3.

Example 52

Synthesis of 9-methoxy-N-(propan-2-yl)-8-[3-(pyrrolidin-1-yl)propoxy]benzo[h]1,6-naphthyridin-5-amine formate

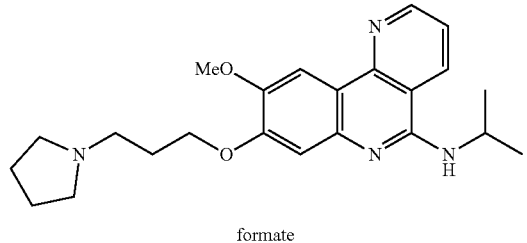 [SMILES: COc1cc2c(cc1OCCCN1CCCC1)nc(NC(C)C)c1cccnc12]

formate

The title compound was made from 1-[3-({5-chloro-9-methoxybenzo[h]1,6-naphthyridin-8-yl}oxy)propyl]pyrrolidine (Intermediate III-3) and propan-2-amine, following a procedure similar as described above in Example 3. The crude product was purified by reverse preparative HPLC (Prep-C18, 5 μM XBridge column, 19×150 mm, Waters; gradient elution of 8-24% MeCN in water over a 7 min period, where both solvents contain 0.1% FA) to provide the title compound as a brown solid. LCMS (ES) [M+1]$^+$ m/z 395.3.

Example 53

Synthesis of 8-methoxy-N,2,2-trimethyl-7-[3-(pyrrolidin-1-yl)propoxy]-1H,2H,3H-cyclopenta[c]quinolin-4-amine formate

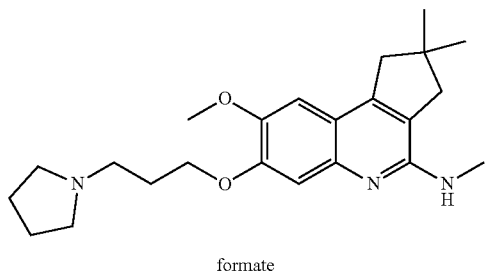 [SMILES: CNc1nc2cc(OCCCN3CCCC3)c(OC)cc2c2c1CC(C)(C)C2]

formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and ethylamine (2.0 M in THF), following a procedure similar as described above in Example 3. The crude product was purified by reverse preparative HPLC ((Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as a brown solid. LCMS (ES) [M+1]$^+$ m/z 384.3.

Example 54

Synthesis of 8-methoxy-2,2-dimethyl-N-(propan-2-yl)-7-[3-(pyrrolidin-1-yl)propoxy]-1H,2H,3H-cyclopenta[c]quinolin-4-amine formate

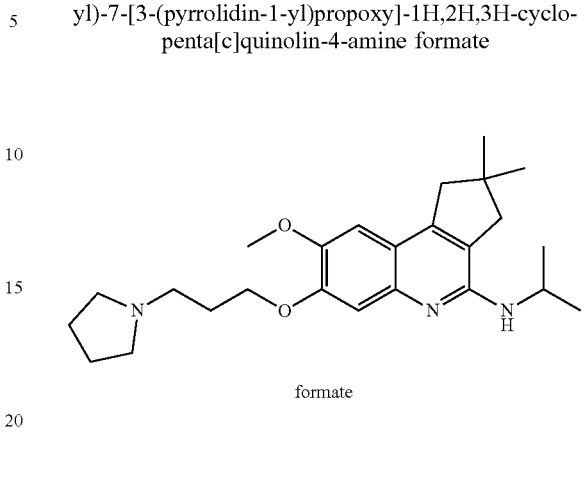

formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and propan-2-amine, following a procedure similar as described above in Example 3. The crude product was purified by reverse preparative HPLC ((Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as a brown solid. LCMS (ES) [M+1]$^+$ m/z 412.3.

Example 55

Synthesis of N-cyclopropyl-9-methoxy-8-[3-(pyrrolidin-1-yl)propoxy]-1H,2H,4H-pyrano[3,4-c]-quinolin-5-amine formate

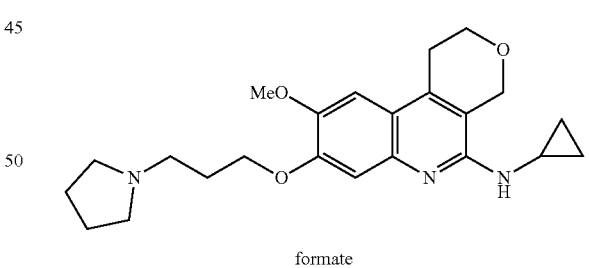

formate

The title compound was made from 1-[3-({5-chloro-9-methoxy-1H,2H,4H-pyrano[3,4-c]quinolin-8-yl}oxy)propyl]pyrrolidine (Intermediate III-6) and cyclopropanamine, following a procedure similar as described above in Example 3, except that reaction was conducted in microwave reactor at 80° C. for 3 h. The crude product was purified by reverse preparative HPLC (Prep-C18, 5 μM XBridge column, 19×150 mm, Waters; gradient elution of 13-35% MeCN in water over a 7 min period, where both solvents contain 0.1% formic acid) to provide the title compound as a yellow solid. LCMS (ES) [M+1]$^+$ m/z 398.2.

Example 56

Synthesis of 9-methoxy-8-[3-(pyrrolidin-1-yl)propoxy]pyrazolo[1,5-c]quinazolin-5-ol formate

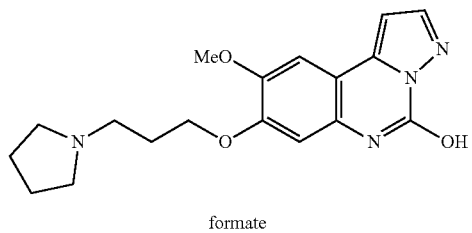 [SMILES: COc1cc2c(cc1OCCCN1CCCC1)nc(O)n1nccc21]

formate

Step 1

A mixture of 1H-pyrazol-5-ylboronic acid (186.90 mg; 1.67 mmol; 1.20 eq.), potassium carbonate (384.17 mg; 2.78 mmol; 2.00 eq.) and 1-[3-(4-bromo-2-methoxy-5-nitrophenoxy)-propyl]pyrrolidine (500.00 mg; 1.39 mmol; 1.00 eq.) in a mixed solvent of dimethylethane (2.0 mL) and water (0.6 mL) in a seal vial was purged with $N_2$ for 10 min. To the mixture was added Pd(PPh$_3$)$_4$ (80 mg, 0.07 mmol, 0.05 eq.) and CuI (27 mg, 0.14 mmol, 0.10 eq.). The vial was sealed and the mixture was allowed to stir at 100° C. for 16 h. The crude reaction mixture was cooled to rt, quenched with water, extracted with 30%$^i$PrOH/chloroform. The organic layers were combined and concentrated under reduced pressure. The residue was purified by flash chromatography on silica gel column eluted with 5-15% solvent A in $CH_2Cl_2$ (Solvent A is 0.1% $NH_4OH$/10% MeOH/$CH_2Cl_2$) to provide 5-(5-methoxy-2-nitro-4-(3-(pyrrolidin-1-yl)propoxy)phenyl)-1H-pyrazole as a brown syrup (310 mg, 64%). LCMS (ES) [M+1]$^+$ m/z 347.3.

Step 2

To a solution of 5-{5-methoxy-2-nitro-4-[3-(pyrrolidin-1-yl)propoxy]phenyl}-1H-pyrazole (310.00 mg; 0.89 mol) in MeOH (8 mL) was added Pd/C (30 mg). The reaction flask was purged with nitrogen once followed with hydrogen twice. The mixture was allowed to stir at 60° C. for 2.5 h. The solid was filtered off through a small pad of celite. Removal of the organic solvent under reduced pressure provided 4-methoxy-2-(1H-pyrazol-5-yl)-5-[3-(pyrrolidin-1-yl)propoxy]aniline as a brown oil (252 mg, 92%). LCMS (ES) [M+1]$^+$ m/z 317.3.

Step 3

To a flask charged with 4-methoxy-2-(1H-pyrazol-5-yl)-5-[3-(pyrrolidin-1-yl)propoxy]aniline (152.00 mg; 0.48 mmol; 1.00 eq.) was added anhydrous $CH_2Cl_2$ (4 mL) followed by N,N-diisopropylethylamine (0.2 mL). The resulting solution was cooled to −78° C. and to the mixture was added bis(trichloromethyl) carbonate (49.90 mg; 0.17 mmol; 0.35 eq.). After stirring at −78° C. for 20 min, the reaction flask was removed from the bath and allowed to stir at rt for 2 h. The reaction mixture was quenched with water and extracted with 30%$^i$PrOH/chloroform thrice. The organic layers were combined and concentrated under reduced pressure. The residue was dissolve din DMSO and subjected to purification by reverse preparative HPLC (Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as a white solid (33 mg, 19%). LCMS (ES) [M+1]$^+$ m/z 343.3.

Example 57

Synthesis of 9-methoxy-N-methyl-8-[3-(pyrrolidin-1-yl)propoxy]-1H,2H,4H-pyrano[3,4-c]quinolin-5-amine formate

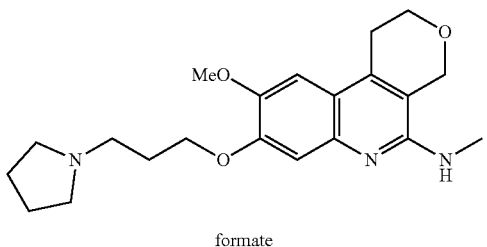 [SMILES: CNc1nc2cc(OCCCN3CCCC3)c(OC)cc2c2c1COCC2]

formate

The title compound was made from 1-[3-({5-chloro-9-methoxy-1H,2H,4H-pyrano[3,4-c]-quinolin-8-yl}oxy)propyl]pyrrolidine (Intermediate III-6) and methyl amine (2.0 M in THF), following a procedure similar as described above in Example 3, except that reaction was conducted in microwave reactor at 120° C. for 1.0 h. The crude product was purified by reverse preparative HPLC (Prep-C18, 5 mM XBridge column, 19×150 mm, Waters; gradient elution of 13-35% MeCN in water over a 7 min period, where both solvents contain 0.1% formic acid) to provide the title compound as a yellow solid. LCMS (ES) [M+1]$^+$ m/z 372.2.

Example 58

Synthesis of N-ethyl-9-methoxy-8-[3-(pyrrolidin-1-yl)propoxy]-1H,2H,4H-pyrano[3,4-c]quinolin-5-amine formate

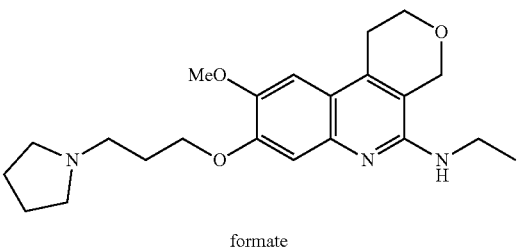 [SMILES: CCNc1nc2cc(OCCCN3CCCC3)c(OC)cc2c2c1COCC2]

formate

The title compound was made from 1-[3-({5-chloro-9-methoxy-1H,2H,4H-pyrano[3,4-c]quinolin-8-yl}oxy)propyl]pyrrolidine (Intermediate III-6) and ethylamine (2.0 M in THF), following a procedure similar as described above in Example 3, except that the reaction was conducted in microwave reactor at 120° C. for 1.0 h. The crude product was purified by reverse preparative HPLC (Prep-C18, 5 mM XBridge column, 19×150 mm, Waters; gradient elution of 13-35% MeCN in water over a 7 min period, where both solvents contain 0.1% formic acid) to provide the title compound as a yellow solid. LCMS (ES) [M+1]$^+$ m/z 386.2.

Example 59

Synthesis of 8-methoxy-N-methyl-7-[3-(pyrrolidin-1-yl)propoxy]-1H,3H-furo[3,4-c]quinolin-4-amine formate

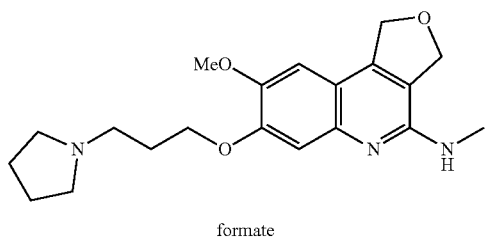 [SMILES: CNc1nc2cc(OCCCN3CCCC3)c(OC)cc2c2c1COC2]

formate

The title compound was made from 1-[3-({4-chloro-8-methoxy-1H,3H-furo[3,4-c]quinolin-7-yl}oxy)propyl]pyrrolidine (Intermediate III-7) and methylamine (2.0 N in THF), following a procedure similar as described above in Example 3, except that the reaction was conducted in microwave reactor at 100° C. for 1.0 h. The crude product was purified by reverse preparative HPLC (Prep-C18, 5 μM XBridge column, 19×150 mm, Waters; gradient elution of 13-35% MeCN in water over a 7 min period, where both solvents contain 0.1% formic acid) to provide the title compound as a light brown solid. $^1$H NMR (300 MHz, CD$_3$OD-d$_6$, ppm): 8.48 (br, 1H), 7.38 (s, 1H), 6.92 (s, 1H), 5.34 (s, 2H), 5.05 (s, 2H), 4.31-4.28 (m, 2H), 3.93 (s, 3H), 3.61-3.47 (m, 6H), 3.10 (s, 3H), 2.38-2.36 (m, 2H), 2.15-2.10 (m, 4H). LCMS (ES) [M+1]$^+$ m/z 358.2.

Example 60

Synthesis of N-ethyl-8-methoxy-7-[3-(pyrrolidin-1-yl)propoxy]-1H,3H-furo[3,4-c]quinolin-4-amine formate

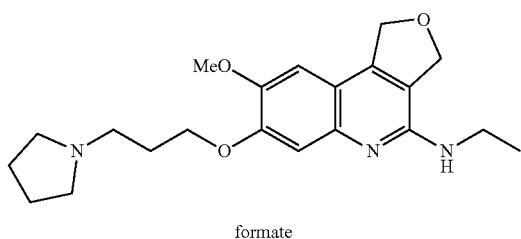 [SMILES: CCNc1nc2cc(OCCCN3CCCC3)c(OC)cc2c2c1COC2]

formate

The title compound was made from 1-[3-({4-chloro-8-methoxy-1H,3H-furo[3,4-c]quinolin-7-yl}oxy)propyl]pyrrolidine (Intermediate III-7) and ethylamine (2.0 N in THF), following a procedure similar as described above in Example 3, except that the reaction was conducted in microwave reactor at 100° C. for 1.0 h. The crude product was purified by reverse preparative HPLC (Prep-C18, 5 μM XBridge column, 19×150 mm, Waters; gradient elution of 13-35% MeCN in water over a 7 min period, where both solvents contain 0.1% formic acid) to provide the title compound as a light brown solid. LCMS (ES) [M+1]$^+$ m/z 372.2.

Example 61

Synthesis of 2-methoxy-6-(methylamino)-3-[3-(pyrrolidin-1-yl)propoxy]-7,8,9,10-tetrahydrophenanthridin-8-ol formate

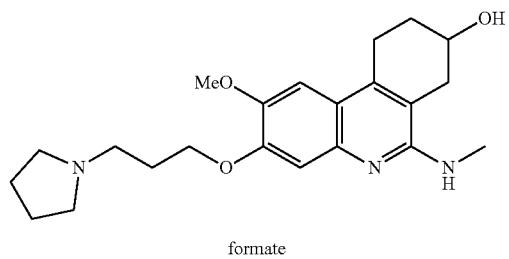 [SMILES: CNc1nc2cc(OCCCN3CCCC3)c(OC)cc2c2c1CC(O)CC2]

formate

Step 1

Into a 40-mL seal tube vial purged and maintained with an inert atmosphere of nitrogen, was placed a mixture of 8-(benzyloxy)-6-chloro-2-methoxy-3-[3-(pyrrolidin-1-yl)propoxy]-7,8,9,10-tetrahydrophenanthridine (Intermediate III-8) (1.00 g, 2.08 mmol, 1.00 eq.), anhydrous 1,4-dioxane (10 mL), MeNH$_2$ (5.2 mL, 2 N in THF, 10.4 mmol, 5.00 eq.), 3rd Brettphos precatalyst (189 mg, 0.208 mmol, 0.10 eq.), t-BuONa (400 mg, 4.16 mmol, 2.00 eq.) and 4 Å MS (400 mg) subsequently. The vial was sealed and the resulting solution was allowed to stir for 16 h at 90° C. under nitrogen atmosphere. The mixture was cooled to rt, diluted with 100 mL of 10% MeOH/CH$_2$Cl$_2$, filtered through a pad of celite. The filtrate was concentrated under reduced pressure to provide a crude product of 8-(benzyloxy)-2-methoxy-N-methyl-3-[3-(pyrrolidin-1-yl)propoxy]-7,8,9,10-tetrahydrophenanthridin-6-amine as a brown crude oil (956 mg). LCMS (ES) [M+1]$^+$ m/z 476.4.

Step 2

Into a 0° C. solution of 8-(benzyloxy)-2-methoxy-N-methyl-3-[3-(pyrrolidin-1-yl)propoxy]-7,8,9,10-tetrahydrophenanthridin-6-amine (500 mg, 1.05 mmol, 1.00 eq.) in CH$_2$Cl$_2$ (8 mL) was added TMSI (421 mg, 2.10 mmol, 2.00 eq.) dropwise with stirring. The resulting mixture was allowed to stir at room temperature for 4 h. The reaction mixture was then quenched by saturated aq. NaHCO$_3$. The mixture was diluted with 10% MeOH/CH$_2$Cl$_2$, dried over anhydrous sodium sulfate, filtered through a pad of celite. The filtrate was concentrated under reduced pressure. The residue was diluted with 5 mL of N,N-dimethylformamide, filtered and subjected to reverse phase preparative HPLC (Prep-C18, 5 μM SunFire column, 19×150 mm, Waters; gradient elution of 18%-22% MeCN in water over a 8 min period, where both solvents contain 0.05% FA) to provide the title compound as a green solid. LCMS (ES) [M+1]$^+$ m/z 386.2.

Example 62

Synthesis of 1-({8-methoxy-7-[3-(pyrrolidin-1-yl)propoxy]-1H,2H,3H-cyclopenta[c]quinolin-4-yl}amino)cyclopropane-1-carboxylic acid formate

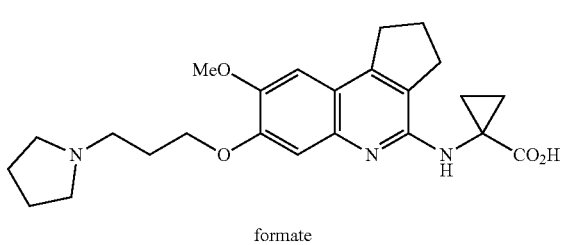 [SMILES: COc1cc2c3c(c(NC4(C(=O)O)CC4)nc2cc1OCCCN1CCCC1)CCC3]

formate

A mixture of 1-[3-({4-chloro-8-methoxy-1H,2H,3H-cyclopenta[c]quinolin-7-yl}oxy)propyl]-pyrrolidine (Intermediate II-1) (150 mg, 0.42 mmol, 1.00 eq.), 1,4-dioxane (5 mL), and t-BuONa (160 mg, 1.66 mmol, 4.00 eq.) in a microwave reaction vial was purged with N₂ for 5 min. To the solution was added 1-aminocyclopropane-1-carbonitrile hydrochloride (103 mg, 0.86 mol, 2.1 eq.), and 3rd Generation BrettPhos pre-catalyst (32 mg, 0.04 mmol, 0.05 eq.). After being purged with N₂ for additional 2 min, the resulting solution was sealed and subjected to microwave reactor (130° C., 2.5 h). The reaction mixture was allowed to cool to rt and quenched with H₂O. The resulting mixture was allowed to stir at rt for 2 h. After removal of the volatiles under reduced pressure, the residue was re-dissolved in DMSO, filtered and subjected to reverse preparative HPLC (Prep-C18, 5 μM OBD column, 19×250 mm, waters; gradient elution of 0-40% MeCN in water over a 20 min period, where both solvents contain 0.1% formic acid, flow rate: 20 mL/min)) to provide the title compound as a brown oil (65 mg, 38%). LCMS (ES) [M+1]⁺ m/z 426.2.

Example 63

Synthesis of 6-fluoro-8-methoxy-N-(propan-2-yl)-7-[3-(pyrrolidin-1-yl)propoxy]-1H,2H,3H-cyclopenta[c]quinolin-4-amine formate

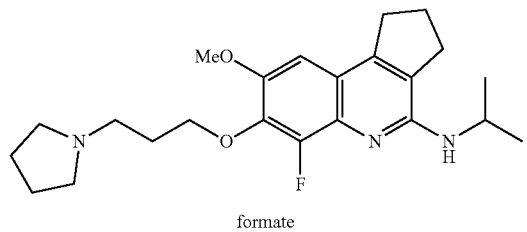 [SMILES: COc1cc2c3c(c(NC(C)C)nc2c(F)c1OCCCN1CCCC1)CCC3]

formate

The title compound was made from 1-[3-({4-chloro-6-fluoro-8-methoxy-1H,2H,3H-cyclopenta[c]quinolin-7-yl}oxy)propyl]pyrrolidine (Intermediate II-7) and propan-2-amine, following a procedure similar as described above in Example 3. The crude product was purified by reverse preparative HPLC (Prep-C18, 5 mM XBridge column, 19×150 mm, Waters; gradient elution of 13-35% MeCN in water over a 7 min period, where both solvents contain 0.1% formic acid) to provide the title compound as a light brown oil. LCMS (ES) [M+1]⁺ m/z 402.2.

Example 64

Synthesis of 3-({2-methoxy-3-[3-(pyrrolidin-1-yl)propoxy]-7,8,9,10-tetrahydrophenanthridin-6-yl}amino)cyclobutan-1-ol formate

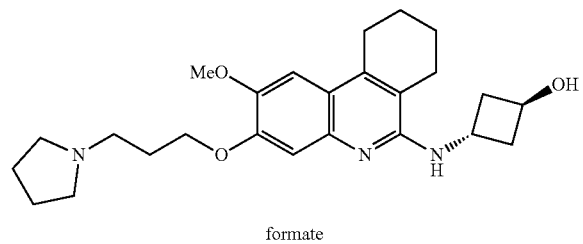 [SMILES: COc1cc2c3c(c(N[C@H]4C[C@H](O)C4)nc2cc1OCCCN1CCCC1)CCCC3]

formate

The title compound was made from 6-chloro-2-methoxy-3-[3-(pyrrolidin-1-yl)propoxy]-7,8,9,10-tetrahydrophenanthridine (Intermediate II-2) and trans-3-aminocyclobutane-1-ol, following a procedure similar as described above in Example 3. The crude product was purified by reverse preparative HPLC (Prep-C18, 5 μM XBridge column, 19×150 mm, Waters; gradient elution of 10-28% MeCN in water over a 7 min period, where both solvents contain 0.1% formic acid (FA)) to provide the title compound as a yellow solid. LCMS (ES) [M+1]⁺ m/z 426.3.

Example 65

Synthesis of 8-methoxy-7-[3-(pyrrolidin-1-yl)propoxy]-N-(2,2,2-trifluoroethyl)-1H,2H,3H-cyclopenta[c]quinolin-4-amine formate

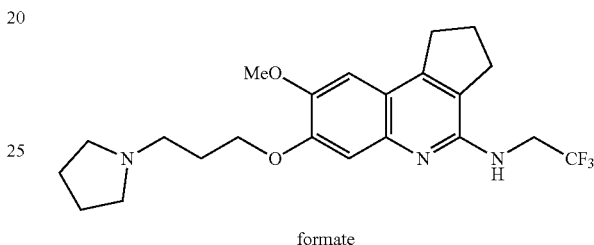

formate

The title compound was made from 1-[3-({4-chloro-8-methoxy-1H,2H,3H-cyclopenta[c]-quinolin-7-yl}oxy)propyl]pyrrolidine (Intermediate II-1) and 2,2,2-trifluoroethan-1-amine, following a procedure similar as described above in Example 3. The crude mixture was filtered and subjected to purification on reverse phase preparative HPLC (Prep-C18, 5 μM XBridge column, 19×150 mm, Waters; gradient elution of 10-25% MeCN in water over a 7 min period, where both solvents contain 0.1% formic acid (FA)) to provide the title compound as an off-white solid. LCMS (ES) [M+1]⁺ m/z 424.3.

Example 66

Synthesis of 8-methoxy-7-[3-(pyrrolidin-1-yl)propoxy]-N-(3,3,3-trifluoropropyl)-1H,2H,3H-cyclopenta[c]quinolin-4-amine

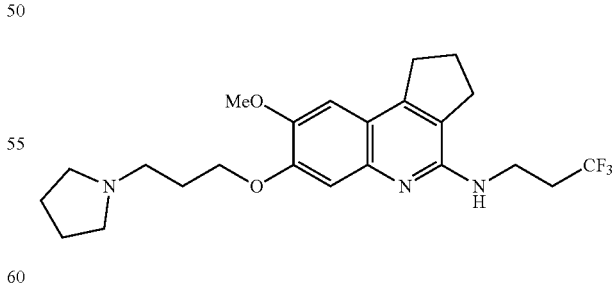

The title compound was made from 1-[3-({4-chloro-8-methoxy-1H,2H,3H-cyclopenta-[c]quinolin-7-yl}oxy)propyl]pyrrolidine (Intermediate II-1) and 3,3,3-trifluoropropan-1-amine, following z procedure similar as described above in Example 3, except that the crude mixture was filtered and concentrated under reduced pressure. The residue was purified by flash chromatography on silica gel

Example 67

Synthesis of 2-methoxy-3-[3-(pyrrolidin-1-yl)propoxy]-N-(2,2,2-trifluoroethyl)-7,8,9,10-tetrahydrophenanthridin-6-amine formate

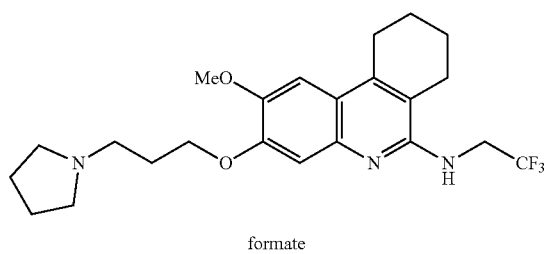 [SMILES: COc1cc2c3c(c(NCC(F)(F)F)nc2cc1OCCCN1CCCC1)CCCC3]

formate

The title compound was made from 6-chloro-2-methoxy-3-[3-(pyrrolidin-1-yl)propoxy]-7,8,9,10-tetrahydrophenanthridine (Intermediate II-2) and 2,2,2-trifluoroethan-1-amine, following a procedure similar described above in Example 3, except that the crude mixture was filtered and subjected to purification on reverse phase preparative HPLC (Prep-C18, 5 μM XBridge column, 19×150 mm, Waters; gradient elution of 12-27% MeCN in water over a 7 min period, where both solvents contain 0.1% formic acid (FA)) to provide the title compound as an off-white solid (116.3 mg, 36%). LCMS (ES) [M+1]$^+$ m/z 438.4.

Example 68

Synthesis of 2-methoxy-6-[(propan-2-yl)amino]-3-[3-(pyrrolidin-1-yl)propoxy]-7,8,9,10-tetrahydrophenanthridin-8-ol trifluoroacetate

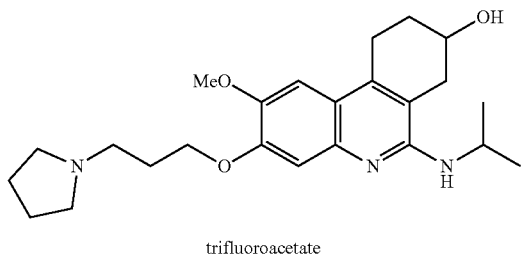 [SMILES: COc1cc2c3c(c(NC(C)C)nc2cc1OCCCN1CCCC1)CC(O)CC3]

trifluoroacetate

The title compound was made from 8-(benzyloxy)-6-chloro-2-methoxy-3-[3-(pyrrolidin-1-yl)propoxy]-7,8,9,10-tetrahydrophenanthridine (Intermediate III-8) following a procedure similar as described above in Example 61, except that propan-2-amine was used in place of MeNH$_2$. The crude product of the final step as purified by reverse preparative HPLC (Prep-C18, 5 μM SunFire column, 19×150 mm, Waters; gradient elution of 8-22% MeCN in water over a 8 min period, where both solvents contain 0.1% trifluoroacetic acid (TFA)) to provide the title compound as a light brown oil (90.0 mg, 18% over 2 steps). $^-$LCMS (ES) [M+1]$^+$ m/z 414.2.

Example 69

Synthesis of 8-methoxy-N-methyl-N-phenyl-7-[3-(pyrrolidin-1-yl)propoxy]-1H,2H,3H-cyclopenta[c]quinolin-4-amine trifluoroacetate

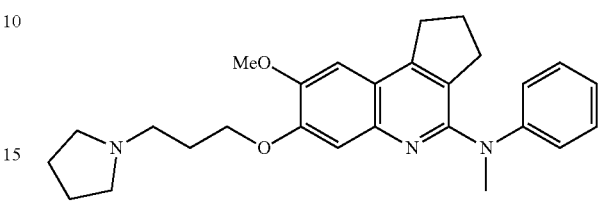

trifluoroacetate

The title compound was made from 1-[3-({4-chloro-8-methoxy-1H,2H,3H-cyclopenta-[c]quinolin-7-yl}oxy)propyl]pyrrolidine (Intermediate II-1) and N-methylaniline following a procedure similar as described above in Example 5, except that reaction solution was allowed to stir at 100° C. under N$_2$ atmosphere for 16 h. The crude mixture was filtered and subjected to purification on reverse phase preparative HPLC (Prep-C18, 5 μM SunFire column, 19×150 mm, Waters; gradient elution of 5-20% MeCN in water over a 1 min period and 20-35% MeCN in water over a 9 min period, where both solvents contain 0.1% trifluoroacetic acid (TFA)) to provide the title compound as a yellow solid. $^-$LCMS (ES) [M+1]$^+$ m/z 432.2.

Example 70

Synthesis of 1-{8-methoxy-7-[3-(pyrrolidin-1-yl)propoxy]-1H,2H,3H-cyclopenta[c]quinolin-4-yl}pyrrolidine formate

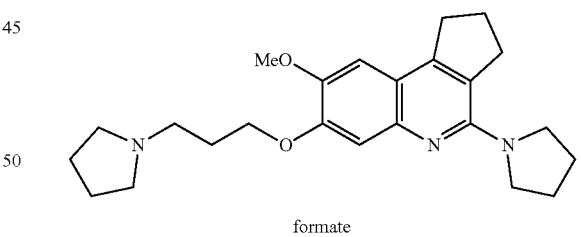

formate

The title compound was made from 1-[3-({4-chloro-8-methoxy-1H,2H,3H-cyclopenta[c]quinolin-7-yl}oxy)propyl]pyrrolidine (Intermediate II-1) and pyrrolidine, following a procedure similar as described above in Example 5, except that reaction solution was allowed to stir at 100° C. under N$_2$ atmosphere for 16 h. The crude reaction mixture was filtered and subjected to purification on reverse phase preparative HPLC (Prep-C18, 5 μM XBridge column, 19×150 mm, Waters; gradient elution of 5-22% MeCN in water over a 7 min period, where both solvents contain 0.1% formic acid (FA)) to provide the title compound as a dark green solid. LCMS (ES) [M+1]$^+$ m/z 396.2.

Example 71

Synthesis of 9-methoxy-3-methyl-N-(propan-2-yl)-8-[3-(pyrrolidin-1-yl)propoxy]-1H,2H,3H,4H-benzo[c]2,7-naphthyridin-5-amine formate

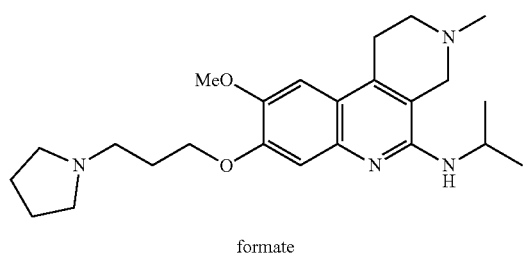 [SMILES: COc1cc2c3c(c(NC(C)C)nc2cc1OCCCN1CCCC1)CN(C)CC3]

formate

Into a 8-mL seal vial, was placed a mixture of 1-[3-({5-chloro-9-methoxy-3-methyl-1H,2H,3H,4H-benzo[c]2,7-naphthyridin-8-yl}oxy)propyl]pyrrolidine (Intermediate III-9) (110 mg, 0.281 mmol, 1.00 eq.), dry 1.4-dioxane (3 mL), propan-2-amine (83 mg, 1.40 mmol, 5.00 eq.), t-BuONa (81 mg, 0.843 mmol, 3.00 eq.) and 3rd-BrettPhos precatalyst (12 mg, 0.013 mmol, 0.05 eq.) subsequently. The resulting mixture was allowed to stir at 100° C. under $N_2$ for 1 h. The mixture was concentrated under reduced pressure and the resulting residue was dissolved in N,N-dimethylformamide (5 mL) and subjected to reverse preparative HPLC (Prep-C18, 5 mM XBridge column, 19×150 mm, Waters; gradient elution of 13-35% MeCN in water over a 7 min period, where both solvents contain 0.1% formic acid) to provide the title compound as a brown solid (72 mg, 62%). LCMS (ES) [M+1]+ m/z 413.3.

Example 72

Synthesis of 8-methoxy-N-methyl-N-(propan-2-yl)-7-[3-(pyrrolidin-1-yl)propoxy]-1H,2H,3H-cyclopenta[c]quinolin-4-amine trifluoroacetate

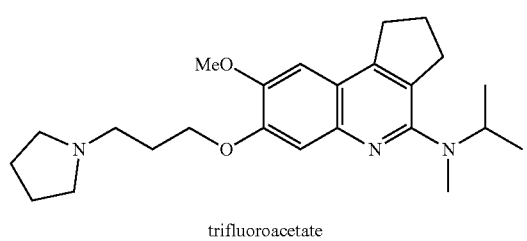

trifluoroacetate

Into a 50-mL sealed tube was placed 8-methoxy-N-(propan-2-yl)-7-[3-(pyrrolidin-1-yl)propoxy]-1H,2H,3H-cyclopenta[c]quinolin-4-amine (Example 3) (110 mg, 0.29 mmol, 1.00 eq.), ethanol (10 mL), $CH_2O$ (aq. 37%) (0.23 mL, 2.90 mmol, 10.00 eq.) and $NaBH_3CN$ (54 mg, 0.86 mmol, 3.00 eq.) subsequently. The resulting solution was allowed to stir at 120° C. for 16 h. The crude reaction mixture was filtered and subjected to purification on reverse phase preparative HPLC (Prep-C18, 5 μM SunFire column, 19×150 mm, Waters; gradient elution of 20-32% MeCN in water over a 9.5 min period, where both solvents contain 0.1% trifluoroacetic acid (TFA)) to provide the title compound as a yellow solid. LCMS (ES) [M+1]+ m/z 398.3.

Example 73

Synthesis of N-cyclopentyl-8-methoxy-N-methyl-7-[3-(pyrrolidin-1-yl)propoxy]-1H,2H,3H-cyclopenta[c]quinolin-4-amine trifluoroacetate

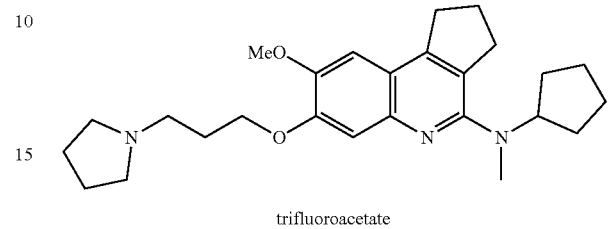

trifluoroacetate

The title compound was made from N-cyclopentyl-8-methoxy-7-[3-(pyrrolidin-1-yl)propoxy]-1H,2H,3H-cyclopenta[c]quinolin-4-amine (Example 8) following a procedure similar as described above in Example 72, except that the reaction solution was allowed to stir at 120° C. for 2 days. The crude reaction mixture was filtered and subjected to purification on reverse phase preparative HPLC (Prep-C18, 5 μM SunFire column, 19×150 mm, Waters; gradient elution of 20-42% MeCN in water over a 9.5 min period, where both solvents contain 0.1% trifluoroacetic acid (TFA)) to provide the title compound as a yellow semi-solid. LCMS (ES) [M+1]+ m/z 424.3.

Example 74

Synthesis of N-ethyl-8-methoxy-2,2-dimethyl-7-[3-(pyrrolidin-1-yl)propoxy]-1H,2H,3H-cyclopenta[c]quinolin-4-amine formate

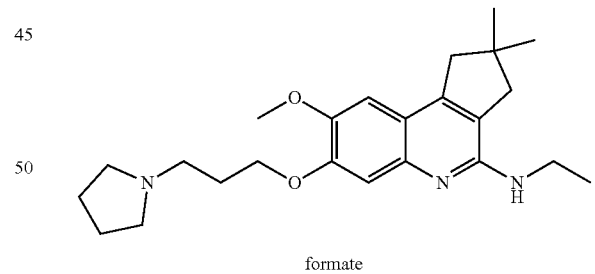

formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and ethylamine (2.0 M in THF), following a procedure similar as described above in Example 3, The crude product was purified by reverse preparative HPLC ((Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as a brown solid. LCMS (ES) [M+1]+ m/z 398.3.

Example 75

Synthesis of 1-[3-({9-methoxy-2,2-dimethyl-1H,2H,3H,4H-benzo[h]1,6-naphthyridin-8-yl}oxy)propyl]pyrrolidine formate

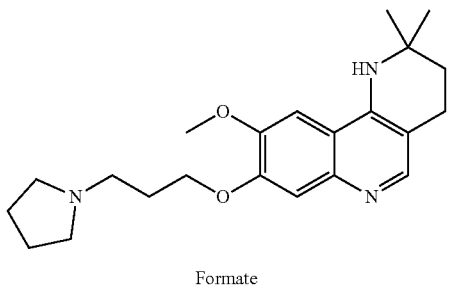 [SMILES: COc1cc2c3c(cnc2cc1OCCCN1CCCC1)CCC(C)(C)N3]

Formate

To a 8-mL vial was added dioxane/H₂O (4 mL, V/V=5/1), 1-[3-([5-chloro-9-methoxy-2,2-dimethyl-1H,2H,3H,4H-benzo[h]1,6-naphthyridin-8-yl]oxy)propyl]pyrrolidine (Intermediate III-10) (200 mg, 0.50 mmol, 1.00 eq.), K₃PO₄ (212 mg, 1.00 mmol, 2.00 eq.) and Pd(Amphos)Cl₂ (35 mg, 0.05 mmol, 0.10 eq.). The resulting mixture was stirred for 16 h at 90° C. under N₂. The mixture was concentrated under vacuum. To the residue was added DMF (5 mL). The mixture was filtered and subjected to reverse phase preparative HPLC (Prep-C18, 5 μM XBridge column, 19×150 mm, Waters; gradient elution of 5% MeCN in water to 15% MeCN in water over a 6 min period, where both solvents contain 0.1% formic acid) to provide the title compound (7.9 mg, 4%) as a brown semi-solid. ¹H NMR (300 MHz, CD₃OD-d₄): δ 8.10 (s, 1H), 7.78 (s, 1H), 7.23 (s, 1H), 4.34 (br, 2H), 4.06 (s, 3H), 3.56-3.48 (m, 6H), 2.96 (t, J=6.3 Hz, 2H), 2.38 (br, 2H), 2.15 (br, 4H), 1.91 (t, J=6.3 Hz, 2H), 1.49 (s, 6H). LCMS (ES) [M+1]⁺ m/z 370.2.

Example 76

Synthesis of 1-[3-({5-cyclopropyl-9-methoxy-2,2-dimethyl-1H,2H,3H,4H-benzo[h]1,6-naphthyridin-8-yl}oxy)propyl]pyrrolidine formate

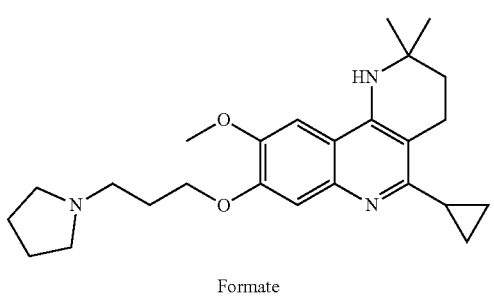 [SMILES: COc1cc2c3c(c(C4CC4)nc2cc1OCCCN1CCCC1)CCC(C)(C)N3]

Formate

Into a 40-mL vial, was placed a mixture of 1-[3-([5-chloro-9-methoxy-2,2-dimethyl-1H,2H,3H,4H-benzo[h]1,6-naphthyridin-8-yl]oxy)propyl]pyrrolidine (Intermediate III-10) (700 mg, 1.73 mmol, 1.00 eq.), toluene (20 mL), water (2 mL), cyclopropylboronic acid (1.09 g, 12.69 mmol, 5.00 eq.), Pd(dppf)Cl₂ (115 mg, 0.16 mmol, 0.10 eq.) and potassium carbonate (1.09 g, 7.89 mmol, 5.00 eq.). The resulting mixture was stirred for 2 h at 90° C. under N₂ and then concentrated under vacuum. The residue was diluted with DMF (5 mL), filtered and subjected to reverse preparative HPLC (Prep-C18, 20-45 μM, 120 g, Tianjin Bonna-Agela Technologies; gradient elution of 5% MeCN in water to 30% MeCN in water over a 10 min period, where both solvents contain 0.1% formic acid) to provide the title compound (59.8 mg, 6%) as a brown semi-solid. ¹H NMR (300 MHz, DMSO-d₆) δ 8.23 (s, 3H), 7.45 (s, 1H), 7.08 (s, 1H), 6.86 (s, 1H), 4.10 (t, J=6.3 Hz, 2H), 3.90 (s, 3H), 2.90 (t, J=6.3 Hz, 2H), 2.76-2.67 (m, 6H), 2.21-2.13 (m, 1H), 2.08-1.96 (m, 2H), 1.77-1.75 (m, 6H), 1.31 (s, 6H), 1.05-0.88 (m, 4H). LCMS (ES) [M+1]⁺ m/z 410.5.

Example 77

Synthesis of 1-(3-{[9-methoxy-2,2-dimethyl-5-(propan-2-yl)-1H,2H,3H,4H-benzo[h]1,6-naphthyridin-8-yl]oxy}propyl)pyrrolidine formate

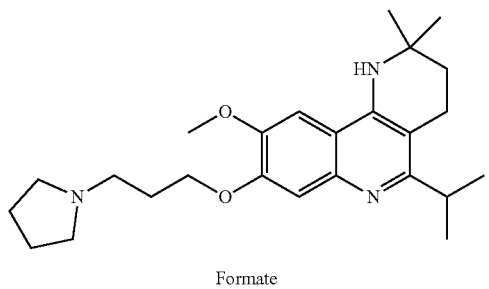 [SMILES: COc1cc2c3c(c(C(C)C)nc2cc1OCCCN1CCCC1)CCC(C)(C)N3]

Formate

Step 1

Into a 40-mL vial, was placed a mixture of 1-[3-([5-chloro-9-methoxy-2,2-dimethyl-1H,2H,3H,4H-benzo[h]1,6-naphthyridin-8-yl]oxy)propyl]pyrrolidine (Intermediate III-10) (700 mg, 1.74 mmol, 1.00 eq.), ethylene glycol dimethyl ether (20 mL), water (2 mL), 4,4,5,5-tetramethyl-2-(prop-1-en-2-yl)-1,3,2-dioxaborolane (1.46 g, 8.70 mmol, 5.00 eq.), Pd(PPh₃)₄ (402 mg, 0.348 mmol, 0.20 eq.) and Cs₂CO₃ (2.83 g, 8.70 mmol, 5.00 eq.). The resulting mixture was stirred for 2 h at 90° C. under N₂. The reaction mixture was cooled to rt and concentrated under vacuum. The residue was diluted with DMF (5 mL), filtered and subjected to reverse preparative HPLC (Prep-C18, 20-45 μM, 120 g, Tianjin Bonna-Agela Technologies; gradient elution of 5% MeCN in water to 30% MeCN in water over a 10 min period, where both solvents contain 0.1% formic acid) to provide 9-methoxy-2,2-dimethyl-5-(prop-1-en-2-yl)-8-(3-(pyrrolidin-1-yl)propoxy)-1,2,3,4-tetrahydrobenzo[h][1,6]naphthyridine (316.0 mg, 45%) as a brown oil. LCMS (ES) [M+1]⁺ m/z 410.5.

Step 2

Into a 25-mL round-bottom flask, was placed a mixture of 1-(3-[[9-methoxy-2,2-dimethyl-5-(prop-1-en-2-yl)-1H,2H,3H,4H-benzo[h]1,6-naphthyridin-8-yl]oxy]propyl)pyrrolidine (316 mg, 0.77 mmol, 1.00 eq.), methanol (10 mL) and 10% Pd/C (300 mg). The mixture was degassed and purged with hydrogen for 3 times. The resulting mixture was stirred for 1 h under H₂ at room temperature. The mixture was filtered, and the filtrate was subjected to reverse preparative HPLC (Prep-C18, 5 μM XBridge column, 19×150 mm, Waters; gradient elution of 9% MeCN in water to 18% MeCN in water over a 6 min period, where both solvents contain 0.1% formic acid) to provide the title compound (17.2 mg, 13%) as a yellow semi-solid. $^1$H NMR (300 MHz, DMSO-$d_6$) δ 8.27 (s, 3H), 7.54 (s, 1H), 7.33 (s, 1H), 7.31 (s, 1H), 4.14 (t, J=6.3 Hz, 2H), 3.92 (s, 3H), 3.40-3.31 (m, 1H), 2.82-2.67 (m, 8H), 2.08-2.01 (m, 2H), 1.76-1.74 (m, 6H), 1.33 (s, 6H), 1.28 (d, J=6.6 Hz, 6H). LCMS (ES) [M+1]$^+$ m/z 412.5.

Example 78

Synthesis of 1-[3-({9-methoxy-2,2,5-trimethyl-1H,2H,3H,4H-benzo[h]1,6-naphthyridin-8-yl}oxy)propyl]pyrrolidine

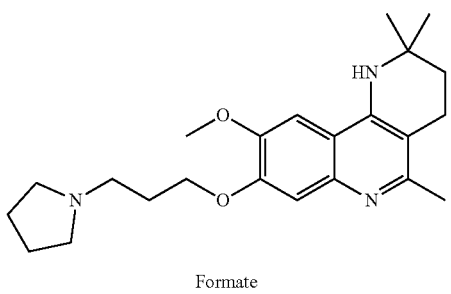 [SMILES: COc1cc2c3c(c(C)nc2cc1OCCCN1CCCC1)CCC(C)(C)N3]

Formate

Into a 40-mL vial, was placed a mixture of 1-[3-([5-chloro-9-methoxy-2,2-dimethyl-1H,2H,3H,4H-benzo[h]1,6-naphthyridin-8-yl]oxy)propyl]pyrrolidine (Intermediate III-10) (700 mg, 1.73 mmol, 1.00 eq.), dioxane (20 mL), water (2 mL), methylboronic acid (1.5 g, 25.06 mmol, 10.00 eq.), Pd(PPh$_3$)$_4$ (402 mg, 0.35 mmol, 0.20 eq.) and potassium carbonate (1.02 g, 7.38 mmol, 5.00 eq.). The resulting mixture was stirred for 2 h at 90° C. under N$_2$. The crude reaction mixture was filtered and subjected to reverse preparative HPLC (Prep-C18, 20-45 µM, 120 g, Tianjin Bonna-Agela Technologies; gradient elution of 5% MeCN in water to 25% MeCN in water over a 8 min period, where both solvents contain 0.1% formic acid) to provide the title compound as a brown semi-solid (114.6, 13%). $^1$H NMR (300 MHz, DMSO-$d_6$) δ 8.29 (s, 3H), 7.75 (s, 1H), 7.63 (s, 1H), 7.31 (s, 1H), 4.13 (t, J=6.0 Hz, 2H), 3.93 (s, 3H), 2.74-2.67 (m, 4H), 2.66-2.61 (m, 4H), 2.50 (s, 3H), 2.08-1.95 (m, 2H), 1.78-1.74 (m, 6H), 1.35 (s, 6H). LCMS (ES) [M+1]$^+$ m/z 384.4

Example 79

Synthesis of 1-[3-({6-cyclopentyl-10-methoxy-1H,2H,3H,4H,5H-azepino[3,2-c]quinolin-9-yl}oxy)propyl]pyrrolidine triflate

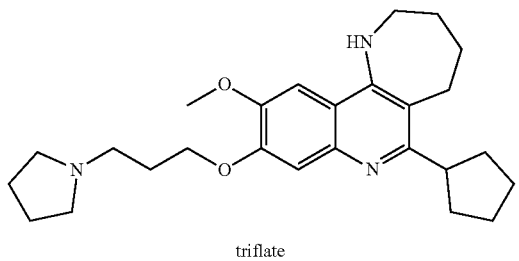 [SMILES: COc1cc2c3c(c(C4CCCC4)nc2cc1OCCCN1CCCC1)CCCCN3]

triflate

The title compound was made from 1-[3-({6-chloro-10-methoxy-1H,2H,3H,4H,5H-azepino[3,2-c]quinolin-9-yl}oxy)propyl]pyrrolidine (Intermediate III-5) and 2-(cyclopent-1-en-1-yl)-4,4,5,5-tetramethyl-1,3,2-dioxaborolane, following a procedure similar as described above in Example 77 above, except that reaction solution was allowed to stir at 100° C. under N$_2$ atmosphere for 16 h. The crude was purified by reverse phase preparative HPLC (Prep-C18, 5 µM XBridge column, 19×150 mm, Waters; gradient elution of 17% MeCN in water to 32% MeCN in water over a 6 min period, where both solvents contain 0.05% TFA) to provide the title compound as a brown viscous oil (88.4 mg, 24%). $^1$H NMR (300 MHz, DMSO-$d_6$) δ 12.23 (br, 1H), 9.69 (br, 1H), 8.48 (br, 1H), 7.65 (s, 1H), 7.53 (s, 1H), 4.21-4.17 (m, 2H), 3.92 (s, 3H), 3.77-3.71 (m, 2H), 3.68-3.58 (m, 2H), 3.56-3.47 (m, 1H), 3.41-3.29 (m, 2H), 3.13-2.97 (m, 4H), 2.29-2.21 (m, 2H), 2.10-1.70 (m, 16H). LCMS (ES) [M+1]$^+$ m/z 424.3.

Example 80

Synthesis of 1-[3-({6-cyclopropyl-10-methoxy-1H,2H,3H,4H,5H-azepino[3,2-c]quinolin-9-yl}oxy)propyl]pyrrolidine trifluoroacetate

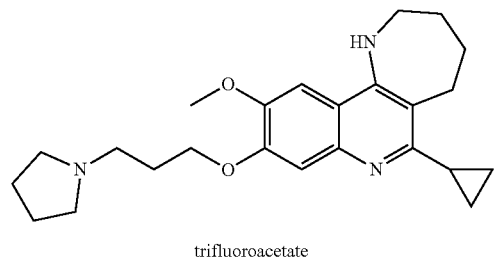 [SMILES: COc1cc2c3c(c(C4CC4)nc2cc1OCCCN1CCCC1)CCCCN3]

trifluoroacetate

Into a 40-mL vial, was placed a mixture of 1-[3-({6-chloro-10-methoxy-1H,2H,3H,4H,5H-azepino[3,2-c]quinolin-9-yl}oxy)propyl]pyrrolidine (Intermediate III-5) (500 mg, 1.28 mmol, 1.00 eq.), toluene (10 mL), cyclopropylboronic acid (222 mg, 2.58 mmol, 2.00 eq.), potassium carbonate (534 mg, 3.86 mmol, 3.00 eq.) and Pd(dppf)Cl$_2$ (98.2 mg, 0.13 mmol, 0.10 eq.). The resulting mixture was stirred for 16 h at 100° C. under N$_2$ and then concentrated under vacuum. The residue was dissolved in DMF (5 mL), filtered and subjected to reverse phase preparative HPLC (Prep-C18, 5 µM XBridge column, 19×150 mm, Waters; gradient elution of 2% MeCN in water to 25% MeCN in water over a 6 min period, where both solvents contain 0.05% TFA) to provide the title compound as a yellow oil (111.1 mg, 14%). $^1$HNMR (300 MHz, DMSO-$d_6$) δ 12.33 (s, 1H), 9.67 (br, 1H), 8.44 (br, 1H), 7.64 (s, 1H), 7.43 (s, 1H), 4.18-4.15 (m, 2H), 3.92 (s, 3H), 3.77-3.71 (m, 2H), 3.69-3.61 (m, 2H), 3.36-3.28 (m, 2H), 3.22-3.17 (m, 2H), 3.13-2.99 (m, 2H), 2.31-2.23 (m, 3H), 2.13-1.98 (m, 6H), 1.89-1.80 (m, 2H), 1.18-1.13 (m, 2H), 1.06-1.00 (m, 2H). LCMS (ES) [M+1]$^+$ m/z 396.3.

Example 81

Synthesis of 1-(3-{[10-methoxy-6-(propan-2-yl)-1H,2H,3H,4H,5H-azepino[3,2-c]quinolin-9-yl]oxy}propyl)pyrrolidine trifluoroacetate

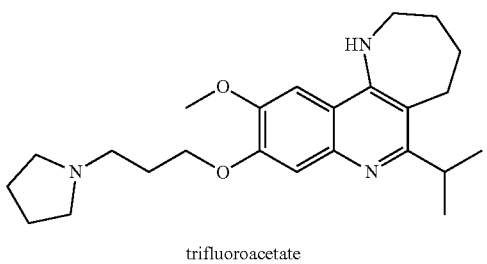 [SMILES: COc1cc2c3c(c(C(C)C)nc2cc1OCCCN1CCCC1)CCCCN3]

trifluoroacetate

The title compound was made from 1-[3-({6-chloro-10-methoxy-1H,2H,3H,4H,5H-azepino[3,2-c]quinolin-9-yl}oxy)propyl]pyrrolidine (Intermediate III-5) and 4,4,5,5-tetramethyl-2-(prop-1-en-2-yl)-1,3,2-dioxaborolane, following a procedure similar as described above in Example 79 above, except that reaction solvents were DME/H$_2$O (V/V=5/1) and allowed to stir at 100° C. under N$_2$ atmosphere for 16 h. The crude product was purified by reverse phase preparative HPLC (Prep-C18, 5 μM XBridge column, 19×150 mm, Waters; gradient elution of 16% MeCN in water to 30% MeCN in water over a 6 min period, where both solvents contain 0.05% TFA) to provide the title compound as a yellow solid (101.4 mg, 40%). $^1$H NMR (300 MHz, DMSO-d$_6$) δ 12.35 (br, 1H), 9.86 (br, 1H), 8.53 (br, 1H), 7.66 (s, 1H), 7.55 (s, 1H), 4.21-4.18 (m, 2H), 3.92 (s, 3H), 3.77-3.71 (m, 2H), 3.68-3.59 (m, 2H), 3.53-3.45 (m, 1H), 3.37-3.30 (m, 2H), 3.12-2.97 (m, 4H), 2.29-2.21 (m, 2H), 2.04-1.82 (m, 8H), 1.36 (d, J=6.9 Hz, 6H). LCMS (ES) [M+1]$^+$ m/z 398.2.

Example 82

Synthesis of 1-[3-({10-methoxy-6-methyl-1H,2H,3H,4H,5H-azepino[3,2-c]quinolin-9-yl}oxy)propyl]pyrrolidine trifluoroacetate

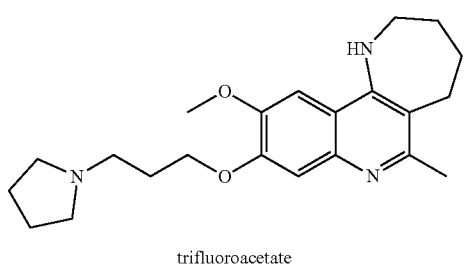 [SMILES: COc1cc2c3c(c(C)nc2cc1OCCCN1CCCC1)CCCCN3]

trifluoroacetate

Into a 40-mL vial, was placed a mixture of 1-[3-({6-chloro-10-methoxy-1H,2H,3H,4H,5H-azepino[3,2-c]quinolin-9-yl}oxy)propyl]pyrrolidine (Intermediate III-5) (500 mg, 1.28 mmol, 1.00 eq.), dioxane (5 mL), methylboronic acid (93 mg, 1.55 mmol, 1.20 eq.), Pd(PPh$_3$)$_4$ (68 mg, 0.064 mmol, 0.05 eq.) and potassium carbonate (534 mg, 3.86 mmol, 3.00 eq.). The mixture was stirred for 16 h at 100° C. under N$_2$ and then concentrated under vacuum. The residue was diluted with DMF (10 mL), filtered and subjected to reverse phase preparative HPLC (Prep-C18, 5 μM X Bridge column, 19×150 mm, Waters; gradient elution of 17% MeCN in water to 32% MeCN in water over a 6 min period, where both solvents contain 0.05% trifluoroacetic acid) to provide the title compound as a yellow oil (114.3 mg, 18%). $^1$H NMR (300 MHz, DMSO-d$_6$) δ 9.76 (br, 1H), 8.42 (br, 1H), 7.66 (s, 1H), 7.23 (s, 1H), 4.19 (t, J=5.7 Hz, 2H), 3.92 (s, 3H), 3.75-3.70 (m, 2H), 3.68-3.63 (m, 2H), 3.36-3.29 (m, 2H), 3.10-3.00 (m, 2H), 2.97-2.94 (m, 2H), 2.55 (s, 3H), 2.27-2.20 (m, 2H), 2.12-1.92 (m, 6H), 1.91-1.88 (m, 2H). LCMS (ES) [M+1]$^+$ m/z 370.2.

Example 83

Synthesis of 1-(3-{[4-(cyclopent-1-en-1-yl)-8-methoxy-2,2-dimethyl-1H,2H,3H-pyrrolo[3,2-c]quinolin-7-yl]oxy}propyl)pyrrolidine

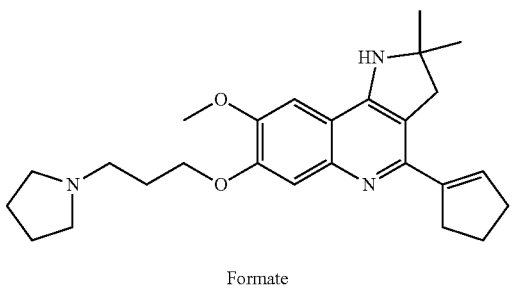 [SMILES: COc1cc2c3c(c(C4=CCCC4)nc2cc1OCCCN1CCCC1)CC(C)(C)N3]

Formate

Into a 8 mL seal tube under N$_2$ was added a mixture of 1-[3-[4-chloro-8-methoxy-2,2-dimethyl-1H,2H,3H-pyrrolo[3,2-c]quinolin-7-yl]oxy)propyl]pyrrolidine (Intermediate III-2) (250.00 mg; 0.64 mmol; 1.00 eq.), 1-cyclopenten-1-ylboronic acid (143.54 mg; 1.28 mmol; 2.00 eq.), 4-[di(tert-butyl)phosphino]-N,N-dimethylaniline compound with dichloropalladium (2:1) (90.80 mg; 0.13 mmol; 0.20 eq.) and K$_3$PO$_4$ (680.48 mg; 3.21 mmol; 5.00 eq.) in toluene (7.50 mL) and water (0.75 mL). The vial was sealed and heated at 60° C. for 90 min. The volatiles were removed under reduced pressure and the residue was redissolved in DMSO, filtered and subjected to purification on reverse phase preparative HPLC (Prep-C18 XSelect, 5 μM column, 19×150 mm, Waters; gradient elution of 0-50% MeCN in water over a 20 min period, where both solvents contain 0.1% hydrochloric acid) to provide the title compound (110 mg, 32%). LCMS (ES) [M+1]$^+$ m/z 422.1.

Example 84

Synthesis of 4-[(propan-2-yl)amino]-7-[3-(pyrrolidin-1-yl)propoxy]-1H,2H,3H-cyclopenta[c]quinolin-8-ol trifluoroacetate

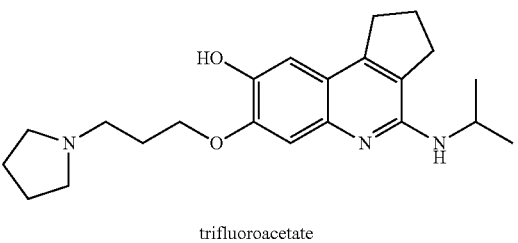 [SMILES: CC(C)Nc1nc2cc(OCCCN3CCCC3)c(O)cc2c2c1CCC2]

trifluoroacetate

Into a 100-mL round-bottom flask, was placed a solution of 8-methoxy-N-(propan-2-yl)-7-[3-(pyrrolidin-1-yl)propoxy]-1H,2H,3H-cyclopenta[c]quinolin-4-amine (1.0 g, 2.61 mmol, 1.00 eq.), AcOH (20 mL) and 48% HBr aqueous solution (20 mL). The resulting solution was stirred for 16 h at 100° C. and then concentrated under vacuum. The residue was diluted with DMF (20 mL), filtered and subjected to reverse phase preparative MPLC (Prep-C18, 20-45 μM, 120 g, Tianjin Bonna-Agela Technologies; gradient elution of 10% MeCN in water to 25% MeCN in water over a 10 min period, where both solvents contain 0.05% TFA) to provide the title compound as a brown solid (750 mg, 48%). $^1$H NMR (300 MHz, DMSO-$d_6$) δ 12.38 (s, 1H), 9.90 (br, 2H), 8.12 (d, J=8.4 Hz, 1H), 7.59 (s, 1H), 7.11 (s, 1H), 4.37-4.28 (m, 1H), 4.18 (t, J=5.4 Hz, 2H), 3.71-3.57 (m, 2H), 3.47-3.33 (m, 2H), 3.21-3.00 (m, 4H), 2.92-2.86 (m, 2H), 2.23-2.10 (m, 4H), 2.07-2.00 (m, 2H), 1.99-1.81 (m, 2H), 1.33 (d, J=6.3 Hz, 6H). LCMS (ES) [M+1]$^+$ m/z 370.3.

Example 85

Synthesis of 8-methoxy-7-[3-(piperidin-1-yl)propoxy]-N-(propan-2-yl)-1H,2H,3H-cyclopenta[c]quinolin-4-amine formate

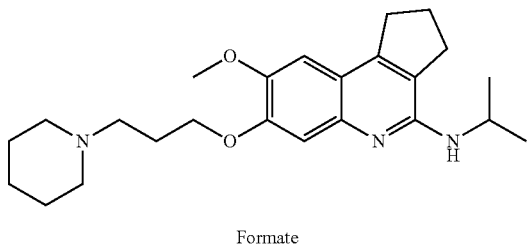 [SMILES: COc1cc2c3c(c(NC(C)C)nc2cc1OCCCN1CCCCC1)CCC3]

Formate

The title compound was made from 4-chloro-8-methoxy-7-(3-(piperidin-1-yl)propoxy)-2,3-dihydro-1H-cyclopenta[c]quinolone (Intermediate III-11) and propan-2-amine, following a procedure similar as described above in Example 5. The crude reaction mixture was filtered and subjected to purification on reverse phase preparative HPLC (Prep-C18, 5 μM, X Bridge column, 19×150 mm, Waters; gradient elution of 7% MeCN in water to 27% MeCN in water over a 6 min period, where both solvents contain 0.1% formic acid) to provide the title compound as a yellow solid (197.7 mg, 38%). $^1$H NMR (300 MHz, DMSO-$d_6$) δ 8.25 (s, 2H), 7.02 (s, 1H), 6.93 (s, 1H), 5.74 (d, J=7.5 Hz, 1H), 4.44-4.34 (m, 1H), 4.09 (t, J=6.0 Hz, 2H), 3.82 (s, 3H), 3.05 (t, J=7.2 Hz, 2H), 2.83-2.75 (m, 8H), 2.20-2.02 (m, 4H), 1.65-1.60 (m, 4H), 1.52-1.47 (m, 2H), 1.21 (d, J=6.9 Hz, 6H). LCMS (ES) [M+1]$^+$ m/z 398.3.

Example 86

Synthesis of 7-[3-(3,3-dimethylpyrrolidin-1-yl)propoxy]-8-methoxy-N-(propan-2-yl)-1H,2H,3H-cyclopenta[c]quinolin-4-amine formate

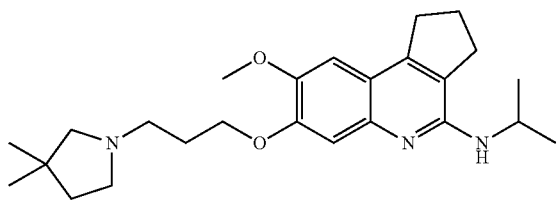

Formate

The title compound was made from 1-[3-([4-chloro-8-methoxy-1H, 2H, 3H-cyclopenta[c]quinolin-7-yl]oxy) propyl]-3, 3-dimethylpyrrolidine (Intermediate III-12) and propan-2-amine, following a procedure similar as described above in Example 5. The crude reaction mixture was filtered and subjected to purification on reverse phase preparative HPLC (Prep-C18, 5 μM XBridge column, 19×150 mm, Waters; gradient elution of 5% MeCN in water to 21% MeCN in water over a 6 min period, where both solvents contain 0.1% formic acid) to provide the title compound as a yellow solid (103.1 mg, 20%). $^1$H NMR (300 MHz, DMSO-$d_6$) δ 8.21 (s, 2H), 7.01 (s, 1H), 6.93 (s, 1H), 5.72 (d, J=8.1 Hz, 1H), 4.47-4.30 (m, 1H), 4.10 (t, J=6.3 Hz, 2H), 3.82 (s, 3H), 3.05 (t, J=7.2 Hz, 2H), 2.87-2.81 (m, 2H), 2.79-2.74 (m, 4H), 2.55-2.51 (m, 2H), 2.19-2.05 (m, 2H), 2.00-1.95 (m, 2H), 1.61 (t, J=7.2 Hz, 2H), 1.21 (d, J=6.3 Hz, 6H), 1.08 (s, 6H). LCMS (ES) m/z 412.3 [M−1]$^+$.

Example 87

Synthesis of 8-methoxy-2,2-dimethyl-N-(3-methylbutyl)-7-[3-(pyrrolidin-1-yl)propoxy]-1H,2H,3H-cyclopenta[c]quinolin-4-amine formate

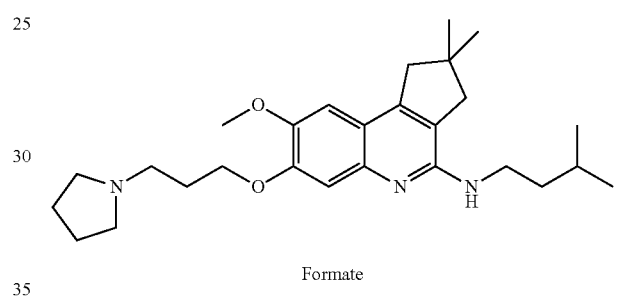

Formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and 3-methyl butanamine, following a procedure similar as described in Example 3 above. The reaction mixture was filtered and concentrated and the crude dissolved in dimethylsulfoxide and subjected to purification on reverse phase preparative HPLC (Prep-C18 XSelect, 5 μM column, 19×150 mm, Waters; gradient elution of 19-35% MeCN in water over a 7 min period, where both solvents contain 0.1% formic acid) to provide the title compound as a white powder (19 mg, 30%). LCMS (ES) [M+1]$^+$ m/z 440.1.

Example 88

Synthesis of N-[(1S)-1-cyclopropylethyl]-8-methoxy-7-[3-(pyrrolidin-1-yl)propoxy]-1H,2H,3H-cyclopenta[c]quinolin-4-amine formate

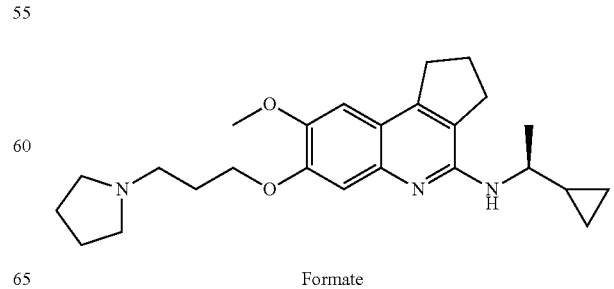

Formate

The title compound was made from 1-[3-({4-chloro-8-methoxy-1H,2H,3H-cyclopenta[c]quinolin-7-yl}oxy)-propyl]pyrrolidine (Intermediate II-1) and (S)-1-cyclopropylethan-1-amine, following a procedure similar as described above in Example 5. The crude reaction mixture was filtered and subjected to purification on reverse phase preparative HPLC (Prep-C18, 5 μM SunFire column, 19×150 mm, Waters; gradient elution of 10% MeCN in water to 20% MeCN in water over a 10 min period, where both solvents contain 0.1% FA) to provide the title compound as an off-white solid (36.2 mg, 14%). $^1$H NMR (300 MHz, DMSO) δ 8.14 (s, 0.4H), 7.00 (s, 1H), 6.95 (s, 1H), 5.91 (br, 1H), 4.14 (t, J=6.0 Hz, 2H), 3.83 (s, 3H), 3.81-3.76 (m, 1H), 3.33-3.23 (m, 6H), 3.09-3.04 (m, 2H), 2.85-2.73 (m, 2H), 2.18-2.13 (m, 4H), 1.95-1.90 (m, 4H), 1.26 (d, J=6.6 Hz, 3H), 1.09-1.01 (m, 1H), 0.49-0.33 (m, 3H), 0.23-0.18 (m, 1H). LCMS (ES) [M+1]$^+$ m/z 410.2.

Example 89

Synthesis of N-[(1R)-1-cyclopropylethyl]-8-methoxy-7-[3-(pyrrolidin-1-yl)propoxy]-1H,2H,3H-cyclopenta[c]quinolin-4-amine formate

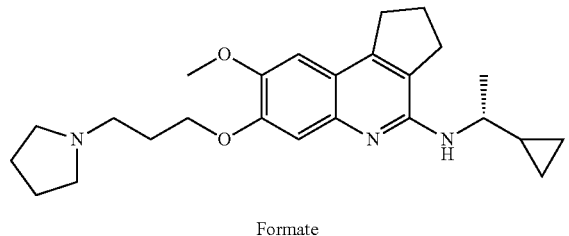 [SMILES: COc1cc2c3c(c(N[C@H](C)C4CC4)nc2cc1OCCCN1CCCC1)CCC3]

Formate

The title compound was made from 1-[3-({4-chloro-8-methoxy-1H,2H,3H-cyclopenta[c]quinolin-7-yl}oxy)-propyl]pyrrolidine (Intermediate II-1) and (R)-1-cyclopropylethan-1-amine, following a procedure similar as described above in Example 5. The crude reaction mixture was filtered and subjected to purification on reverse phase preparative HPLC (Prep-C18, 5 μM SunFire column, 19×150 mm, Waters; gradient elution of 10% MeCN in water to 20% MeCN in water over a 10 min period, where both solvents contain 0.1% FA) to provide the title compound as an off-white solid (43.2 mg, 17%). $^1$H NMR (300 MHz, CD$_3$OD) δ 7.45 (s, 1H), 7.19 (s, 1H), 4.31 (t, J=5.4 Hz, 2H), 3.98 (s, 3H), 3.64-3.55 (m, 2H), 3.49 (t, J=7.2 Hz, 2H), 3.40-3.28 (m, 5H), 3.02-2.97 (m, 2H), 2.39-2.32 (m, 4H), 2.15-2.10 (m, 4H), 1.45 (d, J=6.3 Hz, 3H), 1.24-1.18 (m, 1H), 0.69-0.56 (m, 2H), 0.40-0.33 (m, 2H). LCMS (ES) [M+1]$^+$ m/z 410.2.

Example 90

Synthesis of 1-(3-{[8-methoxy-4-(5-methylfuran-3-yl)-1H,2H,3H-cyclopenta[c]quinolin-7-yl]oxy}propyl)pyrrolidine formate

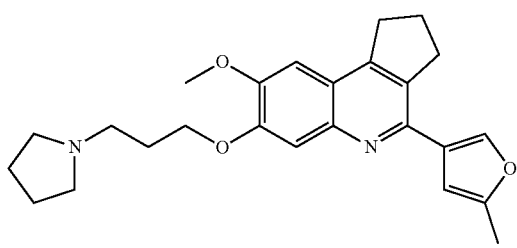

Formate

Step 1

Into a 250-mL round-bottom flask, was placed a mixture of methyl 4-bromofuran-2-carboxylate (3.0 g, 14.63 mmol, 1.00 eq.), 1,4-dioxane (100 mL), 4,4,5,5-tetramethyl-2-(tetramethyl-1,3,2-dioxaborolan-2-yl)-1,3,2-dioxaborolane (11.1 g, 43.89 mmol, 3.00 eq.), KOAc (4.3 g, 43.89 mmol, 3.00 eq.) and Pd(dppf)Cl$_2$ (534 mg, 0.73 mmol, 0.05 eq.). The resulting mixture was stirred for 16 h at 90° C. under N$_2$. The mixture was cooled to at and concentrated under vacuum. The residue was purified by a silica gel column eluted with ethyl acetate/petroleum ether (1/3) to provide methyl 4-(tetramethyl-1,3,2-dioxaborolan-2-yl)furan-2-carboxylate (1.3 g, 35%) as a yellow solid. LCMS (ES) m/z 253.2 [M+1]$^+$.

Step 2

Into a 100-mL round-bottom flask, was placed a mixture of methyl 4-(tetramethyl-1,3,2-dioxaborolan-2-yl)furan-2-carboxylate (500 mg, 1.98 mmol, 1.00 eq.), 1,4-dioxane (60 mL), water (10 mL), 1-[3-({4-chloro-8-methoxy-1H,2H,3H-cyclopenta[c]quinolin-7-yl}oxy)-propyl]pyrrolidine (Intermediate II-1) (568.8 mg, 1.58 mmol, 0.80 eq.), Cs$_2$CO$_3$ (1.9 g, 5.94 mmol, 3.00 eq.) and Pd(PPh$_3$)$_4$ (116 mg, 0.10 mmol, 0.05 eq.). The resulting mixture was stirred for 3 h at 100° C. under N$_2$. The mixture was cooled to rt and concentrated under vacuum. The residue was purified by a silica gel column eluted with dichloromethane/methanol (5/1) to provide methyl 4-[8-methoxy-7-[3-(pyrrolidin-1-yl)propoxy]-1H,2H,3H-cyclopenta[c]quinolin-4-yl]furan-2-carboxylate (335 mg, 37%) as a gray solid. LCMS (ES) m/z 451.2 [M+1]$^+$.

Step 3

Into a stirring solution of methyl 4-[8-methoxy-7-[3-(pyrrolidin-1-yl)propoxy]-1H,2H,3H-cyclopenta[c]quinolin-4-yl]furan-2-carboxylate (330 mg, 0.73 mmol, 1.00 eq.) in THF (20 mL) at 0° C. was added LiAH$_4$ (56 mg, 1.46 mmol, 2.00 eq.). The resulting mixture was stirred for 1 h and then quenched with water (0.06 mL), followed by addition of 15% sodium hydroxide aqueous solution (0.06 mL) and water (0.18 mL) in turn. The mixture was stirred for 30 minutes and then filtered through a pad of celite. The filter cake was washed with THF (2×10 mL). The combined filtrate was concentrated under vacuum to provide 4-[8-methoxy-7-[3-(pyrrolidin-1-yl)propoxy]-1H,2H,3H-cyclopenta[c]quinolin-4-yl]furan-2-yl)methanol (220 mg, 71%) as a yellow solid. LCMS (ES) m/z 423.2 [M+1]$^+$.

Step 4

Into a 50-mL round-bottom flask, was placed a mixture of (4-[8-methoxy-7-[3-(pyrrolidin-1-yl)propoxy]-1H,2H,3H-cyclopenta[c]quinolin-4-yl]furan-2-yl)methanol (220 mg, 0.52 mmol, 1.00 eq.), methanol (20 mL), concentrated hydrogen chloride solution (1.8 mL) and 10% Pd/C (30 mg). The resulting mixture was degassed and purged with H$_2$ for several times and then stirred for 30 min at rt. The crude reaction mixture was filtered and subjected to reverse phase preparative HPLC (Prep-C18, 5 μM XBridge column, 19×150 mm, Waters; gradient elution of 4% MeCN in water to 24% MeCN in water over a 6 min period, where both solvents contain 0.05% FA) to provide the title compound as a yellow solid (29.9 mg, 9%). $^1$H NMR (300 MHz, DMSO-d$_6$): δ 8.23 (s, 2H), 8.04 (s, 1H), 7.34 (s, 1H), 7.11 (s, 1H), 6.80 (s, 1H), 4.20 (t, J=6.0 Hz, 2H), 3.93 (s, 3H), 3.26-3.13 (m, 4H), 2.87-2.78 (m, 6H), 2.35 (s, 3H), 2.28-2.21 (m, 2H), 2.18-2.05 (m, 2H), 1.80-1.72 (m, 4H). LCMS (ES) m/z 407.2 [M+1]$^+$.

Example 91

Synthesis of N-butyl-8-methoxy-2,2-dimethyl-7-[3-(pyrrolidin-1-yl)propoxy]-1H,2H,3H-cyclopenta[c]quinolin-4-amine formate

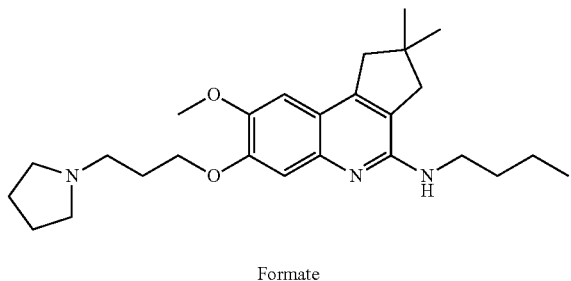 [SMILES: CCCCNc1nc2cc(OCCCN3CCCC3)c(OC)cc2c2c1CC(C)(C)C2]

Formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and 1-butanamine, following a procedure similar as described in Example 3 above. The reaction mixture was filtered and concentrated and the crude dissolved in dimethylsulfoxide and subjected to purification on reverse phase preparative HPLC (Prep-C18 XSelect, 5 µM column, 19×150 mm, Waters; gradient elution of 0-50%% MeCN in water over a 20 min period, where both solvents contain 0.1% formic acid) to provide the title compound as a white powder (19 mg, 30%). LCMS (ES) [M+1]$^+$ m/z 426.1.

Example 92

Synthesis of 7-[3-(dimethylamino)propoxy]-8-methoxy-N-(propan-2-yl)-1H,2H,3H-cyclopenta[c]quinolin-4-amine formate

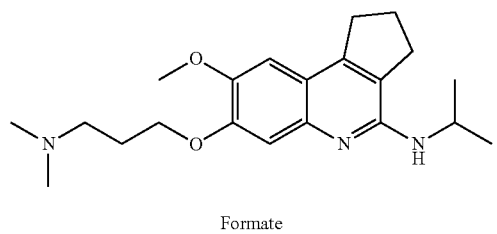 [SMILES: COc1cc2c3c(c(NC(C)C)nc2cc1OCCCN(C)C)CCC3]

Formate

The title compound was made from [3-([4-chloro-8-methoxy-1H,2H,3H-cyclopenta[c]quinolin-7-yl]oxy)propyl]dimethylamine (Intermediate III-13) and propan-2-amine, following a procedure similar as described above in Example 5. The crude reaction mixture was filtered and subjected to purification on reverse phase preparative HPLC (Prep-C18, 5 µM SunFire column, 19×150 mm, Waters; gradient elution of 2% MeCN in water to 19% MeCN in water over a 6 min period, where both solvents contain 0.1% formic acid) to provide the title compound as a yellow solid (98.9 mg, 25%). $^1$H NMR (300 MHz, DMSO-d$_6$): 8.23 (s, 1H), 7.01 (s, 1H), 6.93 (s, 1H), 5.72 (d, J=7.8 Hz, 1H), 4.43-4.32 (m, 1H), 4.09 (t, J=6.3 Hz, 2H), 3.82 (s, 3H), 3.05 (t, J=7.2 Hz, 2H), 2.79-2.70 (m, 4H), 2.42 (s, 6H), 2.19-2.11 (m, 2H), 2.05-1.97 (m, 2H), 1.20 (d, J=6.6 Hz, 6H). LCMS (ES) [M+1]$^+$ m/z 358.2.

Example 93

Synthesis of 7-[3-(diethylamino)propoxy]-8-methoxy-N-(propan-2-yl)-1H,2H,3H-cyclopenta[c]quinolin-4-amine formate

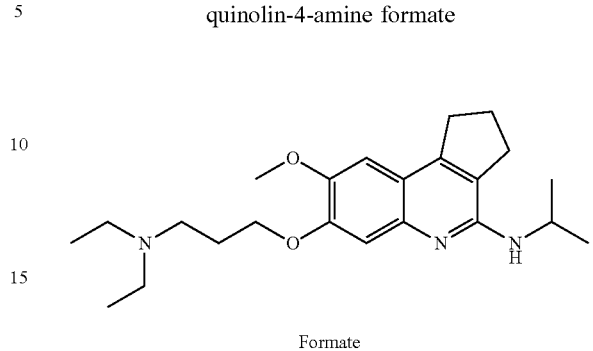

Formate

The title compound was made from [3-([4-chloro-8-methoxy-1H,2H,3H-cyclopenta[c]quinolin-7-yl]oxy)propyl]diethylamine (Intermediate III-14) and propan-2-amine, following a procedure similar as described above in Example 5. The crude reaction mixture was filtered and subjected to purification on reverse phase preparative HPLC (Prep-C18, 5 µm XBridge column, 19×150 mm, Waters; gradient elution of 2% MeCN in water to 18% MeCN in water over a 6 min period, where both solvents contain 0.1% formic acid) to provide the title compound as a yellow solid (76.3 mg, 21%). $^1$H NMR (300 MHz, DMSO-d$_6$): 8.21 (s, 1H), 6.99 (s, 1H), 6.92 (s, 1H), 5.70 (d, J=8.1 Hz, 1H), 4.43-4.32 (m, 1H), 4.09 (t, J=6.3 Hz, 2H), 3.82 (s, 3H), 3.07-3.02 (m, 2H), 2.79-2.58 (m, 8H), 2.18-2.09 (m, 2H), 1.94-1.90 (m, 2H), 1.20 (d, J=6.6 Hz, 6H), 1.02 (t, J=6.9 Hz, 6H). LCMS (ES) [M+1]$^+$ m/z 386.3.

Example 94

Synthesis of N-tert-butyl-8-methoxy-7-[3-(pyrrolidin-1-yl)propoxy]-1H,2H,3H-cyclopenta[c]quinolin-4-amine formate

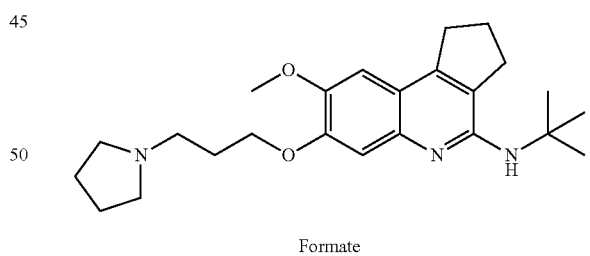

Formate

The title compound was made from 1-[3-({4-chloro-8-methoxy-1H,2H,3H-cyclopenta[c]quinolin-7-yl}oxy)-propyl]pyrrolidine (Intermediate II-1) and 2-methylpropan-2-amine, following a procedure similar as described above in Example 6 above, except that the reaction solution was allowed to stir at 50° C. under N$_2$ atmosphere for 3 h. The crude reaction mixture was filtered and subjected to reverse phase preparative HPLC (Prep-C18, 5 µM SunFire column, 19×150 mm, Waters; gradient elution of 5% MeCN in water to 40% MeCN in water over a 7 min period, where both solvents contain 0.1% FA) to provide the title compound as a gray solid (22.5 mg, 13%). $^1$H NMR (300 MHz, DMSO-d$_6$) δ 8.23 (s, 1H), 7.00 (s, 1H), 6.92 (s, 1H), 5.05 (s, 1H), 4.09 (t, J=6.3 Hz, 2H), 3.82 (s, 3H), 3.05 (t, J=7.5 Hz, 2H), 2.77 (t, J=7.5 Hz, 2H), 2.67 (t, J=7.2 Hz, 2H), 2.62-2.59 (m, 4H), 2.17-2.08 (m, 2H), 2.01-1.95 (m, 2H), 1.77-1.72 (m, 4H), 1.51 (s, 9H). LCMS (ES) [M+1]$^+$ m/z 398.2.

Example 95

Synthesis of N-isobutyl-8-methoxy-2,2-dimethyl-7-(3-(pyrrolidin-1-yl)propoxy)-2,3-dihydro-1H-cyclopenta[c]quinolin-4-amine formate

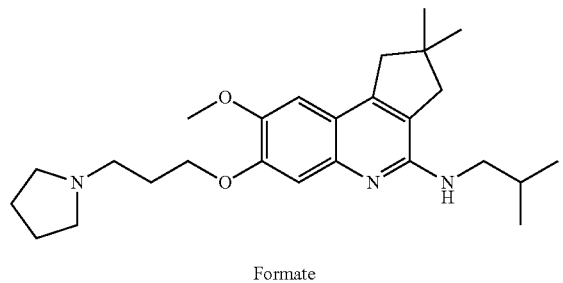 [SMILES: COc1cc2c3c(c(NCC(C)C)nc2cc1OCCCN1CCCC1)CC(C)(C)C3]

Formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and 2-methyl-1-propanamine, following a procedure similar as described in Example 3 above. The reaction mixture was filtered and concentrated under reduced pressure. The residue was dissolved in dimethylsulfoxide and subjected to purification on reverse phase preparative HPLC (Prep-C18 XSelect, 5 µM column, 19×150 mm, Waters; gradient elution of 0-50% MeCN in water over a 20 min period, where both solvents contain 0.1% formic acid) to provide the title compound as a white powder (29 mg, 40%). LCMS (ES) [M+1]$^+$ m/z 426.1.

Example 96

Synthesis of N-(cyclobutylmethyl)-8-methoxy-2,2-dimethyl-7-(3-(pyrrolidin-1-yl)propoxy)-2,3-dihydro-1H-cyclopenta[c]quinolin-4-amine formate

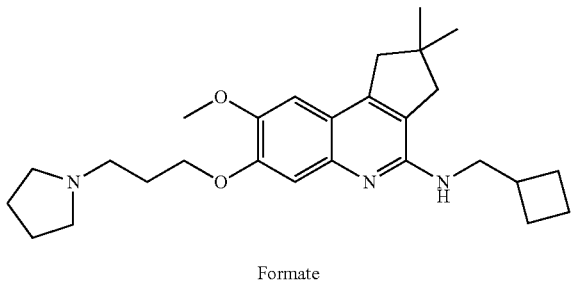 [SMILES: COc1cc2c3c(c(NCC4CCC4)nc2cc1OCCCN1CCCC1)CC(C)(C)C3]

Formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and cyclobutylmethanamine, following a procedure similar as described in Example 3 above. The reaction mixture was filtered and concentrated under reduced pressure. The residue was dissolved in dimethylsulfoxide and subjected to purification on reverse phase preparative HPLC (Prep-C18 XSelect, 5 µM column, 19×150 mm, Waters; gradient elution of 0-50% MeCN in water over a 20 min period, where both solvents contain 0.1% formic acid) to provide the title compound as a white powder (15 mg, 20%). LCMS (ES) [M+1]$^+$ m/z 438.1.

Example 97

Synthesis of N-(cyclopropylmethyl)-8-methoxy-2,2-dimethyl-7-[3-(pyrrolidin-1-yl)propoxy]-1H,2H,3H-cyclopenta[c]quinolin-4-amine formate

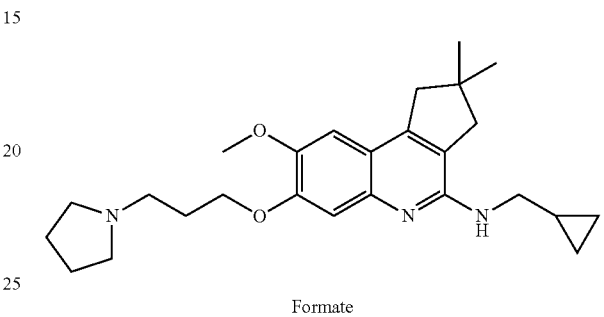

Formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and cyclopropyllmethanamine, following a procedure similar as described in Example 3 above. The reaction mixture was filtered and concentrated under reduced pressure. The residue was dissolved in dimethylsulfoxide and subjected to purification on reverse phase preparative HPLC (Prep-C18 XSelect, 5 µM column, 19×150 mm, Waters; gradient elution of 0-50%% MeCN in water over a 20 min period, where both solvents contain 0.1% formic acid) to provide the title compound as a white powder (24 mg, 33%). LCMS (ES) [M+1]$^+$ m/z 424.1.

Example 98

Synthesis of 1-(3-{[8-methoxy-4-(oxolan-3-yl)-1H,2H,3H-cyclopenta[c]quinolin-7-yl]oxy}propyl)pyrrolidine formate

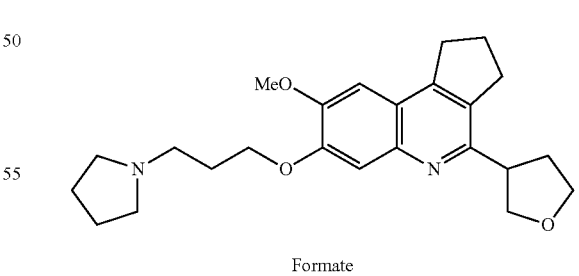

Formate

The title compound was made from 1-[3-({4-chloro-8-methoxy-1H,2H,3H-cyclopenta[c]quinolin-7-yl}oxy)-propyl]pyrrolidine (Intermediate II-1) and 2-(2,5-dihydrofuran-3-yl)-4,4,5,5-tetramethyl-1,3,2-dioxaborolane, following a procedure similar as described above in Example 77 above, except that reaction solution was allowed to stir at 80° C. under N$_2$ atmosphere overnight. The crude reaction mixture was filtered and subjected to reverse phase preparative HPLC (Prep-C18, 5 µM XBridge column, 19×150 mm, Waters; gradient elution of 5% MeCN in water to 15% MeCN in water over a 7 min period, where both solvents contain 0.1% formic acid) to provide the title compound as a light yellow solid (64.1 mg, 27%). $^1$H NMR (300 MHz, DMSO-$d_6$): δ 8.21 (s, 1H), 7.31 (s, 1H), 7.09 (s, 1H), 4.17 (t, J=6.3 Hz, 2H), 4.10 (t, J=7.8 Hz, 1H), 3.99-3.94 (m, 1H), 3.91 (s, 3H), 3.89-3.82 (m, 2H), 3.74-3.66 (m, 1H), 3.19 (t, J=7.5 Hz, 2H), 3.08-3.03 (m, 2H), 2.77-2.67 (m, 6H), 2.36-2.16 (m, 4H), 2.04-1.98 (m, 2H), 1.79-1.76 (m, 4H). LCMS (ES) [M+1]$^+$ m/z 397.2.

Example 99

Synthesis of N-[(2S)-butan-2-yl]-8-methoxy-7-[3-(pyrrolidin-1-yl)propoxy]-1H,2H,3H-cyclopenta[c]quinolin-4-amine formate

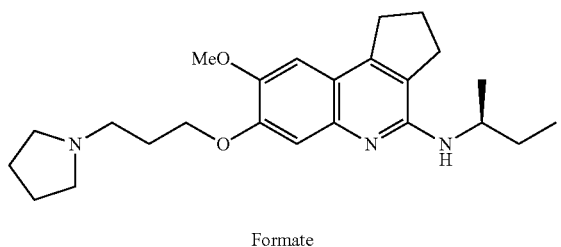 [SMILES: CC[C@H](C)Nc1nc2cc(OCCCN3CCCC3)c(OC)cc2c2c1CCC2]

Formate

The title compound was made from 1-[3-({4-chloro-8-methoxy-1H,2H,3H-cyclopenta[c]quinolin-7-yl}oxy)-propyl]pyrrolidine (Intermediate II-1) and (S)-butan-2-amine, following a procedure similar as described above in Example 5. The crude reaction mixture was filtered and subjected to purification on reverse phase preparative HPLC (Prep-C18, 5 µM XBridge column, 19×150 mm, Waters; gradient elution of 10% MeCN in water to 10% MeCN in water over a 7 min period, where both solvents contain 0.1% formic acid) to provide the title compound (32.3 mg, 13%) as a white solid. $^1$H NMR (300 MHz, DMSO-$d_6$) δ 8.16 (s, 1H), 7.03 (s, 1H), 6.94 (s, 1H), 5.72 (d, J=8.1 Hz, 1H), 4.26-4.19 (m, 1H), 4.14 (t, J=6.0 Hz, 2H), 3.83 (s, 3H), 3.17-3.14 (m, 6H), 3.06 (t, J=7.5 Hz, 2H), 2.79-2.73 (m, 2H), 2.00-2.10 (m, 4H), 1.91-1.88 (m, 4H), 1.68-1.47 (m, 2H), 1.17 (d, J=6.3 Hz, 3H), 0.90 (t, J=7.5 Hz, 3H). LCMS (ES) [M+1]$^+$ m/z: 398.4.

Example 100

Synthesis of N-[(2R)-butan-2-yl]-8-methoxy-7-[3-(pyrrolidin-1-yl)propoxy]-1H,2H,3H-cyclopenta[c]quinolin-4-amine formate

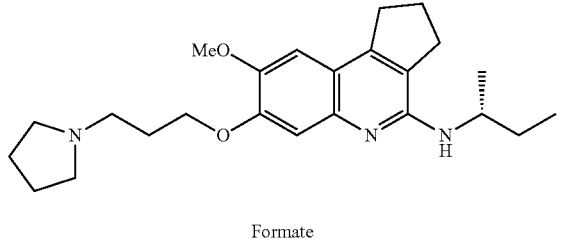 [SMILES: CC[C@@H](C)Nc1nc2cc(OCCCN3CCCC3)c(OC)cc2c2c1CCC2]

Formate

The title compound was made from 1-[3-({4-chloro-8-methoxy-1H,2H,3H-cyclopenta[c]quinolin-7-yl}oxy)-propyl]pyrrolidine (Intermediate II-1) and (R)-butan-2-amine, following a procedure similar as described above in Example 5. The crude reaction mixture was filtered and subjected to purification on reverse phase preparative HPLC (Prep-C18, 5 µM XBridge column, 19×150 mm, Waters; gradient elution of 10% MeCN in water to 20% MeCN in water over a 7 min period, where both solvents contain 0.1% formic acid) to provide the title compound (29.3 mg, 12%) as a white solid. $^1$H NMR (300 MHz, DMSO-$d_6$) δ 8.15 (s, 1H), 7.03 (s, 1H), 6.95 (s, 1H), 5.74 (d, J=7.8 Hz, 1H), 4.26-4.19 (m, 1H), 4.15 (t, J=6.3 Hz, 2H), 3.83 (s, 3H), 3.28-3.15 (m, 6H), 3.06 (t, J=7.5 Hz, 2H), 2.83-2.72 (m, 2H), 2.17-2.06 (m, 4H), 1.93-1.84 (m, 4H), 1.68-1.47 (m, 2H), 1.17 (d, J=6.6 Hz, 3H), 0.90 (t, J=7.5 Hz, 3H). LCMS (ES) [M+1]$^+$ m/z: 398.4.

Example 101

Synthesis of N-(2,2-dimethylpropyl)-8-methoxy-7-[3-(pyrrolidin-1-yl)propoxy]-1H,2H,3H-cyclopenta[c]quinolin-4-amine formate

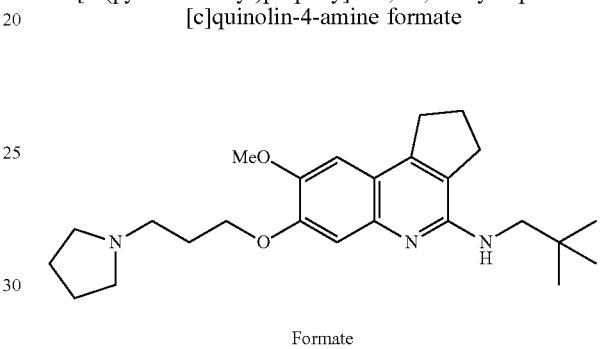

Formate

The title compound was made from 1-[3-({4-chloro-8-methoxy-1H,2H,3H-cyclopenta[c]quinolin-7-yl}oxy)-propyl]pyrrolidine (Intermediate II-1) and 2,2-dimethylpropan-1-amine, following a procedure similar as described above in Example 5. The crude reaction mixture was filtered and subjected to purification on reverse phase preparative HPLC (Prep-C18, 5 µM X Bridge column, 19×150 mm, Waters; gradient elution of 17% MeCN in water to 30% MeCN in water over a 6 min period, where both solvents contain 0.1% formic acid) to provide the title compound (82.5 mg, 30%) as brown oil. $^1$H NMR (300 MHz, DMSO-$d_6$) δ 8.20 (s, 2H), 6.98 (s, 1H), 6.92 (s, 1H), 5.74 (t, J=6.0 Hz, 1H), 4.10 (t, J=6.6 Hz, 2H), 3.82 (s, 3H), 3.36-3.34 (m, 2H), 3.09-3.03 (m, 2H), 2.84-2.80 (m, 2H), 2.79-2.68 (m, 6H), 2.20-2.13 (m, 2H), 2.08-2.02 (m, 2H), 1.83-1.75 (m, 4H), 0.94 (s, 9H). LCMS (ES) [M+1]$^+$ m/z 412.3.

Example 102

Synthesis of 8-methoxy-N-[(2-$^2$H)propan-2-yl]-7-[3-(pyrrolidin-1-yl)propoxy]-1H,2H,3H-cyclopenta[c]quinolin-4-amine hydrochloride

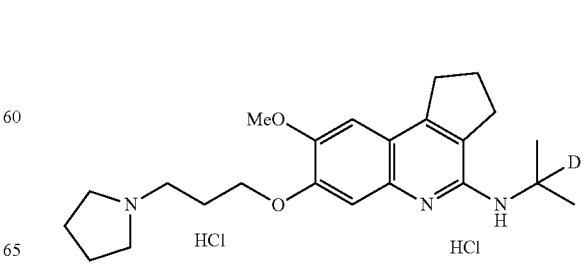

HCl       HCl

Step 1

Into a 50-mL 3-necked round-bottom flask, was placed a mixture of lithio(deuterium)-5-alumane (287.7 mg, 6.85 mmol, 0.50 eq.) in tetrahydrofuran (30 mL). To the mixture was added N-(propan-2-ylidene)hydroxylamine (1.0 g, 13.68 mmol, 1.00 eq.) dropwise. The resulting solution was stirred for 4 h at 70° C. After cooled to 0° C., the reaction was quenched by addition of sodium sulfate decahydrate (2.0 g). The product was purified by distillation at 1.0 atmosphere, and the fractions at 40-60° C. was collected as the desired product. This desired fractions was dissolved in a solution of 1,4-dioxane (5 mL) that freshly saturated with HCl gas. The resulting mixture was allowed to stir at rt for 15 min, concentrated under vacuum to give (2-deuterium) propan-2-amine hydrogen chloride as a yellow solid (320 mg, 24%). $^1$H NMR (300 MHz, DMSO-$d_6$): δ 8.14 (br, 2H), 1.19 (s, 6H).

Step 2

The title compound was made from 1-[3-({4-chloro-8-methoxy-1H,2H,3H-cyclopenta[c]quinolin-7-yl}oxy)-propyl]pyrrolidine (Intermediate II-1) and (2-deuterium)propan-2-amine hydrogen chloride, following a procedure similar as described above in Example 5. The crude reaction mixture was filtered and subjected to purification on reverse phase preparative HPLC (Prep-C18, 5 μM XBridge column, 19×150 mm, Waters; gradient elution of 20% MeCN in water to 31% MeCN in water over a 9 min period, where both solvents contain 0.05% TFA) to provide the title compound (44.8 mg, 4%) as a yellow semi-solid. $^1$H NMR (300 MHz, DMSO-$d_6$): δ 8.26 (s, 2H), 7.01 (s, 1H), 6.93 (s, 1H), 5.72 (s, 1H), 4.11 (t, J=6.3 Hz, 2H), 3.82 (s, 3H), 3.05 (t, J=7.2 Hz, 2H), 2.92-2.86 (m, 6H), 2.79-2.74 (m, 2H), 2.18-2.02 (m, 4H), 1.85-1.77 (m, 4H), 1.20 (s, 6H). LCMS (ES) [M+1]$^+$ m/z 385.2.

Example 103

Synthesis of 8-methoxy-N-(2-methylpropyl)-7-[3-(pyrrolidin-1-yl)propoxy]-1H,2H,3H-cyclopenta[c]quinolin-4-amine trifluoroacetate

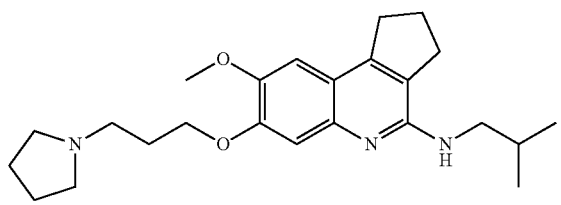

trifluoroacetate

The title compound was made from 1-[3-({4-chloro-8-methoxy-1H,2H,3H-cyclopenta[c]quinolin-7-yl}oxy)-propyl]pyrrolidine (Intermediate II-1) and 2-methylpropan-1-amine, following a procedure similar as described above in Example 5. The crude reaction mixture was filtered and subjected to purification on reverse phase preparative HPLC (Prep-C18, 5 μM XBridge column, 19×150 mm, Waters; gradient elution of 10% MeCN in water to 35% MeCN in water over a 7.5 min period, where both solvents contain 0.1% trifluoroacetic acid) to provide the title compound (179.7 mg, 52%) as a light yellow solid. $^1$H NMR (300 MHz, DMSO-$d_6$) δ 12.56 (s, 1H), 9.77 (br, 1H), 8.49 (br, 1H), 7.63 (s, 1H), 7.20 (s, 1H), 4.19 (t, J=5.7 Hz, 2H), 3.91 (s, 3H), 3.65-3.60 (m, 2H), 3.39-3.30 (m, 4H), 3.27-3.22 (m, 2H), 3.10-2.98 (m, 2H), 2.94-2.89 (m, 2H), 2.27-2.15 (m, 4H), 2.06-1.98 (m, 3H), 1.91-1.85 (m, 2H), 0.97 (d, J=6.6 Hz, 6H). LCMS (ES) [M+1]$^+$ m/z: 398.2.

Example 104

Synthesis of 8-methoxy-N-propyl-7-[3-(pyrrolidin-1-yl)propoxy]-1H,2H,3H-cyclopenta[c]quinolin-4-amine trifluoroacetate

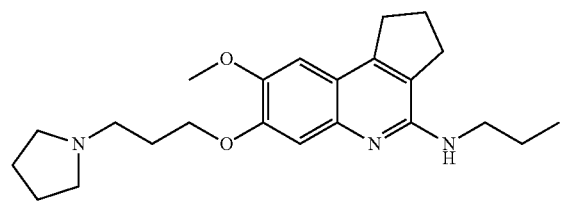

Trifluoroacetic acid

The title compound was made from 1-[3-({4-chloro-8-methoxy-1H,2H,3H-cyclopenta[c]quinolin-7-yl}oxy)-propyl]pyrrolidine (Intermediate II-1) and propan-1-amine, following a procedure similar as described above in Example 5. The crude reaction mixture was filtered and subjected to purification on reverse phase preparative HPLC (Prep-C18, 5 μM XBridge column, 19×150 mm, Waters; gradient elution of 10% MeCN in water to 34% MeCN in water over a 7.5 min period, where both solvents contain 0.1% trifluoroacetic acid) to provide the title compound (126.7 mg, 37%) as a light yellow solid. $^1$H NMR (300 MHz, DMSO-$d_6$) δ 12.54 (s, 1H), 9.80 (br, 1H), 8.53 (t, J=5.4 Hz, 1H), 7.63 (s, 1H), 7.20 (s, 1H), 4.18 (t, J=5.7 Hz, 2H), 3.91 (s, 3H), 3.65-3.59 (m, 2H), 3.56-3.47 (m, 2H), 3.37-3.30 (m, 2H), 3.26-3.21 (m, 2H), 3.10-3.02 (m, 2H), 2.92-2.87 (m, 2H), 2.24-2.17 (m, 4H), 2.08-1.95 (m, 2H), 1.91-1.85 (m, 2H), 1.73-1.67 (m, 2H), 0.98 (t, J=6.9 Hz, 3H). LCMS (ES) [M+1]$^+$ m/z: 384.2.

Example 105

Synthesis of N-cyclopropyl-8-methoxy-7-[3-(pyrrolidin-1-yl)propoxy]-1H,2H,3H-cyclopenta[c]quinolin-4-amine trifluoroacetate

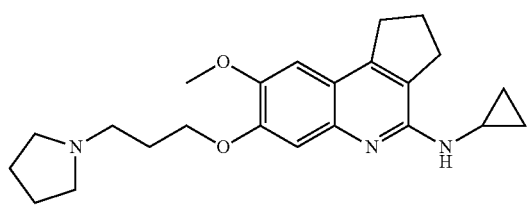

Trifluoroacetic acid

The title compound was made from 1-[3-({4-chloro-8-methoxy-1H,2H,3H-cyclopenta[c]quinolin-7-yl}oxy)-propyl]pyrrolidine (Intermediate II-1) and cyclopropanamine, following a procedure similar as described above in Example 5. The crude reaction mixture was filtered and subjected to purification on reverse phase preparative HPLC (Prep-C18, 5 μM XBridge column, 19×150 mm, Waters; gradient elution of 10% MeCN in water to 30% MeCN in water over a 7 min period, where both solvents contain 0.1% trifluoroacetic acid) to provide the title compound (122.0 mg, 36%) as a light yellow solid. $^1$H NMR (300 MHz, DMSO-d$_6$) δ 12.63 (s, 1H), 9.83 (br, 1H), 8.89 (s, 1H), 7.78 (s, 1H), 7.23 (s, 1H), 4.21 (t, J=5.7 Hz, 2H), 3.92 (s, 3H), 3.66-3.58 (m, 2H), 3.38-3.30 (m, 2H), 3.23-3.18 (m, 2H), 3.13-3.02 (m, 2H), 2.92-2.84 (m, 3H), 2.25-2.15 (m, 4H), 2.08-1.96 (m, 2H), 1.95-1.87 (m, 2H), 1.07-1.01 (m, 2H), 0.82-0.77 (m, 2H). LCMS (ES) [M+1]$^+$ m/z: 382.2.

Example 106

Synthesis of N-ethyl-8-methoxy-7-[3-(pyrrolidin-1-yl)propoxy]-1H,2H,3H-cyclopenta[c]quinolin-4-amine trifluoroacetate

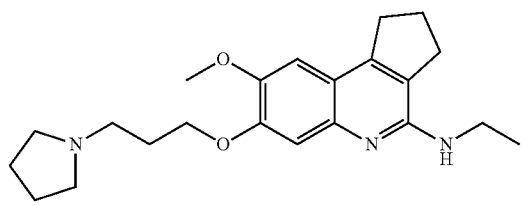

Trifluoroacetic acid

The title compound was made from 1-[3-({4-chloro-8-methoxy-1H,2H,3H-cyclopenta[c]quinolin-7-yl}oxy)-propyl]pyrrolidine (Intermediate II-1) and ethanamine, following a procedure similar as described above in Example 5. The crude reaction mixture was filtered and subjected to purification on reverse phase preparative HPLC (Prep-C18, 5 μM XBridge column, 19×150 mm, Waters; gradient elution of 10% MeCN in water to 35% MeCN in water over a 7.5 min period, where both solvents contain 0.1% trifluoroacetic acid) to provide the title compound (94.7 mg, 29%) as a light yellow solid. $^1$H NMR (300 MHz, DMSO-d$_6$) δ 12.41 (s, 1H), 9.69 (br, 1H), 8.54 (br, 1H), 7.61 (s, 1H), 7.21 (s, 1H), 4.18 (t, J=6.0 Hz, 2H), 3.91 (s, 3H), 3.65-3.54 (m, 4H), 3.37-3.30 (m, 2H), 3.27-3.21 (m, 2H), 3.13-3.02 (m, 2H), 2.92-2.86 (m, 2H), 2.26-2.17 (m, 4H), 2.08-2.05 (m, 2H), 1.92-1.85 (m, 2H), 1.29 (t, J=6.9 Hz, 3H). LCMS (ES) [M+1]$^+$ m/z: 370.2.

Example 107

Synthesis of N-cyclohexyl-8-methoxy-7-[3-(pyrrolidin-1-yl)propoxy]-1H,2H,3H-cyclopenta[c]quinolin-4-amine trifluoroacetate

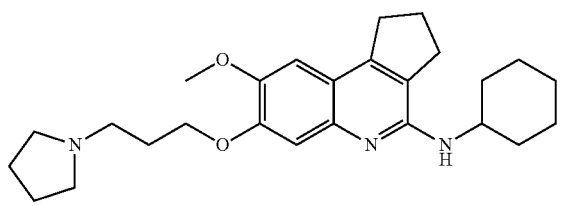

Trifluoroacetic acid

The title compound was made from 1-[3-({4-chloro-8-methoxy-1H,2H,3H-cyclopenta[c]quinolin-7-yl}oxy)-propyl]pyrrolidine (Intermediate II-1) and cyclohexanamine, following a procedure similar as described above in Example 6 above, except that reaction solution was allowed to stir at 100° C. under N$_2$ atmosphere for 2 h. The crude reaction mixture was filtered and subjected to reverse phase preparative HPLC (Prep-C18, 5 μM XBridge column, 19×150 mm, Waters; gradient elution of 10% MeCN in water to 36% MeCN in water over a 9 min period, where both solvents contain 0.05% TFA) to provide the title compound (358.1 mg, 73%) as a solid. $^1$H NMR (300 MHz, DMSO-d$_6$) δ 12.69 (s, 1H), 9.86 (br, 1H), 8.08 (d, J=9.0 Hz, 1H), 7.65 (s, 1H), 7.19 (s, 1H), 4.19 (t, J=5.7 Hz, 2H), 4.07-4.05 (m, 1H), 3.91 (s, 3H), 3.65-3.63 (m, 2H), 3.37-3.35 (m, 2H), 3.23-3.20 (m, 2H), 3.12-3.02 (m, 2H), 2.91 (t, J=7.5 Hz, 2H), 2.27-2.20 (m, 4H), 2.05-1.87 (m, 6H), 1.82-1.78 (m, 2H), 1.71-1.68 (m, 1H), 1.51-1.39 (m, 4H), 1.20-1.11 (m, 1H). LCMS (ES) [M+1]$^+$ m/z 424.4.

Example 108

Synthesis of N-(cyclopropylmethyl)-8-methoxy-7-[3-(pyrrolidin-1-yl)propoxy]-1H,2H,3H-cyclopenta[c]quinolin-4-amine trifluoroacetate

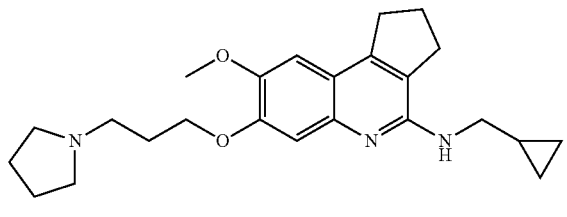

Trifluoroacetic acid

The title compound was made from 1-[3-({4-chloro-8-methoxy-1H,2H,3H-cyclopenta[c]quinolin-7-yl}oxy)-propyl]pyrrolidine (Intermediate II-1) and cyclopropylmethanamine, following a procedure similar as described above in Example 121. The crude reaction mixture was filtered and subjected to reverse phase preparative HPLC (Prep-C18, 5 μM XBridge column, 19×150 mm, Waters; gradient elution of 10% MeCN in water to 36% MeCN in water over a 9 min period, where both solvents contain 0.05% TFA) to provide the title compound (289.4 mg, 59%) as a white solid. $^1$H NMR (300 MHz, DMSO-d$_6$) δ 12.67 (s, 1H), 10.06 (s, 1H), 8.69 (t, J=5.4 Hz, 1H), 7.67 (s, 1H), 7.18 (s, 1H), 4.18 (t, J=5.7 Hz, 2H), 3.90 (s, 3H), 3.66-3.63 (m, 2H), 3.49-3.44 (m, 2H), 3.37-3.35 (m, 2H), 3.23 (t, J=7.5 Hz, 2H), 3.10-3.07 (m, 2H), 2.91 (t, J=6.9 Hz, 2H), 2.24-2.21 (m, 4H), 2.05-2.00 (m, 2H), 1.95-1.87 (m, 2H), 1.25-1.16 (m, 1H), 0.57-0.52 (m, 2H), 0.39-0.33 (m, 2H). LCMS (ES) [M+1]$^+$ m/z 396.4.

Example 109

Synthesis of 1-[3-({4-cyclopentyl-8-methoxy-1H,2H,3H-cyclopenta[c]quinolin-7-yl}oxy)propyl]pyrrolidine formate

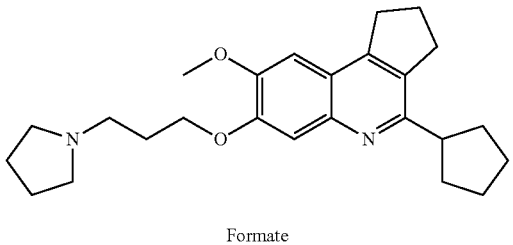 [SMILES: COc1cc2c3c(c(C4CCCC4)nc2cc1OCCCN1CCCC1)CCC3]

Formate

The title compound was made from 1-[3-({4-chloro-8-methoxy-1H,2H,3H-cyclopenta[c]quinolin-7-yl}oxy)-propyl]pyrrolidine (Intermediate II-1) and 2-(cyclopent-1-en-1-yl)-4,4,5,5-tetramethyl-1,3,2-dioxaborolane, following a procedure similar as described above in Example 77 above, except that reaction solution was allowed to stir at 80° C. under $N_2$ atmosphere for 5 h. The crude reaction mixture was filtered and subjected to reverse phase preparative HPLC (Prep-C18, 5 µM XBridge column, 19×150 mm, Waters; gradient elution of 5% MeCN in water to 25% MeCN in water over a 7.5 min period, where both solvents contain 0.1% formic acid) to provide the title compound (143.7 mg, 64%) as a light yellow solid. $^1$H NMR (300 MHz, DMSO-$d_6$): δ 8.23 (s, 1H), 7.29 (s, 1H), 7.07 (s, 1H), 4.17 (t, J=6.3 Hz, 2H), 3.90 (s, 3H), 3.38-3.27 (m, 1H), 3.18 (t, J=7.5 Hz, 2H), 3.04 (t, J=7.5 Hz, 2H), 2.82-2.73 (m, 6H), 2.23-2.15 (m, 2H), 2.08-1.93 (m, 6H), 1.83-1.65 (m, 8H). LCMS (ES) [M+1]$^+$ m/z 395.2.

Example 110

Synthesis of 1-[3-({4-cyclohexyl-8-methoxy-1H,2H,3H-cyclopenta[c]quinolin-7-yl}oxy)propyl]pyrrolidine trifluoroacetate

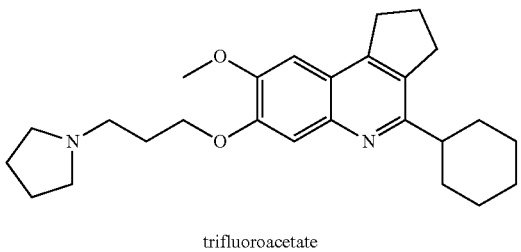 [SMILES: COc1cc2c3c(c(C4CCCCC4)nc2cc1OCCCN1CCCC1)CCC3]

trifluoroacetate

The title compound was made from 1-[3-({4-chloro-8-methoxy-1H,2H,3H-cyclopenta[c]quinolin-7-yl}oxy)-propyl]pyrrolidine (Intermediate II-1) and 2-(cyclohex-1-en-1-yl)-4,4,5,5-tetramethyl-1,3,2-dioxaborolane, following a procedure similar as described above in Example 77 above, except that the reaction solution was allowed to stir at 100° C. under $N_2$ atmosphere for 2 h. The crude product was purified by reverse phase preparative HPLC (Prep-C18, 5 µM XBridge column, 19×150 mm, Waters; gradient elution of 10% MeCN in water to 35% MeCN in water over a 9.5 min period, where both solvents contain 0.1% TFA) to provide the title compound (121.6 mg, 30%) as a white solid. $^1$H NMR (300 MHz, DMSO-$d_6$): δ 9.97 (br, 1H), 7.87 (s, 1H), 7.41 (s, 1H), 4.28 (t, J=5.7 Hz, 2H), 4.00 (s, 3H), 3.67-3.62 (m, 2H), 3.48-3.43 (m, 2H), 3.38-3.31 (m, 2H), 3.25-3.20 (m, 2H), 3.13-3.04 (m, 3H), 2.33-2.24 (m, 4H), 2.10-2.04 (m, 2H), 1.92-1.75 (m, 9H), 1.46-1.31 (m, 3H). LCMS (ES) [M+1]$^+$ m/z 409.3.

Example 111

Synthesis of 1-[3-({8-methoxy-4-phenyl-1H,2H,3H-cyclopenta[c]quinolin-7-yl}oxy)propyl]pyrrolidine formate

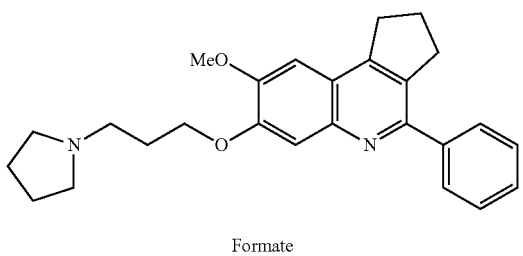 [SMILES: COc1cc2c3c(c(-c4ccccc4)nc2cc1OCCCN1CCCC1)CCC3]

Formate

Into a 25-mL round-bottom flask, was placed 1-[3-({4-chloro-8-methoxy-1H,2H,3H-cyclopenta[c]quinolin-7-yl}oxy)-propyl]pyrrolidine (Intermediate II-1) 1 (200 mg, 0.55 mmol, 1.00 eq.), 1,4-dioxane (5 mL), water (0.5 mL), phenylboronic acid (101 mg, 0.83 mmol, 1.50 eq.), potassium carbonate (153 mg, 1.11 mmol, 2.00 eq.) and Pd(PPh$_3$)$_4$ (64 mg, 0.06 mmol, 0.10 eq.). The mixture was degassed under vacuum and purged with $N_2$ several times. The resulting solution was allowed to stir at 110° C. under $N_2$ for 2 h. The crude reaction mixture was filtered and subjected to reverse preparative HPLC (Prep-C18, 20-45 µM, 120 g, Tianjin Bonna-Agela Technologies; gradient elution of 15% MeCN in water to 15% MeCN in water over a 5 min period, 15% MeCN in water to 30% MeCN in water over another 8 min period, where both solvents contain 0.1% formic acid) to provide the title compound (68.7 mg, 28%) as a white solid. $^1$H NMR (300 MHz, DMSO-$d_6$) δ 8.21 (s, 1H), 7.87 (d, J=6.9 Hz, 2H), 7.57-7.44 (m, 3H), 7.42 (s, 1H), 7.16 (s, 1H), 4.19 (t, J=6.6 Hz, 2H), 3.95 (s, 3H), 3.30-3.17 (m, 4H), 2.67 (t, J=6.9 Hz, 2H), 3.63-3.55 (m, 4H), 2.21 (t, J=7.2 Hz, 2H), 2.02 (t, J=7.2 Hz, 2H), 1.75-1.70 (m, 4H). LCMS (ES) [M+1]$^+$ m/z: 403.1.

Example 112

Synthesis of 8-methoxy-7-[3-(morpholin-4-yl)propoxy]-N-(propan-2-yl)-1H,2H,3H-cyclopenta[c]quinolin-4-amine trifluoroacetate

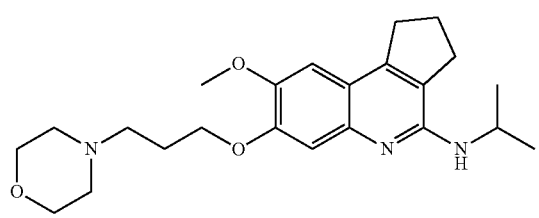

Trifluoroacetate

The title compound was made from 4-[3-([4-chloro-8-methoxy-1H, 2H, 3H-cyclopenta[c]quinolin-7-yl]oxy)propyl]morpholine (Intermediate III-15) and propan-2-amine, following a procedure similar as described above in Example 5. The crude reaction mixture was filtered and subjected to reverse phase preparative HPLC (Prep-C18, 5 µM, X Bridge column, 19×150 mm, Waters; gradient elution of 4% MeCN in water to 24% MeCN in water over a 6 min period, where both solvents contain 0.05% TFA) to provide the title compound (251.4 mg, 38%) as a brown oil. $^1$H NMR (300 MHz, DMSO-$d_6$) δ 12.41 (br, 1H), 9.91 (br, 1H), 8.18 (d, J=8.7 Hz, 1H), 7.63 (s, 1H), 7.21 (s, 1H), 4.41-4.25 (m, 1H), 4.19 (t, J=5.7 Hz, 2H), 4.12-3.96 (m, 2H), 3.91 (s, 3H), 3.72-3.60 (m, 2H), 3.60-3.46 (m, 2H), 3.30-3.28 (m, 2H), 3.26-3.21 (m, 2H), 3.20-3.01 (m, 2H), 2.93-2.88 (m, 2H), 2.31-2.14 (m, 4H), 1.34 (d, J=6.9 Hz, 6H). LCMS (ES) [M+1]$^+$ m/z 400.2.

Example 113

Synthesis of 1-[3-({4-cyclopentyl-8-methoxy-2,2-dimethyl-1H,2H,3H-pyrrolo[3,2-c]quinolin-7-yl}oxy)propyl]pyrrolidine hydrochloride

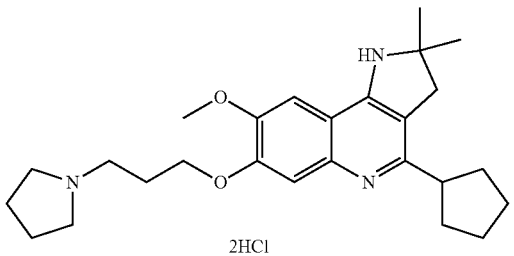 [SMILES: COc1cc2c3c(c(C4CCCC4)nc2cc1OCCCN1CCCC1)CC(C)(C)N3]

2HCl

A solution of 1-(3-{[4-(cyclopent-1-en-1-yl)-8-methoxy-2,2-dimethyl-1H,2H,3H-pyrrolo[3,2-c]quinolin-7-yl]oxy}propyl)pyrrolidine (Example 83, 110.00 mg; 0.26 mmol; 1.00 eq.) in methanol (5.50 mL) was purged with nitrogen. Palladium on carbon (2.78 mg; 0.03 mmol; 0.10 eq.) was added to the solution and the flask was purged with nitrogen once again. The flask was filled with hydrogen and the reaction mixture was allowed to stir under a hydrogen atmosphere at rt overnight. The crude reaction mixture was filtered over celite and subjected to purification on reverse phase preparative HPLC (Prep-C18 XSelect, 5 µM column, 19×150 mm, Waters; gradient elution of 0-50% MeCN in water over a 20 min period, where both solvents contain 0.1% hydrochloric acid) to provide the title compound (88 mg, 80%). LCMS (ES) [M+1]$^+$ m/z 424.1.

Example 114

Synthesis of 1-[3-({8-methoxy-2,2-dimethyl-4-phenyl-1H,2H,3H-pyrrolo[3,2-c]quinolin-7-yl}oxy)propyl]pyrrolidine formate

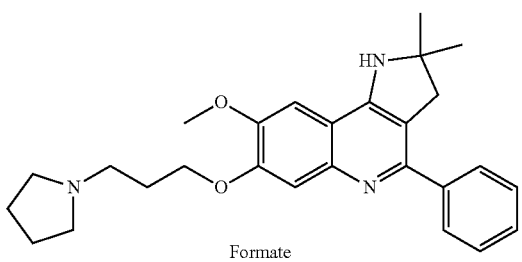 [SMILES: COc1cc2c3c(c(-c4ccccc4)nc2cc1OCCCN1CCCC1)CC(C)(C)N3]

Formate

The title compound was made from 1-[3-({4-chloro-8-methoxy-2,2-dimethyl-1H,2H,3H-pyrrolo[3,2-c]quinolin-7-yl}oxy)-propyl]pyrrolidine (Intermediate III-2) and phenylboronic acid, following a procedure similar as described above in Example 83. The volatiles were removed under reduced pressure and the residue was redissolved in DMSO, filtered and subjected to purification on reverse phase preparative HPLC (Prep-C18 XSelect, 5 µM column, 19×150 mm, Waters; gradient elution of 10-50% MeCN in water over a 20 min period, where both solvents contain 0.1% hydrochloric acid) to provide the title compound as a yellow solid. LCMS (ES) [M+1]$^+$ m/z 432.1.

Example 115

Synthesis of N-[(2,4-dimethoxyphenyl)methyl]-8-methoxy-7-[3-(pyrrolidin-1-yl)propoxy]-1H,2H,3H-cyclopenta[c]quinolin-4-amine formate

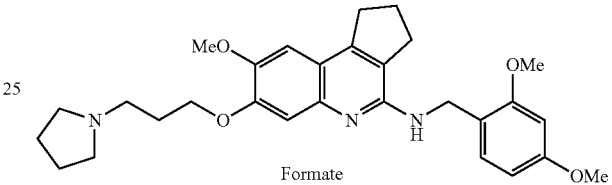

Formate

The title compound was made from 1-[3-({4-chloro-8-methoxy-1H,2H,3H-cyclopenta-[c]quinolin-7-yl}oxy)propyl]pyrrolidine (Intermediate II-1) and (2,4-dimethoxyphenyl)methanamine, following a procedure similar as described in Example 3 above, except that reaction mixture was allowed to stir at 140° C. under $N_2$ for 1.5 h. The crude mixture was treated with water and the volatiles were removed under reduced pressure. The residue were redissolved in DMSO, filtered and subjected to reverse phase preparative HPLC (Prep-C18, 5 µM XBridge column, 19×150 mm, Waters; gradient elution of 0-40% MeCN in water over a 20 min period, where both solvents contain 0.1% formic acid (FA)) to provide the title compound as a white solid. LCMS (ES) [M+1]$^+$ m/z 492.1.

Example 116

Synthesis of 8-methoxy-7-[3-(pyrrolidin-1-yl)propoxy]-1H,2H,3H-cyclopenta[c]quinolin-4-amine formate

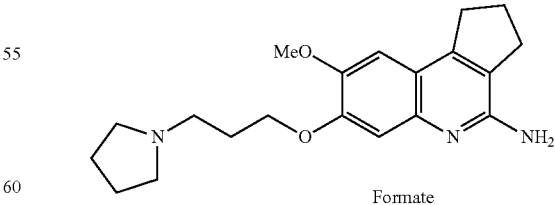

Formate

A mixture of N-[(2,4-dimethoxyphenyl)methyl]-8-methoxy-7-[3-(pyrrolidin-1-yl)propoxy]-1H,2H,3H-cyclopenta[c]quinolin-4-amine formate (Example 115, 228 mg, 0.46 mmol) in TFA (0.5 mL) and CHCl$_3$ (0.8 mL) was allowed to stir at 70° C. for 1.5 hr. The organic volatiles were removed under reduced pressure, and the residues were dissolved in DMSO, filtered and subjected to reverse phase preparative HPLC (Prep-C18, 5 μM XBridge column, 19×150 mm, Waters; gradient elution of 0-40% MeCN in water over a 20 min period, where both solvents contain 0.1% formic acid (FA)) to provide the title compound as a white solid. LCMS (ES) [M+1]⁺ m/z 342.1.

Example 117

Synthesis of N-[(2,4-dimethoxyphenyl)methyl]-8-methoxy-2,2-dimethyl-7-[3-(pyrrolidin-1-yl)propoxy]-1H,2H,3H-cyclopenta[c]quinolin-4-amine formate

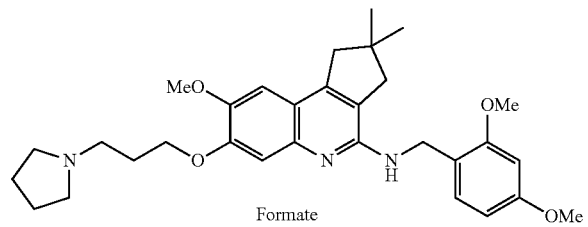 [SMILES: COc1ccc(CNc2nc3cc(OCCCN4CCCC4)c(OC)cc3c3c2CC(C)(C)C3)c(OC)c1]

Formate

The title compound was made from 1-[3-({4-chloro-8-methoxy-2,2-dimethyl-1H,2H,3H-cyclopenta[c]quinolin-7-yl}oxy)propyl]pyrrolidine (Intermediate II-4) and (2,4-dimethoxyphenyl)methanamine, following a procedure similar as described above in Example 115. The crude mixture was treated with water and the volatiles were removed under reduced pressure. The residue were redissolved in DMSO, filtered and subjected to reverse phase preparative HPLC (Prep-C18, 5 μM XBridge column, 19×150 mm, Waters; gradient elution of 0-40% MeCN in water over a 20 min period, where both solvents contain 0.1% formic acid (FA)) to provide the title compound as a white solid. LCMS (ES) [M+1]⁺ m/z 520.1.

Example 118

Synthesis of 8-methoxy-2,2-dimethyl-7-[3-(pyrrolidin-1-yl)propoxy]-1H,2H,3H-cyclopenta[c]quinolin-4-amine formate

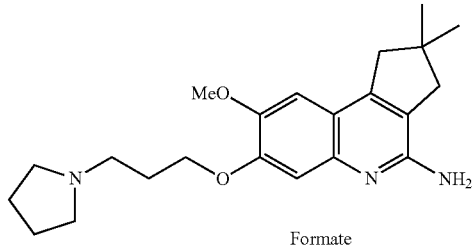 [SMILES: COc1cc2c3c(c(N)nc2cc1OCCCN1CCCC1)CC(C)(C)C3]

Formate

The title compound was made from N-[(2,4-dimethoxyphenyl)methyl]-8-methoxy-2,2-dimethyl-7-[3-(pyrrolidin-1-yl)propoxy]-1H,2H,3H-cyclopenta[c]quinolin-4-amine formate (Example 117) following a procedure similar as described above in Example 116. The crude mixture was treated with water and the volatiles were removed under reduced pressure. The organic volatiles were removed from the crude reaction mixture under reduced pressure, and the residues were dissolved in DMSO, filtered and subjected to reverse phase preparative HPLC (Prep-C18, 5 μM XBridge column, 19×150 mm, Waters; gradient elution of 0-40% MeCN in water over a 20 min period, where both solvents contain 0.1% formic acid (FA)) to provide the title compound as a white solid. LCMS (ES) [M+1]⁺ m/z 370.1.

Example 119

Synthesis of 3-({8-methoxy-7-[3-(pyrrolidin-1-yl)propoxy]-1H,2H,3H-cyclopenta[c]quinolin-4-yl}amino)propanenitrile formate

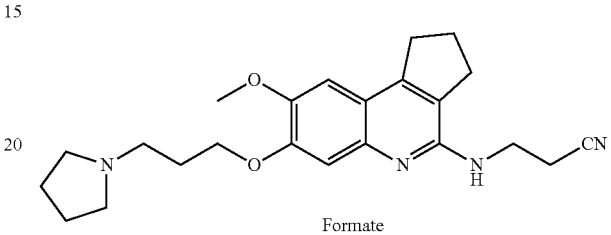

Formate

The title compound was made from 1-[3-({4-chloro-8-methoxy-1H,2H,3H-cyclopenta[c]-quinolin-7-yl}oxy)propyl]pyrrolidine (Intermediate II-1) and 3-aminopropanenitrile, (2E)-but-2-enedioic acetate, following a procedure similar as described in Example 3 above, except that BuONa was used in 10.0 equivalents. The crude product was treated with water and the organic volatiles were removed under reduced pressure. The residues were re-dissolved in DMSO, filtered and subjected to reverse phase preparative HPLC (Prep-C18, 5 μM OBD column, 19×250 mm, waters; gradient elution of 0-25% MeCN in water over a 20 min period, where both solvents contain 0.1% formic acid, flow rate: 20 mL/min) to provide the title compound as a brown syrup. LCMS (ES) [M+1]⁺ m/z 395.2.

Example 120

Synthesis of 8-methoxy-N-[2-(methylsulfanyl)ethyl]-7-[3-(pyrrolidin-1-yl)propoxy]-1H,2H,3H-cyclopenta[c]quinolin-4-amine formate

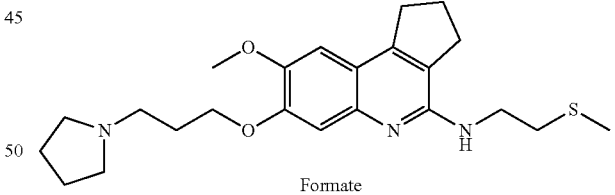

Formate

The title compound was made from 1-[3-({4-chloro-8-methoxy-1H,2H,3H-cyclopenta[c]-quinolin-7-yl}oxy)propyl]pyrrolidine (Intermediate II-1) and 2-(methylsulfanyl)ethanamine, following a procedure similar as described above in Example 3, except that reaction mixture was allowed to stir at 140° C. under N₂ for 1.5 h. The crude product was treated with water and the organic volatiles were removed under reduced pressure. The residues were re-dissolved in DMSO, filtered and subjected to reverse phase preparative HPLC (Prep-C18, 5 μM OBD column, 19×250 mm, waters; gradient elution of 0-40% MeCN in water over a 20 min period, where both solvents contain 0.1% formic acid, flow rate: 20 mL/min) to provide the title compound as a light yellow solid. LCMS (ES) [M+1]⁺ m/z 416.2.

Example 121

Synthesis of (1S,3R)-3-({8-methoxy-7-[3-(pyrrolidin-1-yl)propoxy]-1H,2H,3H-cyclopenta[c]quinolin-4-yl}amino)cyclohexan-1-ol and (1R,3S)-3-({8-methoxy-7-[3-(pyrrolidin-1-yl)propoxy]-1H,2H,3H-cyclopenta[c]quinolin-4-yl}amino)cyclohexan-1-ol (1:1 Mixture in Form of formate Salt) and (1R,3R)-3-({8-methoxy-7-[3-(pyrrolidin-1-yl)propoxy]-1H,2H,3H-cyclopenta[c]quinolin-4-yl}amino)cyclohexan-1-ol formate and (1S,3S)-3-({8-methoxy-7-[3-(pyrrolidin-1-yl)propoxy]-1H,2H,3H-cyclopenta[c]quinolin-4-yl}amino)cyclohexan-1-ol (1:1 Mixture in Form of Formate Salt)

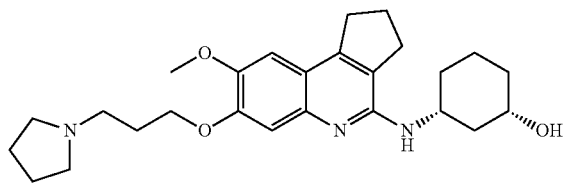

AND

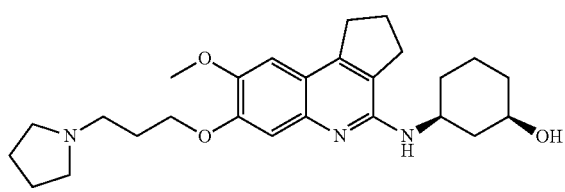

(1:1 mixture as formate salt)     (1:1 mixture as formate salt)

The title compounds as two pairs of 1:1 mixture in form of formate salt, were made from 1-[3-({4-chloro-8-methoxy-1H,2H,3H-cyclopenta[c]-quinolin-7-yl}oxy)propyl]pyrrolidine (Intermediate II-1) and 3-aminocyclohexanol, following a procedure similar as described above in Example 3, except that reaction mixture was allowed to stir at 140° C. under N₂ for 1.5 h. The crude product was treated with water and the organic volatiles were removed under reduced pressure. The residues were re-dissolved in DMSO, filtered and subjected to reverse phase preparative HPLC (Prep-C18, 5 µM OBD column, 19×250 mm, waters; gradient elution of 0-25% MeCN in water over a 20 min period, where both solvents contain 0.1% formic acid, flow rate: 20 mL/min) to provide two fractions with desired mass of LCMS (ES) [M+1]⁺ m/z 440.2. Among them, the fraction came out of the column first was a 1:1 mixture of two isomers, LCMS (ES) [M+1]⁺ m/z 440.2, which was one of two titled mixtures; the fraction came out of the column second was a 1:1 mixture of two isomers, LCMS (ES) [M+1]⁺ m/z 440.2, which was the other of two titled mixtures.

Example 122

Synthesis of (1S,2S)-2-({8-methoxy-7-[3-(pyrrolidin-1-yl)propoxy]-1H,2H,3H-cyclopenta[c]quinolin-4-yl}amino)cyclohexan-1-ol formate

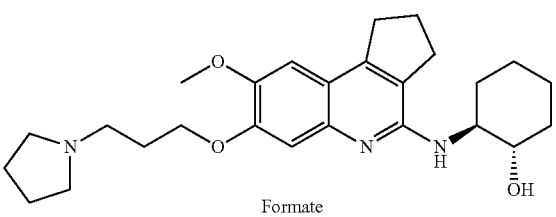 [SMILES: COc1cc2c3c(c(N[C@H]4CCCC[C@@H]4O)nc2cc1OCCCN1CCCC1)CCC3]

Formate

The title compounds was made from 1-[3-({4-chloro-8-methoxy-1H,2H,3H-cyclopenta[c]-quinolin-7-yl}oxy)propyl]pyrrolidine (Intermediate II-1) and (1R,2R)-2-aminocyclohexanol, following a procedure similar as described above in Example 3, except that the reaction mixture was allowed to stir at 130° C. under N₂ for 1.5 h. The crude product was treated with water and the organic volatiles were removed under reduced pressure. The residues were re-dissolved in DMSO, filtered and subjected to reverse phase preparative HPLC (Prep-C18, 5 μM OBD column, 19×250 mm, waters; gradient elution of 0-25% MeCN in water over a 20 min period, where both solvents contain 0.1% formic acid, flow rate: 20 mL/min) to provide the title compound as a white solid. LCMS (ES) [M+1]+ m/z 440.2.

Example 123

Synthesis of (1R,4R)-4-({8-methoxy-7-[3-(pyrrolidin-1-yl)propoxy]-1H,2H,3H-cyclopenta[c]quinolin-4-yl}amino)cyclohexan-1-ol formate

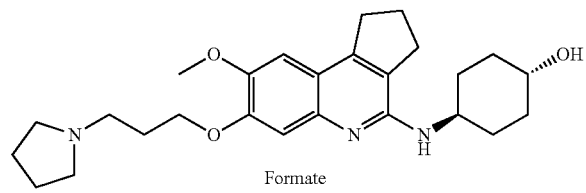 [SMILES: COc1cc2c3c(c(N[C@H]4CC[C@H](O)CC4)nc2cc1OCCCN1CCCC1)CCC3]

Formate

The title compounds was made from 1-[3-({4-chloro-8-methoxy-1H,2H,3H-cyclopenta[c]-quinolin-7-yl}oxy)propyl]pyrrolidine (Intermediate II-1) and trans-4-aminocyclohexan-1-ol, following a procedure similar as described above in Example 3, except that the reaction mixture was allowed to stir at 130° C. under $N_2$ for 1.5 h. The crude product was treated with water and the organic volatiles were removed under reduced pressure. The residues were re-dissolved in DMSO, filtered and subjected to reverse phase preparative HPLC (Prep-C18, 5 μM OBD column, 19×250 mm, waters; gradient elution of 0-25% MeCN in water over a 20 min period, where both solvents contain 0.1% formic acid, flow rate: 20 mL/min) to provide the title compound as a white solid. LCMS (ES) [M+1]+ m/z 440.2.

Example 124

Synthesis of (1S,2S)-2-({8-methoxy-7-[3-(pyrrolidin-1-yl)propoxy]-1H,2H,3H-cyclopenta[c]quinolin-4-yl}amino)cyclopentan-1-ol formate

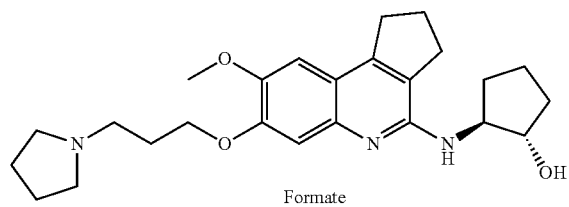 [SMILES: COc1cc2c3c(c(N[C@H]4CCC[C@@H]4O)nc2cc1OCCCN1CCCC1)CCC3]

Formate

The title compounds was made from 1-[3-({4-chloro-8-methoxy-1H,2H,3H-cyclopenta[c]-quinolin-7-yl}oxy)propyl]pyrrolidine (Intermediate II-1) and (1R,2R)-2-aminocyclopentane-1-ol, following a procedure similar as described above in Example 3, except that the reaction mixture was allowed to stir at 140° C. under $N_2$ for 1.5 h. The crude product was treated with water and the organic volatiles were removed under reduced pressure. The residues were re-dissolved in DMSO, filtered and subjected to reverse phase preparative HPLC (Prep-C18, 5 μM OBD column, 19×250 mm, waters; gradient elution of 0-25% MeCN in water over a 20 min period, where both solvents contain 0.1% formic acid, flow rate: 20 mL/min) to provide the title compound as a yellow solid. LCMS (ES) [M+1]+ m/z 426.1.

Example 125

Synthesis of (1R,2S)-2-({8-methoxy-7-[3-(pyrrolidin-1-yl)propoxy]-1H,2H,3H-cyclopenta[c]quinolin-4-yl}amino)cyclopentan-1-ol and (1S,2R)-2-({8-methoxy-7-[3-(pyrrolidin-1-yl)propoxy]-1H,2H,3H-cyclopenta[c]quinolin-4-yl}amino)cyclopentan-1-ol (1:1) mixture as formate salt

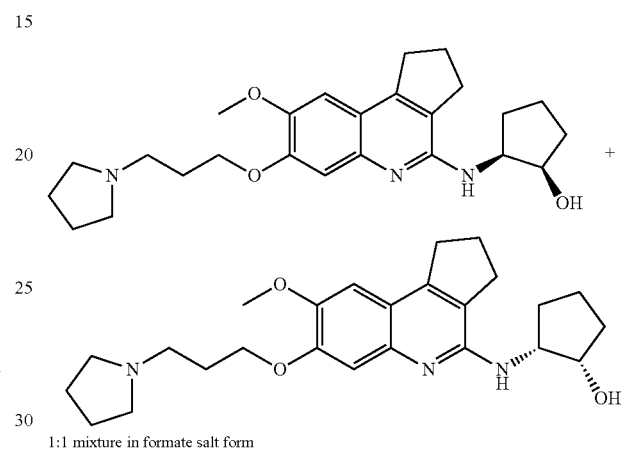

1:1 mixture in formate salt form

The title compounds, as a 1:1 mixture in form of formate salt, was made from 1-[3-({4-chloro-8-methoxy-1H,2H,3H-cyclopenta[c]-quinolin-7-yl}oxy)propyl]pyrrolidine (Intermediate II-1) and cis-2-aminocyclopentane-1-ol, following a procedure similar as described above in Example 3, except that the reaction mixture was allowed to stir at 140° C. under $N_2$ for 1.5 h. The crude product was treated with water and the organic volatiles were removed under reduced pressure. The residues were re-dissolved in DMSO, filtered and subjected to reverse phase preparative HPLC (Prep-C18, 5 μM OBD column, 19×250 mm, waters; gradient elution of 0-25% MeCN in water over a 20 min period, where both solvents contain 0.1% formic acid, flow rate: 20 mL/min) to provide the title compounds as a mixture as a yellow solid. LCMS (ES) [M+1]+ m/z 426.1.

Example 126

Synthesis of 3-({8-methoxy-7-[3-(pyrrolidin-1-yl)propoxy]-1H,2H,3H-cyclopenta[c]quinolin-4-yl}amino)cyclopentan-1-ol formate

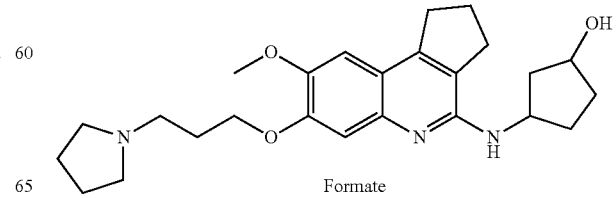

Formate

The title compound was made from 1-[3-({4-chloro-8-methoxy-1H,2H,3H-cyclopenta[c]-quinolin-7-yl}oxy)propyl]pyrrolidine (Intermediate II-1) and 3-aminocyclopentane-1-ol following a procedure similar as described above in Example 3, except that the reaction mixture was allowed to stir at 140° C. under $N_2$ for 1.5 h. The crude product was treated with water and the organic volatiles were removed under reduced pressure. The residues were re-dissolved in DMSO, filtered and subjected to reverse phase preparative HPLC (Prep-C18, 5 μM OBD column, 19×250 mm, waters; gradient elution of 0-25% MeCN in water over a 20 min period, where both solvents contain 0.1% formic acid, flow rate: 20 mL/min) to provide the title compound as a yellow solid. LCMS (ES) $[M+1]^+$ m/z 426.1.

BIOLOGICAL EXAMPLES

Example 1

Determination of G9a Enzymatic Activity Assay

The G9a AlphaLISA assay was used to detect the methyl modifications of a biotinylated histone H3 peptide by the compounds. These modifications are done by the histone methyl transferase activity of the G9a enzyme. The assay consists of reading a chemiluminescent signal at 615 nm; this signal is generated by a laser excitation at 680 nm that transfers a reactive singlet oxygen between the donor beads and acceptor beads. Donor beads are streptavidin conjugated and bind to the biotin on the peptide. Acceptor beads are conjugated with an antibody that recognizes the specific G9a methyl mark on the peptide. If there is a methyl mark on the peptide, the acceptor beads will bind to the peptide. Upon binding, the acceptor beads will be in close proximity (<200 nm) of the donor beads and when the donor beads are excited, the transfer of the oxygen can occur and a strong signal will be generated. If there is no methyl mark, the interaction between beads will not occur and signal will be at background levels.

For the assay, the following buffer was used to set up reactions: 50 mM Tris-HCl pH9, 50 mM NaCl, 0.01% Tween-20 and 1 mM DTT (added fresh prior to starting the reactions). The assay is set up by adding a final concentration of 0.15 nM G9a, 15 uM S-adenosyl-methionine and, 100 nM biotinylated histone 3 peptide (1-21). The reaction is incubated at room temperature for 1 hour, and subsequently quenched by the addition of the acceptor beads (anti-H3k9me2 AlphaLISA acceptor beads, PerkinElmer # AL117) at a final concentration of 20 ug/mL. The acceptor beads are incubated for 1 hour. After 1 hour, the donor beads are added at a final concentration of 20 ug/mL (Alpha Streptavidin donor beads, PerkinElmer #6760002). Donor beads are incubated for 0.5 hours. Both donor and acceptor beads are resuspended in AlphaLISA 5X Epigenetics Buffer 1 Kit (PerkinElmer # AL008) prior to addition to the reaction. All manipulations and incubations with the donor and acceptor beads are done in subdued light. Signal is detected in an EnVision plate reader in Alpha mode (see ACS Med Chem Lett. 2014 Jan. 2; 5(2):205-9. doi: 10.1021/ml400496h. eCollection 2014. Discovery and development of potent and selective inhibitors of histone methyltransferase g9a.)

Percent inhibition was calculated for each compound dilution and the concentration that produced 50% inhibition was calculated. This value is presented as the $IC_{50}$. The $IC_{50}$ values for a representative number of compounds of the disclosure are provided below.

TABLE A

| Cmpd No. (see Cmpd # in Table 1) | G9a in (uM) |
|---|---|
| 1 | 0.031 |
| 2 | 0.029 |
| 3 | 0.015 |
| 4 | 0.04 |
| 5 | 0.15 |
| 6 | 0.027 |
| 7 | 0.045 |
| 8 | 0.04 |
| 9 | 0.69 |
| 10 | 0.19 |
| 11 | 0.27 |
| 12 | 0.52 |
| 13 | 0.042 |
| 14 | 0.19 |
| 15 | 0.19 |
| 16 | 0.11 |
| 17 | 0.21 |
| 18 | 0.11 |
| 19 | 0.057 |
| 20 | 0.14 |
| 21 | 0.62 |
| 22 | 0.003 |
| 23 | 0.003 |
| 24 | 0.006 |
| 25 | 0.005 |
| 26 | 0.004 |
| 27 | 0.006 |
| 28 | 0.006 |
| 29 | 0.009 |
| 30 | 0.008 |
| 31 | 0.009 |
| 32 | 0.022 |
| 33 | 0.012 |
| 34 | 0.010 |
| 35 | 0.012 |
| 36 | 0.009 |
| 37 | 1.3 |
| 38 | 3.0 |
| 39 | 3.0 |
| 40 | 1.3 |
| 41 | 0.50 |
| 42 | 0.52 |
| 43 | 1.70 |
| 44 | 5.8 |
| 45 | 4.3 |
| 46 | 0.26 |
| 47 | 3.1 |
| 48 | 0.97 |
| 49 | 0.046 |
| 50 | 0.24 |
| 51 | 0.88 |
| 52 | 0.34 |
| 53 | 0.043 |
| 54 | 0.048 |
| 55 | 0.32 |
| 56 | 0.46 |
| 57 | 0.21 |
| 58 | 0.17 |
| 59 | 0.23 |
| 60 | 0.21 |
| 61 | 0.14 |
| 62 | 0.12 |
| 63 | 2.3 |
| 64 | 0.50 |
| 65 | 0.74 |
| 66 | 0.22 |
| 67 | 2.0 |
| 68 | 0.11 |
| 69 | >10 |
| 70 | 0.19 |
| 71 | 1.1 |
| 72 | 0.69 |
| 73 | 1.9 |
| 74 | 0.015 |
| 75 | 0.014 |
| 76 | 0.013 |
| 77 | 0.007 |

TABLE A-continued

| Cmpd No.<br>(see Cmpd # in Table 1) | G9a in (uM) |
|---|---|
| 78 | 0.003 |
| 79 | 0.003 |
| 80 | 0.009 |
| 81 | 0.009 |
| 82 | 0.006 |
| 83 | 0.009 |
| 84 | 1.60 |
| 85 | 0.66 |
| 86 | >10.0 |
| 87 | 0.15 |
| 88 | 0.003 |
| 89 | 0.14 |
| 90 | 0.60 |
| 91 | 0.007 |
| 92 | 0.059 |
| 93 | 0.39 |
| 94 | 1.4 |
| 95 | 0.07 |
| 96 | 0.10 |
| 97 | 0.084 |
| 98 | >10.0 |
| 99 | 0.023 |
| 100 | 0.047 |
| 101 | 0.070 |
| 102 | 0.013 |
| 103 | 0.027 |
| 104 | 0.020 |
| 105 | 0.021 |
| 106 | 0.013 |
| 107 | 0.016 |
| 108 | 0.037 |
| 109 | 0.50 |
| 110 | 1.4 |
| 111 | 4.9 |
| 112 | >10 |
| 113 | 0.006 |
| 114 | 0.17 |
| 115 | 0.009 |
| 116 | 0.006 |
| 117 | 0.36 |
| 118 | 0.018 |
| 119 | 0.11 |
| 120 | 0.075 |
| 121 | 0.073 and 0.16 respectively |
| 122 | 0.043 |
| 123 | 0.17 |
| 124 | 4.7 |
| 125 | 1.0 |
| 126 | 0.15 |

Example 2

Fetal Hemoglobin Induction Assay

Cryopreserved bone marrow CD34$^+$ hematopoietic cells obtained from healthy adult human donors were used for all studies. A 21 day ex vivo serum free culture system was utilized that consists of two phases. In culture phase I (culture days 1-7), CD34$^+$ cells were placed in media containing StemPro-34 complete media (1-glutamine, pen-strep and StemPro-34 nutrient supplement) (Invitrogen, Carlsbad, Calif.) supplemented with 50 ng/ml SCF (Human-Zyme, Chicago, Ill.), 50 ng/ml FLT3-Ligand (HumanZyme) and 10 ng/ml IL-3 (HumanZyme). During the first phase of culture (days 0-7), the CD34$^+$ cells differentiate into progenitor cell populations that include erythroblasts. After 7 days, the cells were transferred to erythropoietin (EPO; Stemcell) supplemented medium (phase 2; culture days 7-21) which is comprised of the following: StemPro-34 complete medium, 4 U/ml EPO, 3 µM mifepristone (Sigma Aldrich, St. Louis, Mo.), 10 µg/ml insulin (Sigma Aldrich), 3 U/ml heparin (Sigma Aldrich) and 0.8 mg/ml holo transferrin (Sigma Aldrich). The Compounds are added during phase 2; days 7-21 to test fetal hemoglobin production (see Blood. 2015 Jul. 30; 126(5):665-72. Inhibition of G9a methyltransferase stimulates fetal hemoglobin production by facilitating LCR/γ-globin looping).

Expression levels of α-, ⊕- and γ-globin genes are assessed by quantitative PCR analyses. HbF protein levels are assessed by the human Hemoglobin F enzyme-linked immunosorbent assay (ELISA) Quantitation Kit (Bethyl Laboratory, Montgomery, Tex., USA). Percentages of cells expressing HbF are assessed by flow cytometry analysis. In brief, RNA samples were prepared and complementary DNA was synthesized, according to the manufacturer's instructions (Qiagen, Germany). The qRT-PCR analysis of human globin genes was performed using the TaqMan Gene Expression Master.

Formulation Examples

The following are representative pharmaceutical formulations containing a compound of the present disclosure.

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 μL of spray for each application.

What is claimed:

1. A compound of Formula (I):

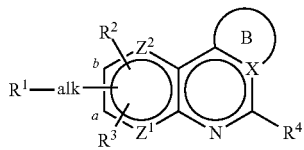

(I)

where:
$Z^1$ is C;
$Z^2$ is CH;
X is C;
alk is —O—$(CH_2)_{2-4}$*, wherein * indicates the point of attachment to —$R^1$;
$R^1$ is unsubstituted heterocyclyl or heterocyclyl substituted with 1 or 2 of $R^a$ and $R^b$ wherein $R^a$ and $R^b$ are independently alkyl or halo;
$R^2$ is an unsubstituted $C_{1-4}$ alkoxy;
wherein, -alk-$R^1$ is attached to carbon (a) and $R^2$ is attached to carbon (b);
$R^3$ is H;
$R^4$ is alkyl or $NR^eR^f$ (where $R^e$ is hydrogen or alkyl, and $R^f$ is hydrogen, alkyl, deuterated alkyl, alkylthioalkyl, acyl, haloalkyl, hydroxyalkyl, alkoxyalkyl, aminoalkyl, cyanoalkyl, carboxyalkyl, alkoxycarbonylalkyl, cycloalkyl, cycloalkylalkyl, aryl, aralkyl, heteroaryl, heteroaralkyl, heterocyclyl, or heterocyclylalkyl), wherein the cycloalkyl, the aryl, the heteroaryl, and the heterocyclyl are independently unsubstituted or substituted with 1, 2, or 3 of $R^g$, $R^h$, and $R^i$, wherein $R^g$, $R^h$, and $R^i$ are independently selected from alkyl, hydroxy, alkoxy, halo, haloalkyl, cyano, carboxy, alkoxycarbonyl, and haloalkoxy;
ring B is unsubstituted 5- or 6-membered cycloalkyl or 5- or 6-membered cycloalkyl substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy;
or,
ring B is an unsubstituted 5-, 6-, or 7-membered saturated heterocyclyl or a 5-, 6-, or 7-membered saturated heterocyclyl substituted with 1, 2, 3, or 4 of $R^j$, $R^k$, $R^l$, and $R^m$ wherein $R^j$, $R^k$, $R^l$, and $R^m$ are independently selected from alkyl, hydroxy, alkoxy, halo, haloalkyl, and haloalkoxy;
or a pharmaceutically acceptable salt thereof.

2. The compound of claim 1, or a pharmaceutically acceptable salt thereof, wherein $R^4$ is $NR^eR^f$ (where $R^e$ is hydrogen or alkyl, and $R^f$ is hydrogen, alkyl, acyl, haloalkyl, hydroxyalkyl, alkoxyalkyl, aminoalkyl, cycloalkyl, cycloalkylalkyl, aryl, aralkyl, heteroaryl, heteroaralkyl, heterocyclyl, or heterocyclylalkyl), wherein the cycloalkyl, the aryl, the heteroaryl, and the heterocyclyl is unsubstituted or substituted with 1, 2, or 3 of $R^g$, $R^h$, and $R^i$ wherein $R^g$, $R^h$, and $R^i$ are independently selected from alkyl, hydroxy, alkoxy, halo, haloalkyl, cyano, carboxy, alkoxycarbonyl, and haloalkoxy.

3. The compound of claim 1, or a pharmaceutically acceptable salt thereof, wherein the compound, or a pharmaceutically acceptable salt thereof, is selected from the group consisting of:

1

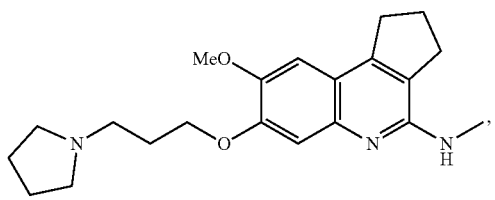

formate

2

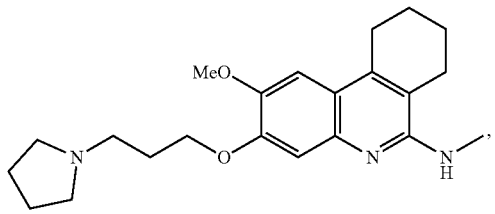

formate

-continued
3
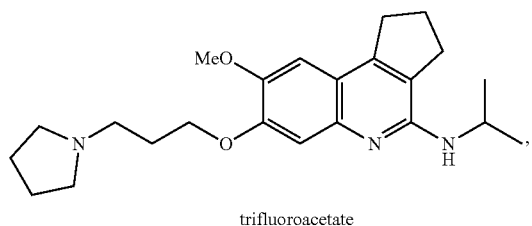 [SMILES: COc1cc2c3c(c(NC(C)C)nc2cc1OCCCN1CCCC1)CCC3]
trifluoroacetate
4
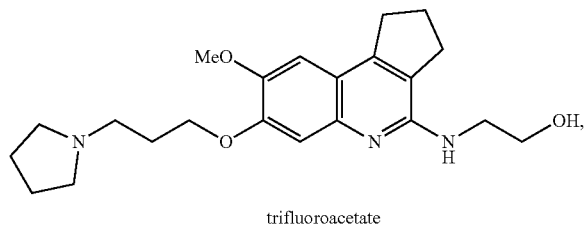 [SMILES: COc1cc2c3c(c(NCCO)nc2cc1OCCCN1CCCC1)CCC3]
trifluoroacetate
5
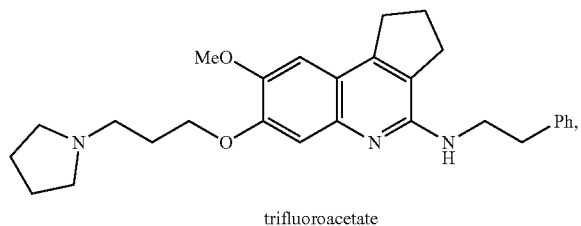 [SMILES: COc1cc2c3c(c(NCCc4ccccc4)nc2cc1OCCCN1CCCC1)CCC3]
trifluoroacetate
6
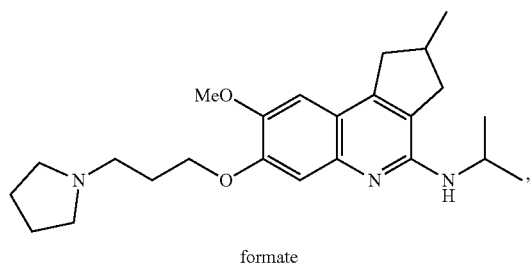 [SMILES: COc1cc2c3c(c(NC(C)C)nc2cc1OCCCN1CCCC1)CC(C)C3]
formate
7
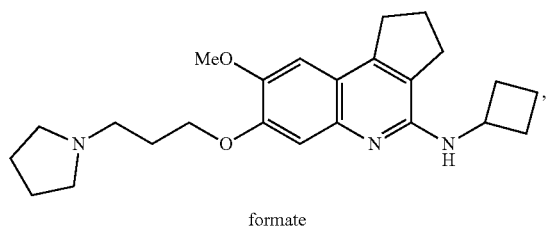
formate
8
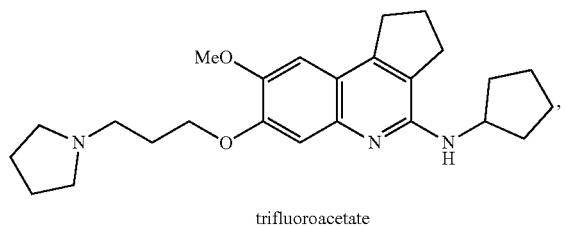 [SMILES: COc1cc2c3c(c(NC4CCCC4)nc2cc1OCCCN1CCCC1)CCC3]
trifluoroacetate 9
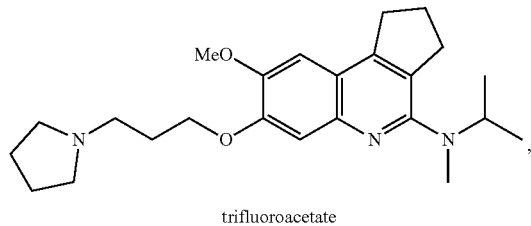 [SMILES: COc1cc2c3c(c(N(C)C(C)C)nc2cc1OCCCN1CCCC1)CCC3]
trifluoroacetate
11
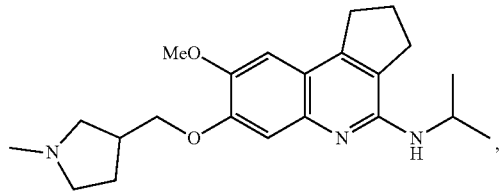
trifluoroacetate
12
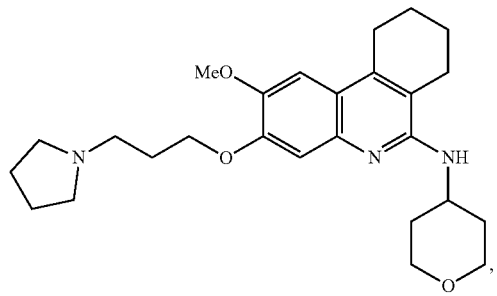
trifluoroacetate
13
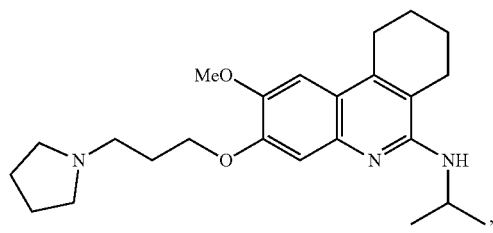
formate
14
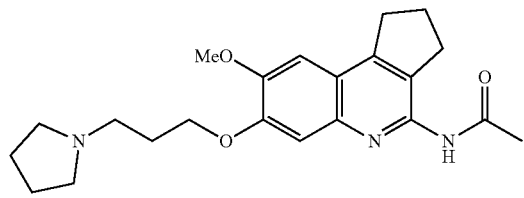
trifluoroacetate
15
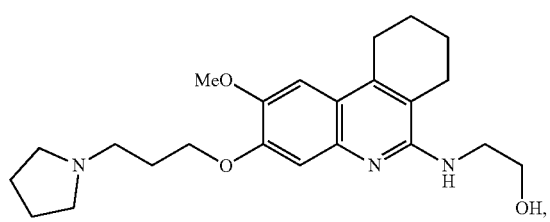
formate 16 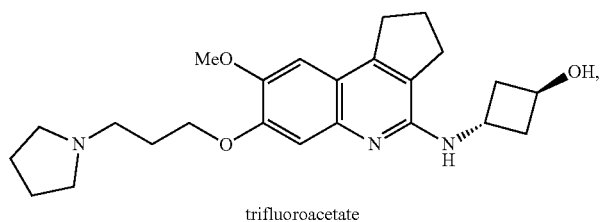 [SMILES: COc1cc2c3c(c(N[C@H]4C[C@H](O)C4)nc2cc1OCCCN1CCCC1)CCC3]
trifluoroacetate
17 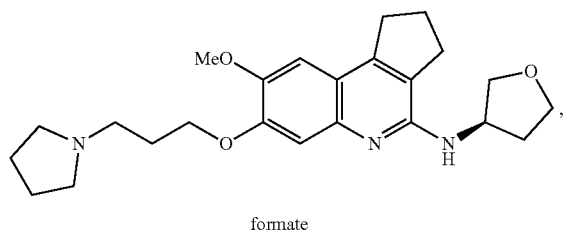 [SMILES: COc1cc2c3c(c(N[C@@H]4CCOC4)nc2cc1OCCCN1CCCC1)CCC3]
formate
18 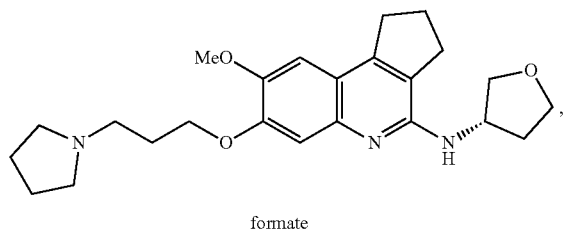 [SMILES: COc1cc2c3c(c(N[C@H]4CCOC4)nc2cc1OCCCN1CCCC1)CCC3]
formate
19 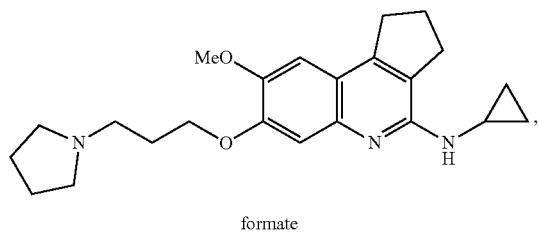 [SMILES: COc1cc2c3c(c(NC4CC4)nc2cc1OCCCN1CCCC1)CCC3]
formate
20 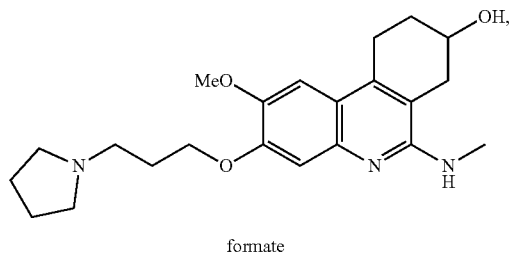 [SMILES: CNc1nc2cc(OCCCN3CCCC3)c(OC)cc2c2c1CC(O)CC2]
formate
22 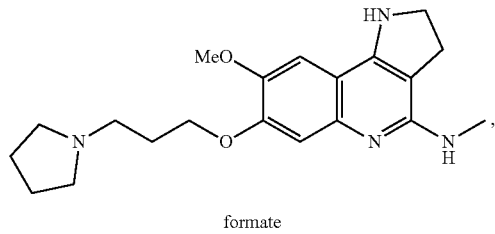 [SMILES: CNc1nc2cc(OCCCN3CCCC3)c(OC)cc2c2c1CCN2]
formate -continued
23
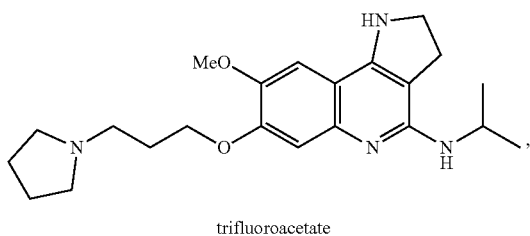 [SMILES: COc1cc2c3c(c(NC(C)C)nc2cc1OCCCN1CCCC1)CCN3]
trifluoroacetate
24
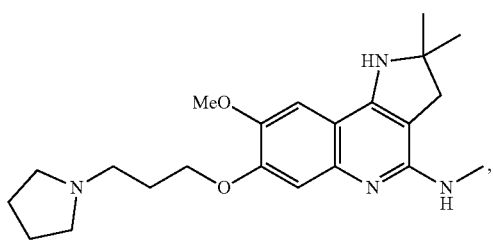
trifluoroacetate
25
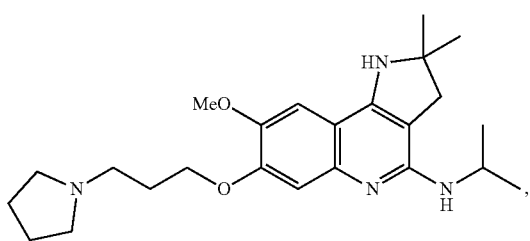
trifluoroacetate
26
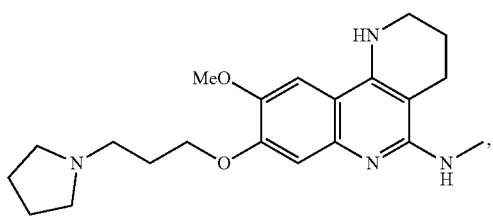
formate
27
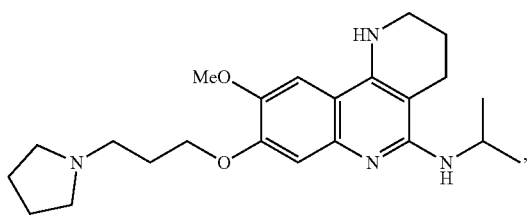
trifluoroacetate
28
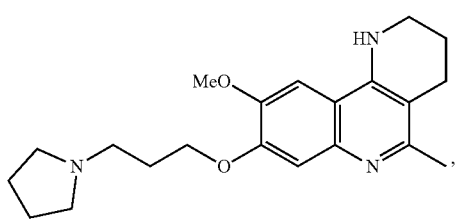
trifluoroacetate 29
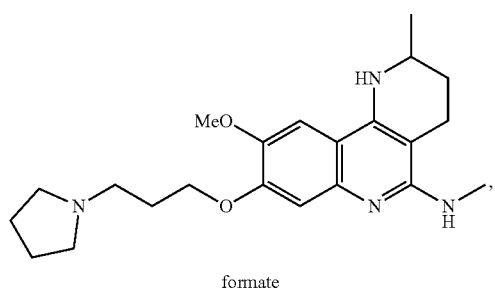 [SMILES: CNc1nc2cc(OCCCN3CCCC3)c(OC)cc2c2c1CCC(C)N2]
formate
30
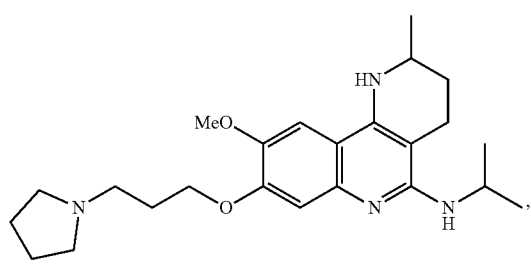
formate
31
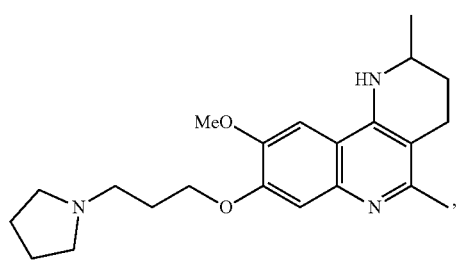
trifluoroacetate
33
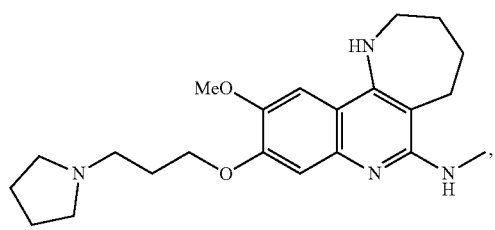
formate
34
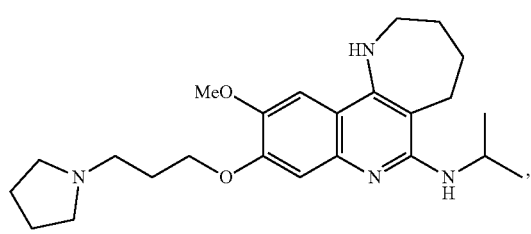
formate 39
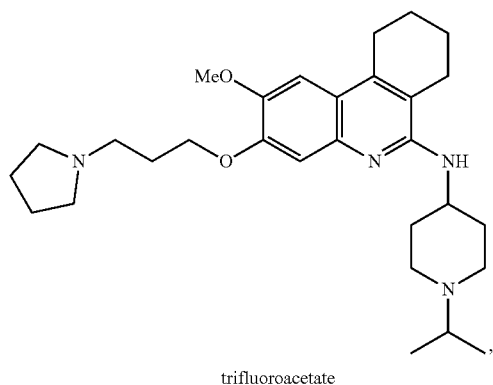 [SMILES: COc1cc2c3c(c(NC4CCN(C(C)C)CC4)nc2cc1OCCCN1CCCC1)CCCC3]
trifluoroacetate
41
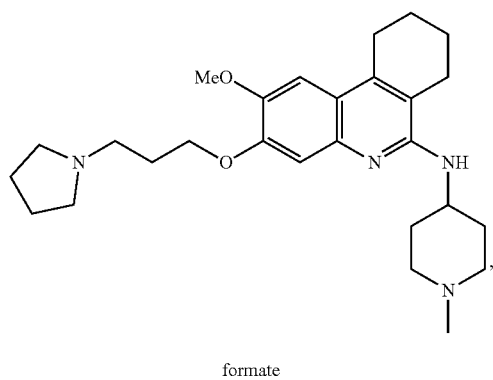 [SMILES: COc1cc2c3c(c(NC4CCN(C)CC4)nc2cc1OCCCN1CCCC1)CCCC3]
formate
42
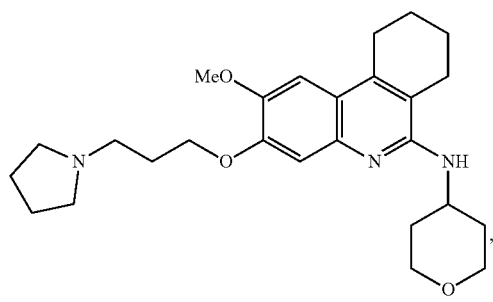
formate
43
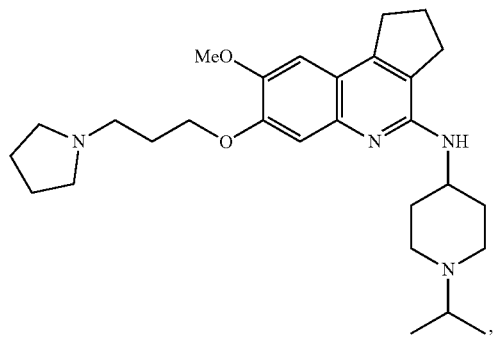
formate 44 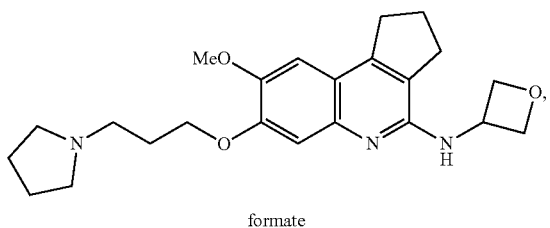 [SMILES: COc1cc2c3c(c(NC4COC4)nc2cc1OCCCN1CCCC1)CCC3]
formate
46 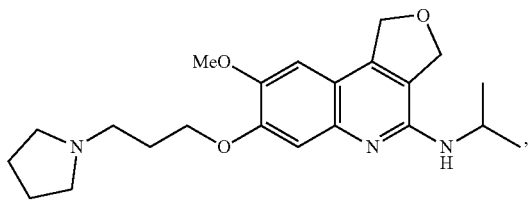 [SMILES: COc1cc2c3c(c(NC(C)C)nc2cc1OCCCN1CCCC1)COC3]
48 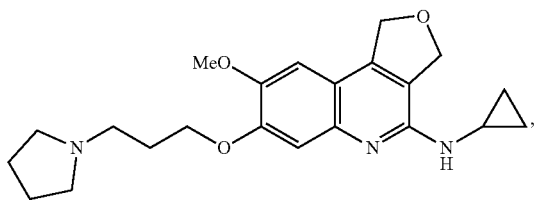 [SMILES: COc1cc2c3c(c(NC4CC4)nc2cc1OCCCN1CCCC1)COC3]
49 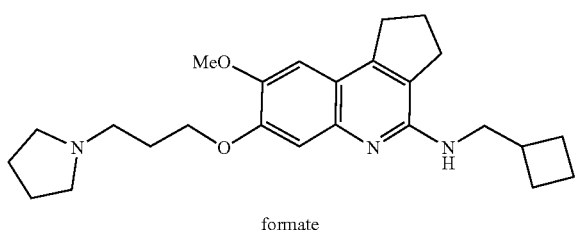 [SMILES: COc1cc2c3c(c(NCC4CCC4)nc2cc1OCCCN1CCCC1)CCC3]
formate
50 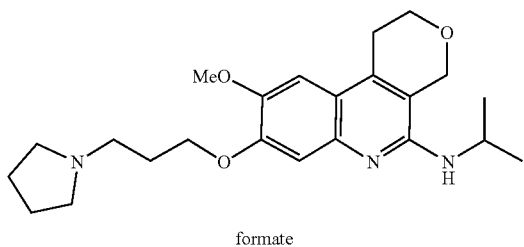 [SMILES: COc1cc2c3c(c(NC(C)C)nc2cc1OCCCN1CCCC1)COCC3]
formate
53 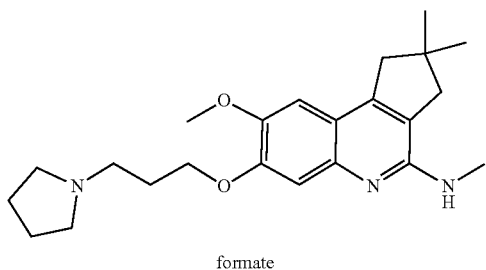 [SMILES: CNc1nc2cc(OCCCN3CCCC3)c(OC)cc2c2c1CC(C)(C)C2]
formate -continued
54 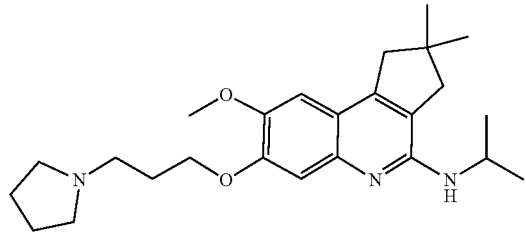
formate
55 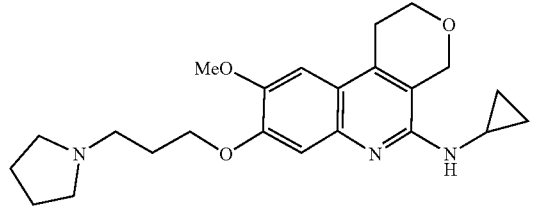
formate
57 formate 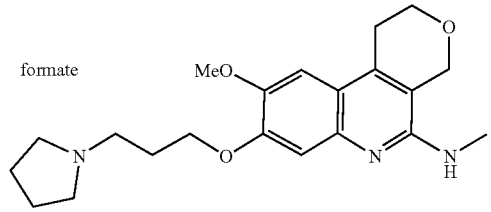 [SMILES: CNc1nc2cc(OCCCN3CCCC3)c(OC)cc2c2c1COCC2]
58 formate 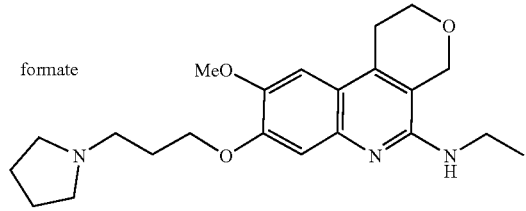 [SMILES: CCNc1nc2cc(OCCCN3CCCC3)c(OC)cc2c2c1COCC2]
59 formate 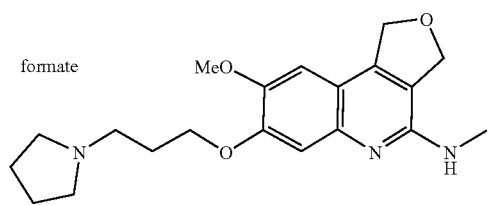 [SMILES: CNc1nc2cc(OCCCN3CCCC3)c(OC)cc2c2c1COC2]
60 formate 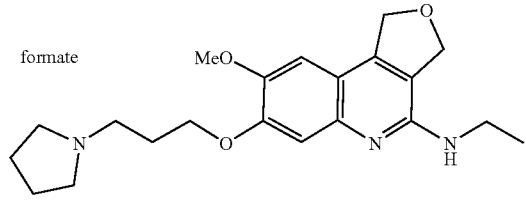 [SMILES: CCNc1nc2cc(OCCCN3CCCC3)c(OC)cc2c2c1COC2]
61 formate 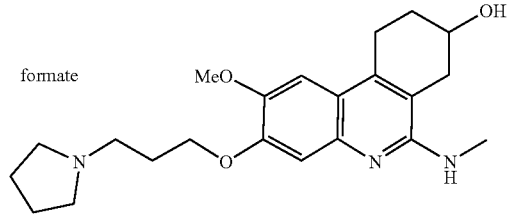 [SMILES: CNc1nc2cc(OCCCN3CCCC3)c(OC)cc2c2c1CC(O)CC2]

-continued
62
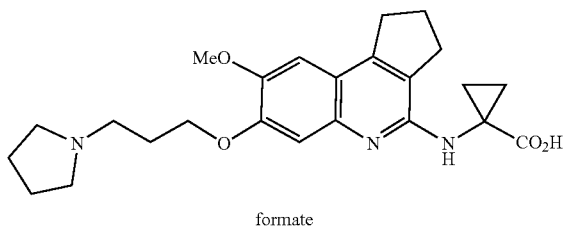 [SMILES: COc1cc2c3c(c(NC4(C(=O)O)CC4)nc2cc1OCCCN1CCCC1)CCC3]
formate
64
formate
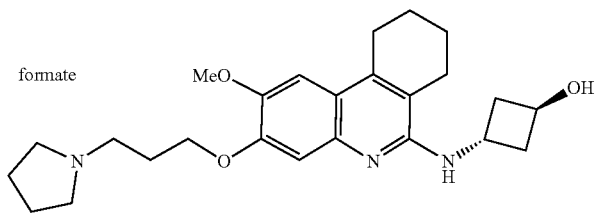 [SMILES: COc1cc2c3c(c(N[C@H]4C[C@H](O)C4)nc2cc1OCCCN1CCCC1)CCCC3]
65
formate
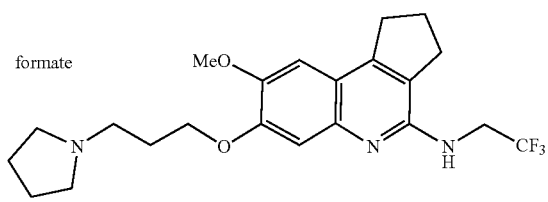 [SMILES: COc1cc2c3c(c(NCC(F)(F)F)nc2cc1OCCCN1CCCC1)CCC3]
66
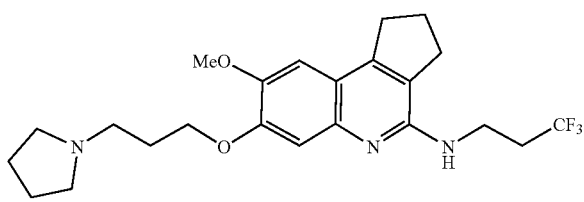 [SMILES: COc1cc2c3c(c(NCCC(F)(F)F)nc2cc1OCCCN1CCCC1)CCC3]
67
formate
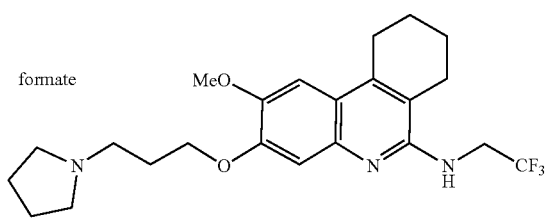 [SMILES: COc1cc2c3c(c(NCC(F)(F)F)nc2cc1OCCCN1CCCC1)CCCC3]
68
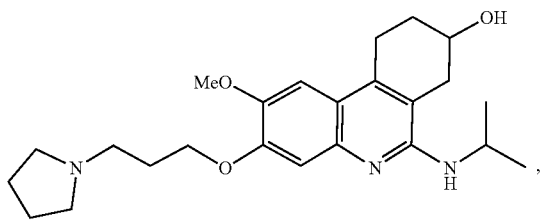
trifluoroacetate
69
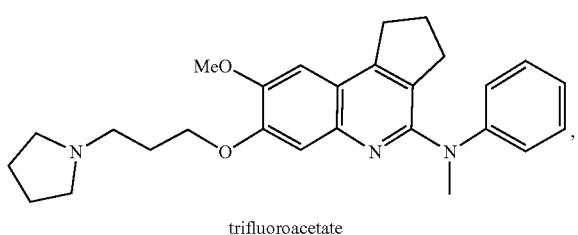 [SMILES: COc1cc2c3c(c(N(C)c4ccccc4)nc2cc1OCCCN1CCCC1)CCC3]
trifluoroacetate -continued
71
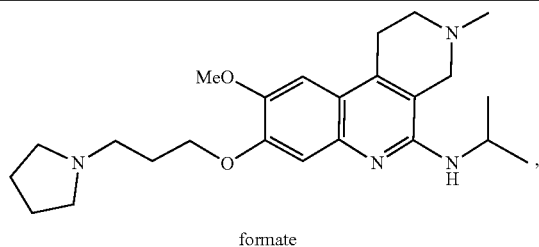
formate
73
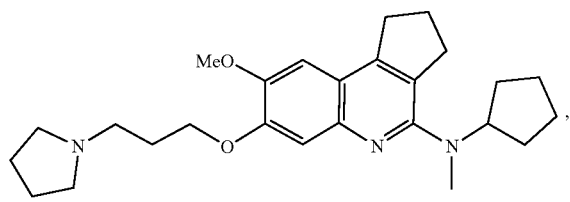
trifluoroacetate
74
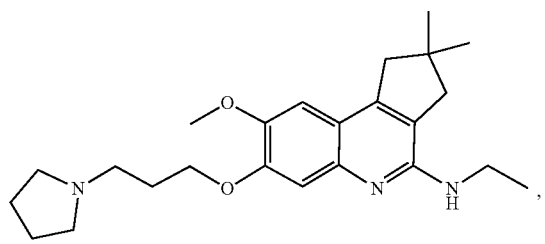
formate
77
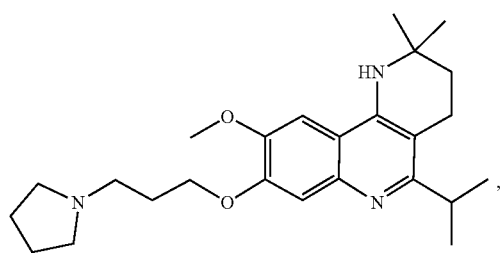
Formate
78
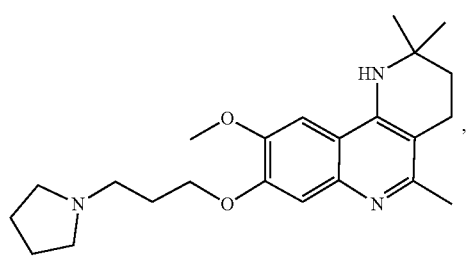
Formate
81
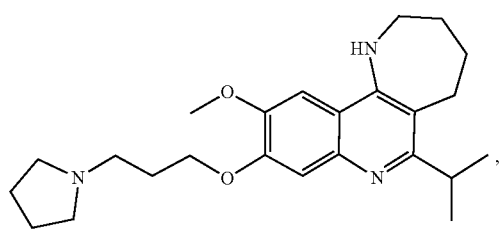
trifluoroacetate 82 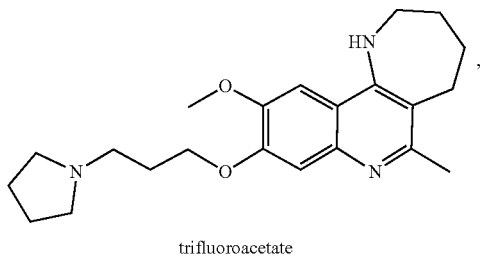 [SMILES: COc1cc2c3c(c(C)nc2cc1OCCCN1CCCC1)CCCCN3]
trifluoroacetate
85 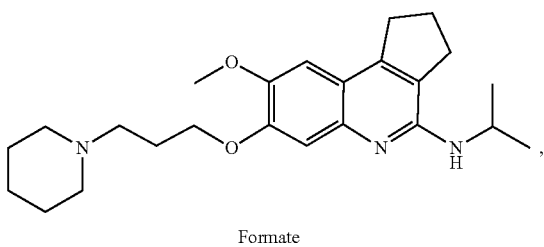 [SMILES: COc1cc2c3c(c(NC(C)C)nc2cc1OCCCN1CCCCC1)CCC3]
Formate
86 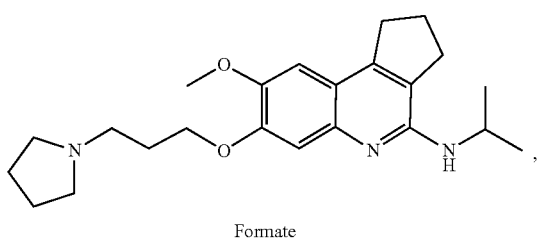 [SMILES: COc1cc2c3c(c(NC(C)C)nc2cc1OCCCN1CCCC1)CCC3]
Formate
87 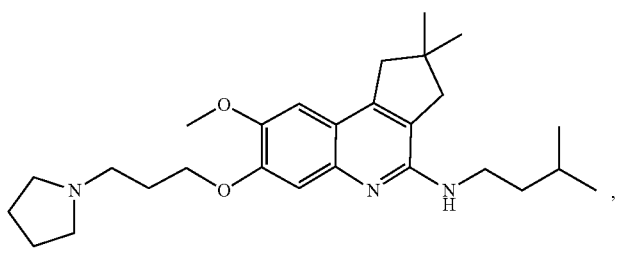
Formate
88 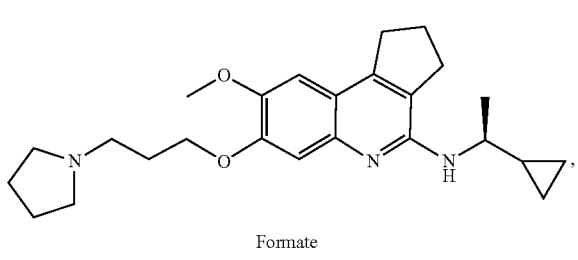 [SMILES: COc1cc2c3c(c(N[C@@H](C)C4CC4)nc2cc1OCCCN1CCCC1)CCC3]
Formate
89 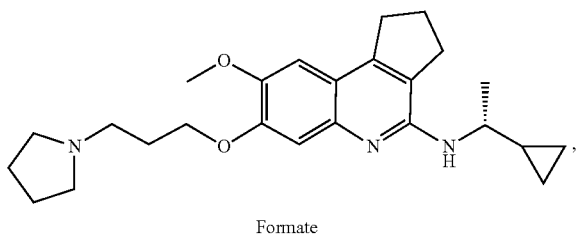 [SMILES: COc1cc2c3c(c(N[C@H](C)C4CC4)nc2cc1OCCCN1CCCC1)CCC3]
Formate -continued
91
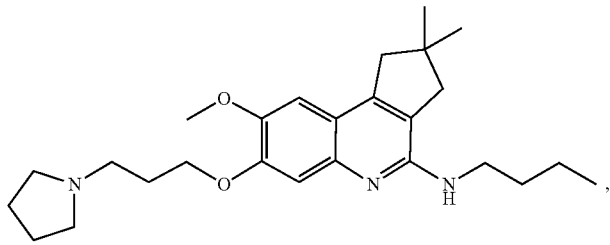
Formate
94
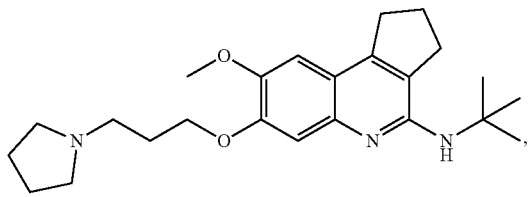
Formate
95
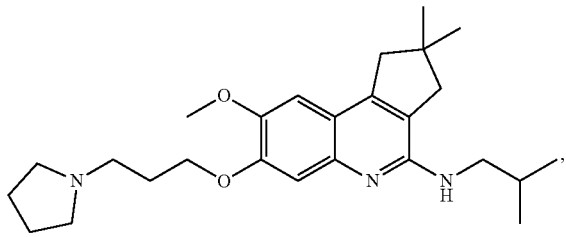
Formate
96
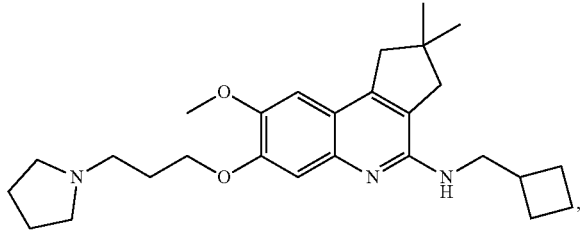
Formate
97
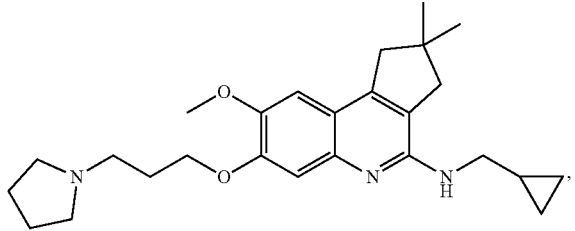
Formate
99
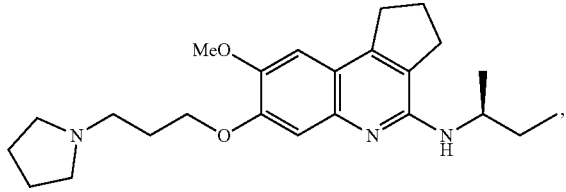
Formate 241
-continued
100
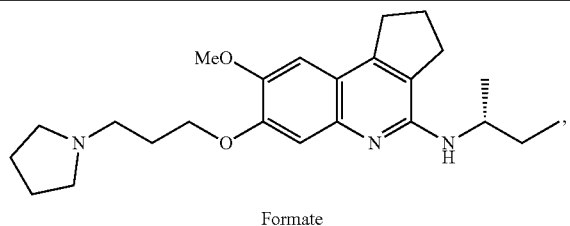
Formate
101
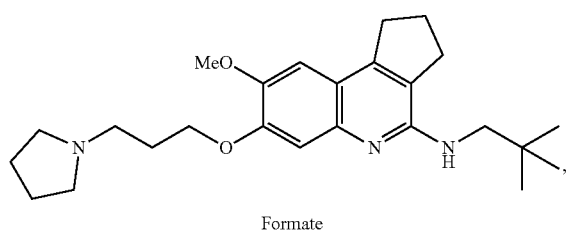 [SMILES: COc1cc2c3c(c(NCC(C)(C)C)nc2cc1OCCCN1CCCC1)CCC3]
Formate
102
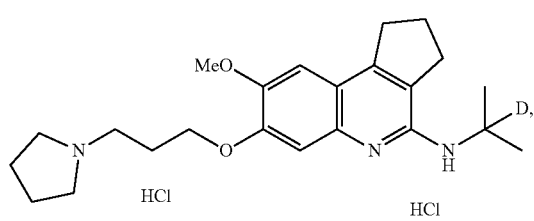
HCl        HCl
103
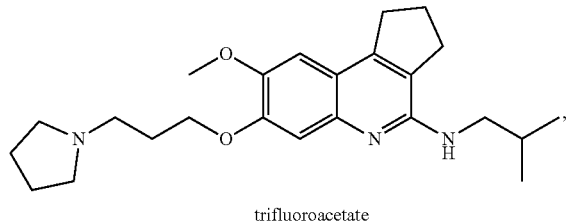 [SMILES: COc1cc2c3c(c(NCC(C)C)nc2cc1OCCCN1CCCC1)CCC3]
trifluoroacetate
104
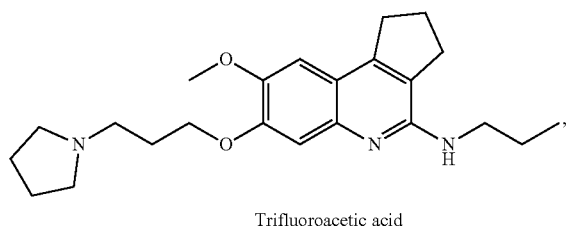 [SMILES: CCCNc1nc2cc(OCCCN3CCCC3)c(OC)cc2c2c1CCC2]
Trifluoroacetic acid
105
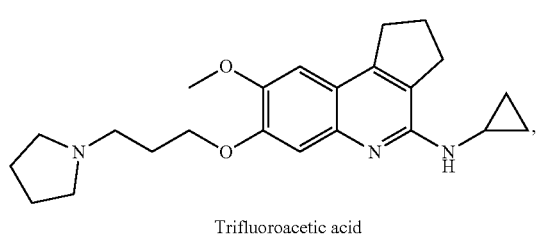 [SMILES: COc1cc2c3c(c(NC4CC4)nc2cc1OCCCN1CCCC1)CCC3]
Trifluoroacetic acid
106
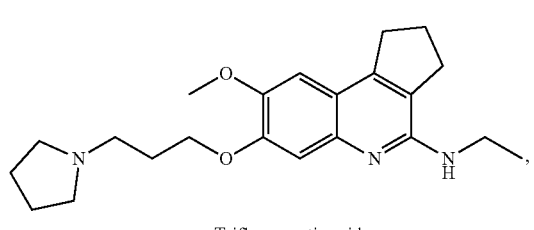
Trifluoroacetic acid -continued
107
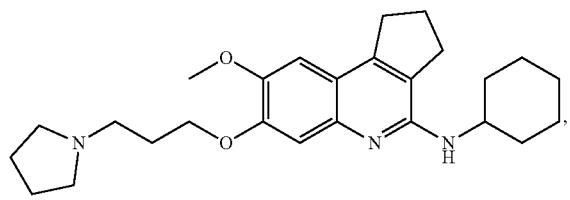
Trifluoroacetic acid
108
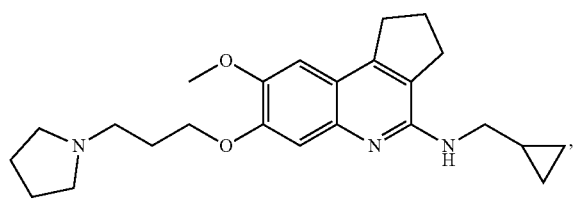
Trifluoroacetic acid
112
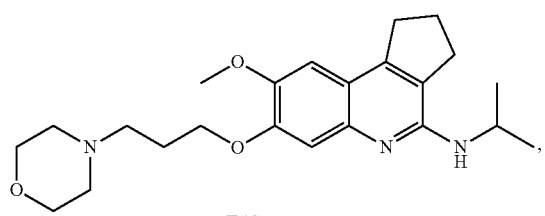
Trifluoroacetate
115
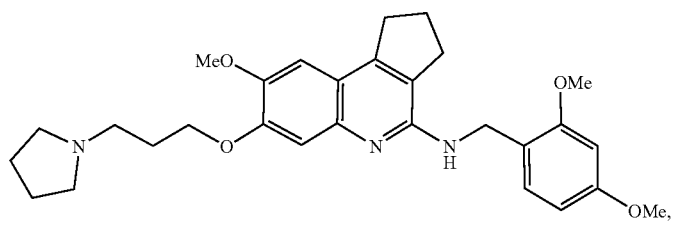
Formate
116
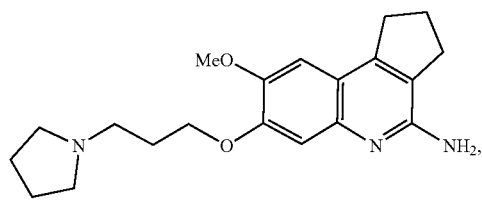
Formate
117
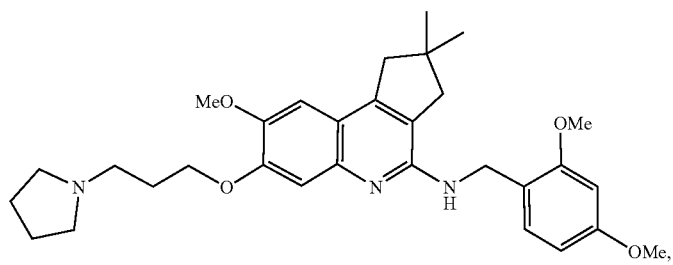
Formate -continued
118
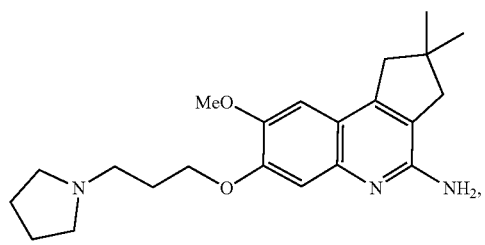
Formate
119
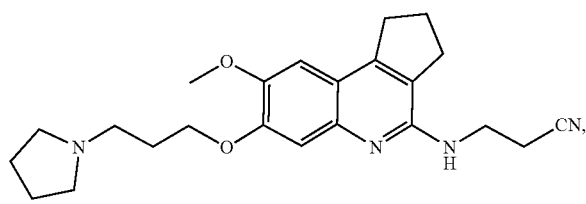
Formate
120
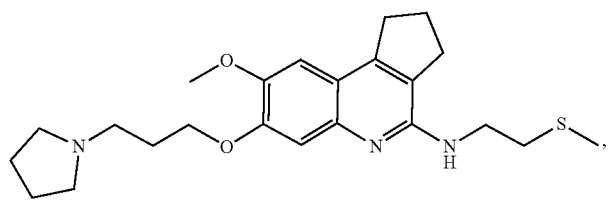
Formate
121a Formate
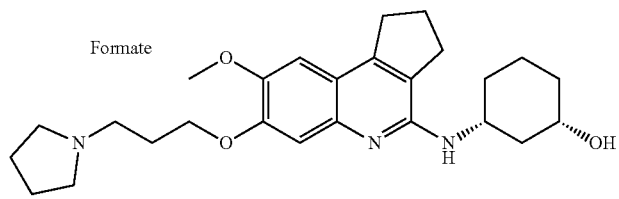 [SMILES: COc1cc2c3c(c(N[C@@H]4CCC[C@H](O)C4)nc2cc1OCCCN1CCCC1)CCC3]
121b
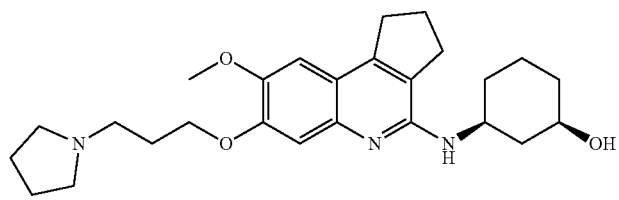
Formate
121c Formate
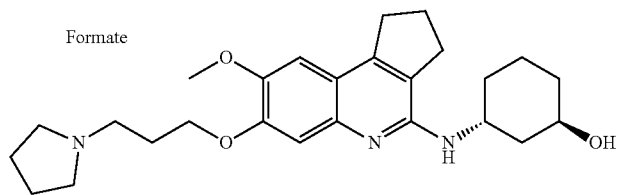 [SMILES: COc1cc2c3c(c(N[C@@H]4CCC[C@@H](O)C4)nc2cc1OCCCN1CCCC1)CCC3]

-continued
121d
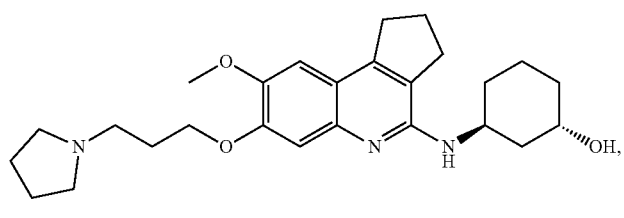
Formate
122
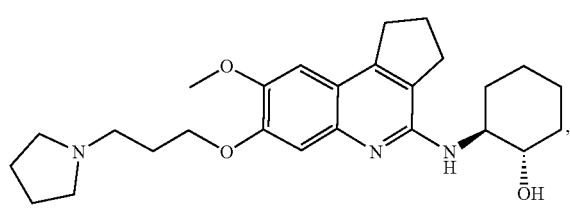
Formate
123
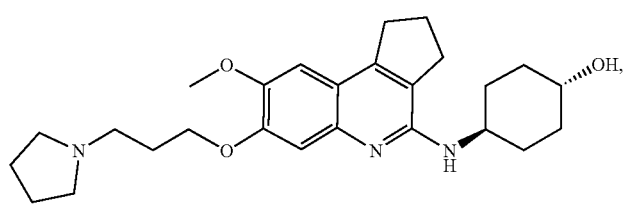
Formate
124
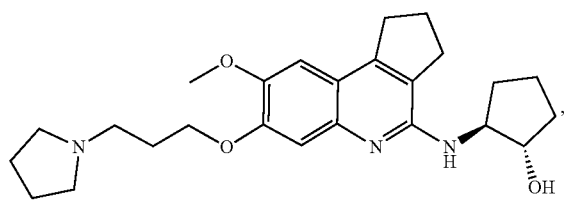
Formate
125a  Formate
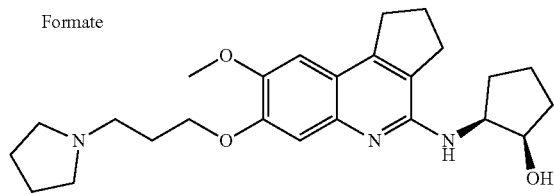 [SMILES: COc1cc2c3c(c(N[C@H]4CCC[C@H]4O)nc2cc1OCCCN1CCCC1)CCC3]
125b
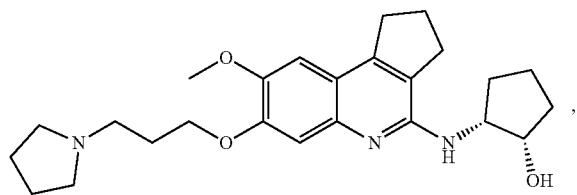
Formate 126
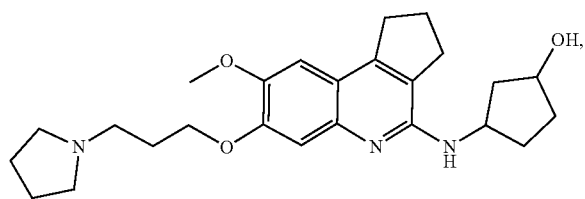
Formate
137
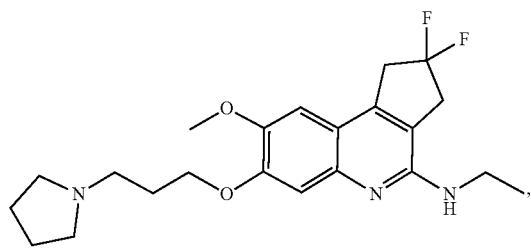 [SMILES: CCNc1nc2cc(OCCCN3CCCC3)c(OC)cc2c2c1CC(F)(F)C2]
149
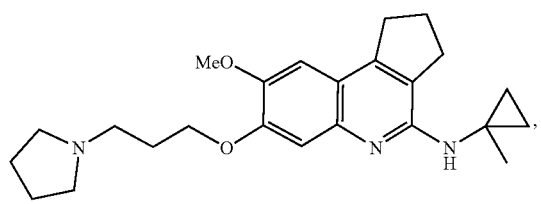 [SMILES: COc1cc2c3c(c(NC4(C)CC4)nc2cc1OCCCN1CCCC1)CCC3]
150
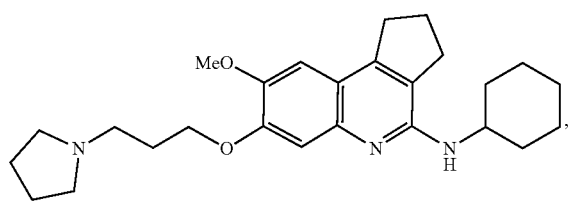 [SMILES: COc1cc2c3c(c(NC4CCCCC4)nc2cc1OCCCN1CCCC1)CCC3]
151
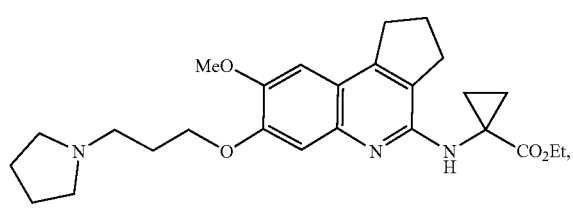 [SMILES: CCOC(=O)C1(Nc2nc3cc(OCCCN4CCCC4)c(OC)cc3c3c2CCC3)CC1]
152
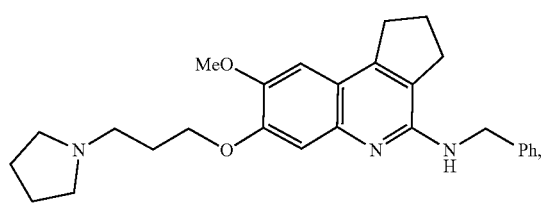 [SMILES: COc1cc2c3c(c(NCc4ccccc4)nc2cc1OCCCN1CCCC1)CCC3]
153
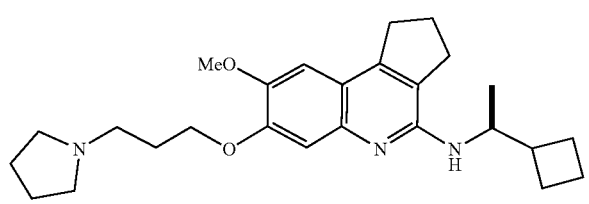 [SMILES: COc1cc2c3c(c(N[C@@H](C)C4CCC4)nc2cc1OCCCN1CCCC1)CCC3]

-continued
154
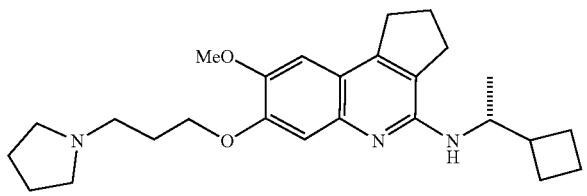 [SMILES: COc1cc2c3c(c(N[C@H](C)C4CCC4)nc2cc1OCCCN1CCCC1)CCC3]
155
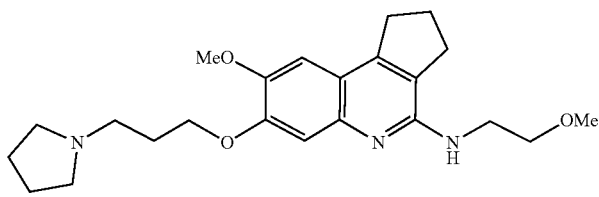 [SMILES: COCCNc1nc2cc(OCCCN3CCCC3)c(OC)cc2c2c1CCC2]
156
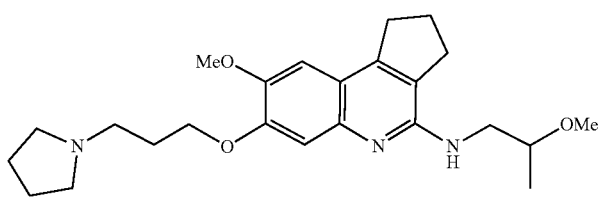 [SMILES: COc1cc2c3c(c(NCC(C)OC)nc2cc1OCCCN1CCCC1)CCC3]
157
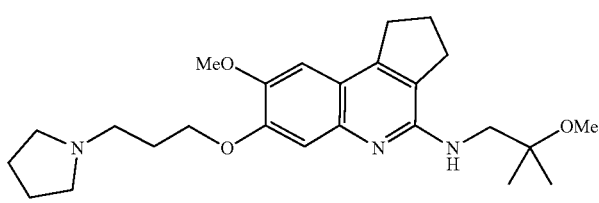 [SMILES: COc1cc2c3c(c(NCC(C)(C)OC)nc2cc1OCCCN1CCCC1)CCC3]
158
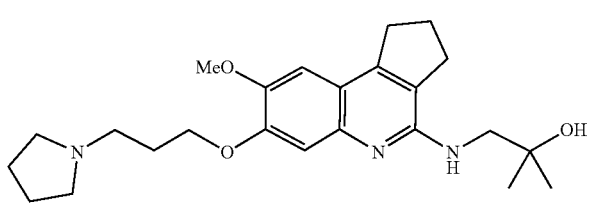 [SMILES: COc1cc2c3c(c(NCC(C)(C)O)nc2cc1OCCCN1CCCC1)CCC3]
159
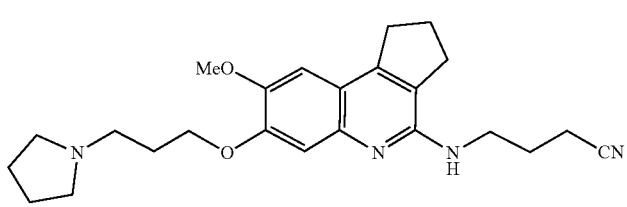 [SMILES: COc1cc2c3c(c(NCCCC#N)nc2cc1OCCCN1CCCC1)CCC3]
160
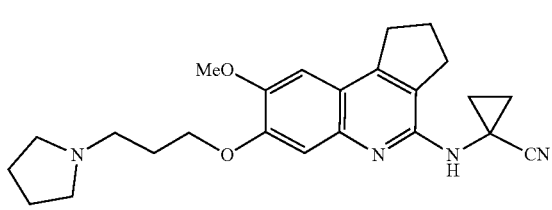 [SMILES: COc1cc2c3c(c(NC4(C#N)CC4)nc2cc1OCCCN1CCCC1)CCC3]
161
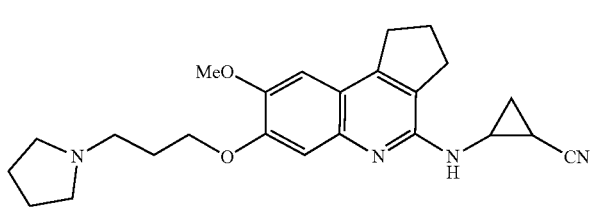 [SMILES: COc1cc2c3c(c(NC4CC4C#N)nc2cc1OCCCN1CCCC1)CCC3]

-continued
| | |
|---|---|
| 162 | 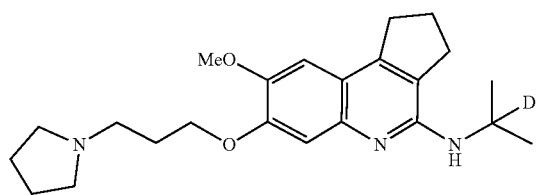 [SMILES: [2H]C(C)(C)Nc1nc2cc(OCCCN3CCCC3)c(OC)cc2c2c1CCC2] |
| 163 | 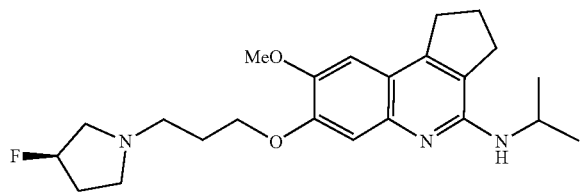 [SMILES: COc1cc2c3c(c(NC(C)C)nc2cc1OCCCN1CC[C@@H](F)C1)CCC3] |
| 164 | 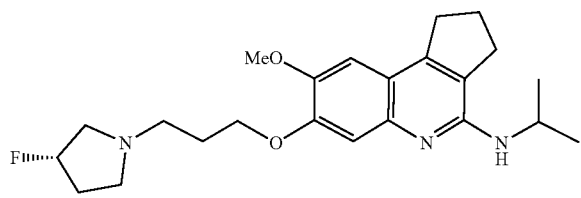 [SMILES: COc1cc2c3c(c(NC(C)C)nc2cc1OCCCN1CC[C@H](F)C1)CCC3] |
| 169 | 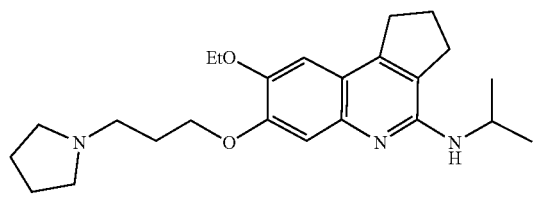 [SMILES: CCOc1cc2c3c(c(NC(C)C)nc2cc1OCCCN1CCCC1)CCC3] |
| 170 | 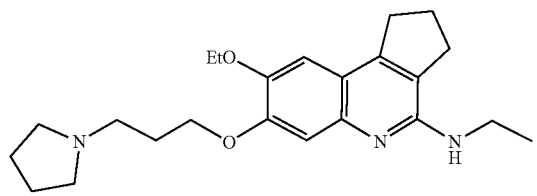 [SMILES: CCNc1nc2cc(OCCCN3CCCC3)c(OCC)cc2c2c1CCC2] |
| 171 | 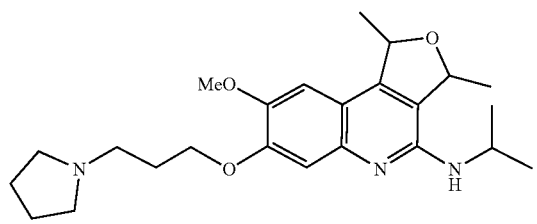 [SMILES: COc1cc2c3c(c(NC(C)C)nc2cc1OCCCN1CCCC1)C(C)OC3C] |
| 172 | 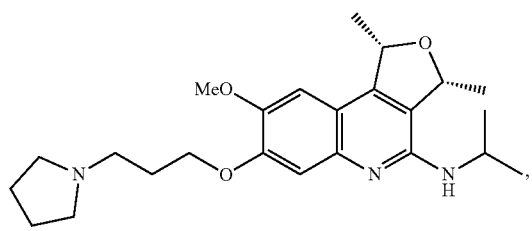 [SMILES: COc1cc2c3c(c(NC(C)C)nc2cc1OCCCN1CCCC1)[C@@H](C)O[C@H]3C] |

-continued
173
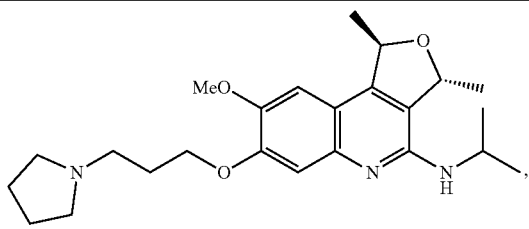
174
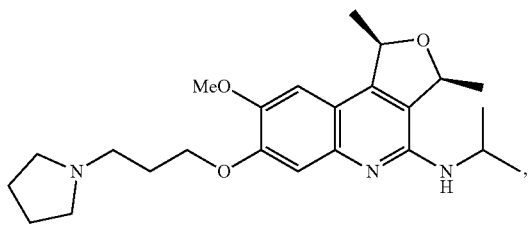 [SMILES: COc1cc2c3c(c(NC(C)C)nc2cc1OCCCN1CCCC1)[C@H](C)O[C@@H]3C]
175
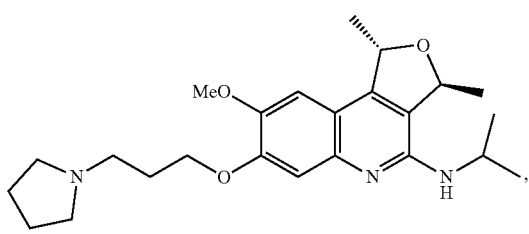 [SMILES: COc1cc2c3c(c(NC(C)C)nc2cc1OCCCN1CCCC1)[C@H](C)O[C@H]3C]
176
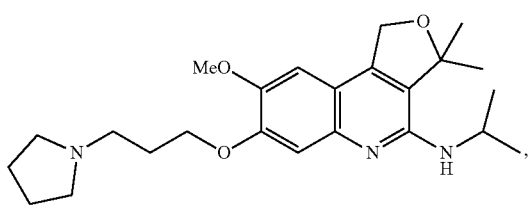 [SMILES: COc1cc2c3c(c(NC(C)C)nc2cc1OCCCN1CCCC1)C(C)(C)OC3]
177
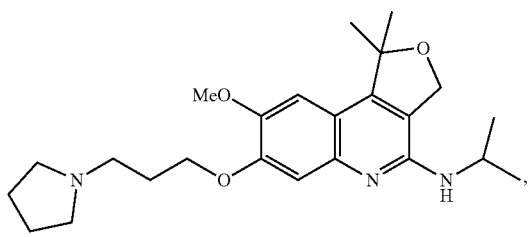 [SMILES: COc1cc2c3c(c(NC(C)C)nc2cc1OCCCN1CCCC1)COC3(C)C]
178
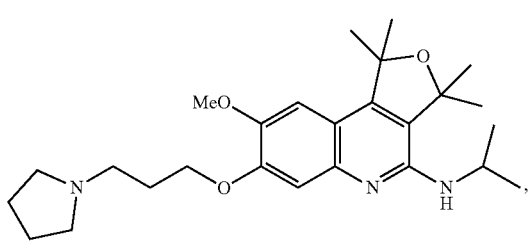 [SMILES: COc1cc2c3c(c(NC(C)C)nc2cc1OCCCN1CCCC1)C(C)(C)OC3(C)C]
179
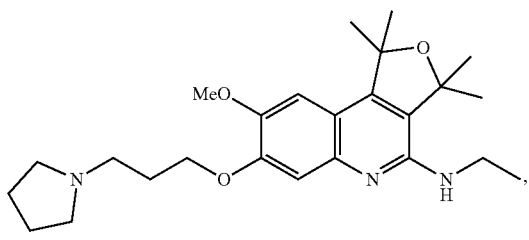 [SMILES: CCNc1nc2cc(OCCCN3CCCC3)c(OC)cc2c2c1C(C)(C)OC2(C)C]

-continued
180
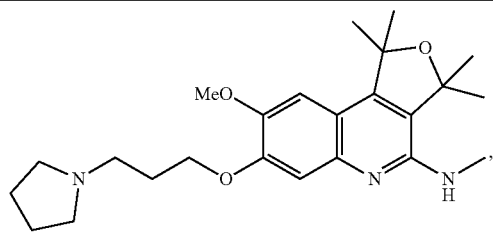
181
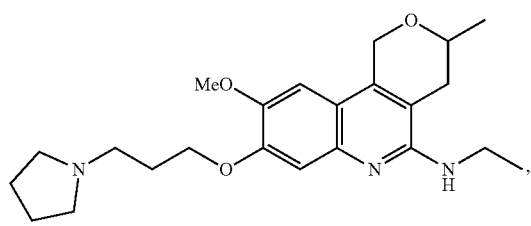 [SMILES: CCNc1nc2cc(OCCCN3CCCC3)c(OC)cc2c2c1CC(C)OC2]
182
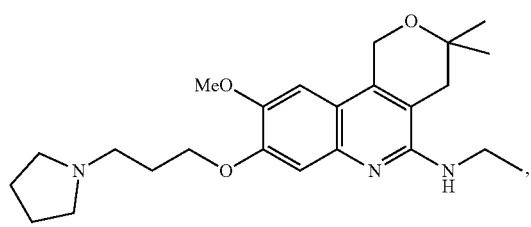 [SMILES: CCNc1nc2cc(OCCCN3CCCC3)c(OC)cc2c2c1CC(C)(C)OC2]
183
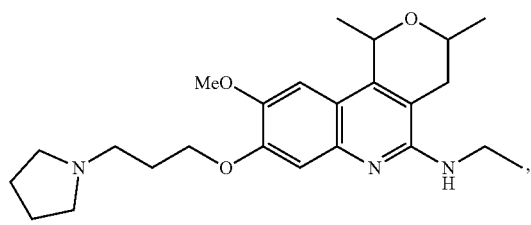 [SMILES: CCNc1nc2cc(OCCCN3CCCC3)c(OC)cc2c2c1CC(C)OC2C]
184
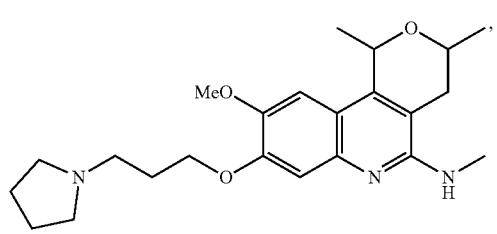 [SMILES: CNc1nc2cc(OCCCN3CCCC3)c(OC)cc2c2c1CC(C)OC2C]
185
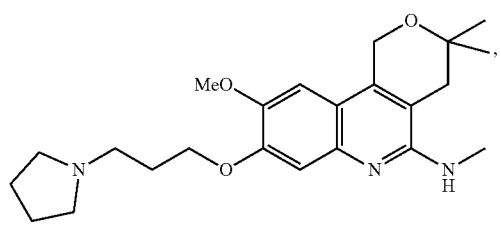 [SMILES: CNc1nc2cc(OCCCN3CCCC3)c(OC)cc2c2c1CC(C)(C)OC2]
186
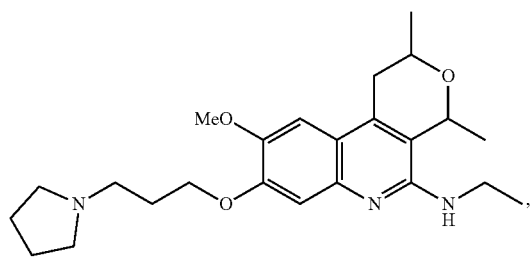 [SMILES: CCNc1nc2cc(OCCCN3CCCC3)c(OC)cc2c2c1C(C)OC(C)C2]

187
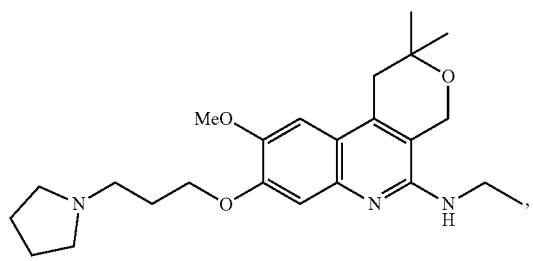 [SMILES: CCNc1nc2cc(OCCCN3CCCC3)c(OC)cc2c2c1COC(C)(C)C2]
188
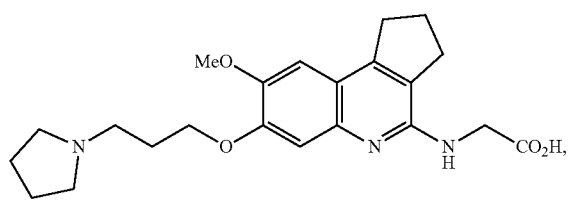 [SMILES: COc1cc2c3c(c(NCC(=O)O)nc2cc1OCCCN1CCCC1)CCC3]
189
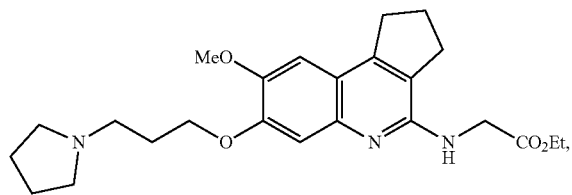 [SMILES: CCOC(=O)CNc1nc2cc(OCCCN3CCCC3)c(OC)cc2c2c1CCC2]
190
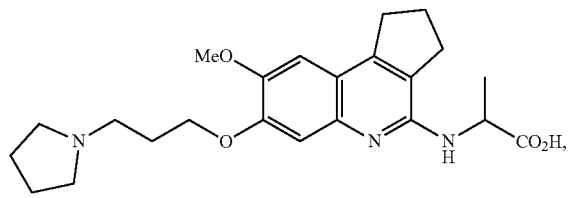 [SMILES: COc1cc2c3c(c(NC(C)C(=O)O)nc2cc1OCCCN1CCCC1)CCC3]
191
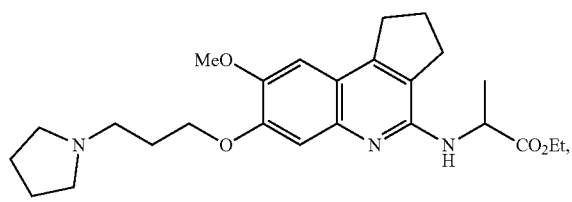 [SMILES: CCOC(=O)C(C)Nc1nc2cc(OCCCN3CCCC3)c(OC)cc2c2c1CCC2]
192
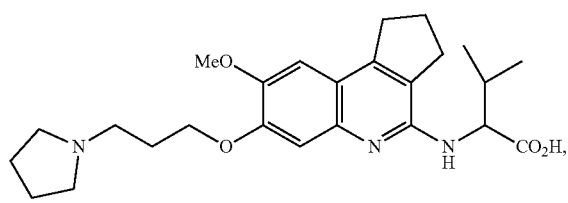 [SMILES: COc1cc2c3c(c(NC(C(=O)O)C(C)C)nc2cc1OCCCN1CCCC1)CCC3]
193
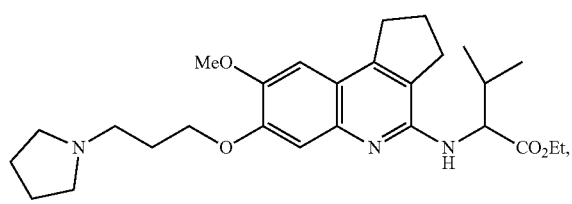 [SMILES: CCOC(=O)C(Nc1nc2cc(OCCCN3CCCC3)c(OC)cc2c2c1CCC2)C(C)C]

-continued

194

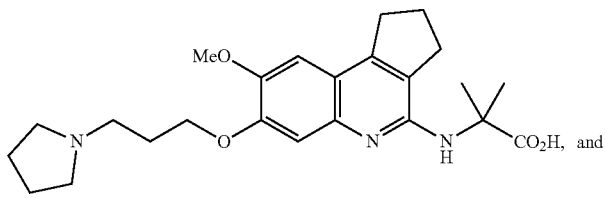 [SMILES: COc1cc2c3c(c(NC(C)(C)C(=O)O)nc2cc1OCCCN1CCCC1)CCC3]

195

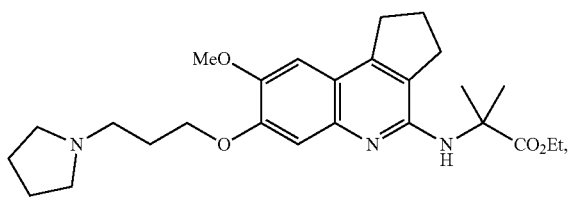 [SMILES: CCOC(=O)C(C)(C)Nc1nc2cc(OCCCN3CCCC3)c(OC)cc2c2c1CCC2]

or a parent compound of any of the salts shown above, or a pharmaceutically acceptable salt of the parent compound.

4. A pharmaceutical composition comprising a compound of claim 1, or a pharmaceutically acceptable salt thereof; and a pharmaceutically acceptable excipient.

5. The compound of claim 3, or a pharmaceutically acceptable salt thereof, wherein the compound, or a pharmaceutically acceptable salt thereof, is selected from the group consisting of:

1

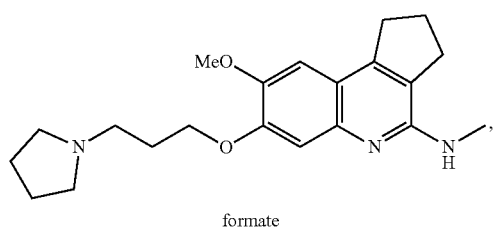 [SMILES: CNc1nc2cc(OCCCN3CCCC3)c(OC)cc2c2c1CCC2]

formate

2

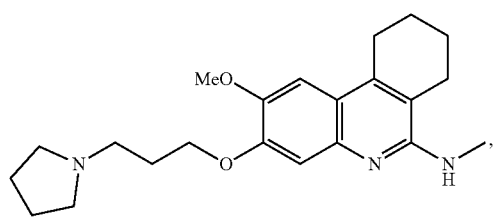

formate

3

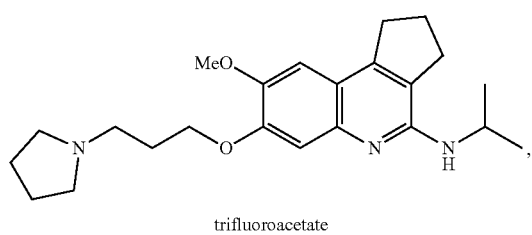 [SMILES: COc1cc2c3c(c(NC(C)C)nc2cc1OCCCN1CCCC1)CCC3]

trifluoroacetate

4

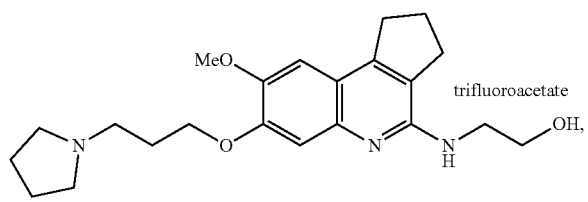 [SMILES: COc1cc2c3c(c(NCCO)nc2cc1OCCCN1CCCC1)CCC3]

trifluoroacetate

5 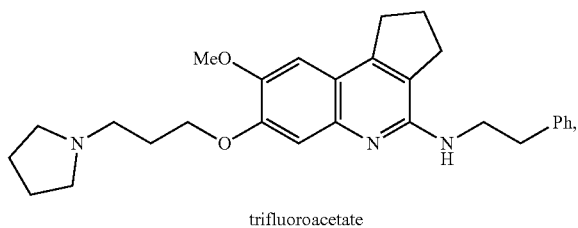 [SMILES: COc1cc2c3c(c(NCCc4ccccc4)nc2cc1OCCCN1CCCC1)CCC3]
trifluoroacetate
6 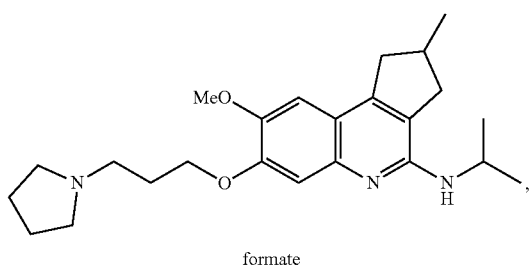 [SMILES: COc1cc2c3c(c(NC(C)C)nc2cc1OCCCN1CCCC1)CC(C)C3]
formate
7 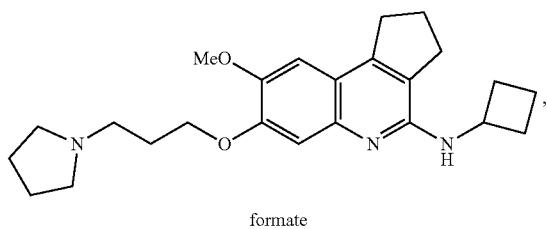 [SMILES: COc1cc2c3c(c(NC4CCC4)nc2cc1OCCCN1CCCC1)CCC3]
formate
8 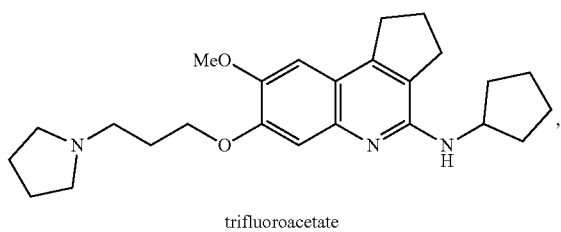 [SMILES: COc1cc2c3c(c(NC4CCCC4)nc2cc1OCCCN1CCCC1)CCC3]
trifluoroacetate
9 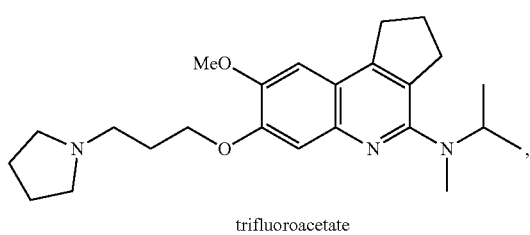 [SMILES: COc1cc2c3c(c(N(C)C(C)C)nc2cc1OCCCN1CCCC1)CCC3]
trifluoroacetate
12 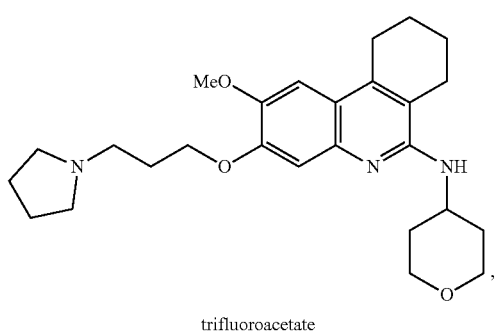 [SMILES: COc1cc2c3c(c(NC4CCOCC4)nc2cc1OCCCN1CCCC1)CCCC3]
trifluoroacetate 13
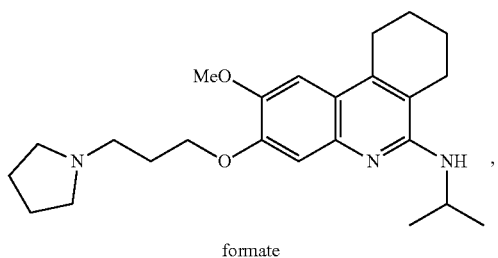 [SMILES: COc1cc2c3c(c(NC(C)C)nc2cc1OCCCN1CCCC1)CCCC3]
formate
14
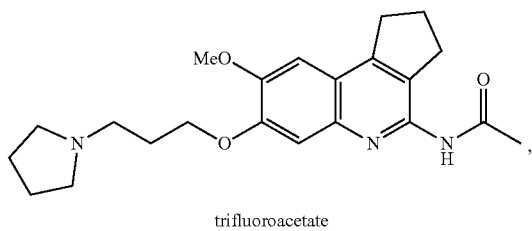 [SMILES: COc1cc2c3c(c(NC(C)=O)nc2cc1OCCCN1CCCC1)CCC3]
trifluoroacetate
15
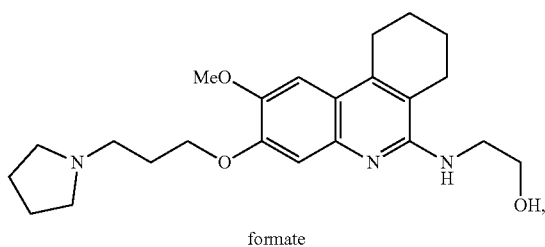 [SMILES: COc1cc2c3c(c(NCCO)nc2cc1OCCCN1CCCC1)CCCC3]
formate
16
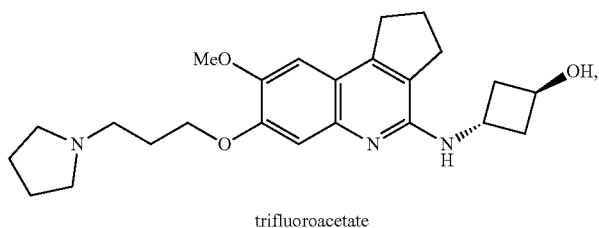 [SMILES: COc1cc2c3c(c(N[C@H]4C[C@H](O)C4)nc2cc1OCCCN1CCCC1)CCC3]
trifluoroacetate
17
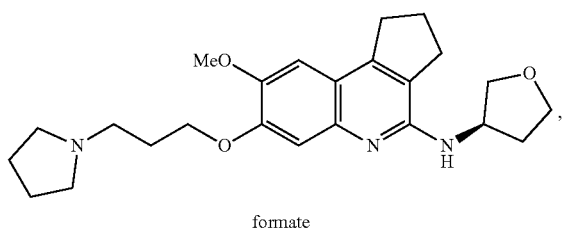 [SMILES: COc1cc2c3c(c(N[C@@H]4CCOC4)nc2cc1OCCCN1CCCC1)CCC3]
formate
18
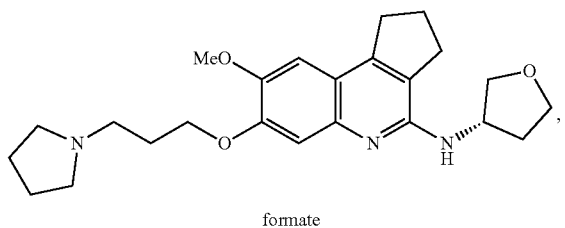 [SMILES: COc1cc2c3c(c(N[C@H]4CCOC4)nc2cc1OCCCN1CCCC1)CCC3]
formate 19 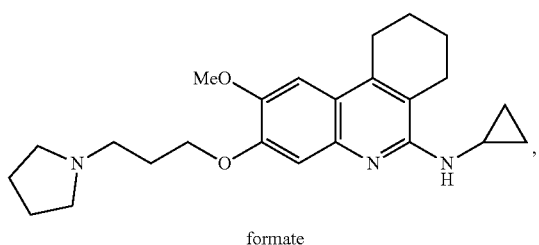 [SMILES: COc1cc2c3c(c(NC4CC4)nc2cc1OCCCN1CCCC1)CCCC3]
formate
20 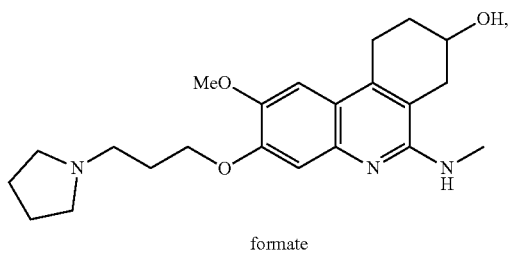 [SMILES: CNc1nc2cc(OCCCN3CCCC3)c(OC)cc2c2c1CC(O)CC2]
formate
22 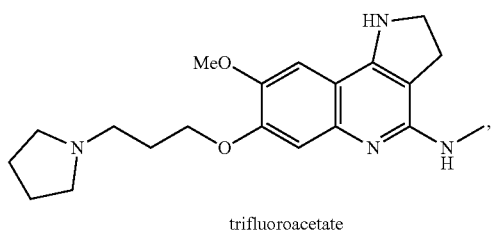 [SMILES: CNc1nc2cc(OCCCN3CCCC3)c(OC)cc2c2c1CCN2]
trifluoroacetate
23 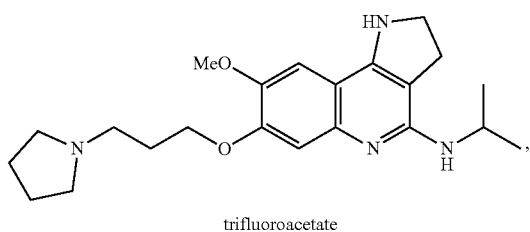 [SMILES: COc1cc2c3c(c(NC(C)C)nc2cc1OCCCN1CCCC1)CCN3]
trifluoroacetate
24 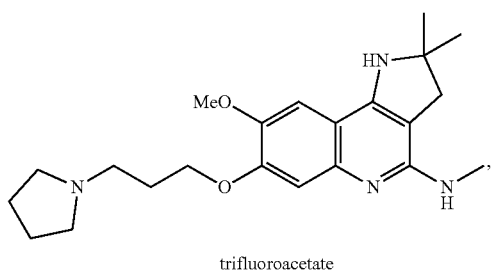 [SMILES: CNc1nc2cc(OCCCN3CCCC3)c(OC)cc2c2c1CC(C)(C)N2]
trifluoroacetate
25 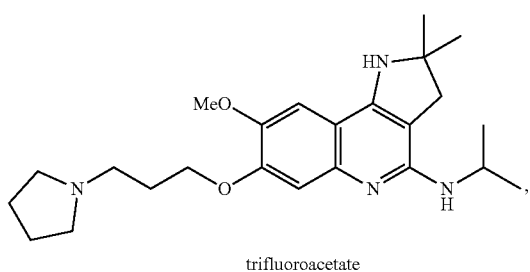 [SMILES: COc1cc2c3c(c(NC(C)C)nc2cc1OCCCN1CCCC1)CC(C)(C)N3]
trifluoroacetate

| | | |
|---|---|---|
| 26 | 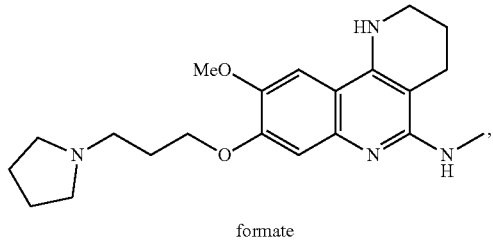 [SMILES: CNc1nc2cc(OCCCN3CCCC3)c(OC)cc2c2c1CCCN2] formate | |
| 27 | 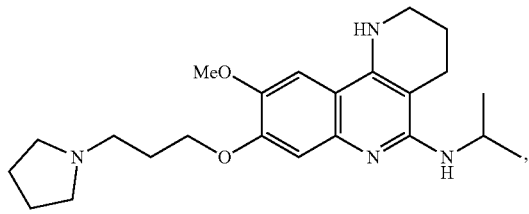 trifluoroacetate | |
| 28 | 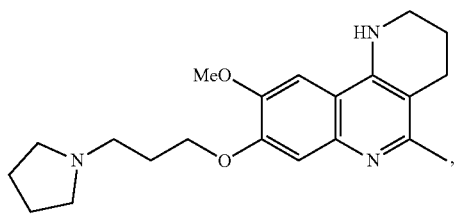 trifluoroacetate | |
| 29 | 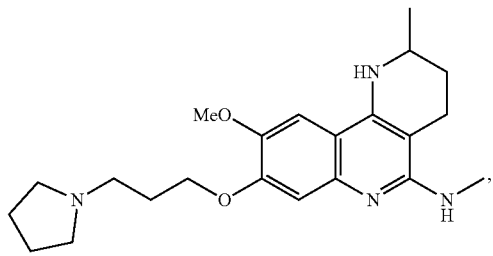 formate | |
| 30 | 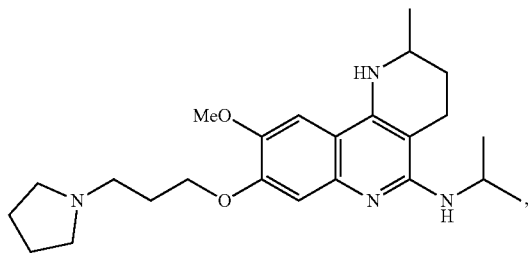 formate | |

31 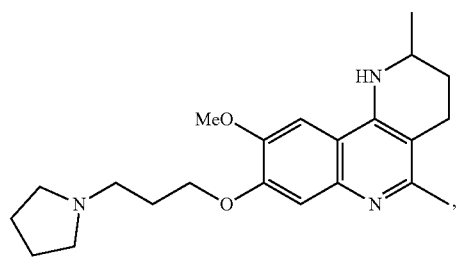
trifluoroacetate
33 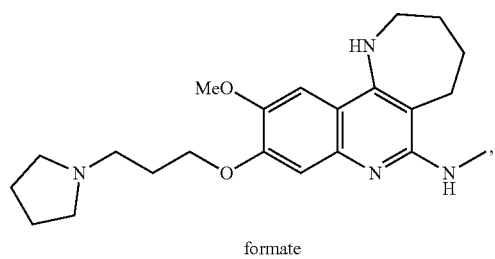 [SMILES: CNc1nc2cc(OCCCN3CCCC3)c(OC)cc2c2c1CCCCN2]
formate
34 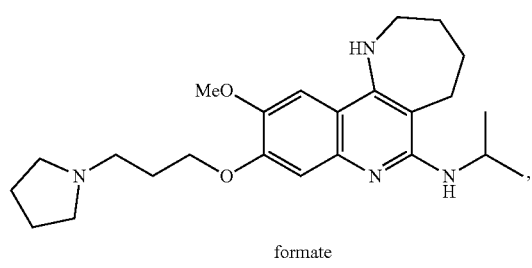 [SMILES: COc1cc2c3c(c(NC(C)C)nc2cc1OCCCN1CCCC1)CCCCN3]
formate
39 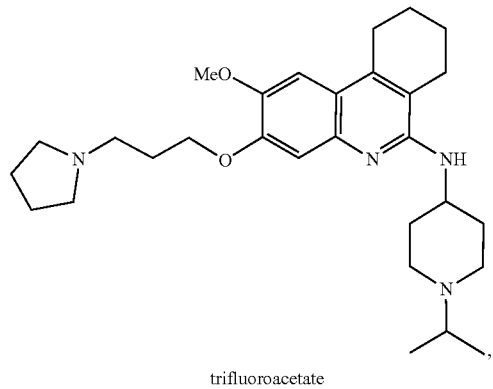 [SMILES: COc1cc2c3c(c(NC4CCN(C(C)C)CC4)nc2cc1OCCCN1CCCC1)CCCC3]
trifluoroacetate
41 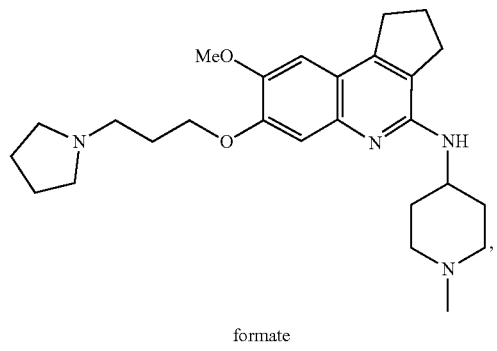 [SMILES: COc1cc2c3c(c(NC4CCN(C)CC4)nc2cc1OCCCN1CCCC1)CCC3]
formate -continued
42
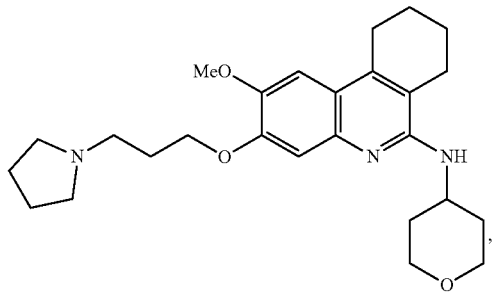
formate
43
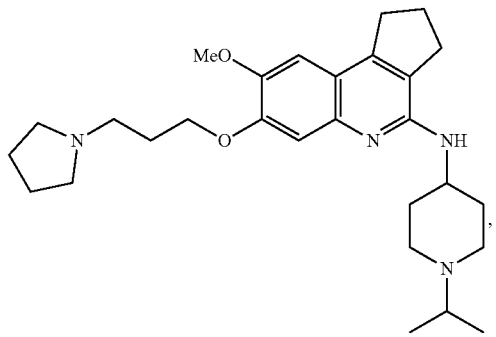
formate
44
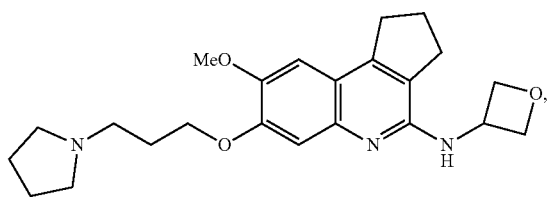
formate
46
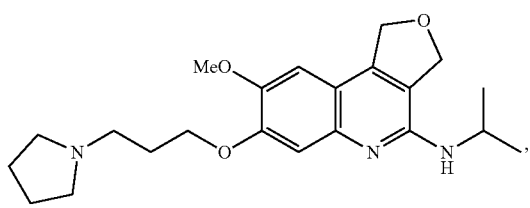
formate
48
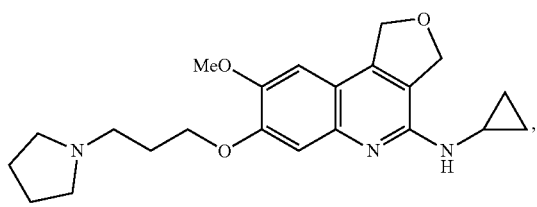 [SMILES: COc1cc2c3c(c(NC4CC4)nc2cc1OCCCN1CCCC1)COC3]
49
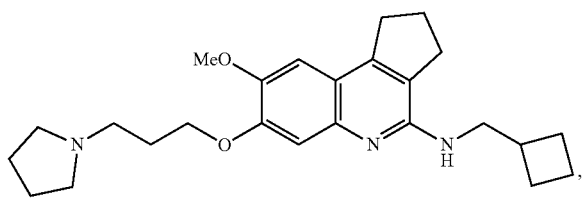
formate 50
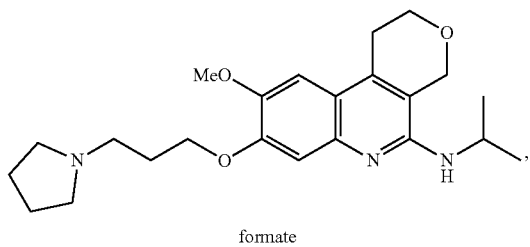 [SMILES: COc1cc2c3c(c(NC(C)C)nc2cc1OCCCN1CCCC1)COCC3]
formate
53
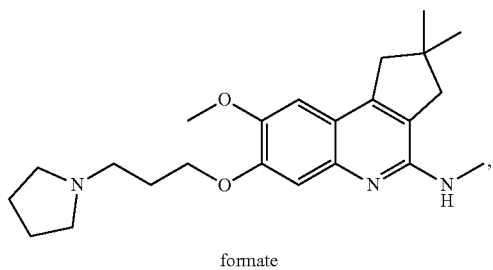 [SMILES: CNc1nc2cc(OCCCN3CCCC3)c(OC)cc2c2c1CC(C)(C)C2]
formate
54
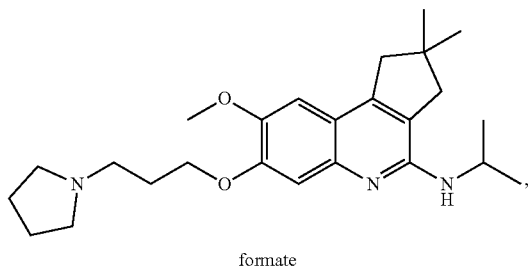 [SMILES: COc1cc2c3c(c(NC(C)C)nc2cc1OCCCN1CCCC1)CC(C)(C)C3]
formate
55
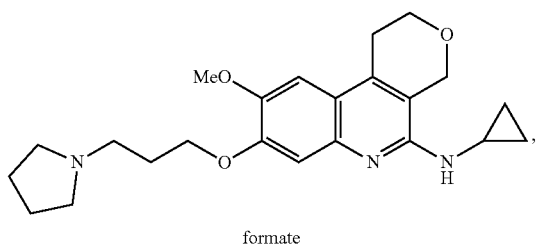 [SMILES: COc1cc2c3c(c(NC4CC4)nc2cc1OCCCN1CCCC1)COCC3]
formate
57
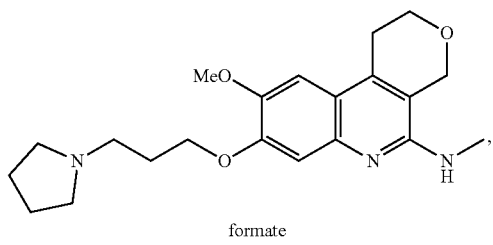 [SMILES: CNc1nc2cc(OCCCN3CCCC3)c(OC)cc2c2c1COCC2]
formate
58
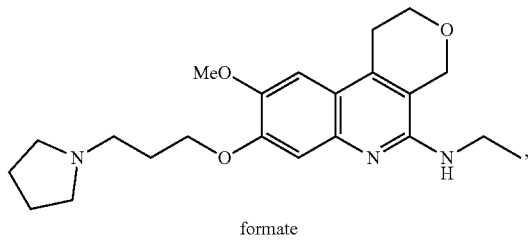 [SMILES: CCNc1nc2cc(OCCCN3CCCC3)c(OC)cc2c2c1COCC2]
formate -continued
59
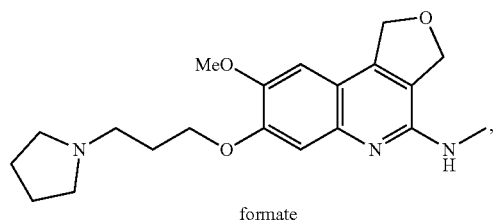 [SMILES: CNc1nc2cc(OCCCN3CCCC3)c(OC)cc2c2c1COC2]
formate
60
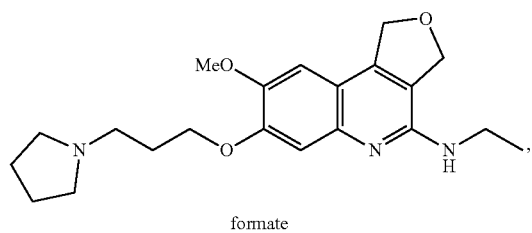 [SMILES: CCNc1nc2cc(OCCCN3CCCC3)c(OC)cc2c2c1COC2]
formate
61
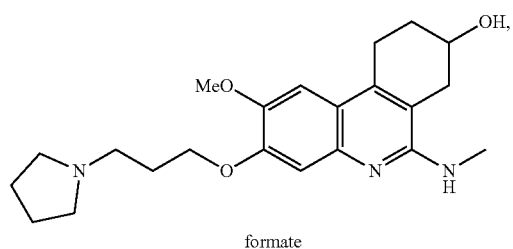 [SMILES: CNc1nc2cc(OCCCN3CCCC3)c(OC)cc2c2c1CC(O)CC2]
formate
62
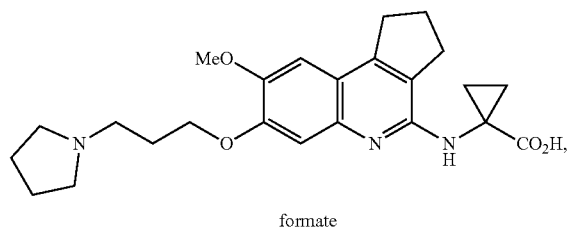 [SMILES: COc1cc2c3c(c(NC4(C(=O)O)CC4)nc2cc1OCCCN1CCCC1)CCC3]
formate
64
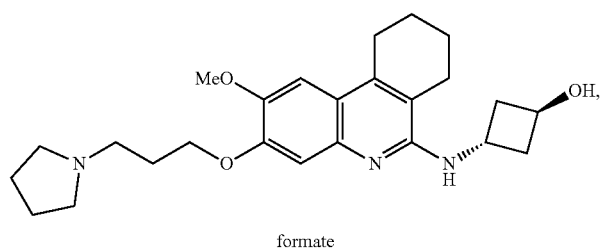 [SMILES: COc1cc2c3c(c(N[C@H]4C[C@H](O)C4)nc2cc1OCCCN1CCCC1)CCCC3]
formate
65
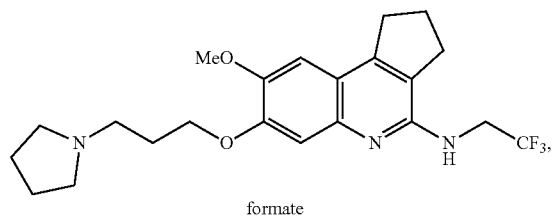 [SMILES: COc1cc2c3c(c(NCC(F)(F)F)nc2cc1OCCCN1CCCC1)CCC3]
formate -continued
66
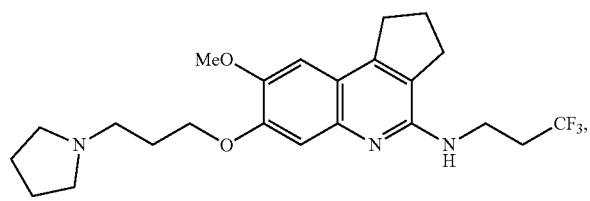 [SMILES: COc1cc2c3c(c(NCCC(F)(F)F)nc2cc1OCCCN1CCCC1)CCC3]
67
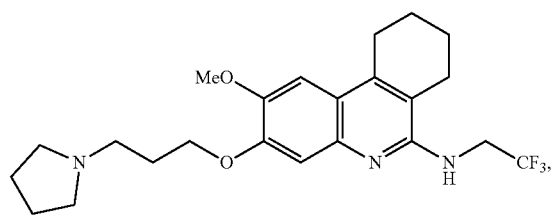
formate
68
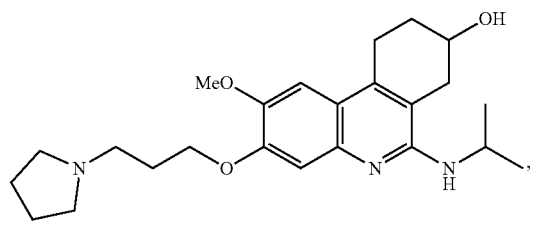
trifluoroacetate
69
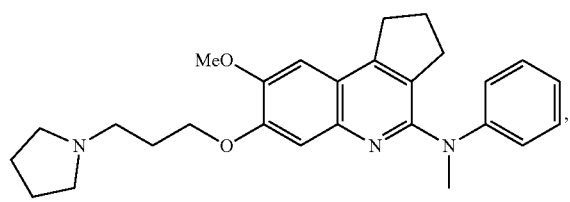
trifluoroacetate
71
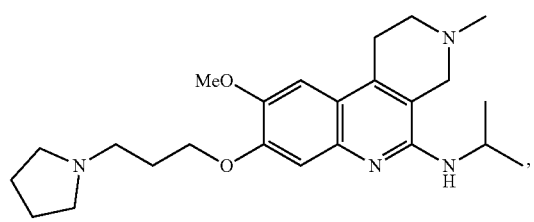
formate
73
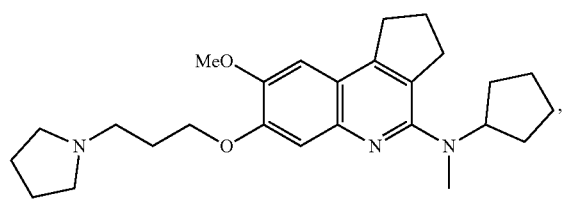
trifluoroacetate -continued
74
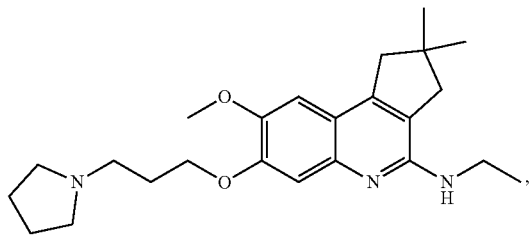
formate
77
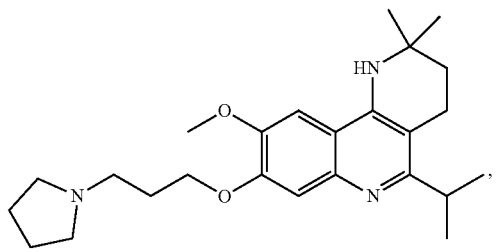
Formate
78
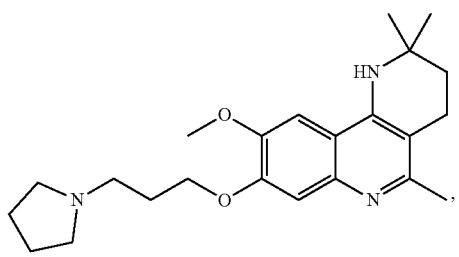
Formate
81
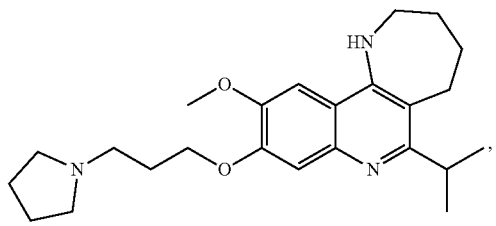
trifluoroacetate
82
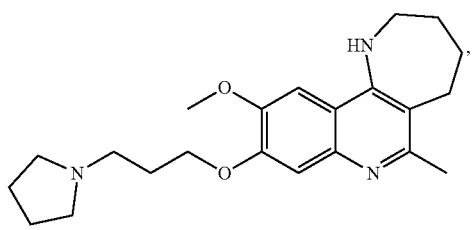
trifluoroacetate
85
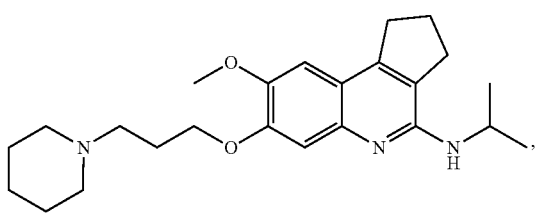
Formate 86
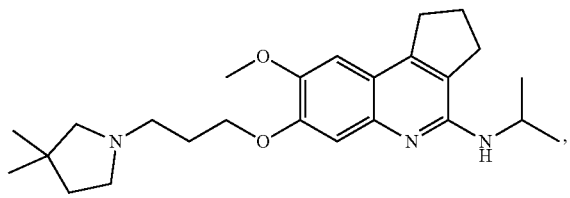
Formate
87
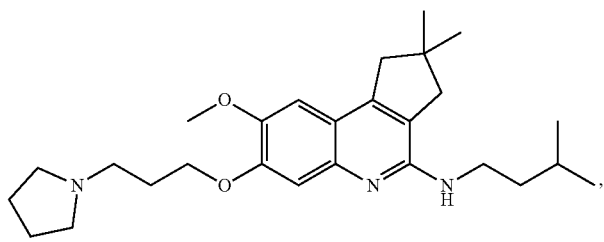
Formate
88
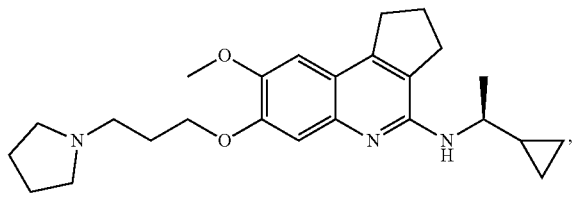
Formate
89
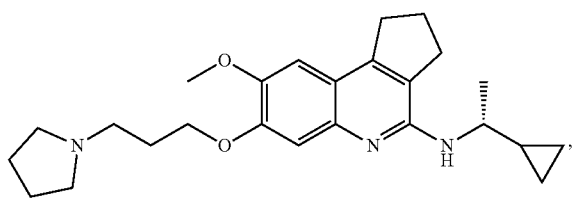
Formate
91
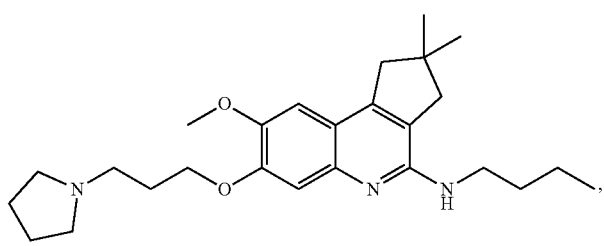
Formate
94
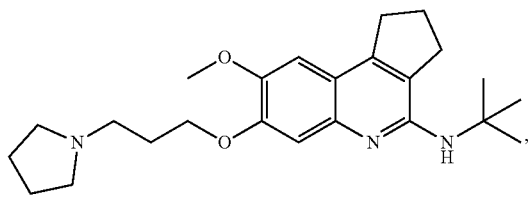
Formate -continued
95
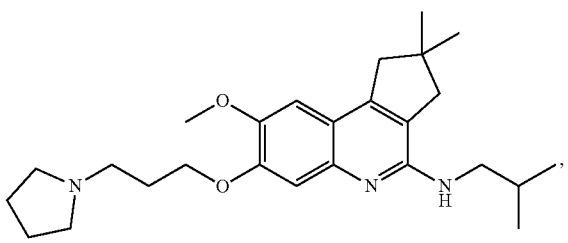
Formate
96
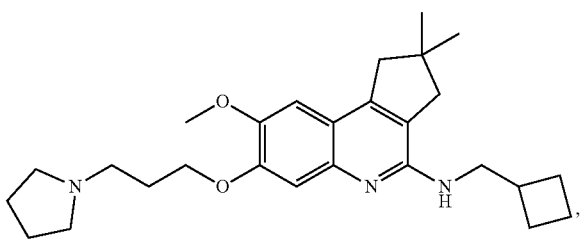
Formate
97
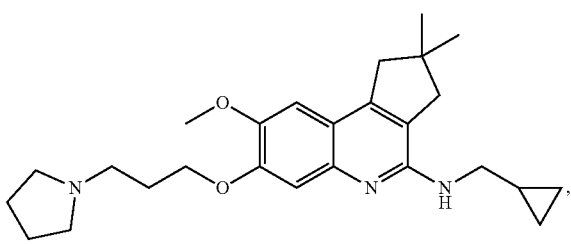
Formate
99
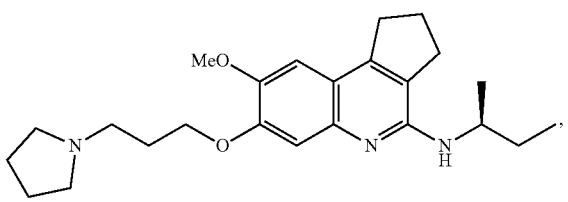
Formate
100
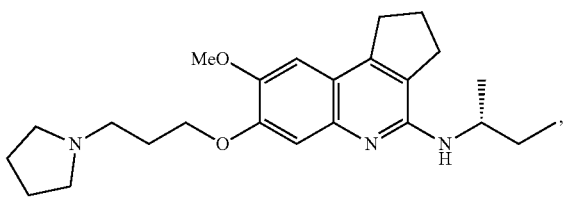
Formate
101
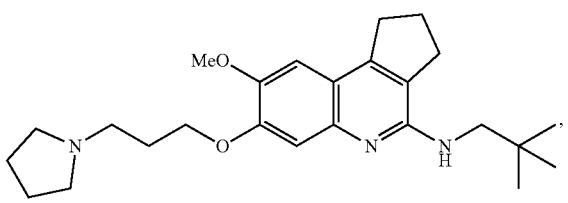
Formate

| | |
|---|---|
| 102 | 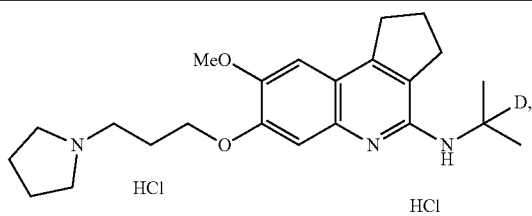
HCl        HCl |
| 103 | 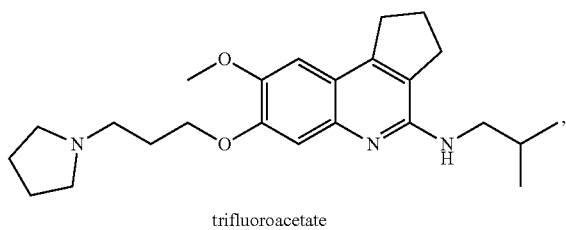 [SMILES: COc1cc2c3c(c(NCC(C)C)nc2cc1OCCCN1CCCC1)CCC3]
trifluoroacetate |
| 104 | 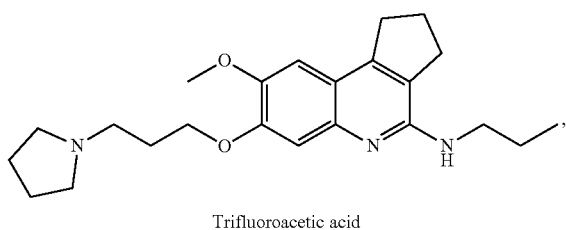 [SMILES: CCCNc1nc2cc(OCCCN3CCCC3)c(OC)cc2c2c1CCC2]
Trifluoroacetic acid |
| 105 | 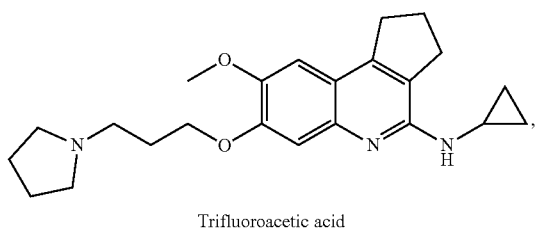 [SMILES: COc1cc2c3c(c(NC4CC4)nc2cc1OCCCN1CCCC1)CCC3]
Trifluoroacetic acid |
| 106 | 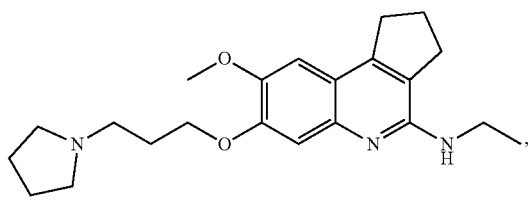
Trifluoroacetic acid |
| 107 | 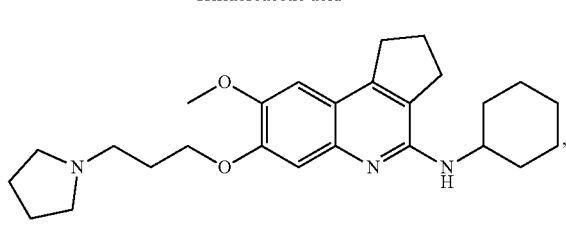
Trifluoroacetic acid |
| 108 | 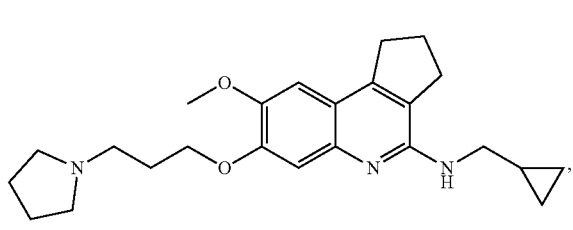
Trifluoroacetic acid |

112
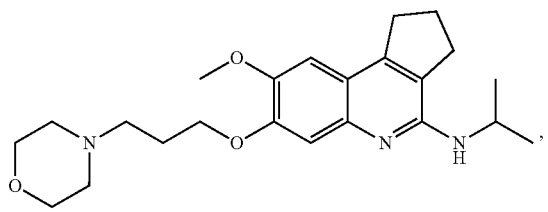
Trifluoroacetic
115
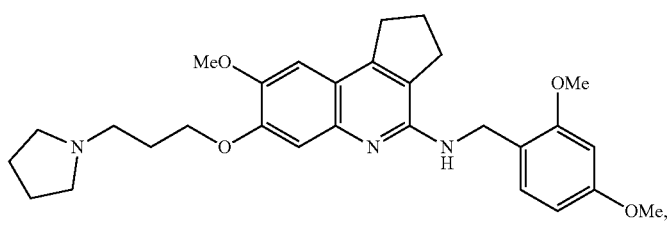
Formate
116
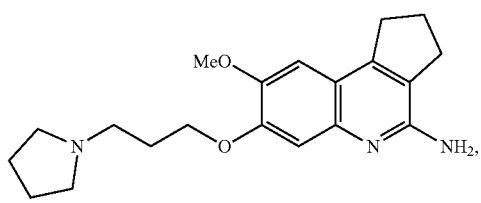
Formate
117
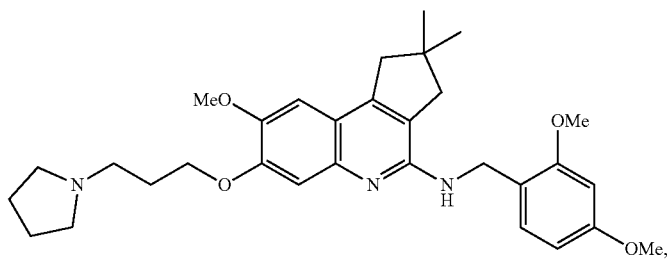
Formate
118
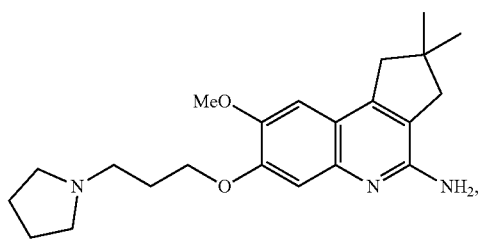
Formate
119
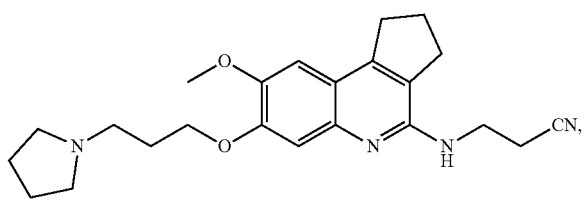
Formate 120
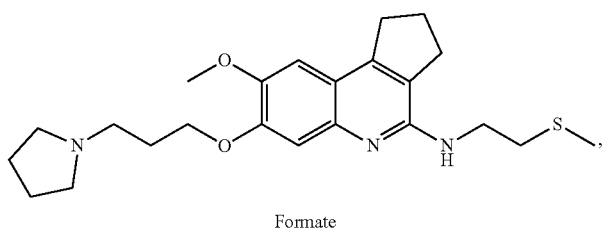 [SMILES: COc1cc2c3c(c(NCCSC)nc2cc1OCCCN1CCCC1)CCC3]
Formate
121a
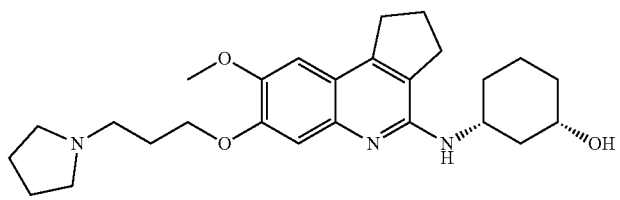
Formate
121b
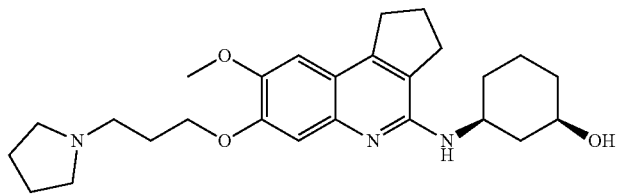
Formate
121c
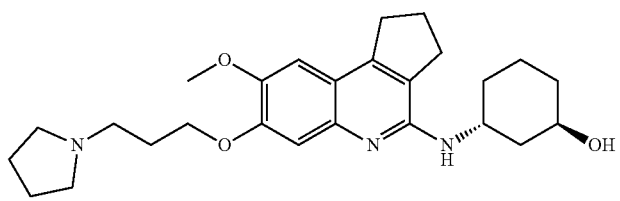
Formate
121d
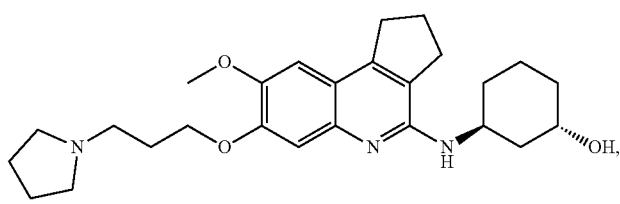
Formate
122
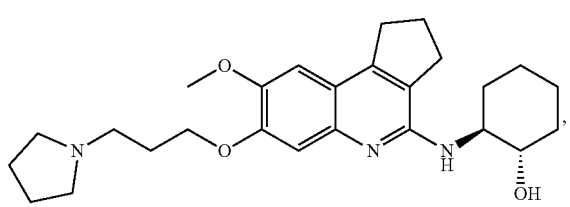
Formate 123 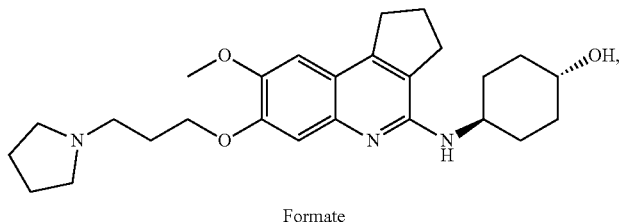 [SMILES: COc1cc2c3c(c(N[C@H]4CC[C@H](O)CC4)nc2cc1OCCCN1CCCC1)CCC3]
Formate 124 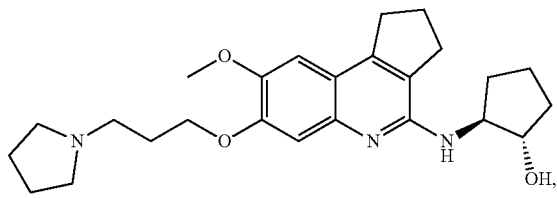
Formate 125a 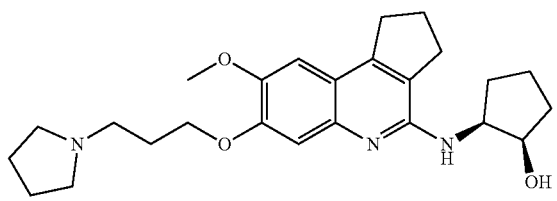
Formate 125b 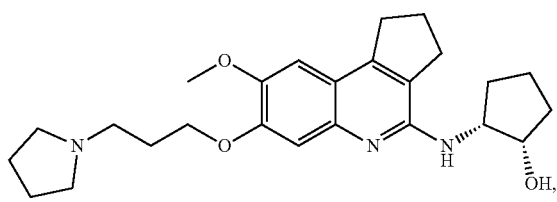
Formate 126 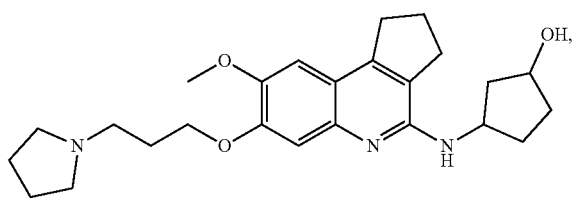
Formate or a parent compound of any of the salts shown above, or a pharmaceutically acceptable salt of the parent compound.

6. The compound of claim 1, or a pharmaceutically acceptable salt thereof, wherein,
alk is —O—(CH$_2$)$_3$*;
R$^1$ is -pyrrolidin-1-yl; and
R$^2$ is methoxy.

7. The compound of claim 6, or a pharmaceutically acceptable salt thereof, wherein R$^4$ is alkyl.

8. The compound of claim 6, or a pharmaceutically acceptable salt thereof, wherein R$^4$ is —NR$^e$R$^f$.

9. The compound of claim 8, or a pharmaceutically acceptable salt thereof, wherein R$^e$ is hydrogen or alkyl, and R$^f$ is alkyl.

10. The compound of claim 9, or a pharmaceutically acceptable salt thereof, wherein said alkyl of R$^e$ or R$^f$ is independently selected from the group consisting of methyl, ethyl, n-propyl, isopropyl, n-butyl, isobutyl, s-butyl and t-butyl.

11. The compound of claim 10, or a pharmaceutically acceptable salt thereof, wherein ring B is unsubstituted 5- or 6-membered cycloalkyl or 5- or 6-membered cycloalkyl substituted with 1 or 2 of R$^j$ and R$^k$, wherein R$^j$ and R$^k$ are each independently alkyl, halo or hydroxy.

12. The compound of claim 11, or a pharmaceutically acceptable salt thereof, wherein ring B is unsubstituted cyclopentyl or cyclopentyl substituted with 1 or 2 of R$^j$ and R$^k$, wherein R$^j$ and R$^k$ are each independently alkyl.

13. The compound of claim 11, or a pharmaceutically acceptable salt thereof, wherein ring B is cyclopentyl or cyclohexyl.

14. The compound of claim 13, or a pharmaceutically acceptable salt thereof, wherein ring B is cyclopentyl.

15. The compound of claim 1, or a pharmaceutically acceptable salt thereof, wherein ring B is a 5, 6 or 7 membered nitrogen containing heterocyclyl.

16. The compound of claim 15, or a pharmaceutically acceptable salt thereof, wherein $R^4$ is alkyl.

* * * * *